US012599665B2

(12) United States Patent
Mock et al.

(10) Patent No.: US 12,599,665 B2
(45) Date of Patent: Apr. 14, 2026

(54) GENE FUSIONS FOR CONTROL OF GENETICALLY MODIFIED CELLS

(71) Applicant: A2 Biotherapeutics, Inc., Agoura Hills, CA (US)

(72) Inventors: Jee Young Mock, North Hollywood, CA (US); Carl Alexander Kamb, Thousand Oaks, CA (US); Agnes Hamburger, Newbury Park, CA (US)

(73) Assignee: A2 Biotherapeutics, Inc., Agoura Hills, CA (US)

( * ) Notice: Subject to any disclaimer, the term of this patent is extended or adjusted under 35 U.S.C. 154(b) by 574 days.

(21) Appl. No.: 18/020,728

(22) PCT Filed: Aug. 12, 2021

(86) PCT No.: PCT/US2021/045704

§ 371 (c)(1),
(2) Date: Feb. 10, 2023

(87) PCT Pub. No.: WO2022/036068

PCT Pub. Date: Feb. 17, 2022

(65) Prior Publication Data

US 2023/0330227 A1 Oct. 19, 2023

Related U.S. Application Data

(60) Provisional application No. 63/065,321, filed on Aug. 13, 2020.

(51) Int. Cl.

| | |
|---|---|
| ***A61K 40/11*** | (2025.01) |
| ***A61K 31/138*** | (2006.01) |
| ***A61K 40/22*** | (2025.01) |
| ***A61K 40/30*** | (2025.01) |
| ***A61K 40/31*** | (2025.01) |
| ***A61K 40/41*** | (2025.01) |
| ***C07K 14/47*** | (2006.01) |
| ***C07K 14/72*** | (2006.01) |
| ***C07K 14/725*** | (2006.01) |
| ***C12N 5/0783*** | (2010.01) |
| ***C12N 15/86*** | (2006.01) |

(52) U.S. Cl.

CPC ............ *A61K 40/11* (2025.01); *A61K 31/138* (2013.01); *A61K 40/22* (2025.01); *A61K 40/30* (2025.01); *A61K 40/31* (2025.01); *A61K 40/412* (2025.01); *C07K 14/4747* (2013.01); *C07K 14/7051* (2013.01); *C07K 14/721* (2013.01); *C12N 5/0636* (2013.01); *C12N 15/86* (2013.01); *A61K 2239/25* (2023.05); *C07K 2319/00* (2013.01); *C12N 2740/15043* (2013.01)

(58) Field of Classification Search

CPC ...... A61K 40/11; A61K 31/138; A61K 40/22; A61K 40/30; A61K 40/31; A61K 40/412; A61K 2239/25; C07K 14/4747; C07K 14/7051; C07K 14/721; C07K 2319/00; C12N 5/0636; C12N 15/86; C12N 2740/15043

See application file for complete search history.

(56) References Cited

U.S. PATENT DOCUMENTS

| | | | | |
|---|---|---|---|---|
| 5,192,525 | A | | 3/1993 | Yang et al. |
| 5,350,674 | A | | 9/1994 | Boenisch et al. |
| 5,585,362 | A | | 12/1996 | Wilson et al. |
| 5,858,358 | A | | 1/1999 | June et al. |
| 5,883,223 | A | | 3/1999 | Gray |
| 5,994,136 | A | | 11/1999 | Naldini et al. |
| 5,998,583 | A | * | 12/1999 | Korsmeyer ............. A61P 25/00 435/69.7 |
| 6,013,516 | A | | 1/2000 | Verma et al. |
| 6,326,193 | B1 | | 12/2001 | Liu et al. |
| 6,352,694 | B1 | | 3/2002 | June et al. |
| 6,534,055 | B1 | | 3/2003 | June et al. |
| 6,692,964 | B1 | | 2/2004 | June et al. |
| 6,797,514 | B2 | | 9/2004 | Berenson et al. |
| 6,867,041 | B2 | | 3/2005 | Berenson et al. |
| 6,887,466 | B2 | | 5/2005 | June et al. |
| 6,905,680 | B2 | | 6/2005 | June et al. |
| 6,905,681 | B1 | | 6/2005 | June et al. |
| 6,905,874 | B2 | | 6/2005 | Berenson et al. |
| 7,067,318 | B2 | | 6/2006 | June et al. |
| 7,144,575 | B2 | | 12/2006 | June et al. |
| 7,172,869 | B2 | | 2/2007 | June et al. |
| 7,175,843 | B2 | | 2/2007 | June et al. |
| 7,232,566 | B2 | | 6/2007 | June et al. |

(Continued)

FOREIGN PATENT DOCUMENTS

| | | | |
|---|---|---|---|
| WO | 0129058 | A1 | 4/2001 |
| WO | 0183692 | A2 | 11/2001 |

(Continued)

OTHER PUBLICATIONS

Picard, Didier. "Posttranslational Regulation of Proteins by Fusions to Steroid-Binding Domains." Methods in Enzymology, vol. 327, Elsevier, 2000, pp. 385-401. (Year: 2000).*
Abraham, Robert T., and Arthur Weiss. "Jurkat T Cells and Development of the T-Cell Receptor Signalling Paradigm." Nature Reviews Immunology, vol. 4, No. 4, Apr. 2004, pp. 301-308. (Year: 2004).*
Alexander et al. (2017) "The Concise Guide to Pharmacology 2017/18: Nuclear Hormone Receptors", British Journal of Pharmacology, 174(Suppl Suppl 1):S208-S224.
Altschul et al. (Oct. 5, 1990) "Basic Local Alignment Search Tool", Journal of Molecular Biology, 215(3):403-410.
Altschul et al. (Sep. 1, 1997) "Gapped BLAST and PSI-BLAST: A New Generation of Protein Database Search Programs", Nucleic Acids Research, 25(17):3389-3402.

(Continued)

*Primary Examiner* — J. E. Angell
*Assistant Examiner* — Sarah E Allen
(74) *Attorney, Agent, or Firm* — Mintz Levin Cohn Ferris Glovsky and Popeo, P.C.; James R. Whittle

(57) ABSTRACT

The disclosure relates to fusion proteins comprising a tBID polypeptide and a steroid hormone receptor domain, and methods of using same to induce apoptosis in cells.

6 Claims, 16 Drawing Sheets

Specification includes a Sequence Listing.

(56) References Cited

U.S. PATENT DOCUMENTS

| | | | | |
|---|---|---|---|---|
| 8,530,168 B2 | | 9/2013 | Chu et al. | |
| 10,040,846 B2 | | 8/2018 | Frigault et al. | |
| 2003/0109683 A1 | | 6/2003 | Omalley et al. | |
| 2004/0101519 A1 | | 5/2004 | June et al. | |
| 2006/0034810 A1 | | 2/2006 | Riley et al. | |
| 2006/0121005 A1 | | 6/2006 | Berenson et al. | |
| 2011/0023137 A1 | | 1/2011 | Chu et al. | |
| 2019/0008797 A1 | * | 1/2019 | Leitman | A61K 31/565 |

FOREIGN PATENT DOCUMENTS

| | | | | | |
|---|---|---|---|---|---|
| WO | 0198584 A2 | | 12/2001 | | |
| WO | 2012138475 A1 | | 10/2012 | | |
| WO | WO-2014121093 A1 | * | 8/2014 | | C07K 14/525 |
| WO | 2017040815 A1 | | 3/2017 | | |
| WO | WO-2017127750 A1 | * | 7/2017 | | A61P 35/00 |
| WO | 2021030149 A1 | | 2/2021 | | |
| WO | 2021030153 A2 | | 2/2021 | | |
| WO | 2021096868 A1 | | 5/2021 | | |
| WO | 2021119489 A1 | | 6/2021 | | |
| WO | 2022036068 A1 | | 2/2022 | | |

OTHER PUBLICATIONS

Berge et al. (Dec. 1998) "Selective Expansion of a Peripheral Blood CD8+ Memory T Cell Subset Expressing Both Granzyme B and L-Selectin During Primary Viral Infection in Renal Allograft Recipients", Transplantation Proceedings, 30(8):3975-3977.

Bonifant et al. (Apr. 20, 2016) "Toxicity and Management in CAR T-Cell Therapy", Molecular Therapy Oncolytics, 16011 (7 pages).

Brocard et al. (Sep. 1, 1998) "A Chimeric Cre Recombinase Inducible by Synthetic, but Not by Natural Ligands of the Glucocorticoid Receptor", Nucleic Acids Research, 26(17):4086-4090.

Brocard et al. (Dec. 23, 1997) "Spatio-Temporally Controlled Site-Specific Somatic Mutagenesis in the Mouse", Proceedings of the National Academy of Sciences of the United States of America, 94(26):14559-14563.

Chu et al. (Oct. 2008) "Novel Caspase-suicide Proteins for Tamoxifen-Inducible Apoptosis", Genesis, 46(10):530-536.

Clackson et al. (Sep. 1, 1998) "Redesigning an FKBP-ligand Interface to Generate Chemical Dimerizers With Novel Specificity", Proceedings of the National Academy of Sciences of the United States of America, 95(18):10437-10442.

Danielian et al. (Feb. 1993) "Identification of Residues in the Estrogen Receptor That Confer Differential Sensitivity to Estrogen and Hydroxytamoxifen", Molecular Endocrinology, 7(2):232-240.

Database Genbank. (Aug. 19, 2022) "BH3-interacting Domain Death Agonist Isoform 2 [*Homo Sapiens*]", Accession No. NP_001187. 1, 3 pages.

Database Genbank. (Dec. 19, 2022) "BH3-interacting Domain Death Agonist Isoform 3 [*Homo Sapiens*]", Accession No. NP_932071. 1, 3 pages.

Database Genbank. (Jul. 26, 2020) "*Homo Sapiens* BH3 Interacting Domain Death Agonist (BID), Transcript Variant 1, mRNA", Accession No. NM_197966.2, 4 pages.

Farzaneh et al. (Apr. 13, 2016) "Estrogen Receptor Ligands: A Review (2013-2015)", Scientia Pharmaceutica, 84(3):409-427.

Feil et al. (Aug. 28, 1997) "Regulation of Cre Recombinase Activity by Mutated Estrogen Receptor Ligand-Binding Domains", Biochemical and Biophysical Research Communications, 237(3):752-757.

Garland et al. (Jul. 30, 1999) "The Use of Teflon Cell Culture Bags to Expand Functionally Active CD8+ Cytotoxic T Lymphocytes", Journal of Immunological Methods, 227(1-2):53-63.

Gross et al. (Jan. 8, 1999) "Caspase Cleaved BID Targets Mitochondria and is Required for Cytochrome C Release, While BCL-XL Prevents This Release but Not Tumor Necrosis Factor-R1/Fas Death", Journal of Biological Chemistry, 274(2):1156-1163.

Haanen et al. (Nov. 1, 1999) "Selective Expansion of Cross-reactive CD8+ Memory T Cells by Viral Variants", Journal of Experimental Medicine, 190(9):1319-1328.

Indra et al. (Nov. 15, 1999) "Temporally-Controlled Site-specific Mutagenesis in the Basal Layer of the Epidermis: Comparison of the Recombinase Activity of the Tamoxifen-inducible Cre-ER(T) and Cre-ER(T2) Recombinases", Nucleic Acids Research, 27(22):4324-4327.

Kaczmarczyk et al. (Aug. 1, 2003) "Induction of Cre Recombinase Activity Using Modified Androgen Receptor Ligand Binding Domains: a Sensitive Assay for Ligand-receptor Interactions", Nucleic Acids Research, 31(15):e86 (8 pages).

Karlin et al. (Jun. 15, 1993) "Applications and Statistics for Multiple High-scoring Segments in Molecular Sequences", Proceedings of the National Academy of Sciences of the United States of America, 90(12):5873-5877.

Karlin et al. (Mar. 1990) "Methods for Assessing the Statistical Significance of Molecular Sequence Features by Using General Scoring Schemes", Proceedings of the National Academy of Sciences of the United States of America, 87(6):2264-2268.

Kellendonk et al. (Jan. 8, 1999) "Inducible Site-Specific Recombination in the Brain", Journal of Molecular Biology, 285(1):175-182.

Kellendonk et al. (Apr. 1, 1996) "Regulation of Cre Recombinase Activity by the Synthetic Steroid RU 486", Nucleic Acids Research, 24(8):1404-1411.

Kumar et al. (May 1999) "The Structure of the Nuclear Hormone Receptors", Steroids, 64(5):310-319.

Li et al. (Aug. 21, 1998) "Cleavage of BID by Caspase 8 Mediates the Mitochondrial Damage in the Fas Pathway of Apoptosis", Cell, 94(4):491-501.

Luo et al. (Aug. 21, 1998) "Bid, a Bcl2 Interacting Protein, Mediates Cytochrome C Release From Mitochondria in Response to Activation of Cell Surface Death Receptors", Cell, 94(4):481-490.

Mangelsdorf et al. (Dec. 15, 1995) "The Nuclear Receptor Superfamily: The Second Decade", Cell, 83(6):835-839.

Marsic et al. (Nov. 2014) "Vector Design Tour De Force: Integrating Combinatorial and Rational Approaches to Derive Novel Adeno-associated Virus Variants", Molecular Therapy, 22(11):1900-1909.

Metzger et al. (Jul. 18, 1995) "Conditional Site-Specific Recombination in Mammalian Cells Using a Ligand-dependent Chimeric Cre Recombinase", Proceedings of the National Academy of Sciences of the United States of America, 92(15):6991-6995.

Miyazaki et al. (Feb. 14, 2012) "Destabilizing Domains Derived from the Human Estrogen Receptor", Journal of the American Chemical Society, 134(9):3942-3945.

Muchmore et al. (May 23, 1996) "X-ray and NMR Structure of Human Bcl-xl, an Inhibitor of Programmed Cell Death", Nature, 381(6580):335-341.

Petros et al. (Mar. 1, 2004) "Structural Biology of the Bcl-2 Family of Proteins", Biochimica et Biophysica Acta, 1644(2-3):83-94.

Spencer et al. (Nov. 12, 1993) "Controlling Signal Transduction with Synthetic Ligands", Science, 262(5136):1019-1024.

Stasi et al. (Nov. 3, 2011) "Inducible Apoptosis as a Safety Switch for Adoptive Cell Therapy", The New England Journal of Medicine, 365(18):1673-1683.

Straathof et al. (Feb. 22, 2005) "An Inducible Caspase 9 Safety Switch for T-cell Therapy", 105(11):4247-4254.

Takebayashi et al. (Sep. 1, 1996) "Hormone-induced Apoptosis by Fas-Nuclear Receptor Fusion Proteins: Novel Biological Tools for Controlling Apoptosis in Vivo", Cancer Research, 56(18):4164-4170.

Tey, Siok-Keen. (Jun. 20, 2014) "Adoptive T-Cell Therapy: Adverse Events and Safety Switches", Clinical & Translational Immunology, 3(6):e17 (7 pages).

Tey et al. (May 29, 2007) "Inducible Caspase 9 Suicide Gene to Improve the Safety of Allodepleted T Cells After Haploidentical Stem Cell Transplantation", Biology of Blood and Marrow Transplantation, 13(8):913-924.

Wang et al. (Aug. 1994) "A Regulatory System for Use in Gene Transfer", Proceedings of the National Academy of Sciences of the United States of America, 91:8180-8184.

(56) References Cited

OTHER PUBLICATIONS

Wootton et al. (Jun. 1993) "Statistics of Local Complexity in Amino Acid Sequences and Sequence Databases", Computers & Chemistry, 17(2):149-163.
Zhou et al. (Nov. 2016) "Improving the Safety of T-Cell Therapies Using an Inducible Caspase-9 Gene", Experimental Hematology, 44(11):1013-1019.

* cited by examiner

SEQUENCE LISTING

```
<160> NUMBER OF SEQ ID NOS: 106

<210> SEQ ID NO 1
<211> LENGTH: 65
<212> TYPE: PRT
<213> ORGANISM: Artificial Sequence
<220> FEATURE:
<223> OTHER INFORMATION: tBID polypeptide

<400> SEQUENCE: 1

Ser Gln Glu Asp Ile Ile Arg Asn Ile Ala Arg His Leu Ala Gln Val
1               5                   10                  15

Gly Asp Ser Met Asp Arg Ser Ile Pro Pro Gly Glu Lys Thr Met Leu
            20                  25                  30

Val Leu Ala Leu Leu Leu Ala Lys Lys Val Ala Ser His Thr Pro Ser
        35                  40                  45

Leu Leu Arg Asp Val Phe His Thr Thr Val Asn Phe Ile Asn Gln Asn
    50                  55                  60

Leu
```

65

<210> SEQ ID NO 2
<211> LENGTH: 87
<212> TYPE: PRT
<213> ORGANISM: Homo sapiens

<400> SEQUENCE: 2

```
Ser Gln Glu Asp Ile Ile Arg Asn Ile Ala Arg His Leu Ala Gln Val
1               5                   10                  15

Gly Asp Ser Met Asp Arg Ser Ile Pro Pro Gly Leu Val Asn Gly Leu
            20                  25                  30

Ala Leu Gln Leu Arg Asn Thr Ser Arg Ser Glu Glu Asp Arg Asn Arg
        35                  40                  45

Asp Leu Ala Thr Ala Leu Glu Gln Leu Leu Gln Ala Tyr Pro Arg Asp
    50                  55                  60

Met Glu Lys Glu Lys Thr Met Leu Val Leu Ala Leu Leu Leu Ala Lys
65                  70                  75                  80

Lys Val Ala Ser His Thr Pro
                85
```

<210> SEQ ID NO 3
<211> LENGTH: 252
<212> TYPE: PRT
<213> ORGANISM: Homo sapiens

<400> SEQUENCE: 3

```
Lys Lys Asn Ser Leu Ala Leu Ser Leu Thr Ala Asp Gln Met Val Ser
1               5                   10                  15

Ala Leu Leu Asp Ala Glu Pro Pro Ile Leu Tyr Ser Glu Tyr Asp Pro
            20                  25                  30

Thr Arg Pro Phe Ser Glu Ala Ser Met Met Gly Leu Leu Thr Asn Leu
        35                  40                  45

Ala Asp Arg Glu Leu Val His Met Ile Asn Trp Ala Lys Arg Val Pro
    50                  55                  60

Gly Phe Val Asp Leu Thr Leu His Asp Gln Val His Leu Leu Glu Cys
65                  70                  75                  80

Ala Trp Leu Glu Ile Leu Met Ile Gly Leu Val Trp Arg Ser Met Glu
                85                  90                  95

His Pro Gly Lys Leu Leu Phe Ala Pro Asn Leu Leu Leu Asp Arg Asn
            100                 105                 110

Gln Gly Lys Cys Val Glu Gly Met Val Glu Ile Phe Asp Met Leu Leu
        115                 120                 125

Ala Thr Ser Ser Arg Phe Arg Met Met Asn Leu Gln Gly Glu Glu Phe
    130                 135                 140

Val Cys Leu Lys Ser Ile Ile Leu Leu Asn Ser Gly Val Tyr Thr Phe
145                 150                 155                 160

Leu Ser Ser Thr Leu Lys Ser Leu Glu Glu Lys Asp His Ile His Arg
                165                 170                 175

Val Leu Asp Lys Ile Thr Asp Thr Leu Ile His Leu Met Ala Lys Ala
            180                 185                 190

Gly Leu Thr Leu Gln Gln Gln His Gln Arg Leu Ala Gln Leu Leu Leu
        195                 200                 205

Ile Leu Ser His Ile Arg His Met Ser Asn Lys Gly Met Glu His Leu
    210                 215                 220

Tyr Ser Met Lys Cys Lys Asn Val Val Pro Leu Tyr Asp Leu Leu Leu
```

```
225                 230                 235                 240

Glu Met Leu Asp Ala His Arg Leu His Ala Pro Thr
                245                 250
```

<210> SEQ ID NO 4
<211> LENGTH: 320
<212> TYPE: PRT
<213> ORGANISM: Artificial Sequence
<220> FEATURE:
<223> OTHER INFORMATION: tBID fusion protein C3445 (ESR1-D)

<400> SEQUENCE: 4

```
Met Lys Lys Asn Ser Leu Ala Leu Ser Leu Thr Ala Asp Gln Met Val
1               5                   10                  15

Ser Ala Leu Leu Asp Ala Glu Pro Pro Ile Leu Tyr Ser Glu Tyr Asp
            20                  25                  30

Pro Thr Arg Pro Phe Ser Glu Ala Ser Met Met Gly Leu Leu Thr Asn
        35                  40                  45

Leu Ala Asp Arg Glu Leu Val His Met Ile Asn Trp Ala Lys Arg Val
    50                  55                  60

Pro Gly Phe Val Asp Leu Thr Leu His Asp Gln Val His Leu Leu Glu
65                  70                  75                  80

Cys Ala Trp Leu Glu Ile Leu Met Ile Gly Leu Val Trp Arg Ser Met
                85                  90                  95

Glu His Pro Gly Lys Leu Leu Phe Ala Pro Asn Leu Leu Leu Asp Arg
            100                 105                 110

Asn Gln Gly Lys Cys Val Glu Gly Met Val Glu Ile Phe Asp Met Leu
        115                 120                 125

Leu Ala Thr Ser Ser Arg Phe Arg Met Met Asn Leu Gln Gly Glu Glu
    130                 135                 140

Phe Val Cys Leu Lys Ser Ile Ile Leu Leu Asn Ser Gly Val Tyr Thr
145                 150                 155                 160

Phe Leu Ser Ser Thr Leu Lys Ser Leu Glu Glu Lys Asp His Ile His
                165                 170                 175

Arg Val Leu Asp Lys Ile Thr Asp Thr Leu Ile His Leu Met Ala Lys
            180                 185                 190

Ala Gly Leu Thr Leu Gln Gln Gln His Gln Arg Leu Ala Gln Leu Leu
        195                 200                 205

Leu Ile Leu Ser His Ile Arg His Met Ser Asn Lys Gly Met Glu His
    210                 215                 220

Leu Tyr Ser Met Lys Cys Lys Asn Val Val Pro Leu Tyr Asp Leu Leu
225                 230                 235                 240

Leu Glu Met Leu Asp Ala His Arg Leu His Ala Pro Thr Gly Ser Ser
                245                 250                 255

Gln Glu Asp Ile Ile Arg Asn Ile Ala Arg His Leu Ala Gln Val Gly
            260                 265                 270

Asp Ser Met Asp Arg Ser Ile Pro Pro Gly Glu Lys Thr Met Leu Val
        275                 280                 285

Leu Ala Leu Leu Leu Ala Lys Lys Val Ala Ser His Thr Pro Ser Leu
    290                 295                 300

Leu Arg Asp Val Phe His Thr Thr Val Asn Phe Ile Asn Gln Asn Leu
305                 310                 315                 320
```

<210> SEQ ID NO 5
<211> LENGTH: 319
<212> TYPE: PRT

-continued

```
<213> ORGANISM: Artificial Sequence
<220> FEATURE:
<223> OTHER INFORMATION: tBID fusion protein C3454 (D-ESR1)

<400> SEQUENCE: 5

Ser Gln Glu Asp Ile Ile Arg Asn Ile Ala Arg His Leu Ala Gln Val
1               5                   10                  15

Gly Asp Ser Met Asp Arg Ser Ile Pro Pro Gly Glu Lys Thr Met Leu
            20                  25                  30

Val Leu Ala Leu Leu Leu Ala Lys Lys Val Ala Ser His Thr Pro Ser
        35                  40                  45

Leu Leu Arg Asp Val Phe His Thr Thr Val Asn Phe Ile Asn Gln Asn
    50                  55                  60

Leu Gly Ser Lys Lys Asn Ser Leu Ala Leu Ser Leu Thr Ala Asp Gln
65                  70                  75                  80

Met Val Ser Ala Leu Leu Asp Ala Glu Pro Pro Ile Leu Tyr Ser Glu
                85                  90                  95

Tyr Asp Pro Thr Arg Pro Phe Ser Glu Ala Ser Met Met Gly Leu Leu
            100                 105                 110

Thr Asn Leu Ala Asp Arg Glu Leu Val His Met Ile Asn Trp Ala Lys
        115                 120                 125

Arg Val Pro Gly Phe Val Asp Leu Thr Leu His Asp Gln Val His Leu
    130                 135                 140

Leu Glu Cys Ala Trp Leu Glu Ile Leu Met Ile Gly Leu Val Trp Arg
145                 150                 155                 160

Ser Met Glu His Pro Gly Lys Leu Leu Phe Ala Pro Asn Leu Leu Leu
                165                 170                 175

Asp Arg Asn Gln Gly Lys Cys Val Glu Gly Met Val Glu Ile Phe Asp
            180                 185                 190

Met Leu Leu Ala Thr Ser Ser Arg Phe Arg Met Met Asn Leu Gln Gly
        195                 200                 205

Glu Glu Phe Val Cys Leu Lys Ser Ile Ile Leu Leu Asn Ser Gly Val
    210                 215                 220

Tyr Thr Phe Leu Ser Ser Thr Leu Lys Ser Leu Glu Glu Lys Asp His
225                 230                 235                 240

Ile His Arg Val Leu Asp Lys Ile Thr Asp Thr Leu Ile His Leu Met
                245                 250                 255

Ala Lys Ala Gly Leu Thr Leu Gln Gln Gln His Gln Arg Leu Ala Gln
            260                 265                 270

Leu Leu Leu Ile Leu Ser His Ile Arg His Met Ser Asn Lys Gly Met
        275                 280                 285

Glu His Leu Tyr Ser Met Lys Cys Lys Asn Val Val Pro Leu Tyr Asp
    290                 295                 300

Leu Leu Leu Glu Met Leu Asp Ala His Arg Leu His Ala Pro Thr
305                 310                 315


<210> SEQ ID NO 6
<211> LENGTH: 342
<212> TYPE: PRT
<213> ORGANISM: Artificial Sequence
<220> FEATURE:
<223> OTHER INFORMATION: tBID fusion protein C3443 (ESR1-C)

<400> SEQUENCE: 6

Met Lys Lys Asn Ser Leu Ala Leu Ser Leu Thr Ala Asp Gln Met Val
1               5                   10                  15
```

-continued

Ser Ala Leu Leu Asp Ala Glu Pro Pro Ile Leu Tyr Ser Glu Tyr Asp
20 25 30

Pro Thr Arg Pro Phe Ser Glu Ala Ser Met Met Gly Leu Leu Thr Asn
35 40 45

Leu Ala Asp Arg Glu Leu Val His Met Ile Asn Trp Ala Lys Arg Val
50 55 60

Pro Gly Phe Val Asp Leu Thr Leu His Asp Gln Val His Leu Leu Glu
65 70 75 80

Cys Ala Trp Leu Glu Ile Leu Met Ile Gly Leu Val Trp Arg Ser Met
85 90 95

Glu His Pro Gly Lys Leu Leu Phe Ala Pro Asn Leu Leu Leu Asp Arg
100 105 110

Asn Gln Gly Lys Cys Val Glu Gly Met Val Glu Ile Phe Asp Met Leu
115 120 125

Leu Ala Thr Ser Ser Arg Phe Arg Met Met Asn Leu Gln Gly Glu Glu
130 135 140

Phe Val Cys Leu Lys Ser Ile Ile Leu Leu Asn Ser Gly Val Tyr Thr
145 150 155 160

Phe Leu Ser Ser Thr Leu Lys Ser Leu Glu Glu Lys Asp His Ile His
165 170 175

Arg Val Leu Asp Lys Ile Thr Asp Thr Leu Ile His Leu Met Ala Lys
180 185 190

Ala Gly Leu Thr Leu Gln Gln Gln His Gln Arg Leu Ala Gln Leu Leu
195 200 205

Leu Ile Leu Ser His Ile Arg His Met Ser Asn Lys Gly Met Glu His
210 215 220

Leu Tyr Ser Met Lys Cys Lys Asn Val Val Pro Leu Tyr Asp Leu Leu
225 230 235 240

Leu Glu Met Leu Asp Ala His Arg Leu His Ala Pro Thr Gly Ser Ser
245 250 255

Gln Glu Asp Ile Ile Arg Asn Ile Ala Arg His Leu Ala Gln Val Gly
260 265 270

Asp Ser Met Asp Arg Ser Ile Pro Pro Gly Leu Val Asn Gly Leu Ala
275 280 285

Leu Gln Leu Arg Asn Thr Ser Arg Ser Glu Glu Asp Arg Asn Arg Asp
290 295 300

Leu Ala Thr Ala Leu Glu Gln Leu Leu Gln Ala Tyr Pro Arg Asp Met
305 310 315 320

Glu Lys Glu Lys Thr Met Leu Val Leu Ala Leu Leu Leu Ala Lys Lys
325 330 335

Val Ala Ser His Thr Pro
340

<210> SEQ ID NO 7
<211> LENGTH: 342
<212> TYPE: PRT
<213> ORGANISM: Artificial Sequence
<220> FEATURE:
<223> OTHER INFORMATION: tBID fusion protein C3452 (C-ESR1)

<400> SEQUENCE: 7

Met Ser Gln Glu Asp Ile Ile Arg Asn Ile Ala Arg His Leu Ala Gln
1 5 10 15

Val Gly Asp Ser Met Asp Arg Ser Ile Pro Pro Gly Leu Val Asn Gly
20 25 30

-continued

```
Leu Ala Leu Gln Leu Arg Asn Thr Ser Arg Ser Glu Glu Asp Arg Asn
        35                  40                  45

Arg Asp Leu Ala Thr Ala Leu Glu Gln Leu Leu Gln Ala Tyr Pro Arg
    50                  55                  60

Asp Met Glu Lys Glu Lys Thr Met Leu Val Leu Ala Leu Leu Leu Ala
65                  70                  75                  80

Lys Lys Val Ala Ser His Thr Pro Gly Ser Lys Lys Asn Ser Leu Ala
                85                  90                  95

Leu Ser Leu Thr Ala Asp Gln Met Val Ser Ala Leu Leu Asp Ala Glu
            100                 105                 110

Pro Pro Ile Leu Tyr Ser Glu Tyr Asp Pro Thr Arg Pro Phe Ser Glu
        115                 120                 125

Ala Ser Met Met Gly Leu Leu Thr Asn Leu Ala Asp Arg Glu Leu Val
    130                 135                 140

His Met Ile Asn Trp Ala Lys Arg Val Pro Gly Phe Val Asp Leu Thr
145                 150                 155                 160

Leu His Asp Gln Val His Leu Leu Glu Cys Ala Trp Leu Glu Ile Leu
                165                 170                 175

Met Ile Gly Leu Val Trp Arg Ser Met Glu His Pro Gly Lys Leu Leu
            180                 185                 190

Phe Ala Pro Asn Leu Leu Leu Asp Arg Asn Gln Gly Lys Cys Val Glu
        195                 200                 205

Gly Met Val Glu Ile Phe Asp Met Leu Leu Ala Thr Ser Ser Arg Phe
    210                 215                 220

Arg Met Met Asn Leu Gln Gly Glu Glu Phe Val Cys Leu Lys Ser Ile
225                 230                 235                 240

Ile Leu Leu Asn Ser Gly Val Tyr Thr Phe Leu Ser Ser Thr Leu Lys
                245                 250                 255

Ser Leu Glu Glu Lys Asp His Ile His Arg Val Leu Asp Lys Ile Thr
            260                 265                 270

Asp Thr Leu Ile His Leu Met Ala Lys Ala Gly Leu Thr Leu Gln Gln
        275                 280                 285

Gln His Gln Arg Leu Ala Gln Leu Leu Leu Ile Leu Ser His Ile Arg
    290                 295                 300

His Met Ser Asn Lys Gly Met Glu His Leu Tyr Ser Met Lys Cys Lys
305                 310                 315                 320

Asn Val Val Pro Leu Tyr Asp Leu Leu Leu Glu Met Leu Asp Ala His
                325                 330                 335

Arg Leu His Ala Pro Thr
            340


<210> SEQ ID NO 8
<211> LENGTH: 241
<212> TYPE: PRT
<213> ORGANISM: Homo sapiens

<400> SEQUENCE: 8

Met Cys Ser Gly Ala Gly Val Met Met Ala Arg Trp Ala Ala Arg Gly
1               5                   10                  15

Arg Ala Gly Trp Arg Ser Thr Val Arg Ile Leu Ser Pro Leu Gly His
            20                  25                  30

Cys Glu Pro Gly Val Ser Arg Ser Cys Arg Ala Ala Gln Ala Met Asp
        35                  40                  45

Cys Glu Val Asn Asn Gly Ser Ser Leu Arg Asp Glu Cys Ile Thr Asn
    50                  55                  60
```

Leu Leu Val Phe Gly Phe Leu Gln Ser Cys Ser Asp Asn Ser Phe Arg
65 70 75 80

Arg Glu Leu Asp Ala Leu Gly His Glu Leu Pro Val Leu Ala Pro Gln
85 90 95

Trp Glu Gly Tyr Asp Glu Leu Gln Thr Asp Gly Asn Arg Ser Ser His
100 105 110

Ser Arg Leu Gly Arg Ile Glu Ala Asp Ser Glu Ser Gln Glu Asp Ile
115 120 125

Ile Arg Asn Ile Ala Arg His Leu Ala Gln Val Gly Asp Ser Met Asp
130 135 140

Arg Ser Ile Pro Pro Gly Leu Val Asn Gly Leu Ala Leu Gln Leu Arg
145 150 155 160

Asn Thr Ser Arg Ser Glu Glu Asp Arg Asn Arg Asp Leu Ala Thr Ala
165 170 175

Leu Glu Gln Leu Leu Gln Ala Tyr Pro Arg Asp Met Glu Lys Glu Lys
180 185 190

Thr Met Leu Val Leu Ala Leu Leu Leu Ala Lys Lys Val Ala Ser His
195 200 205

Thr Pro Ser Leu Leu Arg Asp Val Phe His Thr Thr Val Asn Phe Ile
210 215 220

Asn Gln Asn Leu Arg Thr Tyr Val Arg Ser Leu Ala Arg Asn Gly Met
225 230 235 240

Asp

<210> SEQ ID NO 9
<211> LENGTH: 195
<212> TYPE: PRT
<213> ORGANISM: Homo sapiens

<400> SEQUENCE: 9

Met Asp Cys Glu Val Asn Asn Gly Ser Ser Leu Arg Asp Glu Cys Ile
1 5 10 15

Thr Asn Leu Leu Val Phe Gly Phe Leu Gln Ser Cys Ser Asp Asn Ser
20 25 30

Phe Arg Arg Glu Leu Asp Ala Leu Gly His Glu Leu Pro Val Leu Ala
35 40 45

Pro Gln Trp Glu Gly Tyr Asp Glu Leu Gln Thr Asp Gly Asn Arg Ser
50 55 60

Ser His Ser Arg Leu Gly Arg Ile Glu Ala Asp Ser Glu Ser Gln Glu
65 70 75 80

Asp Ile Ile Arg Asn Ile Ala Arg His Leu Ala Gln Val Gly Asp Ser
85 90 95

Met Asp Arg Ser Ile Pro Pro Gly Leu Val Asn Gly Leu Ala Leu Gln
100 105 110

Leu Arg Asn Thr Ser Arg Ser Glu Glu Asp Arg Asn Arg Asp Leu Ala
115 120 125

Thr Ala Leu Glu Gln Leu Leu Gln Ala Tyr Pro Arg Asp Met Glu Lys
130 135 140

Glu Lys Thr Met Leu Val Leu Ala Leu Leu Leu Ala Lys Lys Val Ala
145 150 155 160

Ser His Thr Pro Ser Leu Leu Arg Asp Val Phe His Thr Thr Val Asn
165 170 175

Phe Ile Asn Gln Asn Leu Arg Thr Tyr Val Arg Ser Leu Ala Arg Asn
180 185 190

```
Gly Met Asp
        195


<210> SEQ ID NO 10
<211> LENGTH: 99
<212> TYPE: PRT
<213> ORGANISM: Homo sapiens

<400> SEQUENCE: 10

Met Asp Arg Ser Ile Pro Pro Gly Leu Val Asn Gly Leu Ala Leu Gln
1               5                   10                  15

Leu Arg Asn Thr Ser Arg Ser Glu Glu Asp Arg Asn Arg Asp Leu Ala
            20                  25                  30

Thr Ala Leu Glu Gln Leu Leu Gln Ala Tyr Pro Arg Asp Met Glu Lys
        35                  40                  45

Glu Lys Thr Met Leu Val Leu Ala Leu Leu Leu Ala Lys Lys Val Ala
    50                  55                  60

Ser His Thr Pro Ser Leu Leu Arg Asp Val Phe His Thr Thr Val Asn
65                  70                  75                  80

Phe Ile Asn Gln Asn Leu Arg Thr Tyr Val Arg Ser Leu Ala Arg Asn
                85                  90                  95

Gly Met Asp


<210> SEQ ID NO 11
<211> LENGTH: 13
<212> TYPE: PRT
<213> ORGANISM: Homo sapiens

<400> SEQUENCE: 11

Cys Ile Thr Asn Leu Leu Val Phe Gly Phe Leu Gln Ser
1               5                   10


<210> SEQ ID NO 12
<211> LENGTH: 10
<212> TYPE: PRT
<213> ORGANISM: Homo sapiens

<400> SEQUENCE: 12

Arg Arg Glu Leu Asp Ala Leu Gly His Glu
1               5                   10


<210> SEQ ID NO 13
<211> LENGTH: 23
<212> TYPE: PRT
<213> ORGANISM: Homo sapiens

<400> SEQUENCE: 13

Gln Glu Asp Ile Ile Arg Asn Ile Ala Arg His Leu Ala Gln Val Gly
1               5                   10                  15

Asp Ser Met Asp Arg Ser Ile
            20


<210> SEQ ID NO 14
<211> LENGTH: 10
<212> TYPE: PRT
<213> ORGANISM: Homo sapiens

<400> SEQUENCE: 14

Leu Val Asn Gly Leu Ala Leu Gln Leu Arg
1               5                   10
```

<210> SEQ ID NO 15
<211> LENGTH: 18
<212> TYPE: PRT
<213> ORGANISM: Homo sapiens

<400> SEQUENCE: 15

Ser Glu Glu Asp Arg Asn Arg Asp Leu Ala Thr Ala Leu Glu Gln Leu
1 5 10 15

Leu Gln

<210> SEQ ID NO 16
<211> LENGTH: 18
<212> TYPE: PRT
<213> ORGANISM: Homo sapiens

<400> SEQUENCE: 16

Glu Lys Thr Met Leu Val Leu Ala Leu Leu Leu Ala Lys Lys Val Ala
1 5 10 15

Ser His

<210> SEQ ID NO 17
<211> LENGTH: 14
<212> TYPE: PRT
<213> ORGANISM: Homo sapiens

<400> SEQUENCE: 17

Leu Arg Asp Val Phe His Thr Thr Val Asn Phe Ile Asn Gln
1 5 10

<210> SEQ ID NO 18
<211> LENGTH: 10
<212> TYPE: PRT
<213> ORGANISM: Homo sapiens

<400> SEQUENCE: 18

Arg Thr Tyr Val Arg Ser Leu Ala Arg Asn
1 5 10

<210> SEQ ID NO 19
<211> LENGTH: 114
<212> TYPE: PRT
<213> ORGANISM: Homo sapiens

<400> SEQUENCE: 19

Gln Glu Asp Ile Ile Arg Asn Ile Ala Arg His Leu Ala Gln Val Gly
1 5 10 15

Asp Ser Met Asp Arg Ser Ile Pro Pro Gly Leu Val Asn Gly Leu Ala
20 25 30

Leu Gln Leu Arg Asn Thr Ser Arg Ser Glu Glu Asp Arg Asn Arg Asp
35 40 45

Leu Ala Thr Ala Leu Glu Gln Leu Leu Gln Ala Tyr Pro Arg Asp Met
50 55 60

Glu Lys Glu Lys Thr Met Leu Val Leu Ala Leu Leu Leu Ala Lys Lys
65 70 75 80

Val Ala Ser His Thr Pro Ser Leu Leu Arg Asp Val Phe His Thr Thr
85 90 95

Val Asn Phe Ile Asn Gln Asn Leu Arg Thr Tyr Val Arg Ser Leu Ala
100 105 110

Arg Asn

<210> SEQ ID NO 20
<211> LENGTH: 134
<212> TYPE: PRT
<213> ORGANISM: Homo sapiens

<400> SEQUENCE: 20

```
Asn Arg Ser Ser His Ser Arg Leu Gly Arg Ile Glu Ala Asp Ser Glu
1               5                   10                  15

Ser Gln Glu Asp Ile Ile Arg Asn Ile Ala Arg His Leu Ala Gln Val
            20                  25                  30

Gly Asp Ser Met Asp Arg Ser Ile Pro Pro Gly Leu Val Asn Gly Leu
        35                  40                  45

Ala Leu Gln Leu Arg Asn Thr Ser Arg Ser Glu Glu Asp Arg Asn Arg
    50                  55                  60

Asp Leu Ala Thr Ala Leu Glu Gln Leu Leu Gln Ala Tyr Pro Arg Asp
65                  70                  75                  80

Met Glu Lys Glu Lys Thr Met Leu Val Leu Ala Leu Leu Leu Ala Lys
                85                  90                  95

Lys Val Ala Ser His Thr Pro Ser Leu Leu Arg Asp Val Phe His Thr
            100                 105                 110

Thr Val Asn Phe Ile Asn Gln Asn Leu Arg Thr Tyr Val Arg Ser Leu
        115                 120                 125

Ala Arg Asn Gly Met Asp
    130
```

<210> SEQ ID NO 21
<211> LENGTH: 136
<212> TYPE: PRT
<213> ORGANISM: Homo sapiens

<400> SEQUENCE: 21

```
Asp Gly Asn Arg Ser Ser His Ser Arg Leu Gly Arg Ile Glu Ala Asp
1               5                   10                  15

Ser Glu Ser Gln Glu Asp Ile Ile Arg Asn Ile Ala Arg His Leu Ala
            20                  25                  30

Gln Val Gly Asp Ser Met Asp Arg Ser Ile Pro Pro Gly Leu Val Asn
        35                  40                  45

Gly Leu Ala Leu Gln Leu Arg Asn Thr Ser Arg Ser Glu Glu Asp Arg
    50                  55                  60

Asn Arg Asp Leu Ala Thr Ala Leu Glu Gln Leu Leu Gln Ala Tyr Pro
65                  70                  75                  80

Arg Asp Met Glu Lys Glu Lys Thr Met Leu Val Leu Ala Leu Leu Leu
                85                  90                  95

Ala Lys Lys Val Ala Ser His Thr Pro Ser Leu Leu Arg Asp Val Phe
            100                 105                 110

His Thr Thr Val Asn Phe Ile Asn Gln Asn Leu Arg Thr Tyr Val Arg
        115                 120                 125

Ser Leu Ala Arg Asn Gly Met Asp
    130                 135
```

<210> SEQ ID NO 22
<211> LENGTH: 86
<212> TYPE: PRT
<213> ORGANISM: Homo sapiens

<400> SEQUENCE: 22

```
Gln Glu Asp Ile Ile Arg Asn Ile Ala Arg His Leu Ala Gln Val Gly
```

-continued

```
1               5                   10                  15

Asp Ser Met Asp Arg Ser Ile Pro Pro Gly Leu Val Asn Gly Leu Ala
            20                  25                  30

Leu Gln Leu Arg Asn Thr Ser Arg Ser Glu Glu Asp Arg Asn Arg Asp
        35                  40                  45

Leu Ala Thr Ala Leu Glu Gln Leu Leu Gln Ala Tyr Pro Arg Asp Met
    50                  55                  60

Glu Lys Glu Lys Thr Met Leu Val Leu Ala Leu Leu Leu Ala Lys Lys
65                  70                  75                  80

Val Ala Ser His Thr Pro
                85
```

<210> SEQ ID NO 23
<211> LENGTH: 261
<212> TYPE: DNA
<213> ORGANISM: Homo sapiens

<400> SEQUENCE: 23

```
agtcaagaag acatcatccg gaatattgcc aggcacctcg cccaggtcgg ggacagcatg     60

gaccgtagca tccctccggg cctggtgaac ggcctggccc tgcagctcag gaacaccagc    120

cggtcggagg aggaccggaa cagggacctg gccactgccc tggagcagct gctgcaggcc    180

taccctagag acatggagaa ggagaagacc atgctggtgc tggccctgct gctggccaag    240

aaggtggcca gtcacacgcc g                                              261
```

<210> SEQ ID NO 24
<211> LENGTH: 195
<212> TYPE: DNA
<213> ORGANISM: Artificial Sequence
<220> FEATURE:
<223> OTHER INFORMATION: encodes tBID polypeptide

<400> SEQUENCE: 24

```
agtcaagaag acatcatccg gaatattgcc aggcacctcg cccaggtcgg ggacagcatg     60

gaccgtagca tccctccggg cgagaagacc atgctggtgc tggccctgct gctggccaag    120

aaggtggcca gtcacacgcc gtccttgctc cgtgatgtct ttcacacaac agtgaatttt    180

attaaccaga accta                                                     195
```

<210> SEQ ID NO 25
<211> LENGTH: 490
<212> TYPE: PRT
<213> ORGANISM: Homo sapiens

<400> SEQUENCE: 25

```
Met Glu Gln Lys Pro Ser Lys Val Glu Cys Gly Ser Asp Pro Glu Glu
1               5                   10                  15

Asn Ser Ala Arg Ser Pro Asp Gly Lys Arg Lys Arg Lys Asn Gly Gln
            20                  25                  30

Cys Ser Leu Lys Thr Ser Met Ser Gly Tyr Ile Pro Ser Tyr Leu Asp
        35                  40                  45

Lys Asp Glu Gln Cys Val Val Cys Gly Asp Lys Ala Thr Gly Tyr His
    50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95
```

-continued

```
Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
        115                 120                 125

Ser Lys Arg Val Ala Lys Arg Lys Leu Ile Glu Gln Asn Arg Glu Arg
    130                 135                 140

Arg Arg Lys Glu Glu Met Ile Arg Ser Leu Gln Gln Arg Pro Glu Pro
145                 150                 155                 160

Thr Pro Glu Glu Trp Asp Leu Ile His Ile Ala Thr Glu Ala His Arg
                165                 170                 175

Ser Thr Asn Ala Gln Gly Ser His Trp Lys Gln Arg Arg Lys Phe Leu
            180                 185                 190

Pro Asp Asp Ile Gly Gln Ser Pro Ile Val Ser Met Pro Asp Gly Asp
        195                 200                 205

Lys Val Asp Leu Glu Ala Phe Ser Glu Phe Thr Lys Ile Ile Thr Pro
    210                 215                 220

Ala Ile Thr Arg Val Val Asp Phe Ala Lys Lys Leu Pro Met Phe Ser
225                 230                 235                 240

Glu Leu Pro Cys Glu Asp Gln Ile Ile Leu Leu Lys Gly Cys Cys Met
                245                 250                 255

Glu Ile Met Ser Leu Arg Ala Ala Val Arg Tyr Asp Pro Glu Ser Asp
            260                 265                 270

Thr Leu Thr Leu Ser Gly Glu Met Ala Val Lys Arg Glu Gln Leu Lys
        275                 280                 285

Asn Gly Gly Leu Gly Val Val Ser Asp Ala Ile Phe Glu Leu Gly Lys
    290                 295                 300

Ser Leu Ser Ala Phe Asn Leu Asp Asp Thr Glu Val Ala Leu Leu Gln
305                 310                 315                 320

Ala Val Leu Leu Met Ser Thr Asp Arg Ser Gly Leu Leu Cys Val Asp
                325                 330                 335

Lys Ile Glu Lys Ser Gln Glu Ala Tyr Leu Leu Ala Phe Glu His Tyr
            340                 345                 350

Val Asn His Arg Lys His Asn Ile Pro His Phe Trp Pro Lys Leu Leu
        355                 360                 365

Met Lys Glu Arg Glu Val Gln Ser Ser Ile Leu Tyr Lys Gly Ala Ala
    370                 375                 380

Ala Glu Gly Arg Pro Gly Gly Ser Leu Gly Val His Pro Glu Gly Gln
385                 390                 395                 400

Gln Leu Leu Gly Met His Val Val Gln Gly Pro Gln Val Arg Gln Leu
                405                 410                 415

Glu Gln Gln Leu Gly Glu Ala Gly Ser Leu Gln Gly Pro Val Leu Gln
            420                 425                 430

His Gln Ser Pro Lys Ser Pro Gln Gln Arg Leu Leu Glu Leu Leu His
        435                 440                 445

Arg Ser Gly Ile Leu His Ala Arg Ala Val Cys Gly Glu Asp Asp Ser
    450                 455                 460

Ser Glu Ala Asp Ser Pro Ser Ser Ser Glu Glu Glu Pro Glu Val Cys
465                 470                 475                 480

Glu Asp Leu Ala Gly Asn Ala Ala Ser Pro
                485                 490
```

<210> SEQ ID NO 26
<211> LENGTH: 461
<212> TYPE: PRT

<213> ORGANISM: Homo sapiens

<400> SEQUENCE: 26

Met Thr Pro Asn Ser Met Thr Glu Asn Gly Leu Thr Ala Trp Asp Lys
1               5                   10                  15

Pro Lys His Cys Pro Asp Arg Glu His Asp Trp Lys Leu Val Gly Met
            20                  25                  30

Ser Glu Ala Cys Leu His Arg Lys Ser His Ser Glu Arg Arg Ser Thr
        35                  40                  45

Leu Lys Asn Glu Gln Ser Ser Pro His Leu Ile Gln Thr Thr Trp Thr
    50                  55                  60

Ser Ser Ile Phe His Leu Asp His Asp Asp Val Asn Asp Gln Ser Val
65                  70                  75                  80

Ser Ser Ala Gln Thr Phe Gln Thr Glu Glu Lys Lys Cys Lys Gly Tyr
                85                  90                  95

Ile Pro Ser Tyr Leu Asp Lys Asp Glu Leu Cys Val Val Cys Gly Asp
            100                 105                 110

Lys Ala Thr Gly Tyr His Tyr Arg Cys Ile Thr Cys Glu Gly Cys Lys
        115                 120                 125

Gly Phe Phe Arg Arg Thr Ile Gln Lys Asn Leu His Pro Ser Tyr Ser
    130                 135                 140

Cys Lys Tyr Glu Gly Lys Cys Val Ile Asp Lys Val Thr Arg Asn Gln
145                 150                 155                 160

Cys Gln Glu Cys Arg Phe Lys Lys Cys Ile Tyr Val Gly Met Ala Thr
                165                 170                 175

Asp Leu Val Leu Asp Asp Ser Lys Arg Leu Ala Lys Arg Lys Leu Ile
            180                 185                 190

Glu Glu Asn Arg Glu Lys Arg Arg Arg Glu Glu Leu Gln Lys Ser Ile
        195                 200                 205

Gly His Lys Pro Glu Pro Thr Asp Glu Glu Trp Glu Leu Ile Lys Thr
    210                 215                 220

Val Thr Glu Ala His Val Ala Thr Asn Ala Gln Gly Ser His Trp Lys
225                 230                 235                 240

Gln Lys Arg Lys Phe Leu Pro Glu Asp Ile Gly Gln Ala Pro Ile Val
                245                 250                 255

Asn Ala Pro Glu Gly Gly Lys Val Asp Leu Glu Ala Phe Ser His Phe
            260                 265                 270

Thr Lys Ile Ile Thr Pro Ala Ile Thr Arg Val Val Asp Phe Ala Lys
        275                 280                 285

Lys Leu Pro Met Phe Cys Glu Leu Pro Cys Glu Asp Gln Ile Ile Leu
    290                 295                 300

Leu Lys Gly Cys Cys Met Glu Ile Met Ser Leu Arg Ala Ala Val Arg
305                 310                 315                 320

Tyr Asp Pro Glu Ser Glu Thr Leu Thr Leu Asn Gly Glu Met Ala Val
                325                 330                 335

Thr Arg Gly Gln Leu Lys Asn Gly Gly Leu Gly Val Val Ser Asp Ala
            340                 345                 350

Ile Phe Asp Leu Gly Met Ser Leu Ser Ser Phe Asn Leu Asp Asp Thr
        355                 360                 365

Glu Val Ala Leu Leu Gln Ala Val Leu Leu Met Ser Ser Asp Arg Pro
    370                 375                 380

Gly Leu Ala Cys Val Glu Arg Ile Glu Lys Tyr Gln Asp Ser Phe Leu
385                 390                 395                 400

```
Leu Ala Phe Glu His Tyr Ile Asn Tyr Arg Lys His His Val Thr His
                405                 410                 415

Phe Trp Pro Lys Leu Leu Met Lys Val Thr Asp Leu Arg Met Ile Gly
            420                 425                 430

Ala Cys His Ala Ser Arg Phe Leu His Met Lys Val Glu Cys Pro Thr
        435                 440                 445

Glu Leu Phe Pro Pro Leu Phe Leu Glu Val Phe Glu Asp
    450                 455                 460


<210> SEQ ID NO 27
<211> LENGTH: 462
<212> TYPE: PRT
<213> ORGANISM: Homo sapiens

<400> SEQUENCE: 27

Met Ala Ser Asn Ser Ser Ser Cys Pro Thr Pro Gly Gly Gly His Leu
1               5                   10                  15

Asn Gly Tyr Pro Val Pro Pro Tyr Ala Phe Phe Phe Pro Pro Met Leu
            20                  25                  30

Gly Gly Leu Ser Pro Pro Gly Ala Leu Thr Thr Leu Gln His Gln Leu
        35                  40                  45

Pro Val Ser Gly Tyr Ser Thr Pro Ser Pro Ala Thr Ile Glu Thr Gln
    50                  55                  60

Ser Ser Ser Ser Glu Glu Ile Val Pro Ser Pro Pro Ser Pro Pro Pro
65                  70                  75                  80

Leu Pro Arg Ile Tyr Lys Pro Cys Phe Val Cys Gln Asp Lys Ser Ser
                85                  90                  95

Gly Tyr His Tyr Gly Val Ser Ala Cys Glu Gly Cys Lys Gly Phe Phe
            100                 105                 110

Arg Arg Ser Ile Gln Lys Asn Met Val Tyr Thr Cys His Arg Asp Lys
        115                 120                 125

Asn Cys Ile Ile Asn Lys Val Thr Arg Asn Arg Cys Gln Tyr Cys Arg
    130                 135                 140

Leu Gln Lys Cys Phe Glu Val Gly Met Ser Lys Glu Ser Val Arg Asn
145                 150                 155                 160

Asp Arg Asn Lys Lys Lys Lys Glu Val Pro Lys Pro Glu Cys Ser Glu
                165                 170                 175

Ser Tyr Thr Leu Thr Pro Glu Val Gly Glu Leu Ile Glu Lys Val Arg
            180                 185                 190

Lys Ala His Gln Glu Thr Phe Pro Ala Leu Cys Gln Leu Gly Lys Tyr
        195                 200                 205

Thr Thr Asn Asn Ser Ser Glu Gln Arg Val Ser Leu Asp Ile Asp Leu
    210                 215                 220

Trp Asp Lys Phe Ser Glu Leu Ser Thr Lys Cys Ile Ile Lys Thr Val
225                 230                 235                 240

Glu Phe Ala Lys Gln Leu Pro Gly Phe Thr Thr Leu Thr Ile Ala Asp
                245                 250                 255

Gln Ile Thr Leu Leu Lys Ala Ala Cys Leu Asp Ile Leu Ile Leu Arg
            260                 265                 270

Ile Cys Thr Arg Tyr Thr Pro Glu Gln Asp Thr Met Thr Phe Ser Asp
        275                 280                 285

Gly Leu Thr Leu Asn Arg Thr Gln Met His Asn Ala Gly Phe Gly Pro
    290                 295                 300

Leu Thr Asp Leu Val Phe Ala Phe Ala Asn Gln Leu Leu Pro Leu Glu
305                 310                 315                 320
```

```
Met Asp Asp Ala Glu Thr Gly Leu Leu Ser Ala Ile Cys Leu Ile Cys
                325                 330                 335

Gly Asp Arg Gln Asp Leu Glu Gln Pro Asp Arg Val Asp Met Leu Gln
            340                 345                 350

Glu Pro Leu Leu Glu Ala Leu Lys Val Tyr Val Arg Lys Arg Arg Pro
        355                 360                 365

Ser Arg Pro His Met Phe Pro Lys Met Leu Met Lys Ile Thr Asp Leu
    370                 375                 380

Arg Ser Ile Ser Ala Lys Gly Ala Glu Arg Val Ile Thr Leu Lys Met
385                 390                 395                 400

Glu Ile Pro Gly Ser Met Pro Pro Leu Ile Gln Glu Met Leu Glu Asn
                405                 410                 415

Ser Glu Gly Leu Asp Thr Leu Ser Gly Gln Pro Gly Gly Gly Gly Arg
            420                 425                 430

Asp Gly Gly Gly Leu Ala Pro Pro Pro Gly Ser Cys Ser Pro Ser Leu
        435                 440                 445

Ser Pro Ser Ser Asn Arg Ser Ser Pro Ala Thr His Ser Pro
    450                 455                 460


<210> SEQ ID NO 28
<211> LENGTH: 455
<212> TYPE: PRT
<213> ORGANISM: Homo sapiens

<400> SEQUENCE: 28

Met Thr Thr Ser Gly His Ala Cys Pro Val Pro Ala Val Asn Gly His
1               5                   10                  15

Met Thr His Tyr Pro Ala Thr Pro Tyr Pro Leu Leu Phe Pro Pro Val
            20                  25                  30

Ile Gly Gly Leu Ser Leu Pro Pro Leu His Gly Leu His Gly His Pro
        35                  40                  45

Pro Pro Ser Gly Cys Ser Thr Pro Ser Pro Ala Thr Ile Glu Thr Gln
    50                  55                  60

Ser Thr Ser Ser Glu Glu Leu Val Pro Ser Pro Pro Ser Pro Leu Pro
65                  70                  75                  80

Pro Pro Arg Val Tyr Lys Pro Cys Phe Val Cys Gln Asp Lys Ser Ser
                85                  90                  95

Gly Tyr His Tyr Gly Val Ser Ala Cys Glu Gly Cys Lys Gly Phe Phe
            100                 105                 110

Arg Arg Ser Ile Gln Lys Asn Met Ile Tyr Thr Cys His Arg Asp Lys
        115                 120                 125

Asn Cys Val Ile Asn Lys Val Thr Arg Asn Arg Cys Gln Tyr Cys Arg
    130                 135                 140

Leu Gln Lys Cys Phe Glu Val Gly Met Ser Lys Glu Ser Val Arg Asn
145                 150                 155                 160

Asp Arg Asn Lys Lys Lys Lys Glu Thr Ser Lys Gln Glu Cys Thr Glu
                165                 170                 175

Ser Tyr Glu Met Thr Ala Glu Leu Asp Asp Leu Thr Glu Lys Ile Arg
            180                 185                 190

Lys Ala His Gln Glu Thr Phe Pro Ser Leu Cys Gln Leu Gly Lys Tyr
        195                 200                 205

Thr Thr Asn Ser Ser Ala Asp His Arg Val Arg Leu Asp Leu Gly Leu
    210                 215                 220

Trp Asp Lys Phe Ser Glu Leu Ala Thr Lys Cys Ile Ile Lys Ile Val
```

-continued

```
225                 230                 235                 240

Glu Phe Ala Lys Arg Leu Pro Gly Phe Thr Gly Leu Thr Ile Ala Asp
                245                 250                 255

Gln Ile Thr Leu Leu Lys Ala Ala Cys Leu Asp Ile Leu Ile Leu Arg
            260                 265                 270

Ile Cys Thr Arg Tyr Thr Pro Glu Gln Asp Thr Met Thr Phe Ser Asp
        275                 280                 285

Gly Leu Thr Leu Asn Arg Thr Gln Met His Asn Ala Gly Phe Gly Pro
    290                 295                 300

Leu Thr Asp Leu Val Phe Thr Phe Ala Asn Gln Leu Leu Pro Leu Glu
305                 310                 315                 320

Met Asp Asp Thr Glu Thr Gly Leu Leu Ser Ala Ile Cys Leu Ile Cys
                325                 330                 335

Gly Asp Arg Gln Asp Leu Glu Glu Pro Thr Lys Val Asp Lys Leu Gln
            340                 345                 350

Glu Pro Leu Leu Glu Ala Leu Lys Ile Tyr Ile Arg Lys Arg Arg Pro
        355                 360                 365

Ser Lys Pro His Met Phe Pro Lys Ile Leu Met Lys Ile Thr Asp Leu
    370                 375                 380

Arg Ser Ile Ser Ala Lys Gly Ala Glu Arg Val Ile Thr Leu Lys Met
385                 390                 395                 400

Glu Ile Pro Gly Ser Met Pro Pro Leu Ile Gln Glu Met Leu Glu Asn
                405                 410                 415

Ser Glu Gly His Glu Pro Leu Thr Pro Ser Ser Ser Gly Asn Thr Ala
            420                 425                 430

Glu His Ser Pro Ser Ile Ser Pro Ser Ser Val Glu Asn Ser Gly Val
        435                 440                 445

Ser Gln Ser Pro Leu Val Gln
    450                 455


<210> SEQ ID NO 29
<211> LENGTH: 454
<212> TYPE: PRT
<213> ORGANISM: Homo sapiens

<400> SEQUENCE: 29

Met Ala Thr Asn Lys Glu Arg Leu Phe Ala Ala Gly Ala Leu Gly Pro
1               5                   10                  15

Gly Ser Gly Tyr Pro Gly Ala Gly Phe Pro Phe Ala Phe Pro Gly Ala
            20                  25                  30

Leu Arg Gly Ser Pro Pro Phe Glu Met Leu Ser Pro Ser Phe Arg Gly
        35                  40                  45

Leu Gly Gln Pro Asp Leu Pro Lys Glu Met Ala Ser Leu Ser Val Glu
    50                  55                  60

Thr Gln Ser Thr Ser Ser Glu Glu Met Val Pro Ser Ser Pro Ser Pro
65                  70                  75                  80

Pro Pro Pro Pro Arg Val Tyr Lys Pro Cys Phe Val Cys Asn Asp Lys
                85                  90                  95

Ser Ser Gly Tyr His Tyr Gly Val Ser Ser Cys Glu Gly Cys Lys Gly
            100                 105                 110

Phe Phe Arg Arg Ser Ile Gln Lys Asn Met Val Tyr Thr Cys His Arg
        115                 120                 125

Asp Lys Asn Cys Ile Ile Asn Lys Val Thr Arg Asn Arg Cys Gln Tyr
    130                 135                 140
```

-continued

Cys Arg Leu Gln Lys Cys Phe Glu Val Gly Met Ser Lys Glu Ala Val
145 150 155 160

Arg Asn Asp Arg Asn Lys Lys Lys Lys Glu Val Lys Glu Glu Gly Ser
165 170 175

Pro Asp Ser Tyr Glu Leu Ser Pro Gln Leu Glu Glu Leu Ile Thr Lys
180 185 190

Val Ser Lys Ala His Gln Glu Thr Phe Pro Ser Leu Cys Gln Leu Gly
195 200 205

Lys Tyr Thr Thr Asn Ser Ser Ala Asp His Arg Val Gln Leu Asp Leu
210 215 220

Gly Leu Trp Asp Lys Phe Ser Glu Leu Ala Thr Lys Cys Ile Ile Lys
225 230 235 240

Ile Val Glu Phe Ala Lys Arg Leu Pro Gly Phe Thr Gly Leu Ser Ile
245 250 255

Ala Asp Gln Ile Thr Leu Leu Lys Ala Ala Cys Leu Asp Ile Leu Met
260 265 270

Leu Arg Ile Cys Thr Arg Tyr Thr Pro Glu Gln Asp Thr Met Thr Phe
275 280 285

Ser Asp Gly Leu Thr Leu Asn Arg Thr Gln Met His Asn Ala Gly Phe
290 295 300

Gly Pro Leu Thr Asp Leu Val Phe Ala Phe Ala Gly Gln Leu Leu Pro
305 310 315 320

Leu Glu Met Asp Asp Thr Glu Thr Gly Leu Leu Ser Ala Ile Cys Leu
325 330 335

Ile Cys Gly Asp Arg Met Asp Leu Glu Glu Pro Glu Lys Val Asp Lys
340 345 350

Leu Gln Glu Pro Leu Leu Glu Ala Leu Arg Leu Tyr Ala Arg Arg Arg
355 360 365

Arg Pro Ser Gln Pro Tyr Met Phe Pro Arg Met Leu Met Lys Ile Thr
370 375 380

Asp Leu Arg Gly Ile Ser Thr Lys Gly Ala Glu Arg Ala Ile Thr Leu
385 390 395 400

Lys Met Glu Ile Pro Gly Pro Met Pro Pro Leu Ile Arg Glu Met Leu
405 410 415

Glu Asn Pro Glu Met Phe Glu Asp Asp Ser Ser Gln Pro Gly Pro His
420 425 430

Pro Asn Ala Ser Ser Glu Asp Glu Val Pro Gly Gly Gln Gly Lys Gly
435 440 445

Gly Leu Lys Ser Pro Ala
450

<210> SEQ ID NO 30
<211> LENGTH: 468
<212> TYPE: PRT
<213> ORGANISM: Homo sapiens

<400> SEQUENCE: 30

Met Val Asp Thr Glu Ser Pro Leu Cys Pro Leu Ser Pro Leu Glu Ala
1 5 10 15

Gly Asp Leu Glu Ser Pro Leu Ser Glu Glu Phe Leu Gln Glu Met Gly
20 25 30

Asn Ile Gln Glu Ile Ser Gln Ser Ile Gly Glu Asp Ser Ser Gly Ser
35 40 45

Phe Gly Phe Thr Glu Tyr Gln Tyr Leu Gly Ser Cys Pro Gly Ser Asp
50 55 60

-continued

```
Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Ala Glu Val Arg Ile
            260                 265                 270

Phe His Cys Cys Gln Cys Thr Ser Val Glu Thr Val Thr Glu Leu Thr
        275                 280                 285

Glu Phe Ala Lys Ala Ile Pro Gly Phe Ala Asn Leu Asp Leu Asn Asp
    290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
            340                 345                 350

Asp Ile Met Glu Pro Lys Phe Asp Phe Ala Met Lys Phe Asn Ala Leu
        355                 360                 365

Glu Leu Asp Asp Ser Asp Ile Ser Leu Phe Val Ala Ala Ile Ile Cys
    370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
            420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
    450                 455                 460

Arg Asp Met Tyr
465
```

<210> SEQ ID NO 31
<211> LENGTH: 441
<212> TYPE: PRT
<213> ORGANISM: Homo sapiens

<400> SEQUENCE: 31

```
Met Glu Gln Pro Gln Glu Glu Ala Pro Glu Val Arg Glu Glu Glu Glu
1               5                   10                  15

Lys Glu Glu Val Ala Glu Ala Glu Gly Ala Pro Glu Leu Asn Gly Gly
            20                  25                  30

Pro Gln His Ala Leu Pro Ser Ser Ser Tyr Thr Asp Leu Ser Arg Ser
        35                  40                  45

Ser Ser Pro Pro Ser Leu Leu Asp Gln Leu Gln Met Gly Cys Asp Gly
    50                  55                  60

Ala Ser Cys Gly Ser Leu Asn Met Glu Cys Arg Val Cys Gly Asp Lys
65                  70                  75                  80

Ala Ser Gly Phe His Tyr Gly Val His Ala Cys Glu Gly Cys Lys Gly
                85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
        115                 120                 125

Arg Phe Gln Lys Cys Leu Ala Leu Gly Met Ser His Asn Ala Ile Arg
    130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
                165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
        195                 200                 205

Ala Pro Phe Val Ile His Asp Ile Glu Thr Leu Trp Gln Ala Glu Lys
    210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
                245                 250                 255

Val Arg Glu Leu Thr Glu Phe Ala Lys Ser Ile Pro Ser Phe Ser Ser
            260                 265                 270

Leu Phe Leu Asn Asp Gln Val Thr Leu Leu Lys Tyr Gly Val His Glu
        275                 280                 285

Ala Ile Phe Ala Met Leu Ala Ser Ile Val Asn Lys Asp Gly Leu Leu
    290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
                325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
        355                 360                 365

Arg Val Glu Ala Ile Gln Asp Thr Ile Leu Arg Ala Leu Glu Phe His
    370                 375                 380
```

-continued

```
Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
                405                 410                 415

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440


<210> SEQ ID NO 32
<211> LENGTH: 505
<212> TYPE: PRT
<213> ORGANISM: Homo sapiens

<400> SEQUENCE: 32

Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
    210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
    290                 295                 300

Val Ala Ile Arg Ile Phe Gln Gly Cys Gln Phe Arg Ser Val Glu Ala
```

305 310 315 320

Val Gln Glu Ile Thr Glu Tyr Ala Lys Ser Ile Pro Gly Phe Val Asn
325 330 335

Leu Asp Leu Asn Asp Gln Val Thr Leu Leu Lys Tyr Gly Val His Glu
340 345 350

Ile Ile Tyr Thr Met Leu Ala Ser Leu Met Asn Lys Asp Gly Val Leu
355 360 365

Ile Ser Glu Gly Gln Gly Phe Met Thr Arg Glu Phe Leu Lys Ser Leu
370 375 380

Arg Lys Pro Phe Gly Asp Phe Met Glu Pro Lys Phe Glu Phe Ala Val
385 390 395 400

Lys Phe Asn Ala Leu Glu Leu Asp Asp Ser Asp Leu Ala Ile Phe Ile
405 410 415

Ala Val Ile Ile Leu Ser Gly Asp Arg Pro Gly Leu Leu Asn Val Lys
420 425 430

Pro Ile Glu Asp Ile Gln Asp Asn Leu Leu Gln Ala Leu Glu Leu Gln
435 440 445

Leu Lys Leu Asn His Pro Glu Ser Ser Gln Leu Phe Ala Lys Leu Leu
450 455 460

Gln Lys Met Thr Asp Leu Arg Gln Ile Val Thr Glu His Val Gln Leu
465 470 475 480

Leu Gln Val Ile Lys Lys Thr Glu Thr Asp Met Ser Leu His Pro Leu
485 490 495

Leu Gln Glu Ile Tyr Lys Asp Leu Tyr
500 505

<210> SEQ ID NO 33
<211> LENGTH: 614
<212> TYPE: PRT
<213> ORGANISM: Homo sapiens

<400> SEQUENCE: 33

Met Thr Thr Leu Asp Ser Asn Asn Asn Thr Gly Gly Val Ile Thr Tyr
1 5 10 15

Ile Gly Ser Ser Gly Ser Ser Pro Ser Arg Thr Ser Pro Glu Ser Leu
20 25 30

Tyr Ser Asp Asn Ser Asn Gly Ser Phe Gln Ser Leu Thr Gln Gly Cys
35 40 45

Pro Thr Tyr Phe Pro Pro Ser Pro Thr Gly Ser Leu Thr Gln Asp Pro
50 55 60

Ala Arg Ser Phe Gly Ser Ile Pro Pro Ser Leu Ser Asp Asp Gly Ser
65 70 75 80

Pro Ser Ser Ser Ser Ser Ser Ser Ser Ser Ser Ser Ser Phe Tyr Asn
85 90 95

Gly Ser Pro Pro Gly Ser Leu Gln Val Ala Met Glu Asp Ser Ser Arg
100 105 110

Val Ser Pro Ser Lys Ser Thr Ser Asn Ile Thr Lys Leu Asn Gly Met
115 120 125

Val Leu Leu Cys Lys Val Cys Gly Asp Val Ala Ser Gly Phe His Tyr
130 135 140

Gly Val His Ala Cys Glu Gly Cys Lys Gly Phe Phe Arg Arg Ser Ile
145 150 155 160

Gln Gln Asn Ile Gln Tyr Lys Arg Cys Leu Lys Asn Glu Asn Cys Ser
165 170 175

-continued

```
Ile Val Arg Ile Asn Arg Asn Arg Cys Gln Gln Cys Arg Phe Lys Lys
            180                 185                 190

Cys Leu Ser Val Gly Met Ser Arg Asp Ala Val Arg Phe Gly Arg Ile
        195                 200                 205

Pro Lys Arg Glu Lys Gln Arg Met Leu Ala Glu Met Gln Ser Ala Met
    210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
                245                 250                 255

Ala Pro Val Pro Ser Pro Leu Val Gly Phe Ser Gln Phe Pro Gln Gln
            260                 265                 270

Leu Thr Pro Pro Arg Ser Pro Ser Pro Glu Pro Thr Val Glu Asp Val
        275                 280                 285

Ile Ser Gln Val Ala Arg Ala His Arg Glu Ile Phe Thr Tyr Ala His
    290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
                325                 330                 335

Pro Pro Ala Pro Asn Asp Asn Asn Thr Leu Ala Ala Gln Arg His Asn
            340                 345                 350

Glu Ala Leu Asn Gly Leu Arg Gln Ala Pro Ser Ser Tyr Pro Pro Thr
        355                 360                 365

Trp Pro Pro Gly Pro Ala His His Ser Cys His Gln Ser Asn Ser Asn
    370                 375                 380

Gly His Arg Leu Cys Pro Thr His Val Tyr Ala Ala Pro Glu Gly Lys
385                 390                 395                 400

Ala Pro Ala Asn Ser Pro Arg Gln Gly Asn Ser Lys Asn Val Leu Leu
                405                 410                 415

Ala Cys Pro Met Asn Met Tyr Pro His Gly Arg Ser Gly Arg Thr Val
            420                 425                 430

Gln Glu Ile Trp Glu Asp Phe Ser Met Ser Phe Thr Pro Ala Val Arg
        435                 440                 445

Glu Val Val Glu Phe Ala Lys His Ile Pro Gly Phe Arg Asp Leu Ser
    450                 455                 460

Gln His Asp Gln Val Thr Leu Leu Lys Ala Gly Thr Phe Glu Val Leu
465                 470                 475                 480

Met Val Arg Phe Ala Ser Leu Phe Asn Val Lys Asp Gln Thr Val Met
                485                 490                 495

Phe Leu Ser Arg Thr Thr Tyr Ser Leu Gln Glu Leu Gly Ala Met Gly
            500                 505                 510

Met Gly Asp Leu Leu Ser Ala Met Phe Asp Phe Ser Glu Lys Leu Asn
        515                 520                 525

Ser Leu Ala Leu Thr Glu Glu Glu Leu Gly Leu Phe Thr Ala Val Val
    530                 535                 540

Leu Val Ser Ala Asp Arg Ser Gly Met Glu Asn Ser Ala Ser Val Glu
545                 550                 555                 560

Gln Leu Gln Glu Thr Leu Leu Arg Ala Leu Arg Ala Leu Val Leu Lys
                565                 570                 575

Asn Arg Pro Leu Glu Thr Ser Arg Phe Thr Lys Leu Leu Leu Lys Leu
            580                 585                 590

Pro Asp Leu Arg Thr Leu Asn Asn Met His Ser Glu Lys Leu Leu Ser
```

```
        595                 600                 605

Phe Arg Val Asp Ala Gln
    610


<210> SEQ ID NO 34
<211> LENGTH: 579
<212> TYPE: PRT
<213> ORGANISM: Homo sapiens

<400> SEQUENCE: 34

Met Glu Val Asn Ala Gly Gly Val Ile Ala Tyr Ile Ser Ser Ser Ser
1               5                   10                  15

Ser Ala Ser Ser Pro Ala Ser Cys His Ser Glu Gly Ser Glu Asn Ser
            20                  25                  30

Phe Gln Ser Ser Ser Ser Ser Val Pro Ser Ser Pro Asn Ser Ser Asn
        35                  40                  45

Ser Asp Thr Asn Gly Asn Pro Lys Asn Gly Asp Leu Ala Asn Ile Glu
    50                  55                  60

Gly Ile Leu Lys Asn Asp Arg Ile Asp Cys Ser Met Lys Thr Ser Lys
65                  70                  75                  80

Ser Ser Ala Pro Gly Met Thr Lys Ser His Ser Gly Val Thr Lys Phe
                85                  90                  95

Ser Gly Met Val Leu Leu Cys Lys Val Cys Gly Asp Val Ala Ser Gly
            100                 105                 110

Phe His Tyr Gly Val His Ala Cys Glu Gly Cys Lys Gly Phe Phe Arg
        115                 120                 125

Arg Ser Ile Gln Gln Asn Ile Gln Tyr Lys Lys Cys Leu Lys Asn Glu
    130                 135                 140

Asn Cys Ser Ile Met Arg Met Asn Arg Asn Arg Cys Gln Gln Cys Arg
145                 150                 155                 160

Phe Lys Lys Cys Leu Ser Val Gly Met Ser Arg Asp Ala Val Arg Phe
                165                 170                 175

Gly Arg Ile Pro Lys Arg Glu Lys Gln Arg Met Leu Ile Glu Met Gln
            180                 185                 190

Ser Ala Met Lys Thr Met Met Asn Ser Gln Phe Ser Gly His Leu Gln
        195                 200                 205

Asn Asp Thr Leu Val Glu His His Glu Gln Thr Ala Leu Pro Ala Gln
    210                 215                 220

Glu Gln Leu Arg Pro Lys Pro Gln Leu Glu Gln Glu Asn Ile Lys Ser
225                 230                 235                 240

Ser Ser Pro Pro Ser Ser Asp Phe Ala Lys Glu Glu Val Ile Gly Met
                245                 250                 255

Val Thr Arg Ala His Lys Asp Thr Phe Met Tyr Asn Gln Glu Gln Gln
            260                 265                 270

Glu Asn Ser Ala Glu Ser Met Gln Pro Gln Arg Gly Glu Arg Ile Pro
        275                 280                 285

Lys Asn Met Glu Gln Tyr Asn Leu Asn His Asp His Cys Gly Asn Gly
    290                 295                 300

Leu Ser Ser His Phe Pro Cys Ser Glu Ser Gln Gln His Leu Asn Gly
305                 310                 315                 320

Gln Phe Lys Gly Arg Asn Ile Met His Tyr Pro Asn Gly His Ala Ile
                325                 330                 335

Cys Ile Ala Asn Gly His Cys Met Asn Phe Ser Asn Ala Tyr Thr Gln
            340                 345                 350
```

```
Arg Val Cys Asp Arg Val Pro Ile Asp Gly Phe Ser Gln Asn Glu Asn
        355                 360                 365

Lys Asn Ser Tyr Leu Cys Asn Thr Gly Gly Arg Met His Leu Val Cys
    370                 375                 380

Pro Leu Ser Lys Ser Pro Tyr Val Asp Pro His Lys Ser Gly His Glu
385                 390                 395                 400

Ile Trp Glu Glu Phe Ser Met Ser Phe Thr Pro Ala Val Lys Glu Val
                405                 410                 415

Val Glu Phe Ala Lys Arg Ile Pro Gly Phe Arg Asp Leu Ser Gln His
            420                 425                 430

Asp Gln Val Asn Leu Leu Lys Ala Gly Thr Phe Glu Val Leu Met Val
        435                 440                 445

Arg Phe Ala Ser Leu Phe Asp Ala Lys Glu Arg Thr Val Thr Phe Leu
    450                 455                 460

Ser Gly Lys Lys Tyr Ser Val Asp Asp Leu His Ser Met Gly Ala Gly
465                 470                 475                 480

Asp Leu Leu Asn Ser Met Phe Glu Phe Ser Glu Lys Leu Asn Ala Leu
                485                 490                 495

Gln Leu Ser Asp Glu Glu Met Ser Leu Phe Thr Ala Val Val Leu Val
            500                 505                 510

Ser Ala Asp Arg Ser Gly Ile Glu Asn Val Asn Ser Val Glu Ala Leu
        515                 520                 525

Gln Glu Thr Leu Ile Arg Ala Leu Arg Thr Leu Ile Met Lys Asn His
    530                 535                 540

Pro Asn Glu Ala Ser Ile Phe Thr Lys Leu Leu Leu Lys Leu Pro Asp
545                 550                 555                 560

Leu Arg Ser Leu Asn Asn Met His Ser Glu Glu Leu Leu Ala Phe Lys
                565                 570                 575

Val His Pro


<210> SEQ ID NO 35
<211> LENGTH: 523
<212> TYPE: PRT
<213> ORGANISM: Homo sapiens

<400> SEQUENCE: 35

Met Glu Ser Ala Pro Ala Ala Pro Asp Pro Ala Ala Ser Glu Pro Gly
1               5                   10                  15

Ser Ser Gly Ala Asp Ala Ala Ala Gly Ser Arg Glu Thr Pro Leu Asn
            20                  25                  30

Gln Glu Ser Ala Arg Lys Ser Glu Pro Pro Ala Pro Val Arg Arg Gln
        35                  40                  45

Ser Tyr Ser Ser Thr Ser Arg Gly Ile Ser Val Thr Lys Lys Thr His
    50                  55                  60

Thr Ser Gln Ile Glu Ile Ile Pro Cys Lys Ile Cys Gly Asp Lys Ser
65                  70                  75                  80

Ser Gly Ile His Tyr Gly Val Ile Thr Cys Glu Gly Cys Lys Gly Phe
                85                  90                  95

Phe Arg Arg Ser Gln Gln Ser Asn Ala Thr Tyr Ser Cys Pro Arg Gln
            100                 105                 110

Lys Asn Cys Leu Ile Asp Arg Thr Ser Arg Asn Arg Cys Gln His Cys
        115                 120                 125

Arg Leu Gln Lys Cys Leu Ala Val Gly Met Ser Arg Asp Ala Val Lys
    130                 135                 140
```

-continued

```
Phe Gly Arg Met Ser Lys Lys Gln Arg Asp Ser Leu Tyr Ala Glu Val
145                 150                 155                 160

Gln Lys His Arg Met Gln Gln Gln Gln Arg Asp His Gln Gln Gln Pro
                165                 170                 175

Gly Glu Ala Glu Pro Leu Thr Pro Thr Tyr Asn Ile Ser Ala Asn Gly
            180                 185                 190

Leu Thr Glu Leu His Asp Asp Leu Ser Asn Tyr Ile Asp Gly His Thr
        195                 200                 205

Pro Glu Gly Ser Lys Ala Asp Ser Ala Val Ser Ser Phe Tyr Leu Asp
    210                 215                 220

Ile Gln Pro Ser Pro Asp Gln Ser Gly Leu Asp Ile Asn Gly Ile Lys
225                 230                 235                 240

Pro Glu Pro Ile Cys Asp Tyr Thr Pro Ala Ser Gly Phe Phe Pro Tyr
                245                 250                 255

Cys Ser Phe Thr Asn Gly Glu Thr Ser Pro Thr Val Ser Met Ala Glu
            260                 265                 270

Leu Glu His Leu Ala Gln Asn Ile Ser Lys Ser His Leu Glu Thr Cys
        275                 280                 285

Gln Tyr Leu Arg Glu Glu Leu Gln Gln Ile Thr Trp Gln Thr Phe Leu
    290                 295                 300

Gln Glu Glu Ile Glu Asn Tyr Gln Asn Lys Gln Arg Glu Val Met Trp
305                 310                 315                 320

Gln Leu Cys Ala Ile Lys Ile Thr Glu Ala Ile Gln Tyr Val Val Glu
                325                 330                 335

Phe Ala Lys Arg Ile Asp Gly Phe Met Glu Leu Cys Gln Asn Asp Gln
            340                 345                 350

Ile Val Leu Leu Lys Ala Gly Ser Leu Glu Val Val Phe Ile Arg Met
        355                 360                 365

Cys Arg Ala Phe Asp Ser Gln Asn Asn Thr Val Tyr Phe Asp Gly Lys
    370                 375                 380

Tyr Ala Ser Pro Asp Val Phe Lys Ser Leu Gly Cys Glu Asp Phe Ile
385                 390                 395                 400

Ser Phe Val Phe Glu Phe Gly Lys Ser Leu Cys Ser Met His Leu Thr
                405                 410                 415

Glu Asp Glu Ile Ala Leu Phe Ser Ala Phe Val Leu Met Ser Ala Asp
            420                 425                 430

Arg Ser Trp Leu Gln Glu Lys Val Lys Ile Glu Lys Leu Gln Gln Lys
        435                 440                 445

Ile Gln Leu Ala Leu Gln His Val Leu Gln Lys Asn His Arg Glu Asp
    450                 455                 460

Gly Ile Leu Thr Lys Leu Ile Cys Lys Val Ser Thr Leu Arg Ala Leu
465                 470                 475                 480

Cys Gly Arg His Thr Glu Lys Leu Met Ala Phe Lys Ala Ile Tyr Pro
                485                 490                 495

Asp Ile Val Arg Leu His Phe Pro Pro Leu Tyr Lys Glu Leu Phe Thr
            500                 505                 510

Ser Glu Phe Glu Pro Ala Met Gln Ile Asp Gly
        515                 520
```

<210> SEQ ID NO 36
<211> LENGTH: 470
<212> TYPE: PRT
<213> ORGANISM: Homo sapiens

<400> SEQUENCE: 36

-continued

```
Met Cys Glu Asn Gln Leu Lys Thr Lys Ala Asp Ala Thr Ala Gln Ile
1               5                   10                  15

Glu Val Ile Pro Cys Lys Ile Cys Gly Asp Lys Ser Ser Gly Ile His
            20                  25                  30

Tyr Gly Val Ile Thr Cys Glu Gly Cys Lys Gly Phe Phe Arg Arg Ser
        35                  40                  45

Gln Gln Asn Asn Ala Ser Tyr Ser Cys Pro Arg Gln Arg Asn Cys Leu
    50                  55                  60

Ile Asp Arg Thr Asn Arg Asn Arg Cys Gln His Cys Arg Leu Gln Lys
65                  70                  75                  80

Cys Leu Ala Leu Gly Met Ser Arg Asp Ala Val Lys Phe Gly Arg Met
                85                  90                  95

Ser Lys Lys Gln Arg Asp Ser Leu Tyr Ala Glu Val Gln Lys His Gln
            100                 105                 110

Gln Arg Leu Gln Glu Gln Arg Gln Gln Gln Ser Gly Glu Ala Glu Ala
        115                 120                 125

Leu Ala Arg Val Tyr Ser Ser Ser Ile Ser Asn Gly Leu Ser Asn Leu
    130                 135                 140

Asn Asn Glu Thr Ser Gly Thr Tyr Ala Asn Gly His Val Ile Asp Leu
145                 150                 155                 160

Pro Lys Ser Glu Gly Tyr Tyr Asn Val Asp Ser Gly Gln Pro Ser Pro
                165                 170                 175

Asp Gln Ser Gly Leu Asp Met Thr Gly Ile Lys Gln Ile Lys Gln Glu
            180                 185                 190

Pro Ile Tyr Asp Leu Thr Ser Val Pro Asn Leu Phe Thr Tyr Ser Ser
        195                 200                 205

Phe Asn Asn Gly Gln Leu Ala Pro Gly Ile Thr Met Thr Glu Ile Asp
    210                 215                 220

Arg Ile Ala Gln Asn Ile Ile Lys Ser His Leu Glu Thr Cys Gln Tyr
225                 230                 235                 240

Thr Met Glu Glu Leu His Gln Leu Ala Trp Gln Thr His Thr Tyr Glu
                245                 250                 255

Glu Ile Lys Ala Tyr Gln Ser Lys Ser Arg Glu Ala Leu Trp Gln Gln
            260                 265                 270

Cys Ala Ile Gln Ile Thr His Ala Ile Gln Tyr Val Val Glu Phe Ala
        275                 280                 285

Lys Arg Ile Thr Gly Phe Met Glu Leu Cys Gln Asn Asp Gln Ile Leu
    290                 295                 300

Leu Leu Lys Ser Gly Cys Leu Glu Val Val Leu Val Arg Met Cys Arg
305                 310                 315                 320

Ala Phe Asn Pro Leu Asn Asn Thr Val Leu Phe Glu Gly Lys Tyr Gly
                325                 330                 335

Gly Met Gln Met Phe Lys Ala Leu Gly Ser Asp Asp Leu Val Asn Glu
            340                 345                 350

Ala Phe Asp Phe Ala Lys Asn Leu Cys Ser Leu Gln Leu Thr Glu Glu
        355                 360                 365

Glu Ile Ala Leu Phe Ser Ser Ala Val Leu Ile Ser Pro Asp Arg Ala
    370                 375                 380

Trp Leu Ile Glu Pro Arg Lys Val Gln Lys Leu Gln Glu Lys Ile Tyr
385                 390                 395                 400

Phe Ala Leu Gln His Val Ile Gln Lys Asn His Leu Asp Asp Glu Thr
                405                 410                 415
```

```
Leu Ala Lys Leu Ile Ala Lys Ile Pro Thr Ile Thr Ala Val Cys Asn
            420                 425                 430

Leu His Gly Glu Lys Leu Gln Val Phe Lys Gln Ser His Pro Glu Ile
        435                 440                 445

Val Asn Thr Leu Phe Pro Pro Leu Tyr Lys Glu Leu Phe Asn Pro Asp
    450                 455                 460

Cys Ala Thr Gly Cys Lys
465                 470
```

<210> SEQ ID NO 37
<211> LENGTH: 518
<212> TYPE: PRT
<213> ORGANISM: Homo sapiens

<400> SEQUENCE: 37

```
Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Arg Cys Asn Ala Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
    130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
        275                 280                 285

Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320
```

```
Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
        355                 360                 365

Tyr Asn Ala Asp Asn Arg Thr Val Phe Phe Glu Gly Lys Tyr Gly Gly
    370                 375                 380

Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
                405                 410                 415

Ile Ala Leu Tyr Thr Ala Leu Val Leu Ile Asn Ala His Arg Pro Gly
            420                 425                 430

Leu Gln Glu Lys Arg Lys Val Glu Gln Leu Gln Tyr Asn Leu Glu Leu
        435                 440                 445

Ala Phe His His His Leu Cys Lys Thr His Arg Gln Ser Ile Leu Ala
    450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
            500                 505                 510

Pro Val Gly Leu Ser Lys
        515


<210> SEQ ID NO 38
<211> LENGTH: 486
<212> TYPE: PRT
<213> ORGANISM: Homo sapiens

<400> SEQUENCE: 38

Met Val Met Gln Phe Gln Gly Leu Glu Asn Pro Ile Gln Ile Ser Pro
1               5                   10                  15

His Cys Ser Cys Thr Pro Ser Gly Phe Phe Met Glu Met Met Ser Met
            20                  25                  30

Lys Pro Ala Lys Gly Val Leu Thr Glu Gln Val Ala Gly Pro Leu Gly
        35                  40                  45

Gln Asn Leu Glu Val Glu Pro Tyr Ser Gln Tyr Ser Asn Val Gln Phe
    50                  55                  60

Pro Gln Val Gln Pro Gln Ile Ser Ser Ser Ser Tyr Tyr Ser Asn Leu
65                  70                  75                  80

Gly Phe Tyr Pro Gln Gln Pro Glu Glu Trp Tyr Ser Pro Gly Ile Tyr
                85                  90                  95

Glu Leu Arg Arg Met Pro Ala Glu Thr Leu Tyr Gln Gly Glu Thr Glu
            100                 105                 110

Val Ala Glu Met Pro Val Thr Lys Lys Pro Arg Met Gly Ala Ser Ala
        115                 120                 125

Gly Arg Ile Lys Gly Asp Glu Leu Cys Val Val Cys Gly Asp Arg Ala
    130                 135                 140

Ser Gly Tyr His Tyr Asn Ala Leu Thr Cys Glu Gly Cys Lys Gly Phe
145                 150                 155                 160

Phe Arg Arg Ser Ile Thr Lys Asn Ala Val Tyr Lys Cys Lys Asn Gly
```

-continued

```
                165                 170                 175

Gly Asn Cys Val Met Asp Met Tyr Met Arg Arg Lys Cys Gln Glu Cys
            180                 185                 190

Arg Leu Arg Lys Cys Lys Glu Met Gly Met Leu Ala Glu Cys Met Tyr
        195                 200                 205

Thr Gly Leu Leu Thr Glu Ile Gln Cys Lys Ser Lys Arg Leu Arg Lys
    210                 215                 220

Asn Val Lys Gln His Ala Asp Gln Thr Val Asn Glu Asp Ser Glu Gly
225                 230                 235                 240

Arg Asp Leu Arg Gln Val Thr Ser Thr Thr Lys Ser Cys Arg Glu Lys
                245                 250                 255

Thr Glu Leu Thr Pro Asp Gln Gln Thr Leu Leu His Phe Ile Met Asp
            260                 265                 270

Ser Tyr Asn Lys Gln Arg Met Pro Gln Glu Ile Thr Asn Lys Ile Leu
        275                 280                 285

Lys Glu Glu Phe Ser Ala Glu Glu Asn Phe Leu Ile Leu Thr Glu Met
    290                 295                 300

Ala Thr Asn His Val Gln Val Leu Val Glu Phe Thr Lys Lys Leu Pro
305                 310                 315                 320

Gly Phe Gln Thr Leu Asp His Glu Asp Gln Ile Ala Leu Leu Lys Gly
                325                 330                 335

Ser Ala Val Glu Ala Met Phe Leu Arg Ser Ala Glu Ile Phe Asn Lys
            340                 345                 350

Lys Leu Pro Ser Gly His Ser Asp Leu Leu Glu Glu Arg Ile Arg Asn
        355                 360                 365

Ser Gly Ile Ser Asp Glu Tyr Ile Thr Pro Met Phe Ser Phe Tyr Lys
    370                 375                 380

Ser Ile Gly Glu Leu Lys Met Thr Gln Glu Glu Tyr Ala Leu Leu Thr
385                 390                 395                 400

Ala Ile Val Ile Leu Ser Pro Asp Arg Gln Tyr Ile Lys Asp Arg Glu
                405                 410                 415

Ala Val Glu Lys Leu Gln Glu Pro Leu Leu Asp Val Leu Gln Lys Leu
            420                 425                 430

Cys Lys Ile His Gln Pro Glu Asn Pro Gln His Phe Ala Cys Leu Leu
        435                 440                 445

Gly Arg Leu Thr Glu Leu Arg Thr Phe Asn His His His Ala Glu Met
    450                 455                 460

Leu Met Ser Trp Arg Val Asn Asp His Lys Phe Thr Pro Leu Leu Cys
465                 470                 475                 480

Glu Ile Trp Asp Val Gln
                485


<210> SEQ ID NO 39
<211> LENGTH: 505
<212> TYPE: PRT
<213> ORGANISM: Mus musculus

<400> SEQUENCE: 39

Met Ala Asn Thr Tyr Val Ala Thr Ser Asp Gly Tyr Tyr Leu Ala Glu
1               5                   10                  15

Pro Thr Gln Tyr Tyr Asp Ile Leu Pro Glu Gln Phe His Tyr Gln Leu
            20                  25                  30

Cys Asp Thr Asp Phe Gln Glu Pro Pro Tyr Cys Gln Tyr Ser Thr Ala
        35                  40                  45
```

-continued

```
Gln Phe Pro Pro Ala Leu Gln Ser Pro Ser Leu Gln Ser His Phe Asn
    50                  55                  60

Thr His Gly Leu Asp Pro Gln Tyr Ser Gly Gly Ser Trp Cys Gly Leu
65                  70                  75                  80

Asp Ala Arg Glu Ser Gly Gln Ser Thr Tyr Val Val Val His Asp Asp
                85                  90                  95

Glu Asp Glu Phe Pro Gly Ala Gln Arg Cys Arg Ala Thr Cys Ser Leu
            100                 105                 110

Arg Trp Lys Gly Gln Asp Asp Met Leu Cys Met Val Cys Gly Asp Lys
        115                 120                 125

Ala Ser Gly Tyr His Tyr Asn Ala Leu Thr Cys Glu Gly Cys Lys Gly
    130                 135                 140

Phe Phe Arg Arg Ser Ile Thr Lys Asn Ala Val Tyr Ser Cys Lys Asn
145                 150                 155                 160

Gly Gly His Cys Glu Met Asp Met Tyr Met Arg Arg Lys Cys Gln Glu
                165                 170                 175

Cys Arg Leu Lys Lys Cys Lys Ala Val Gly Met Leu Ala Glu Cys Leu
            180                 185                 190

Leu Thr Glu Ile Gln Cys Lys Ser Lys Arg Leu Arg Lys Asn Phe Lys
        195                 200                 205

His Gly Pro Ala Leu Tyr Pro Ala Ile Gln Val Glu Asp Glu Gly Ala
    210                 215                 220

Asp Thr Lys His Val Ser Ser Ser Thr Arg Ser Gly Lys Gly Val Gln
225                 230                 235                 240

Asp Asn Met Thr Leu Thr Gln Glu Glu His Arg Leu Leu Asn Thr Ile
                245                 250                 255

Val Thr Val His Gln Lys Ser Met Ile Pro Leu Gly Glu Thr Ser Lys
            260                 265                 270

Leu Leu Gln Glu Gly Ser Asn Pro Glu Leu Ser Phe Leu Arg Leu Ser
        275                 280                 285

Glu Val Ser Val Leu His Ile Gln Gly Leu Met Lys Phe Thr Lys Gly
    290                 295                 300

Leu Pro Gly Phe Glu Asn Leu Thr Thr Glu Asp Gln Ala Ala Leu Gln
305                 310                 315                 320

Lys Ala Ser Lys Thr Glu Val Met Phe Leu His Val Ala Gln Leu Tyr
                325                 330                 335

Gly Gly Lys Asp Ser Thr Ser Gly Ser Thr Met Arg Pro Ala Lys Pro
            340                 345                 350

Ser Ala Gly Thr Leu Glu Val His Asn Pro Ser Ala Asp Glu Ser Val
        355                 360                 365

His Ser Pro Glu Asn Phe Leu Lys Glu Gly Tyr Pro Ser Ala Pro Leu
    370                 375                 380

Thr Asp Ile Thr Lys Glu Phe Ile Ala Ser Leu Ser Tyr Phe Tyr Arg
385                 390                 395                 400

Arg Met Ser Glu Leu His Val Ser Asp Thr Glu Tyr Ala Leu Leu Thr
                405                 410                 415

Ala Thr Thr Val Leu Phe Ser Asp Arg Pro Cys Leu Lys Asn Lys Gln
            420                 425                 430

His Ile Glu Asn Leu Gln Glu Pro Val Leu Gln Leu Leu Phe Lys Phe
        435                 440                 445

Ser Lys Met Tyr His Pro Glu Asp Pro Gln His Phe Ala His Leu Ile
    450                 455                 460

Gly Arg Leu Thr Glu Leu Arg Thr Leu Ser His Ser His Ser Glu Ile
```

465 470 475 480

Leu Arg Met Trp Lys Thr Lys Asp Pro Arg Leu Val Met Leu Phe Ser
485 490 495

Glu Lys Trp Asp Leu His Ser Phe Ser
500 505

<210> SEQ ID NO 40
<211> LENGTH: 447
<212> TYPE: PRT
<213> ORGANISM: Homo sapiens

<400> SEQUENCE: 40

Met Ser Leu Trp Leu Gly Ala Pro Val Pro Asp Ile Pro Pro Asp Ser
1 5 10 15

Ala Val Glu Leu Trp Lys Pro Gly Ala Gln Asp Ala Ser Ser Gln Ala
20 25 30

Gln Gly Gly Ser Ser Cys Ile Leu Arg Glu Glu Ala Arg Met Pro His
35 40 45

Ser Ala Gly Gly Thr Ala Gly Val Gly Leu Glu Ala Ala Glu Pro Thr
50 55 60

Ala Leu Leu Thr Arg Ala Glu Pro Pro Ser Glu Pro Thr Glu Ile Arg
65 70 75 80

Pro Gln Lys Arg Lys Lys Gly Pro Ala Pro Lys Met Leu Gly Asn Glu
85 90 95

Leu Cys Ser Val Cys Gly Asp Lys Ala Ser Gly Phe His Tyr Asn Val
100 105 110

Leu Ser Cys Glu Gly Cys Lys Gly Phe Phe Arg Arg Ser Val Ile Lys
115 120 125

Gly Ala His Tyr Ile Cys His Ser Gly Gly His Cys Pro Met Asp Thr
130 135 140

Tyr Met Arg Arg Lys Cys Gln Glu Cys Arg Leu Arg Lys Cys Arg Gln
145 150 155 160

Ala Gly Met Arg Glu Glu Cys Val Leu Ser Glu Glu Gln Ile Arg Leu
165 170 175

Lys Lys Leu Lys Arg Gln Glu Glu Glu Gln Ala His Ala Thr Ser Leu
180 185 190

Pro Pro Arg Ala Ser Ser Pro Pro Gln Ile Leu Pro Gln Leu Ser Pro
195 200 205

Glu Gln Leu Gly Met Ile Glu Lys Leu Val Ala Ala Gln Gln Gln Cys
210 215 220

Asn Arg Arg Ser Phe Ser Asp Arg Leu Arg Val Thr Pro Trp Pro Met
225 230 235 240

Ala Pro Asp Pro His Ser Arg Glu Ala Arg Gln Gln Arg Phe Ala His
245 250 255

Phe Thr Glu Leu Ala Ile Val Ser Val Gln Glu Ile Val Asp Phe Ala
260 265 270

Lys Gln Leu Pro Gly Phe Leu Gln Leu Ser Arg Glu Asp Gln Ile Ala
275 280 285

Leu Leu Lys Thr Ser Ala Ile Glu Val Met Leu Leu Glu Thr Ser Arg
290 295 300

Arg Tyr Asn Pro Gly Ser Glu Ser Ile Thr Phe Leu Lys Asp Phe Ser
305 310 315 320

Tyr Asn Arg Glu Asp Phe Ala Lys Ala Gly Leu Gln Val Glu Phe Ile
325 330 335

```
Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

Arg Leu Met Phe Pro Arg Met Leu Met Lys Leu Val Ser Leu Arg Thr
                405                 410                 415

Leu Ser Ser Val His Ser Glu Gln Val Phe Ala Leu Arg Leu Gln Asp
            420                 425                 430

Lys Lys Leu Pro Pro Leu Leu Ser Glu Ile Trp Asp Val His Glu
        435                 440                 445


<210> SEQ ID NO 41
<211> LENGTH: 460
<212> TYPE: PRT
<213> ORGANISM: Homo sapiens

<400> SEQUENCE: 41

Met Ser Ser Pro Thr Thr Ser Ser Leu Asp Thr Pro Leu Pro Gly Asn
1               5                   10                  15

Gly Pro Pro Gln Pro Gly Ala Pro Ser Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Glu
                165                 170                 175

Ser Gln Ser Gln Ser Gln Ser Pro Val Gly Pro Gln Gly Ser Ser Ser
            180                 185                 190

Ser Ala Ser Gly Pro Gly Ala Ser Pro Gly Gly Ser Glu Ala Gly Ser
        195                 200                 205

Gln Gly Ser Gly Glu Gly Glu Gly Val Gln Leu Thr Ala Ala Gln Glu
    210                 215                 220

Leu Met Ile Gln Gln Leu Val Ala Ala Gln Leu Gln Cys Asn Lys Arg
225                 230                 235                 240

Ser Phe Ser Asp Gln Pro Lys Val Thr Pro Trp Pro Leu Gly Ala Asp
                245                 250                 255

Pro Gln Ser Arg Asp Ala Arg Gln Gln Arg Phe Ala His Phe Thr Glu
            260                 265                 270
```

Leu Ala Ile Ile Ser Val Gln Glu Ile Val Asp Phe Ala Lys Gln Val
275 280 285

Pro Gly Phe Leu Gln Leu Gly Arg Glu Asp Gln Ile Ala Leu Leu Lys
290 295 300

Ala Ser Thr Ile Glu Ile Met Leu Leu Glu Thr Ala Arg Arg Tyr Asn
305 310 315 320

His Glu Thr Glu Cys Ile Thr Phe Leu Lys Asp Phe Thr Tyr Ser Lys
325 330 335

Asp Asp Phe His Arg Ala Gly Leu Gln Val Glu Phe Ile Asn Pro Ile
340 345 350

Phe Glu Phe Ser Arg Ala Met Arg Arg Leu Gly Leu Asp Asp Ala Glu
355 360 365

Tyr Ala Leu Leu Ile Ala Ile Asn Ile Phe Ser Ala Asp Arg Pro Asn
370 375 380

Val Gln Glu Pro Gly Arg Val Glu Ala Leu Gln Gln Pro Tyr Val Glu
385 390 395 400

Ala Leu Leu Ser Tyr Thr Arg Ile Lys Arg Pro Gln Asp Gln Leu Arg
405 410 415

Phe Pro Arg Met Leu Met Lys Leu Val Ser Leu Arg Thr Leu Ser Ser
420 425 430

Val His Ser Glu Gln Val Phe Ala Leu Arg Leu Gln Asp Lys Lys Leu
435 440 445

Pro Pro Leu Leu Ser Glu Ile Trp Asp Val His Glu
450 455 460

<210> SEQ ID NO 42
<211> LENGTH: 427
<212> TYPE: PRT
<213> ORGANISM: Homo sapiens

<400> SEQUENCE: 42

Met Glu Ala Met Ala Ala Ser Thr Ser Leu Pro Asp Pro Gly Asp Phe
1 5 10 15

Asp Arg Asn Val Pro Arg Ile Cys Gly Val Cys Gly Asp Arg Ala Thr
20 25 30

Gly Phe His Phe Asn Ala Met Thr Cys Glu Gly Cys Lys Gly Phe Phe
35 40 45

Arg Arg Ser Met Lys Arg Lys Ala Leu Phe Thr Cys Pro Phe Asn Gly
50 55 60

Asp Cys Arg Ile Thr Lys Asp Asn Arg Arg His Cys Gln Ala Cys Arg
65 70 75 80

Leu Lys Arg Cys Val Asp Ile Gly Met Met Lys Glu Phe Ile Leu Thr
85 90 95

Asp Glu Glu Val Gln Arg Lys Arg Glu Met Ile Leu Lys Arg Lys Glu
100 105 110

Glu Glu Ala Leu Lys Asp Ser Leu Arg Pro Lys Leu Ser Glu Glu Gln
115 120 125

Gln Arg Ile Ile Ala Ile Leu Leu Asp Ala His His Lys Thr Tyr Asp
130 135 140

Pro Thr Tyr Ser Asp Phe Cys Gln Phe Arg Pro Pro Val Arg Val Asn
145 150 155 160

Asp Gly Gly Gly Ser His Pro Ser Arg Pro Asn Ser Arg His Thr Pro
165 170 175

Ser Phe Ser Gly Asp Ser Ser Ser Ser Cys Ser Asp His Cys Ile Thr

```
            180                 185                 190

Ser Ser Asp Met Met Asp Ser Ser Ser Phe Ser Asn Leu Asp Leu Ser
        195                 200                 205

Glu Glu Asp Ser Asp Asp Pro Ser Val Thr Leu Glu Leu Ser Gln Leu
    210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
    290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Pro Gly Ser His Leu Leu Tyr Ala Lys Met Ile
    370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425


<210> SEQ ID NO 43
<211> LENGTH: 434
<212> TYPE: PRT
<213> ORGANISM: Homo sapiens

<400> SEQUENCE: 43

Met Glu Val Arg Pro Lys Glu Ser Trp Asn His Ala Asp Phe Val His
1               5                   10                  15

Cys Glu Asp Thr Glu Ser Val Pro Gly Lys Pro Ser Val Asn Ala Asp
            20                  25                  30

Glu Glu Val Gly Gly Pro Gln Ile Cys Arg Val Cys Gly Asp Lys Ala
        35                  40                  45

Thr Gly Tyr His Phe Asn Val Met Thr Cys Glu Gly Cys Lys Gly Phe
    50                  55                  60

Phe Arg Arg Ala Met Lys Arg Asn Ala Arg Leu Arg Cys Pro Phe Arg
65                  70                  75                  80

Lys Gly Ala Cys Glu Ile Thr Arg Lys Thr Arg Arg Gln Cys Gln Ala
                85                  90                  95

Cys Arg Leu Arg Lys Cys Leu Glu Ser Gly Met Lys Lys Glu Met Ile
            100                 105                 110

Met Ser Asp Glu Ala Val Glu Glu Arg Arg Ala Leu Ile Lys Arg Lys
        115                 120                 125
```

-continued

```
Lys Ser Glu Arg Thr Gly Thr Gln Pro Leu Gly Val Gln Gly Leu Thr
    130                 135                 140

Glu Glu Gln Arg Met Met Ile Arg Glu Leu Met Asp Ala Gln Met Lys
145                 150                 155                 160

Thr Phe Asp Thr Thr Phe Ser His Phe Lys Asn Phe Arg Leu Pro Gly
                165                 170                 175

Val Leu Ser Ser Gly Cys Glu Leu Pro Glu Ser Leu Gln Ala Pro Ser
            180                 185                 190

Arg Glu Glu Ala Ala Lys Trp Ser Gln Val Arg Lys Asp Leu Cys Ser
        195                 200                 205

Leu Lys Val Ser Leu Gln Leu Arg Gly Glu Asp Gly Ser Val Trp Asn
    210                 215                 220

Tyr Lys Pro Pro Ala Asp Ser Gly Gly Lys Glu Ile Phe Ser Leu Leu
225                 230                 235                 240

Pro His Met Ala Asp Met Ser Thr Tyr Met Phe Lys Gly Ile Ile Ser
                245                 250                 255

Phe Ala Lys Val Ile Ser Tyr Phe Arg Asp Leu Pro Ile Glu Asp Gln
            260                 265                 270

Ile Ser Leu Leu Lys Gly Ala Ala Phe Glu Leu Cys Gln Leu Arg Phe
        275                 280                 285

Asn Thr Val Phe Asn Ala Glu Thr Gly Thr Trp Glu Cys Gly Arg Leu
    290                 295                 300

Ser Tyr Cys Leu Glu Asp Thr Ala Gly Gly Phe Gln Gln Leu Leu Leu
305                 310                 315                 320

Glu Pro Met Leu Lys Phe His Tyr Met Leu Lys Lys Leu Gln Leu His
                325                 330                 335

Glu Glu Glu Tyr Val Leu Met Gln Ala Ile Ser Leu Phe Ser Pro Asp
            340                 345                 350

Arg Pro Gly Val Leu Gln His Arg Val Val Asp Gln Leu Gln Glu Gln
        355                 360                 365

Phe Ala Ile Thr Leu Lys Ser Tyr Ile Glu Cys Asn Arg Pro Gln Pro
    370                 375                 380

Ala His Arg Phe Leu Phe Leu Lys Ile Met Ala Met Leu Thr Glu Leu
385                 390                 395                 400

Arg Ser Ile Asn Ala Gln His Thr Gln Arg Leu Leu Arg Ile Gln Asp
                405                 410                 415

Ile His Pro Phe Ala Thr Pro Leu Met Gln Glu Leu Phe Gly Ile Thr
            420                 425                 430

Gly Ser
```

<210> SEQ ID NO 44
<211> LENGTH: 352
<212> TYPE: PRT
<213> ORGANISM: Homo sapiens

<400> SEQUENCE: 44

```
Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60
```

-continued

Ala Cys Arg Leu Gln Lys Cys Leu Asp Ala Gly Met Arg Lys Asp Met
65 70 75 80

Ile Leu Ser Ala Glu Ala Leu Ala Leu Arg Arg Ala Lys Gln Ala Gln
85 90 95

Arg Arg Ala Gln Gln Thr Pro Val Gln Leu Ser Lys Glu Gln Glu Glu
100 105 110

Leu Ile Arg Thr Leu Leu Gly Ala His Thr Arg His Met Gly Thr Met
115 120 125

Phe Glu Gln Phe Val Gln Phe Arg Pro Pro Ala His Leu Phe Ile His
130 135 140

His Gln Pro Leu Pro Thr Leu Ala Pro Val Leu Pro Leu Val Thr His
145 150 155 160

Phe Ala Asp Ile Asn Thr Phe Met Val Leu Gln Val Ile Lys Phe Thr
165 170 175

Lys Asp Leu Pro Val Phe Arg Ser Leu Pro Ile Glu Asp Gln Ile Ser
180 185 190

Leu Leu Lys Gly Ala Ala Val Glu Ile Cys His Ile Val Leu Asn Thr
195 200 205

Thr Phe Cys Leu Gln Thr Gln Asn Phe Leu Cys Gly Pro Leu Arg Tyr
210 215 220

Thr Ile Glu Asp Gly Ala Arg Val Ser Pro Thr Val Gly Phe Gln Val
225 230 235 240

Glu Phe Leu Glu Leu Leu Phe His Phe His Gly Thr Leu Arg Lys Leu
245 250 255

Gln Leu Gln Glu Pro Glu Tyr Val Leu Leu Ala Ala Met Ala Leu Phe
260 265 270

Ser Pro Asp Arg Pro Gly Val Thr Gln Arg Asp Glu Ile Asp Gln Leu
275 280 285

Gln Glu Glu Met Ala Leu Thr Leu Gln Ser Tyr Ile Lys Gly Gln Gln
290 295 300

Arg Arg Pro Arg Asp Arg Phe Leu Tyr Ala Lys Leu Leu Gly Leu Leu
305 310 315 320

Ala Glu Leu Arg Ser Ile Asn Glu Ala Tyr Gly Tyr Gln Ile Gln His
325 330 335

Ile Gln Gly Leu Ser Ala Met Met Pro Leu Leu Gln Glu Ile Cys Ser
340 345 350

<210> SEQ ID NO 45
<211> LENGTH: 474
<212> TYPE: PRT
<213> ORGANISM: Homo sapiens

<400> SEQUENCE: 45

Met Arg Leu Ser Lys Thr Leu Val Asp Met Asp Met Ala Asp Tyr Ser
1 5 10 15

Ala Ala Leu Asp Pro Ala Tyr Thr Thr Leu Glu Phe Glu Asn Val Gln
20 25 30

Val Leu Thr Met Gly Asn Asp Thr Ser Pro Ser Glu Gly Thr Asn Leu
35 40 45

Asn Ala Pro Asn Ser Leu Gly Val Ser Ala Leu Cys Ala Ile Cys Gly
50 55 60

Asp Arg Ala Thr Gly Lys His Tyr Gly Ala Ser Ser Cys Asp Gly Cys
65 70 75 80

Lys Gly Phe Phe Arg Arg Ser Val Arg Lys Asn His Met Tyr Ser Cys
85 90 95

```
Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Pro Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Tyr
        275                 280                 285

Leu Lys Ala Ile Ile Phe Phe Asp Pro Asp Ala Lys Gly Leu Ser Asp
    290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
        355                 360                 365

Leu Leu Gln Glu Met Leu Leu Gly Gly Ser Pro Ser Asp Ala Pro His
    370                 375                 380

Ala His His Pro Leu His Pro His Leu Met Gln Glu His Met Gly Thr
385                 390                 395                 400

Asn Val Ile Val Ala Asn Thr Met Pro Thr His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Gly Gly Ser Gly Ser Glu Pro Tyr Lys Leu
        435                 440                 445

Leu Pro Gly Ala Val Ala Thr Ile Val Lys Pro Leu Ser Ala Ile Pro
    450                 455                 460

Gln Pro Thr Ile Thr Lys Gln Glu Val Ile
465                 470
```

<210> SEQ ID NO 46
<211> LENGTH: 408
<212> TYPE: PRT
<213> ORGANISM: Homo sapiens -continued

<400> SEQUENCE: 46

```
Met Asn Thr Thr Asp Asn Gly Val Asn Cys Leu Cys Ala Ile Cys Gly
1               5                   10                  15

Asp Arg Ala Thr Gly Lys His Tyr Gly Ala Ser Ser Cys Asp Gly Cys
            20                  25                  30

Lys Gly Phe Phe Arg Arg Ser Ile Arg Lys Ser His Val Tyr Ser Cys
        35                  40                  45

Arg Phe Ser Arg Gln Cys Val Val Asp Lys Asp Lys Arg Asn Gln Cys
    50                  55                  60

Arg Tyr Cys Arg Leu Arg Lys Cys Phe Arg Ala Gly Met Lys Lys Glu
65                  70                  75                  80

Ala Val Gln Asn Glu Arg Asp Arg Ile Ser Thr Arg Arg Ser Thr Phe
                85                  90                  95

Asp Gly Ser Asn Ile Pro Ser Ile Asn Thr Leu Ala Gln Ala Glu Val
            100                 105                 110

Arg Ser Arg Gln Ile Ser Val Ser Ser Pro Gly Ser Ser Thr Asp Ile
        115                 120                 125

Asn Val Lys Lys Ile Ala Ser Ile Gly Asp Val Cys Glu Ser Met Lys
    130                 135                 140

Gln Gln Leu Leu Val Leu Val Glu Trp Ala Lys Tyr Ile Pro Ala Phe
145                 150                 155                 160

Cys Glu Leu Pro Leu Asp Asp Gln Val Ala Leu Leu Arg Ala His Ala
                165                 170                 175

Gly Glu His Leu Leu Leu Gly Ala Thr Lys Arg Ser Met Met Tyr Lys
            180                 185                 190

Asp Ile Leu Leu Leu Gly Asn Asn Tyr Val Ile His Arg Asn Ser Cys
        195                 200                 205

Glu Val Glu Ile Ser Arg Val Ala Asn Arg Val Leu Asp Glu Leu Val
    210                 215                 220

Arg Pro Phe Gln Glu Ile Gln Ile Asp Asp Asn Glu Tyr Ala Cys Leu
225                 230                 235                 240

Lys Ala Ile Val Phe Phe Asp Pro Asp Ala Lys Gly Leu Ser Asp Pro
                245                 250                 255

Val Lys Ile Lys Asn Met Arg Phe Gln Val Gln Ile Gly Leu Glu Asp
            260                 265                 270

Tyr Ile Asn Asp Arg Gln Tyr Asp Ser Arg Gly Arg Phe Gly Glu Leu
        275                 280                 285

Leu Leu Leu Leu Pro Thr Leu Gln Ser Ile Thr Trp Gln Met Ile Glu
    290                 295                 300

Gln Ile Gln Phe Val Lys Leu Phe Gly Met Val Lys Ile Asp Asn Leu
305                 310                 315                 320

Leu Gln Glu Met Leu Leu Gly Gly Ala Ser Asn Asp Gly Ser His Leu
                325                 330                 335

His His Pro Met His Pro His Leu Ser Gln Asp Pro Leu Thr Gly Gln
            340                 345                 350

Thr Ile Leu Leu Gly Pro Met Ser Thr Leu Val His Ala Asp Gln Ile
        355                 360                 365

Ser Thr Pro Glu Thr Pro Leu Pro Ser Pro Pro Gln Gly Ser Gly Gln
    370                 375                 380

Glu Gln Tyr Lys Ile Ala Ala Asn Gln Ala Ser Val Ile Ser His Gln
385                 390                 395                 400

His Leu Ser Lys Gln Lys Gln Leu
                405
```

<210> SEQ ID NO 47
<211> LENGTH: 462
<212> TYPE: PRT
<213> ORGANISM: Homo sapiens

<400> SEQUENCE: 47

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser 370 375 380

Asn Pro Ala Glu Val Glu Ala Leu Arg Glu Lys Val Tyr Ala Ser Leu
385 390 395 400

Glu Ala Tyr Cys Lys His Lys Tyr Pro Glu Gln Pro Gly Arg Phe Ala
405 410 415

Lys Leu Leu Leu Arg Leu Pro Ala Leu Arg Ser Ile Gly Leu Lys Cys
420 425 430

Leu Glu His Leu Phe Phe Phe Lys Leu Ile Gly Asp Thr Pro Ile Asp
435 440 445

Thr Phe Leu Met Glu Met Leu Glu Ala Pro His Gln Met Thr
450 455 460

<210> SEQ ID NO 48
<211> LENGTH: 533
<212> TYPE: PRT
<213> ORGANISM: Homo sapiens

<400> SEQUENCE: 48

Met Ser Trp Ala Ala Arg Pro Pro Phe Leu Pro Gln Arg His Ala Ala
1 5 10 15

Gly Gln Cys Gly Pro Val Gly Val Arg Lys Glu Met His Cys Gly Val
20 25 30

Ala Ser Arg Trp Arg Arg Arg Arg Pro Trp Leu Asp Pro Ala Ala Ala
35 40 45

Ala Ala Ala Ala Val Ala Gly Gly Glu Gln Gln Thr Pro Glu Pro Glu
50 55 60

Pro Gly Glu Ala Gly Arg Asp Gly Met Gly Asp Ser Gly Arg Asp Ser
65 70 75 80

Arg Ser Pro Asp Ser Ser Ser Pro Asn Pro Leu Pro Gln Gly Val Pro
85 90 95

Pro Pro Ser Pro Pro Gly Pro Pro Leu Pro Pro Ser Thr Ala Pro Ser
100 105 110

Leu Gly Gly Ser Gly Ala Pro Pro Pro Pro Pro Met Pro Pro Pro Pro
115 120 125

Leu Gly Ser Pro Phe Pro Val Ile Ser Ser Ser Met Gly Ser Pro Gly
130 135 140

Leu Pro Pro Pro Ala Pro Pro Gly Phe Ser Gly Pro Val Ser Ser Pro
145 150 155 160

Gln Ile Asn Ser Thr Val Ser Leu Pro Gly Gly Gly Ser Gly Pro Pro
165 170 175

Glu Asp Val Lys Pro Pro Val Leu Gly Val Arg Gly Leu His Cys Pro
180 185 190

Pro Pro Pro Gly Gly Pro Gly Ala Gly Lys Arg Leu Cys Ala Ile Cys
195 200 205

Gly Asp Arg Ser Ser Gly Lys His Tyr Gly Val Tyr Ser Cys Glu Gly
210 215 220

Cys Lys Gly Phe Phe Lys Arg Thr Ile Arg Lys Asp Leu Thr Tyr Ser
225 230 235 240

Cys Arg Asp Asn Lys Asp Cys Thr Val Asp Lys Arg Gln Arg Asn Arg
245 250 255

Cys Gln Tyr Cys Arg Tyr Gln Lys Cys Leu Ala Thr Gly Met Lys Arg
260 265 270

Glu Ala Val Gln Glu Glu Arg Gln Arg Gly Lys Asp Lys Asp Gly Asp
275 280 285

-continued

```
Gly Glu Gly Ala Gly Gly Ala Pro Glu Glu Met Pro Val Asp Arg Ile
    290                 295                 300

Leu Glu Ala Glu Leu Ala Val Glu Gln Lys Ser Asp Gln Gly Val Glu
305                 310                 315                 320

Gly Pro Gly Gly Thr Gly Gly Ser Gly Ser Ser Pro Asn Asp Pro Val
                325                 330                 335

Thr Asn Ile Cys Gln Ala Ala Asp Lys Gln Leu Phe Thr Leu Val Glu
            340                 345                 350

Trp Ala Lys Arg Ile Pro His Phe Ser Ser Leu Pro Leu Asp Asp Gln
        355                 360                 365

Val Ile Leu Leu Arg Ala Gly Trp Asn Glu Leu Leu Ile Ala Ser Phe
    370                 375                 380

Ser His Arg Ser Ile Asp Val Arg Asp Gly Ile Leu Leu Ala Thr Gly
385                 390                 395                 400

Leu His Val His Arg Asn Ser Ala His Ser Ala Gly Val Gly Ala Ile
                405                 410                 415

Phe Asp Arg Val Leu Thr Glu Leu Val Ser Lys Met Arg Asp Met Arg
            420                 425                 430

Met Asp Lys Thr Glu Leu Gly Cys Leu Arg Ala Ile Ile Leu Phe Asn
        435                 440                 445

Pro Asp Ala Lys Gly Leu Ser Asn Pro Ser Glu Val Glu Val Leu Arg
    450                 455                 460

Glu Lys Val Tyr Ala Ser Leu Glu Thr Tyr Cys Lys Gln Lys Tyr Pro
465                 470                 475                 480

Glu Gln Gln Gly Arg Phe Ala Lys Leu Leu Leu Arg Leu Pro Ala Leu
                485                 490                 495

Arg Ser Ile Gly Leu Lys Cys Leu Glu His Leu Phe Phe Phe Lys Leu
            500                 505                 510

Ile Gly Asp Thr Pro Ile Asp Thr Phe Leu Met Glu Met Leu Glu Ala
        515                 520                 525

Pro His Gln Leu Ala
    530
```

<210> SEQ ID NO 49
<211> LENGTH: 463
<212> TYPE: PRT
<213> ORGANISM: Homo sapiens

<400> SEQUENCE: 49

```
Met Tyr Gly Asn Tyr Ser His Phe Met Lys Phe Pro Ala Gly Tyr Gly
1               5                   10                  15

Gly Ser Pro Gly His Thr Gly Ser Thr Ser Met Ser Pro Ser Ala Ala
            20                  25                  30

Leu Ser Thr Gly Lys Pro Met Asp Ser His Pro Ser Tyr Thr Asp Thr
        35                  40                  45

Pro Val Ser Ala Pro Arg Thr Leu Ser Ala Val Gly Thr Pro Leu Asn
    50                  55                  60

Ala Leu Gly Ser Pro Tyr Arg Val Ile Thr Ser Ala Met Gly Pro Pro
65                  70                  75                  80

Ser Gly Ala Leu Ala Ala Pro Pro Gly Ile Asn Leu Val Ala Pro Pro
                85                  90                  95

Ser Ser Gln Leu Asn Val Val Asn Ser Val Ser Ser Ser Glu Asp Ile
            100                 105                 110

Lys Pro Leu Pro Gly Leu Pro Gly Ile Gly Asn Met Asn Tyr Pro Ser
        115                 120                 125
```

Thr Ser Pro Gly Ser Leu Val Lys His Ile Cys Ala Ile Cys Gly Asp
130 135 140

Arg Ser Ser Gly Lys His Tyr Gly Val Tyr Ser Cys Glu Gly Cys Lys
145 150 155 160

Gly Phe Phe Lys Arg Thr Ile Arg Lys Asp Leu Ile Tyr Thr Cys Arg
165 170 175

Asp Asn Lys Asp Cys Leu Ile Asp Lys Arg Gln Arg Asn Arg Cys Gln
180 185 190

Tyr Cys Arg Tyr Gln Lys Cys Leu Val Met Gly Met Lys Arg Glu Ala
195 200 205

Val Gln Glu Glu Arg Gln Arg Ser Arg Glu Arg Ala Glu Ser Glu Ala
210 215 220

Glu Cys Ala Thr Ser Gly His Glu Asp Met Pro Val Glu Arg Ile Leu
225 230 235 240

Glu Ala Glu Leu Ala Val Glu Pro Lys Thr Glu Ser Tyr Gly Asp Met
245 250 255

Asn Met Glu Asn Ser Thr Asn Asp Pro Val Thr Asn Ile Cys His Ala
260 265 270

Ala Asp Lys Gln Leu Phe Thr Leu Val Glu Trp Ala Lys Arg Ile Pro
275 280 285

His Phe Ser Asp Leu Thr Leu Glu Asp Gln Val Ile Leu Leu Arg Ala
290 295 300

Gly Trp Asn Glu Leu Leu Ile Ala Ser Phe Ser His Arg Ser Val Ser
305 310 315 320

Val Gln Asp Gly Ile Leu Leu Ala Thr Gly Leu His Val His Arg Ser
325 330 335

Ser Ala His Ser Ala Gly Val Gly Ser Ile Phe Asp Arg Val Leu Thr
340 345 350

Glu Leu Val Ser Lys Met Lys Asp Met Gln Met Asp Lys Ser Glu Leu
355 360 365

Gly Cys Leu Arg Ala Ile Val Leu Phe Asn Pro Asp Ala Lys Gly Leu
370 375 380

Ser Asn Pro Ser Glu Val Glu Thr Leu Arg Glu Lys Val Tyr Ala Thr
385 390 395 400

Leu Glu Ala Tyr Thr Lys Gln Lys Tyr Pro Glu Gln Pro Gly Arg Phe
405 410 415

Ala Lys Leu Leu Leu Arg Leu Pro Ala Leu Arg Ser Ile Gly Leu Lys
420 425 430

Cys Leu Glu His Leu Phe Phe Phe Lys Leu Ile Gly Asp Thr Pro Ile
435 440 445

Asp Thr Phe Leu Met Glu Met Leu Glu Thr Pro Leu Gln Ile Thr
450 455 460

<210> SEQ ID NO 50
<211> LENGTH: 603
<212> TYPE: PRT
<213> ORGANISM: Homo sapiens

<400> SEQUENCE: 50

Met Ala Thr Ile Glu Glu Ile Ala His Gln Ile Ile Glu Gln Gln Met
1 5 10 15

Gly Glu Ile Val Thr Glu Gln Gln Thr Gly Gln Lys Ile Gln Ile Val
20 25 30

Thr Ala Leu Asp His Asn Thr Gln Gly Lys Gln Phe Ile Leu Thr Asn

-continued

```
        35                  40                  45

His Asp Gly Ser Thr Pro Ser Lys Val Ile Leu Ala Arg Gln Asp Ser
    50                  55                  60

Thr Pro Gly Lys Val Phe Leu Thr Thr Pro Asp Ala Ala Gly Val Asn
65                  70                  75                  80

Gln Leu Phe Phe Thr Thr Pro Asp Leu Ser Ala Gln His Leu Gln Leu
                85                  90                  95

Leu Thr Asp Asn Ser Pro Asp Gln Gly Pro Asn Lys Val Phe Asp Leu
            100                 105                 110

Cys Val Val Cys Gly Asp Lys Ala Ser Gly Arg His Tyr Gly Ala Val
        115                 120                 125

Thr Cys Glu Gly Cys Lys Gly Phe Phe Lys Arg Ser Ile Arg Lys Asn
    130                 135                 140

Leu Val Tyr Ser Cys Arg Gly Ser Lys Asp Cys Ile Ile Asn Lys His
145                 150                 155                 160

His Arg Asn Arg Cys Gln Tyr Cys Arg Leu Gln Arg Cys Ile Ala Phe
                165                 170                 175

Gly Met Lys Gln Asp Ser Val Gln Cys Glu Arg Lys Pro Ile Glu Val
            180                 185                 190

Ser Arg Glu Lys Ser Ser Asn Cys Ala Ala Ser Thr Glu Lys Ile Tyr
        195                 200                 205

Ile Arg Lys Asp Leu Arg Ser Pro Leu Thr Ala Thr Pro Thr Phe Val
    210                 215                 220

Thr Asp Ser Glu Ser Thr Arg Ser Thr Gly Leu Leu Asp Ser Gly Met
225                 230                 235                 240

Phe Met Asn Ile His Pro Ser Gly Val Lys Thr Glu Ser Ala Val Leu
                245                 250                 255

Met Thr Ser Asp Lys Ala Glu Ser Cys Gln Gly Asp Leu Ser Thr Leu
            260                 265                 270

Ala Asn Val Val Thr Ser Leu Ala Asn Leu Gly Lys Thr Lys Asp Leu
        275                 280                 285

Ser Gln Asn Ser Asn Glu Met Ser Met Ile Glu Ser Leu Ser Asn Asp
    290                 295                 300

Asp Thr Ser Leu Cys Glu Phe Gln Glu Met Gln Thr Asn Gly Asp Val
305                 310                 315                 320

Ser Arg Ala Phe Asp Thr Leu Ala Lys Ala Leu Asn Pro Gly Glu Ser
                325                 330                 335

Thr Ala Cys Gln Ser Ser Val Ala Gly Met Glu Gly Ser Val His Leu
            340                 345                 350

Ile Thr Gly Asp Ser Ser Ile Asn Tyr Thr Glu Lys Glu Gly Pro Leu
        355                 360                 365

Leu Ser Asp Ser His Val Ala Phe Arg Leu Thr Met Pro Ser Pro Met
    370                 375                 380

Pro Glu Tyr Leu Asn Val His Tyr Ile Gly Glu Ser Ala Ser Arg Leu
385                 390                 395                 400

Leu Phe Leu Ser Met His Trp Ala Leu Ser Ile Pro Ser Phe Gln Ala
                405                 410                 415

Leu Gly Gln Glu Asn Ser Ile Ser Leu Val Lys Ala Tyr Trp Asn Glu
            420                 425                 430

Leu Phe Thr Leu Gly Leu Ala Gln Cys Trp Gln Val Met Asn Val Ala
        435                 440                 445

Thr Ile Leu Ala Thr Phe Val Asn Cys Leu His Asn Ser Leu Gln Gln
    450                 455                 460
```

```
Asp Lys Met Ser Thr Glu Arg Arg Lys Leu Leu Met Glu His Ile Phe
465                 470                 475                 480

Lys Leu Gln Glu Phe Cys Asn Ser Met Val Lys Leu Cys Ile Asp Gly
                485                 490                 495

Tyr Glu Tyr Ala Tyr Leu Lys Ala Ile Val Leu Phe Ser Pro Asp His
            500                 505                 510

Pro Ser Leu Glu Asn Met Glu Gln Ile Glu Lys Phe Gln Glu Lys Ala
        515                 520                 525

Tyr Val Glu Phe Gln Asp Tyr Ile Thr Lys Thr Tyr Pro Asp Asp Thr
    530                 535                 540

Tyr Arg Leu Ser Arg Leu Leu Leu Arg Leu Pro Ala Leu Arg Leu Met
545                 550                 555                 560

Asn Ala Thr Ile Thr Glu Glu Leu Phe Phe Lys Gly Leu Ile Gly Asn
                565                 570                 575

Ile Arg Ile Asp Ser Val Ile Pro His Ile Leu Lys Met Glu Pro Ala
            580                 585                 590

Asp Tyr Asn Ser Gln Ile Ile Gly His Ser Ile
        595                 600


<210> SEQ ID NO 51
<211> LENGTH: 596
<212> TYPE: PRT
<213> ORGANISM: Homo sapiens

<400> SEQUENCE: 51

Met Thr Ser Pro Ser Pro Arg Ile Gln Ile Ile Ser Thr Asp Ser Ala
1               5                   10                  15

Val Ala Ser Pro Gln Arg Ile Gln Ile Val Thr Asp Gln Gln Thr Gly
            20                  25                  30

Gln Lys Ile Gln Ile Val Thr Ala Val Asp Ala Ser Gly Ser Pro Lys
        35                  40                  45

Gln Gln Phe Ile Leu Thr Ser Pro Asp Gly Ala Gly Thr Gly Lys Val
    50                  55                  60

Ile Leu Ala Ser Pro Glu Thr Ser Ser Ala Lys Gln Leu Ile Phe Thr
65                  70                  75                  80

Thr Ser Asp Asn Leu Val Pro Gly Arg Ile Gln Ile Val Thr Asp Ser
                85                  90                  95

Ala Ser Val Glu Arg Leu Leu Gly Lys Thr Asp Val Gln Arg Pro Gln
            100                 105                 110

Val Val Glu Tyr Cys Val Val Cys Gly Asp Lys Ala Ser Gly Arg His
        115                 120                 125

Tyr Gly Ala Val Ser Cys Glu Gly Cys Lys Gly Phe Phe Lys Arg Ser
    130                 135                 140

Val Arg Lys Asn Leu Thr Tyr Ser Cys Arg Ser Asn Gln Asp Cys Ile
145                 150                 155                 160

Ile Asn Lys His His Arg Asn Arg Cys Gln Phe Cys Arg Leu Lys Lys
                165                 170                 175

Cys Leu Glu Met Gly Met Lys Met Glu Ser Val Gln Ser Glu Arg Lys
            180                 185                 190

Pro Phe Asp Val Gln Arg Glu Lys Pro Ser Asn Cys Ala Ala Ser Thr
        195                 200                 205

Glu Lys Ile Tyr Ile Arg Lys Asp Leu Arg Ser Pro Leu Ile Ala Thr
    210                 215                 220

Pro Thr Phe Val Ala Asp Lys Asp Gly Ala Arg Gln Thr Gly Leu Leu
```

-continued 225 230 235 240

Asp Pro Gly Met Leu Val Asn Ile Gln Gln Pro Leu Ile Arg Glu Asp
245 250 255

Gly Thr Val Leu Leu Ala Thr Asp Ser Lys Ala Glu Thr Ser Gln Gly
260 265 270

Ala Leu Gly Thr Leu Ala Asn Val Val Thr Ser Leu Ala Asn Leu Ser
275 280 285

Glu Ser Leu Asn Asn Gly Asp Thr Ser Glu Ile Gln Pro Glu Asp Gln
290 295 300

Ser Ala Ser Glu Ile Thr Arg Ala Phe Asp Thr Leu Ala Lys Ala Leu
305 310 315 320

Asn Thr Thr Asp Ser Ser Ser Ser Pro Ser Leu Ala Asp Gly Ile Asp
325 330 335

Thr Ser Gly Gly Gly Ser Ile His Val Ile Ser Arg Asp Gln Ser Thr
340 345 350

Pro Ile Ile Glu Val Glu Gly Pro Leu Leu Ser Asp Thr His Val Thr
355 360 365

Phe Lys Leu Thr Met Pro Ser Pro Met Pro Glu Tyr Leu Asn Val His
370 375 380

Tyr Ile Cys Glu Ser Ala Ser Arg Leu Leu Phe Leu Ser Met His Trp
385 390 395 400

Ala Arg Ser Ile Pro Ala Phe Gln Ala Leu Gly Gln Asp Cys Asn Thr
405 410 415

Ser Leu Val Arg Ala Cys Trp Asn Glu Leu Phe Thr Leu Gly Leu Ala
420 425 430

Gln Cys Ala Gln Val Met Ser Leu Ser Thr Ile Leu Ala Ala Ile Val
435 440 445

Asn His Leu Gln Asn Ser Ile Gln Glu Asp Lys Leu Ser Gly Asp Arg
450 455 460

Ile Lys Gln Val Met Glu His Ile Trp Lys Leu Gln Glu Phe Cys Asn
465 470 475 480

Ser Met Ala Lys Leu Asp Ile Asp Gly Tyr Glu Tyr Ala Tyr Leu Lys
485 490 495

Ala Ile Val Leu Phe Ser Pro Asp His Pro Gly Leu Thr Ser Thr Ser
500 505 510

Gln Ile Glu Lys Phe Gln Glu Lys Ala Gln Met Glu Leu Gln Asp Tyr
515 520 525

Val Gln Lys Thr Tyr Ser Glu Asp Thr Tyr Arg Leu Ala Arg Ile Leu
530 535 540

Val Arg Leu Pro Ala Leu Arg Leu Met Ser Ser Asn Ile Thr Glu Glu
545 550 555 560

Leu Phe Phe Thr Gly Leu Ile Gly Asn Val Ser Ile Asp Ser Ile Ile
565 570 575

Pro Tyr Ile Leu Lys Met Glu Thr Ala Glu Tyr Asn Gly Gln Ile Thr
580 585 590

Gly Ala Ser Leu
595

<210> SEQ ID NO 52
<211> LENGTH: 385
<212> TYPE: PRT
<213> ORGANISM: Papio anubis

<400> SEQUENCE: 52

```
Met Ser Lys Pro Ala Gly Ser Thr Ser Arg Ile Leu Asp Ile Pro Cys
1               5                   10                  15

Lys Val Cys Gly Asp Arg Ser Ser Gly Lys His Tyr Gly Val Tyr Ala
            20                  25                  30

Cys Asp Gly Cys Ser Gly Phe Phe Lys Arg Ser Ile Arg Arg Asn Arg
        35                  40                  45

Thr Tyr Val Cys Lys Ser Gly Asn Gln Gly Gly Cys Pro Val Asp Lys
    50                  55                  60

Thr His Arg Asn Gln Cys Arg Ala Cys Arg Leu Lys Lys Cys Leu Glu
65                  70                  75                  80

Val Asn Met Asn Lys Asp Ala Val Gln His Glu Arg Gly Pro Arg Thr
                85                  90                  95

Ser Thr Ile Arg Lys Gln Val Ala Leu Tyr Phe Arg Gly His Lys Glu
            100                 105                 110

Glu Asn Gly Ala Ala Ala His Phe Pro Ser Ala Ala Leu Pro Ala Pro
        115                 120                 125

Ala Phe Phe Thr Ala Val Thr Gln Leu Glu Pro His Gly Leu Glu Leu
    130                 135                 140

Ala Ala Val Ser Thr Thr Pro Glu Arg Gln Thr Leu Val Ser Leu Ala
145                 150                 155                 160

Gln Pro Thr Pro Lys Tyr Pro His Glu Val Asn Gly Thr Pro Met Tyr
                165                 170                 175

Leu Tyr Glu Val Ala Thr Glu Ser Val Cys Glu Ser Ala Ala Arg Leu
            180                 185                 190

Leu Phe Met Ser Ile Lys Trp Ala Lys Ser Val Pro Ala Phe Ser Thr
        195                 200                 205

Leu Ser Leu Gln Asp Gln Leu Met Leu Leu Glu Asp Ala Trp Arg Glu
    210                 215                 220

Leu Phe Val Leu Gly Ile Ala Gln Trp Ala Ile Pro Val Asp Ala Asn
225                 230                 235                 240

Thr Leu Leu Ala Val Ser Gly Met Asn Gly Asp Asn Thr Asp Ser Gln
                245                 250                 255

Lys Leu Asn Lys Ile Ile Ser Glu Ile Gln Ala Leu Gln Glu Val Val
            260                 265                 270

Ala Arg Phe Arg Gln Leu Arg Leu Asp Ala Thr Glu Phe Ala Cys Leu
        275                 280                 285

Lys Cys Ile Val Thr Phe Lys Ala Val Pro Thr His Ser Gly Ser Glu
    290                 295                 300

Leu Arg Ser Phe Arg Asn Ala Ala Ala Ile Ala Ala Leu Gln Asp Glu
305                 310                 315                 320

Ala Gln Leu Thr Leu Asn Ser Tyr Ile His Thr Arg Tyr Pro Thr Gln
                325                 330                 335

Pro Cys Arg Phe Gly Lys Leu Leu Leu Leu Leu Pro Ala Leu Arg Ser
            340                 345                 350

Ile Ser Pro Ser Thr Ile Glu Glu Val Phe Phe Lys Lys Thr Ile Gly
        355                 360                 365

Asn Val Pro Ile Thr Arg Leu Leu Ser Asp Met Tyr Lys Ser Ser Asp
    370                 375                 380

Ile
385

<210> SEQ ID NO 53
<211> LENGTH: 410
<212> TYPE: PRT
```

<213> ORGANISM: Homo sapiens

<400> SEQUENCE: 53

Met Glu Thr Arg Pro Thr Ala Leu Met Ser Ser Thr Val Ala Ala Ala
1 5 10 15

Ala Pro Ala Ala Gly Ala Ala Ser Arg Lys Glu Ser Pro Gly Arg Trp
20 25 30

Gly Leu Gly Glu Asp Pro Thr Gly Val Ser Pro Ser Leu Gln Cys Arg
35 40 45

Val Cys Gly Asp Ser Ser Ser Gly Lys His Tyr Gly Ile Tyr Ala Cys
50 55 60

Asn Gly Cys Ser Gly Phe Phe Lys Arg Ser Val Arg Arg Arg Leu Ile
65 70 75 80

Tyr Arg Cys Gln Val Gly Ala Gly Met Cys Pro Val Asp Lys Ala His
85 90 95

Arg Asn Gln Cys Gln Ala Cys Arg Leu Lys Lys Cys Leu Gln Ala Gly
100 105 110

Met Asn Gln Asp Ala Val Gln Asn Glu Arg Gln Pro Arg Ser Thr Ala
115 120 125

Gln Val His Leu Asp Ser Met Glu Ser Asn Thr Glu Ser Arg Pro Glu
130 135 140

Ser Leu Val Ala Pro Pro Ala Pro Ala Gly Arg Ser Pro Arg Gly Pro
145 150 155 160

Thr Pro Met Ser Ala Ala Arg Ala Leu Gly His His Phe Met Ala Ser
165 170 175

Leu Ile Thr Ala Glu Thr Cys Ala Lys Leu Glu Pro Glu Asp Ala Asp
180 185 190

Glu Asn Ile Asp Val Thr Ser Asn Asp Pro Glu Phe Pro Ser Ser Pro
195 200 205

Tyr Ser Ser Ser Ser Pro Cys Gly Leu Asp Ser Ile His Glu Thr Ser
210 215 220

Ala Arg Leu Leu Phe Met Ala Val Lys Trp Ala Lys Asn Leu Pro Val
225 230 235 240

Phe Ser Ser Leu Pro Phe Arg Asp Gln Val Ile Leu Leu Glu Glu Ala
245 250 255

Trp Ser Glu Leu Phe Leu Leu Gly Ala Ile Gln Trp Ser Leu Pro Leu
260 265 270

Asp Ser Cys Pro Leu Leu Ala Pro Pro Glu Ala Ser Ala Ala Gly Gly
275 280 285

Ala Gln Gly Arg Leu Thr Leu Ala Ser Met Glu Thr Arg Val Leu Gln
290 295 300

Glu Thr Ile Ser Arg Phe Arg Ala Leu Ala Val Asp Pro Thr Glu Phe
305 310 315 320

Ala Cys Met Lys Ala Leu Val Leu Phe Lys Pro Glu Thr Arg Gly Leu
325 330 335

Lys Asp Pro Glu His Val Glu Ala Leu Gln Asp Gln Ser Gln Val Met
340 345 350

Leu Ser Gln His Ser Lys Ala His His Pro Ser Gln Pro Val Arg Phe
355 360 365

Gly Lys Leu Leu Leu Leu Leu Pro Ser Leu Arg Phe Ile Thr Ala Glu
370 375 380

Arg Ile Glu Leu Leu Phe Phe Arg Lys Thr Ile Gly Asn Thr Pro Met
385 390 395 400

```
Glu Lys Leu Leu Cys Asp Met Phe Lys Asn
                405                 410


<210> SEQ ID NO 54
<211> LENGTH: 423
<212> TYPE: PRT
<213> ORGANISM: Homo sapiens

<400> SEQUENCE: 54

Met Ala Met Val Val Ser Ser Trp Arg Asp Pro Gln Asp Asp Val Ala
1               5                   10                  15

Gly Gly Asn Pro Gly Gly Pro Asn Pro Ala Ala Gln Ala Ala Arg Gly
            20                  25                  30

Gly Gly Gly Gly Ala Gly Glu Gln Gln Gln Gln Ala Gly Ser Gly Ala
        35                  40                  45

Pro His Thr Pro Gln Thr Pro Gly Gln Pro Gly Ala Pro Ala Thr Pro
    50                  55                  60

Gly Thr Ala Gly Asp Lys Gly Gln Gly Pro Pro Gly Ser Gly Gln Ser
65                  70                  75                  80

Gln Gln His Ile Glu Cys Val Val Cys Gly Asp Lys Ser Ser Gly Lys
                85                  90                  95

His Tyr Gly Gln Phe Thr Cys Glu Gly Cys Lys Ser Phe Phe Lys Arg
            100                 105                 110

Ser Val Arg Arg Asn Leu Thr Tyr Thr Cys Arg Ala Asn Arg Asn Cys
        115                 120                 125

Pro Ile Asp Gln His His Arg Asn Gln Cys Gln Tyr Cys Arg Leu Lys
    130                 135                 140

Lys Cys Leu Lys Val Gly Met Arg Arg Glu Ala Val Gln Arg Gly Arg
145                 150                 155                 160

Met Pro Pro Thr Gln Pro Asn Pro Gly Gln Tyr Ala Leu Thr Asn Gly
                165                 170                 175

Asp Pro Leu Asn Gly His Cys Tyr Leu Ser Gly Tyr Ile Ser Leu Leu
            180                 185                 190

Leu Arg Ala Glu Pro Tyr Pro Thr Ser Arg Tyr Gly Ser Gln Cys Met
        195                 200                 205

Gln Pro Asn Asn Ile Met Gly Ile Glu Asn Ile Cys Glu Leu Ala Ala
    210                 215                 220

Arg Leu Leu Phe Ser Ala Val Glu Trp Ala Arg Asn Ile Pro Phe Phe
225                 230                 235                 240

Pro Asp Leu Gln Ile Thr Asp Gln Val Ser Leu Leu Arg Leu Thr Trp
                245                 250                 255

Ser Glu Leu Phe Val Leu Asn Ala Ala Gln Cys Ser Met Pro Leu His
            260                 265                 270

Val Ala Pro Leu Leu Ala Ala Ala Gly Leu His Ala Ser Pro Met Ser
        275                 280                 285

Ala Asp Arg Val Val Ala Phe Met Asp His Ile Arg Ile Phe Gln Glu
    290                 295                 300

Gln Val Glu Lys Leu Lys Ala Leu His Val Asp Ser Ala Glu Tyr Ser
305                 310                 315                 320

Cys Leu Lys Ala Ile Val Leu Phe Thr Ser Asp Ala Cys Gly Leu Ser
                325                 330                 335

Asp Ala Ala His Ile Glu Ser Leu Gln Glu Lys Ser Gln Cys Ala Leu
            340                 345                 350

Glu Glu Tyr Val Arg Ser Gln Tyr Pro Asn Gln Pro Ser Arg Phe Gly
        355                 360                 365
```

```
Lys Leu Leu Leu Arg Leu Pro Ser Leu Arg Thr Val Ser Ser Ser Val
    370                 375                 380

Ile Glu Gln Leu Phe Phe Val Arg Leu Val Gly Lys Thr Pro Ile Glu
385                 390                 395                 400

Thr Leu Ile Arg Asp Met Leu Leu Ser Gly Ser Ser Phe Asn Trp Pro
                405                 410                 415

Tyr Met Ser Ile Gln Cys Ser
            420


<210> SEQ ID NO 55
<211> LENGTH: 414
<212> TYPE: PRT
<213> ORGANISM: Mus musculus

<400> SEQUENCE: 55

Met Ala Met Val Val Ser Thr Trp Arg Asp Pro Gln Asp Glu Val Pro
1               5                   10                  15

Gly Ser Gln Gly Ser Gln Ala Ser Gln Ala Pro Pro Val Pro Gly Pro
            20                  25                  30

Pro Pro Gly Ala Pro His Thr Pro Gln Thr Pro Gly Gln Gly Gly Pro
        35                  40                  45

Ala Ser Thr Pro Ala Gln Thr Ala Ala Gly Gly Gln Gly Gly Pro Gly
    50                  55                  60

Gly Pro Gly Ser Asp Lys Gln Gln Gln Gln Gln His Ile Glu Cys Val
65                  70                  75                  80

Val Cys Gly Asp Lys Ser Ser Gly Lys His Tyr Gly Gln Phe Thr Cys
                85                  90                  95

Glu Gly Cys Lys Ser Phe Phe Lys Arg Ser Val Arg Arg Asn Leu Ser
            100                 105                 110

Tyr Thr Cys Arg Ala Asn Arg Asn Cys Pro Ile Asp Gln His His Arg
        115                 120                 125

Asn Gln Cys Gln Tyr Cys Arg Leu Lys Lys Cys Leu Lys Val Gly Met
    130                 135                 140

Arg Arg Glu Ala Val Gln Arg Gly Arg Met Pro Pro Thr Gln Pro Thr
145                 150                 155                 160

His Gly Gln Phe Ala Leu Thr Asn Gly Asp Pro Leu Asn Cys His Ser
                165                 170                 175

Tyr Leu Ser Gly Tyr Ile Ser Leu Leu Leu Arg Ala Glu Pro Tyr Pro
            180                 185                 190

Thr Ser Arg Phe Gly Ser Gln Cys Met Gln Pro Asn Asn Ile Met Gly
        195                 200                 205

Ile Glu Asn Ile Cys Glu Leu Ala Ala Arg Met Leu Phe Ser Ala Val
    210                 215                 220

Glu Trp Ala Arg Asn Ile Pro Phe Phe Pro Asp Leu Gln Ile Thr Asp
225                 230                 235                 240

Gln Val Ala Leu Leu Arg Leu Thr Trp Ser Glu Leu Phe Val Leu Asn
                245                 250                 255

Ala Ala Gln Cys Ser Met Pro Leu His Val Ala Pro Leu Leu Ala Ala
            260                 265                 270

Ala Gly Leu His Ala Ser Pro Met Ser Ala Asp Arg Val Val Ala Phe
        275                 280                 285

Met Asp His Ile Arg Ile Phe Gln Glu Gln Val Glu Lys Leu Lys Ala
    290                 295                 300

Leu His Val Asp Ser Ala Glu Tyr Ser Cys Leu Lys Ala Ile Val Leu
```

305 310 315 320

Phe Thr Ser Asp Ala Cys Gly Leu Ser Asp Val Ala His Val Glu Ser
325 330 335

Leu Gln Glu Lys Ser Gln Cys Ala Leu Glu Glu Tyr Val Arg Ser Gln
340 345 350

Tyr Pro Asn Gln Pro Thr Arg Phe Gly Lys Leu Leu Leu Arg Leu Pro
355 360 365

Ser Leu Arg Thr Val Ser Ser Ser Val Ile Glu Gln Leu Phe Phe Val
370 375 380

Arg Leu Val Gly Lys Thr Pro Ile Glu Thr Leu Ile Arg Asp Met Leu
385 390 395 400

Leu Ser Gly Ser Ser Phe Asn Trp Pro Tyr Met Ala Ile Gln
405 410

<210> SEQ ID NO 56
<211> LENGTH: 404
<212> TYPE: PRT
<213> ORGANISM: Homo sapiens

<400> SEQUENCE: 56

Met Ala Met Val Thr Gly Gly Trp Gly Gly Pro Gly Gly Asp Thr Asn
1 5 10 15

Gly Val Asp Lys Ala Gly Gly Tyr Pro Arg Ala Ala Glu Asp Asp Ser
20 25 30

Ala Ser Pro Pro Gly Ala Ala Ser Asp Ala Glu Pro Gly Asp Glu Glu
35 40 45

Arg Pro Gly Leu Gln Val Asp Cys Val Val Cys Gly Asp Lys Ser Ser
50 55 60

Gly Lys His Tyr Gly Val Phe Thr Cys Glu Gly Cys Lys Ser Phe Phe
65 70 75 80

Lys Arg Ser Ile Arg Arg Asn Leu Ser Tyr Thr Cys Arg Ser Asn Arg
85 90 95

Asp Cys Gln Ile Asp Gln His His Arg Asn Gln Cys Gln Tyr Cys Arg
100 105 110

Leu Lys Lys Cys Phe Arg Val Gly Met Arg Lys Glu Ala Val Gln Arg
115 120 125

Gly Arg Ile Pro His Ser Leu Pro Gly Ala Val Ala Ala Ser Ser Gly
130 135 140

Ser Pro Pro Gly Ser Ala Leu Ala Ala Val Ala Ser Gly Gly Asp Leu
145 150 155 160

Phe Pro Gly Gln Pro Val Ser Glu Leu Ile Ala Gln Leu Leu Arg Ala
165 170 175

Glu Pro Tyr Pro Ala Ala Ala Gly Arg Phe Gly Ala Gly Gly Gly Ala
180 185 190

Ala Gly Ala Val Leu Gly Ile Asp Asn Val Cys Glu Leu Ala Ala Arg
195 200 205

Leu Leu Phe Ser Thr Val Glu Trp Ala Arg His Ala Pro Phe Phe Pro
210 215 220

Glu Leu Pro Val Ala Asp Gln Val Ala Leu Leu Arg Leu Ser Trp Ser
225 230 235 240

Glu Leu Phe Val Leu Asn Ala Ala Gln Ala Ala Leu Pro Leu His Thr
245 250 255

Ala Pro Leu Leu Ala Ala Ala Gly Leu His Ala Ala Pro Met Ala Ala
260 265 270

```
Glu Arg Ala Val Ala Phe Met Asp Gln Val Arg Ala Phe Gln Glu Gln
        275                 280                 285

Val Asp Lys Leu Gly Arg Leu Gln Val Asp Ser Ala Glu Tyr Gly Cys
    290                 295                 300

Leu Lys Ala Ile Ala Leu Phe Thr Pro Asp Ala Cys Gly Leu Ser Asp
305                 310                 315                 320

Pro Ala His Val Glu Ser Leu Gln Glu Lys Ala Gln Val Ala Leu Thr
                325                 330                 335

Glu Tyr Val Arg Ala Gln Tyr Pro Ser Gln Pro Gln Arg Phe Gly Arg
            340                 345                 350

Leu Leu Leu Arg Leu Pro Ala Leu Arg Ala Val Pro Ala Ser Leu Ile
        355                 360                 365

Ser Gln Leu Phe Phe Met Arg Leu Val Gly Lys Thr Pro Ile Glu Thr
    370                 375                 380

Leu Ile Arg Asp Met Leu Leu Ser Gly Ser Thr Phe Asn Trp Pro Tyr
385                 390                 395                 400

Gly Ser Gly Gln


<210> SEQ ID NO 57
<211> LENGTH: 423
<212> TYPE: PRT
<213> ORGANISM: Homo sapiens

<400> SEQUENCE: 57

Met Ser Ser Gln Val Val Gly Ile Glu Pro Leu Tyr Ile Lys Ala Glu
1               5                   10                  15

Pro Ala Ser Pro Asp Ser Pro Lys Gly Ser Ser Glu Thr Glu Thr Glu
            20                  25                  30

Pro Pro Val Ala Leu Ala Pro Gly Pro Ala Pro Thr Arg Cys Leu Pro
        35                  40                  45

Gly His Lys Glu Glu Glu Asp Gly Glu Gly Ala Gly Pro Gly Glu Gln
    50                  55                  60

Gly Gly Gly Lys Leu Val Leu Ser Ser Leu Pro Lys Arg Leu Cys Leu
65                  70                  75                  80

Val Cys Gly Asp Val Ala Ser Gly Tyr His Tyr Gly Val Ala Ser Cys
                85                  90                  95

Glu Ala Cys Lys Ala Phe Phe Lys Arg Thr Ile Gln Gly Ser Ile Glu
            100                 105                 110

Tyr Ser Cys Pro Ala Ser Asn Glu Cys Glu Ile Thr Lys Arg Arg Arg
        115                 120                 125

Lys Ala Cys Gln Ala Cys Arg Phe Thr Lys Cys Leu Arg Val Gly Met
    130                 135                 140

Leu Lys Glu Gly Val Arg Leu Asp Arg Val Arg Gly Gly Arg Gln Lys
145                 150                 155                 160

Tyr Lys Arg Arg Pro Glu Val Asp Pro Leu Pro Phe Pro Gly Pro Phe
                165                 170                 175

Pro Ala Gly Pro Leu Ala Val Ala Gly Gly Pro Arg Lys Thr Ala Ala
            180                 185                 190

Pro Val Asn Ala Leu Val Ser His Leu Leu Val Val Glu Pro Glu Lys
        195                 200                 205

Leu Tyr Ala Met Pro Asp Pro Ala Gly Pro Asp Gly His Leu Pro Ala
    210                 215                 220

Val Ala Thr Leu Cys Asp Leu Phe Asp Arg Glu Ile Val Val Thr Ile
225                 230                 235                 240
```

-continued

Ser Trp Ala Lys Ser Ile Pro Gly Phe Ser Ser Leu Ser Leu Ser Asp
245 250 255

Gln Met Ser Val Leu Gln Ser Val Trp Met Glu Val Leu Val Leu Gly
260 265 270

Val Ala Gln Arg Ser Leu Pro Leu Gln Asp Glu Leu Ala Phe Ala Glu
275 280 285

Asp Leu Val Leu Asp Glu Glu Gly Ala Arg Ala Ala Gly Leu Gly Glu
290 295 300

Leu Gly Ala Ala Leu Leu Gln Leu Val Arg Arg Leu Gln Ala Leu Arg
305 310 315 320

Leu Glu Arg Glu Glu Tyr Val Leu Leu Lys Ala Leu Ala Leu Ala Asn
325 330 335

Ser Asp Ser Val His Ile Glu Asp Ala Glu Ala Val Glu Gln Leu Arg
340 345 350

Glu Ala Leu His Glu Ala Leu Leu Glu Tyr Glu Ala Gly Arg Ala Gly
355 360 365

Pro Gly Gly Gly Ala Glu Arg Arg Arg Ala Gly Arg Leu Leu Leu Thr
370 375 380

Leu Pro Leu Leu Arg Gln Thr Ala Gly Lys Val Leu Ala His Phe Tyr
385 390 395 400

Gly Val Lys Leu Glu Gly Lys Val Pro Met His Lys Leu Phe Leu Glu
405 410 415

Met Leu Glu Ala Met Met Asp
420

<210> SEQ ID NO 58
<211> LENGTH: 433
<212> TYPE: PRT
<213> ORGANISM: Homo sapiens

<400> SEQUENCE: 58

Met Ser Ser Asp Asp Arg His Leu Gly Ser Ser Cys Gly Ser Phe Ile
1 5 10 15

Lys Thr Glu Pro Ser Ser Pro Ser Ser Gly Ile Asp Ala Leu Ser His
20 25 30

His Ser Pro Ser Gly Ser Ser Asp Ala Ser Gly Gly Phe Gly Leu Ala
35 40 45

Leu Gly Thr His Ala Asn Gly Leu Asp Ser Pro Pro Met Phe Ala Gly
50 55 60

Ala Gly Leu Gly Gly Thr Pro Cys Arg Lys Ser Tyr Glu Asp Cys Ala
65 70 75 80

Ser Gly Ile Met Glu Asp Ser Ala Ile Lys Cys Glu Tyr Met Leu Asn
85 90 95

Ala Ile Pro Lys Arg Leu Cys Leu Val Cys Gly Asp Ile Ala Ser Gly
100 105 110

Tyr His Tyr Gly Val Ala Ser Cys Glu Ala Cys Lys Ala Phe Phe Lys
115 120 125

Arg Thr Ile Gln Gly Asn Ile Glu Tyr Ser Cys Pro Ala Thr Asn Glu
130 135 140

Cys Glu Ile Thr Lys Arg Arg Arg Lys Ser Cys Gln Ala Cys Arg Phe
145 150 155 160

Met Lys Cys Leu Lys Val Gly Met Leu Lys Glu Gly Val Arg Leu Asp
165 170 175

Arg Val Arg Gly Gly Arg Gln Lys Tyr Lys Arg Arg Leu Asp Ser Glu
180 185 190

Ser Ser Pro Tyr Leu Ser Leu Gln Ile Ser Pro Pro Ala Lys Lys Pro
195 200 205

Leu Thr Lys Ile Val Ser Tyr Leu Leu Val Ala Glu Pro Asp Lys Leu
210 215 220

Tyr Ala Met Pro Pro Pro Gly Met Pro Glu Gly Asp Ile Lys Ala Leu
225 230 235 240

Thr Thr Leu Cys Asp Leu Ala Asp Arg Glu Leu Val Val Ile Ile Gly
245 250 255

Trp Ala Lys His Ile Pro Gly Phe Ser Ser Leu Ser Leu Gly Asp Gln
260 265 270

Met Ser Leu Leu Gln Ser Ala Trp Met Glu Ile Leu Ile Leu Gly Ile
275 280 285

Val Tyr Arg Ser Leu Pro Tyr Asp Asp Lys Leu Val Tyr Ala Glu Asp
290 295 300

Tyr Ile Met Asp Glu Glu His Ser Arg Leu Ala Gly Leu Leu Glu Leu
305 310 315 320

Tyr Arg Ala Ile Leu Gln Leu Val Arg Arg Tyr Lys Lys Leu Lys Val
325 330 335

Glu Lys Glu Glu Phe Val Thr Leu Lys Ala Leu Ala Leu Ala Asn Ser
340 345 350

Asp Ser Met Tyr Ile Glu Asp Leu Glu Ala Val Gln Lys Leu Gln Asp
355 360 365

Leu Leu His Glu Ala Leu Gln Asp Tyr Glu Leu Ser Gln Arg His Glu
370 375 380

Glu Pro Trp Arg Thr Gly Lys Leu Leu Leu Thr Leu Pro Leu Leu Arg
385 390 395 400

Gln Thr Ala Ala Lys Ala Val Gln His Phe Tyr Ser Val Lys Leu Gln
405 410 415

Gly Lys Val Pro Met His Lys Leu Phe Leu Glu Met Leu Glu Ala Lys
420 425 430

Val

<210> SEQ ID NO 59
<211> LENGTH: 458
<212> TYPE: PRT
<213> ORGANISM: Homo sapiens

<400> SEQUENCE: 59

Met Asp Ser Val Glu Leu Cys Leu Pro Glu Ser Phe Ser Leu His Tyr
1 5 10 15

Glu Glu Glu Leu Leu Cys Arg Met Ser Asn Lys Asp Arg His Ile Asp
20 25 30

Ser Ser Cys Ser Ser Phe Ile Lys Thr Glu Pro Ser Ser Pro Ala Ser
35 40 45

Leu Thr Asp Ser Val Asn His His Ser Pro Gly Gly Ser Ser Asp Ala
50 55 60

Ser Gly Ser Tyr Ser Ser Thr Met Asn Gly His Gln Asn Gly Leu Asp
65 70 75 80

Ser Pro Pro Leu Tyr Pro Ser Ala Pro Ile Leu Gly Gly Ser Gly Pro
85 90 95

Val Arg Lys Leu Tyr Asp Asp Cys Ser Ser Thr Ile Val Glu Asp Pro
100 105 110

Gln Thr Lys Cys Glu Tyr Met Leu Asn Ser Met Pro Lys Arg Leu Cys
115 120 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
    210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
        275                 280                 285

Phe Ser Thr Leu Ser Leu Ala Asp Gln Met Ser Leu Leu Gln Ser Ala
    290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
        355                 360                 365

Leu Lys Ala Ile Ala Leu Ala Asn Ser Asp Ser Met His Ile Glu Asp
    370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
        435                 440                 445

Leu Phe Leu Glu Met Leu Glu Ala Lys Val
    450                 455

<210> SEQ ID NO 60
<211> LENGTH: 598
<212> TYPE: PRT
<213> ORGANISM: Homo sapiens

<400> SEQUENCE: 60

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Ala Pro Ala Ala Pro Thr

-continued

```
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ser Ala Thr Ser Pro
                85                  90                  95

Ala Ser Ala Ser Phe Lys Phe Glu Asp Phe Gln Val Tyr Gly Cys Tyr
            100                 105                 110

Pro Gly Pro Leu Ser Gly Pro Val Asp Glu Ala Leu Ser Ser Ser Gly
        115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
        275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
    450                 455                 460
```

```
Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Pro Ile Ile Asp Lys Ile Phe
            580                 585                 590

Met Asp Thr Leu Pro Phe
        595


<210> SEQ ID NO 61
<211> LENGTH: 598
<212> TYPE: PRT
<213> ORGANISM: Homo sapiens

<400> SEQUENCE: 61

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
```

-continued 225 230 235 240

Ser Gln Leu Leu Asp Thr Gln Val Pro Ser Pro Pro Ser Arg Gly Ser
245 250 255

Pro Ser Asn Glu Gly Leu Cys Ala Val Cys Gly Asp Asn Ala Ala Cys
260 265 270

Gln His Tyr Gly Val Arg Thr Cys Glu Gly Cys Lys Gly Phe Phe Lys
275 280 285

Arg Thr Val Gln Lys Asn Ala Lys Tyr Val Cys Leu Ala Asn Lys Asn
290 295 300

Cys Pro Val Asp Lys Arg Arg Arg Asn Arg Cys Gln Tyr Cys Arg Phe
305 310 315 320

Gln Lys Cys Leu Ala Val Gly Met Val Lys Glu Val Val Arg Thr Asp
325 330 335

Ser Leu Lys Gly Arg Arg Gly Arg Leu Pro Ser Lys Pro Lys Ser Pro
340 345 350

Gln Glu Pro Ser Pro Pro Ser Pro Pro Val Ser Leu Ile Ser Ala Leu
355 360 365

Val Arg Ala His Val Asp Ser Asn Pro Ala Met Thr Ser Leu Asp Tyr
370 375 380

Ser Arg Phe Gln Ala Asn Pro Asp Tyr Gln Met Ser Gly Asp Asp Thr
385 390 395 400

Gln His Ile Gln Gln Phe Tyr Asp Leu Leu Thr Gly Ser Met Glu Ile
405 410 415

Ile Arg Gly Trp Ala Glu Lys Ile Pro Gly Phe Ala Asp Leu Pro Lys
420 425 430

Ala Asp Gln Asp Leu Leu Phe Glu Ser Ala Phe Leu Glu Leu Phe Val
435 440 445

Leu Arg Leu Ala Tyr Arg Ser Asn Pro Val Glu Gly Lys Leu Ile Phe
450 455 460

Cys Asn Gly Val Val Leu His Arg Leu Gln Cys Val Arg Gly Phe Gly
465 470 475 480

Glu Trp Ile Asp Ser Ile Val Glu Phe Ser Ser Asn Leu Gln Asn Met
485 490 495

Asn Ile Asp Ile Ser Ala Phe Ser Cys Ile Ala Ala Leu Ala Met Val
500 505 510

Thr Glu Arg His Gly Leu Lys Glu Pro Lys Arg Val Glu Glu Leu Gln
515 520 525

Asn Lys Ile Val Asn Cys Leu Lys Asp His Val Thr Phe Asn Asn Gly
530 535 540

Gly Leu Asn Arg Pro Asn Tyr Leu Ser Lys Leu Leu Gly Lys Leu Pro
545 550 555 560

Glu Leu Arg Thr Leu Cys Thr Gln Gly Leu Gln Arg Ile Phe Tyr Leu
565 570 575

Lys Leu Glu Asp Leu Val Pro Pro Pro Ala Ile Ile Asp Lys Leu Phe
580 585 590

Leu Asp Thr Leu Pro Phe
595

<210> SEQ ID NO 62
<211> LENGTH: 626
<212> TYPE: PRT
<213> ORGANISM: Homo sapiens

<400> SEQUENCE: 62

-continued

```
Met Pro Cys Val Gln Ala Gln Tyr Ser Pro Ser Pro Pro Gly Ser Ser
1               5                   10                  15

Tyr Ala Ala Gln Thr Tyr Ser Ser Glu Tyr Thr Thr Glu Ile Met Asn
            20                  25                  30

Pro Asp Tyr Thr Lys Leu Thr Met Asp Leu Gly Ser Thr Glu Ile Thr
        35                  40                  45

Ala Thr Ala Thr Thr Ser Leu Pro Ser Ile Ser Thr Phe Val Glu Gly
    50                  55                  60

Tyr Ser Ser Asn Tyr Glu Leu Lys Pro Ser Cys Val Tyr Gln Met Gln
65                  70                  75                  80

Arg Pro Leu Ile Lys Val Glu Glu Gly Arg Ala Pro Ser Tyr His His
                85                  90                  95

His His His His His His His His His His His His Gln Gln Gln His
            100                 105                 110

Gln Gln Pro Ser Ile Pro Pro Ala Ser Ser Pro Glu Asp Glu Val Leu
        115                 120                 125

Pro Ser Thr Ser Met Tyr Phe Lys Gln Ser Pro Pro Ser Thr Pro Thr
    130                 135                 140

Thr Pro Ala Phe Pro Pro Gln Ala Gly Ala Leu Trp Asp Glu Ala Leu
145                 150                 155                 160

Pro Ser Ala Pro Gly Cys Ile Ala Pro Gly Pro Leu Leu Asp Pro Pro
                165                 170                 175

Met Lys Ala Val Pro Thr Val Ala Gly Ala Arg Phe Pro Leu Phe His
            180                 185                 190

Phe Lys Pro Ser Pro Pro His Pro Pro Ala Pro Ser Pro Ala Gly Gly
        195                 200                 205

His His Leu Gly Tyr Asp Pro Thr Ala Ala Ala Ala Leu Ser Leu Pro
    210                 215                 220

Leu Gly Ala Ala Ala Ala Ala Gly Ser Gln Ala Ala Ala Leu Glu Ser
225                 230                 235                 240

His Pro Tyr Gly Leu Pro Leu Ala Lys Arg Ala Ala Pro Leu Ala Phe
                245                 250                 255

Pro Pro Leu Gly Leu Thr Pro Ser Pro Thr Ala Ser Ser Leu Leu Gly
            260                 265                 270

Glu Ser Pro Ser Leu Pro Ser Pro Pro Ser Arg Ser Ser Ser Ser Gly
        275                 280                 285

Glu Gly Thr Cys Ala Val Cys Gly Asp Asn Ala Ala Cys Gln His Tyr
    290                 295                 300

Gly Val Arg Thr Cys Glu Gly Cys Lys Gly Phe Phe Lys Arg Thr Val
305                 310                 315                 320

Gln Lys Asn Ala Lys Tyr Val Cys Leu Ala Asn Lys Asn Cys Pro Val
                325                 330                 335

Asp Lys Arg Arg Arg Asn Arg Cys Gln Tyr Cys Arg Phe Gln Lys Cys
            340                 345                 350

Leu Ser Val Gly Met Val Lys Glu Val Val Arg Thr Asp Ser Leu Lys
        355                 360                 365

Gly Arg Arg Gly Arg Leu Pro Ser Lys Pro Lys Ser Pro Leu Gln Gln
    370                 375                 380

Glu Pro Ser Gln Pro Ser Pro Pro Ser Pro Pro Ile Cys Met Met Asn
385                 390                 395                 400

Ala Leu Val Arg Ala Leu Thr Asp Ser Thr Pro Arg Asp Leu Asp Tyr
                405                 410                 415

Ser Arg Tyr Cys Pro Thr Asp Gln Ala Ala Ala Gly Thr Asp Ala Glu
```

```
            420                 425                 430

His Val Gln Gln Phe Tyr Asn Leu Leu Thr Ala Ser Ile Asp Val Ser
        435                 440                 445

Arg Ser Trp Ala Glu Lys Ile Pro Gly Phe Thr Asp Leu Pro Lys Glu
    450                 455                 460

Asp Gln Thr Leu Leu Ile Glu Ser Ala Phe Leu Glu Leu Phe Val Leu
465                 470                 475                 480

Arg Leu Ser Ile Arg Ser Asn Thr Ala Glu Asp Lys Phe Val Phe Cys
                485                 490                 495

Asn Gly Leu Val Leu His Arg Leu Gln Cys Leu Arg Gly Phe Gly Glu
            500                 505                 510

Trp Leu Asp Ser Ile Lys Asp Phe Ser Leu Asn Leu Gln Ser Leu Asn
        515                 520                 525

Leu Asp Ile Gln Ala Leu Ala Cys Leu Ser Ala Leu Ser Met Ile Thr
    530                 535                 540

Glu Arg His Gly Leu Lys Glu Pro Lys Arg Val Glu Glu Leu Cys Asn
545                 550                 555                 560

Lys Ile Thr Ser Ser Leu Lys Asp His Gln Ser Lys Gly Gln Ala Leu
                565                 570                 575

Glu Pro Thr Glu Ser Lys Val Leu Gly Ala Leu Val Glu Leu Arg Lys
            580                 585                 590

Ile Cys Thr Leu Gly Leu Gln Arg Ile Phe Tyr Leu Lys Leu Glu Asp
        595                 600                 605

Leu Val Ser Pro Pro Ser Ile Ile Asp Lys Leu Phe Leu Asp Thr Leu
    610                 615                 620

Pro Phe
625


<210> SEQ ID NO 63
<211> LENGTH: 461
<212> TYPE: PRT
<213> ORGANISM: Homo sapiens

<400> SEQUENCE: 63

Met Asp Tyr Ser Tyr Asp Glu Asp Leu Asp Glu Leu Cys Pro Val Cys
1               5                   10                  15

Gly Asp Lys Val Ser Gly Tyr His Tyr Gly Leu Leu Thr Cys Glu Ser
            20                  25                  30

Cys Lys Gly Phe Phe Lys Arg Thr Val Gln Asn Asn Lys His Tyr Thr
        35                  40                  45

Cys Thr Glu Ser Gln Ser Cys Lys Ile Asp Lys Thr Gln Arg Lys Arg
    50                  55                  60

Cys Pro Phe Cys Arg Phe Gln Lys Cys Leu Thr Val Gly Met Arg Leu
65                  70                  75                  80

Glu Ala Val Arg Ala Asp Arg Met Arg Gly Gly Arg Asn Lys Phe Gly
                85                  90                  95

Pro Met Tyr Lys Arg Asp Arg Ala Leu Lys Gln Gln Lys Lys Ala Gln
            100                 105                 110

Ile Arg Ala Asn Gly Phe Lys Leu Glu Thr Gly Pro Pro Met Gly Val
        115                 120                 125

Pro Pro Pro Pro Pro Pro Ala Pro Asp Tyr Val Leu Pro Pro Ser Leu
    130                 135                 140

His Gly Pro Glu Pro Lys Gly Leu Ala Ala Gly Pro Pro Ala Gly Pro
145                 150                 155                 160
```

```
Leu Gly Asp Phe Gly Ala Pro Ala Leu Pro Met Ala Val Pro Gly Ala
                165                 170                 175

His Gly Pro Leu Ala Gly Tyr Leu Tyr Pro Ala Phe Pro Gly Arg Ala
            180                 185                 190

Ile Lys Ser Glu Tyr Pro Glu Pro Tyr Ala Ser Pro Pro Gln Pro Gly
        195                 200                 205

Leu Pro Tyr Gly Tyr Pro Glu Pro Phe Ser Gly Gly Pro Asn Val Pro
    210                 215                 220

Glu Leu Ile Leu Gln Leu Leu Gln Leu Glu Pro Asp Glu Asp Gln Val
225                 230                 235                 240

Arg Ala Arg Ile Leu Gly Cys Leu Gln Glu Pro Thr Lys Ser Arg Pro
                245                 250                 255

Asp Gln Pro Ala Ala Phe Gly Leu Leu Cys Arg Met Ala Asp Gln Thr
            260                 265                 270

Phe Ile Ser Ile Val Asp Trp Ala Arg Arg Cys Met Val Phe Lys Glu
        275                 280                 285

Leu Glu Val Ala Asp Gln Met Thr Leu Leu Gln Asn Cys Trp Ser Glu
    290                 295                 300

Leu Leu Val Phe Asp His Ile Tyr Arg Gln Val Gln His Gly Lys Glu
305                 310                 315                 320

Gly Ser Ile Leu Leu Val Thr Gly Gln Glu Val Glu Leu Thr Thr Val
                325                 330                 335

Ala Thr Gln Ala Gly Ser Leu Leu His Ser Leu Val Leu Arg Ala Gln
            340                 345                 350

Glu Leu Val Leu Gln Leu Leu Ala Leu Gln Leu Asp Arg Gln Glu Phe
        355                 360                 365

Val Cys Leu Lys Phe Ile Ile Leu Phe Ser Leu Asp Leu Lys Phe Leu
    370                 375                 380

Asn Asn His Ile Leu Val Lys Asp Ala Gln Glu Lys Ala Asn Ala Ala
385                 390                 395                 400

Leu Leu Asp Tyr Thr Leu Cys His Tyr Pro His Cys Gly Asp Lys Phe
                405                 410                 415

Gln Gln Leu Leu Leu Cys Leu Val Glu Val Arg Ala Leu Ser Met Gln
            420                 425                 430

Ala Lys Glu Tyr Leu Tyr His Lys His Leu Gly Asn Glu Met Pro Arg
        435                 440                 445

Asn Asn Leu Leu Ile Glu Met Leu Gln Ala Lys Gln Thr
    450                 455                 460
```

<210> SEQ ID NO 64
<211> LENGTH: 541
<212> TYPE: PRT
<213> ORGANISM: Homo sapiens

<400> SEQUENCE: 64

```
Met Ser Ser Asn Ser Asp Thr Gly Asp Leu Gln Glu Ser Leu Lys His
1               5                   10                  15

Gly Leu Thr Pro Ile Gly Ala Gly Leu Pro Asp Arg His Gly Ser Pro
            20                  25                  30

Ile Pro Ala Arg Gly Arg Leu Val Met Leu Pro Lys Val Glu Thr Glu
        35                  40                  45

Ala Leu Gly Leu Ala Arg Ser His Gly Glu Gln Gly Gln Met Pro Glu
    50                  55                  60

Asn Met Gln Val Ser Gln Phe Lys Met Val Asn Tyr Ser Tyr Asp Glu
65                  70                  75                  80
```

-continued

```
Asp Leu Glu Glu Leu Cys Pro Val Cys Gly Asp Lys Val Ser Gly Tyr
                85                  90                  95

His Tyr Gly Leu Leu Thr Cys Glu Ser Cys Lys Gly Phe Phe Lys Arg
            100                 105                 110

Thr Val Gln Asn Asn Lys Arg Tyr Thr Cys Ile Glu Asn Gln Asn Cys
        115                 120                 125

Gln Ile Asp Lys Thr Gln Arg Lys Arg Cys Pro Tyr Cys Arg Phe Gln
    130                 135                 140

Lys Cys Leu Ser Val Gly Met Lys Leu Glu Ala Val Arg Ala Asp Arg
145                 150                 155                 160

Met Arg Gly Gly Arg Asn Lys Phe Gly Pro Met Tyr Lys Arg Asp Arg
                165                 170                 175

Ala Leu Lys Gln Gln Lys Lys Ala Leu Ile Arg Ala Asn Gly Leu Lys
            180                 185                 190

Leu Glu Ala Met Ser Gln Val Ile Gln Ala Met Pro Ser Asp Leu Thr
        195                 200                 205

Ile Ser Ser Ala Ile Gln Asn Ile His Ser Ala Ser Lys Gly Leu Pro
    210                 215                 220

Leu Asn His Ala Ala Leu Pro Pro Thr Asp Tyr Asp Arg Ser Pro Phe
225                 230                 235                 240

Val Thr Ser Pro Ile Ser Met Thr Met Pro Pro His Gly Ser Leu Gln
                245                 250                 255

Gly Tyr Gln Thr Tyr Gly His Phe Pro Ser Arg Ala Ile Lys Ser Glu
            260                 265                 270

Tyr Pro Asp Pro Tyr Thr Ser Ser Pro Glu Ser Ile Met Gly Tyr Ser
        275                 280                 285

Tyr Met Asp Ser Tyr Gln Thr Ser Ser Pro Ala Ser Ile Pro His Leu
    290                 295                 300

Ile Leu Glu Leu Leu Lys Cys Glu Pro Asp Glu Pro Gln Val Gln Ala
305                 310                 315                 320

Lys Ile Met Ala Tyr Leu Gln Gln Glu Gln Ala Asn Arg Ser Lys His
                325                 330                 335

Glu Lys Leu Ser Thr Phe Gly Leu Met Cys Lys Met Ala Asp Gln Thr
            340                 345                 350

Leu Phe Ser Ile Val Glu Trp Ala Arg Ser Ser Ile Phe Phe Arg Glu
        355                 360                 365

Leu Lys Val Asp Asp Gln Met Lys Leu Leu Gln Asn Cys Trp Ser Glu
    370                 375                 380

Leu Leu Ile Leu Asp His Ile Tyr Arg Gln Val Val His Gly Lys Glu
385                 390                 395                 400

Gly Ser Ile Phe Leu Val Thr Gly Gln Gln Val Asp Tyr Ser Ile Ile
                405                 410                 415

Ala Ser Gln Ala Gly Ala Thr Leu Asn Asn Leu Met Ser His Ala Gln
            420                 425                 430

Glu Leu Val Ala Lys Leu Arg Ser Leu Gln Phe Asp Gln Arg Glu Phe
        435                 440                 445

Val Cys Leu Lys Phe Leu Val Leu Phe Ser Leu Asp Val Lys Asn Leu
    450                 455                 460

Glu Asn Phe Gln Leu Val Glu Gly Val Gln Glu Gln Val Asn Ala Ala
465                 470                 475                 480

Leu Leu Asp Tyr Thr Met Cys Asn Tyr Pro Gln Gln Thr Glu Lys Phe
                485                 490                 495
```

-continued

```
Gly Gln Leu Leu Leu Arg Leu Pro Glu Ile Arg Ala Ile Ser Met Gln
            500                 505                 510

Ala Glu Glu Tyr Leu Tyr Tyr Lys His Leu Asn Gly Asp Val Pro Tyr
        515                 520                 525

Asn Asn Leu Leu Ile Glu Met Leu His Ala Lys Arg Ala
    530                 535                 540


<210> SEQ ID NO 65
<211> LENGTH: 480
<212> TYPE: PRT
<213> ORGANISM: Homo sapiens

<400> SEQUENCE: 65

Met Glu Arg Asp Glu Pro Pro Pro Ser Gly Gly Gly Gly Gly Gly Gly
1               5                   10                  15

Ser Ala Gly Phe Leu Glu Pro Pro Ala Ala Leu Pro Pro Pro Pro Arg
            20                  25                  30

Asn Gly Phe Cys Gln Asp Glu Leu Ala Glu Leu Asp Pro Gly Thr Ile
        35                  40                  45

Ser Val Ser Asp Asp Arg Ala Glu Gln Arg Thr Cys Leu Ile Cys Gly
    50                  55                  60

Asp Arg Ala Thr Gly Leu His Tyr Gly Ile Ile Ser Cys Glu Gly Cys
65                  70                  75                  80

Lys Gly Phe Phe Lys Arg Ser Ile Cys Asn Lys Arg Val Tyr Arg Cys
                85                  90                  95

Ser Arg Asp Lys Asn Cys Val Met Ser Arg Lys Gln Arg Asn Arg Cys
            100                 105                 110

Gln Tyr Cys Arg Leu Leu Lys Cys Leu Gln Met Gly Met Asn Arg Lys
        115                 120                 125

Ala Ile Arg Glu Asp Gly Met Pro Gly Gly Arg Asn Lys Ser Ile Gly
    130                 135                 140

Pro Val Gln Ile Ser Glu Glu Glu Ile Glu Arg Ile Met Ser Gly Gln
145                 150                 155                 160

Glu Phe Glu Glu Glu Ala Asn His Trp Ser Asn His Gly Asp Ser Asp
                165                 170                 175

His Ser Ser Pro Gly Asn Arg Ala Ser Glu Ser Asn Gln Pro Ser Pro
            180                 185                 190

Gly Ser Thr Leu Ser Ser Ser Arg Ser Val Glu Leu Asn Gly Phe Met
        195                 200                 205

Ala Phe Arg Glu Gln Tyr Met Gly Met Ser Val Pro Pro His Tyr Gln
    210                 215                 220

Tyr Ile Pro His Leu Phe Ser Tyr Ser Gly His Ser Pro Leu Leu Pro
225                 230                 235                 240

Gln Gln Ala Arg Ser Leu Asp Pro Gln Ser Tyr Ser Leu Ile His Gln
                245                 250                 255

Leu Leu Ser Ala Glu Asp Leu Glu Pro Leu Gly Thr Pro Met Leu Ile
            260                 265                 270

Glu Asp Gly Tyr Ala Val Thr Gln Ala Glu Leu Phe Ala Leu Leu Cys
        275                 280                 285

Arg Leu Ala Asp Glu Leu Leu Phe Arg Gln Ile Ala Trp Ile Lys Lys
    290                 295                 300

Leu Pro Phe Phe Cys Glu Leu Ser Ile Lys Asp Tyr Thr Cys Leu Leu
305                 310                 315                 320

Ser Ser Thr Trp Gln Glu Leu Ile Leu Leu Ser Ser Leu Thr Val Tyr
                325                 330                 335
```

Ser Lys Gln Ile Phe Gly Glu Leu Ala Asp Val Thr Ala Lys Tyr Ser
340 345 350

Pro Ser Asp Glu Glu Leu His Arg Phe Ser Asp Glu Gly Met Glu Val
355 360 365

Ile Glu Arg Leu Ile Tyr Leu Tyr His Lys Phe His Gln Leu Lys Val
370 375 380

Ser Asn Glu Glu Tyr Ala Cys Met Lys Ala Ile Asn Phe Leu Asn Gln
385 390 395 400

Asp Ile Arg Gly Leu Thr Ser Ala Ser Gln Leu Glu Gln Leu Asn Lys
405 410 415

Arg Tyr Trp Tyr Ile Cys Gln Asp Phe Thr Glu Tyr Lys Tyr Thr His
420 425 430

Gln Pro Asn Arg Phe Pro Asp Leu Met Met Cys Leu Pro Glu Ile Arg
435 440 445

Tyr Ile Ala Gly Lys Met Val Asn Val Pro Leu Glu Gln Leu Pro Leu
450 455 460

Leu Phe Lys Val Val Leu His Ser Cys Lys Thr Ser Val Gly Lys Glu
465 470 475 480

<210> SEQ ID NO 66
<211> LENGTH: 470
<212> TYPE: PRT
<213> ORGANISM: Homo sapiens

<400> SEQUENCE: 66

Met Ala Gly Glu Asn His Gln Trp Gln Gly Ser Ile Leu Tyr Asn Met
1 5 10 15

Leu Met Ser Ala Lys Gln Thr Arg Ala Ala Pro Glu Ala Pro Glu Thr
20 25 30

Arg Leu Val Asp Gln Cys Trp Gly Cys Ser Cys Gly Asp Glu Pro Gly
35 40 45

Val Gly Arg Glu Gly Leu Leu Gly Gly Arg Asn Val Ala Leu Leu Tyr
50 55 60

Arg Cys Cys Phe Cys Gly Lys Asp His Pro Arg Gln Gly Ser Ile Leu
65 70 75 80

Tyr Ser Met Leu Thr Ser Ala Lys Gln Thr Tyr Ala Ala Pro Lys Ala
85 90 95

Pro Glu Ala Thr Leu Gly Pro Cys Trp Gly Cys Ser Cys Gly Ser Asp
100 105 110

Pro Gly Val Gly Arg Ala Gly Leu Pro Gly Gly Arg Pro Val Ala Leu
115 120 125

Leu Tyr Arg Cys Cys Phe Cys Gly Glu Asp His Pro Arg Gln Gly Ser
130 135 140

Ile Leu Tyr Ser Leu Leu Thr Ser Ser Lys Gln Thr His Val Ala Pro
145 150 155 160

Ala Ala Pro Glu Ala Arg Pro Gly Gly Ala Trp Trp Asp Arg Ser Tyr
165 170 175

Phe Ala Gln Arg Pro Gly Gly Lys Glu Ala Leu Pro Gly Gly Arg Ala
180 185 190

Thr Ala Leu Leu Tyr Arg Cys Cys Phe Cys Gly Glu Asp His Pro Gln
195 200 205

Gln Gly Ser Thr Leu Tyr Cys Val Pro Thr Ser Thr Asn Gln Ala Gln
210 215 220

Ala Ala Pro Glu Glu Arg Pro Arg Ala Pro Trp Trp Asp Thr Ser Ser

```
225                 230                 235                 240

Gly Ala Leu Arg Pro Val Ala Leu Lys Ser Pro Gln Val Val Cys Glu
                245                 250                 255

Ala Ala Ser Ala Gly Leu Leu Lys Thr Leu Arg Phe Val Lys Tyr Leu
            260                 265                 270

Pro Cys Phe Gln Val Leu Pro Leu Asp Gln Gln Leu Val Leu Val Arg
        275                 280                 285

Asn Cys Trp Ala Ser Leu Leu Met Leu Glu Leu Ala Gln Asp Arg Leu
    290                 295                 300

Gln Phe Glu Thr Val Glu Val Ser Glu Pro Ser Met Leu Gln Lys Ile
305                 310                 315                 320

Leu Thr Thr Arg Arg Arg Glu Thr Gly Gly Asn Glu Pro Leu Pro Val
                325                 330                 335

Pro Thr Leu Gln His His Leu Ala Pro Pro Ala Glu Ala Arg Lys Val
            340                 345                 350

Pro Ser Ala Ser Gln Val Gln Ala Ile Lys Cys Phe Leu Ser Lys Cys
        355                 360                 365

Trp Ser Leu Asn Ile Ser Thr Lys Glu Tyr Ala Tyr Leu Lys Gly Thr
    370                 375                 380

Val Leu Phe Asn Pro Asp Val Pro Gly Leu Gln Cys Val Lys Tyr Ile
385                 390                 395                 400

Gln Gly Leu Gln Trp Gly Thr Gln Gln Ile Leu Ser Glu His Thr Arg
                405                 410                 415

Met Thr His Gln Gly Pro His Asp Arg Phe Ile Glu Leu Asn Ser Thr
            420                 425                 430

Leu Phe Leu Leu Arg Phe Ile Asn Ala Asn Val Ile Ala Glu Leu Phe
        435                 440                 445

Phe Arg Pro Ile Ile Gly Thr Val Ser Met Asp Asp Met Met Leu Glu
    450                 455                 460

Met Leu Cys Thr Lys Ile
465                 470


<210> SEQ ID NO 67
<211> LENGTH: 257
<212> TYPE: PRT
<213> ORGANISM: Homo sapiens

<400> SEQUENCE: 67

Met Ser Thr Ser Gln Pro Gly Ala Cys Pro Cys Gln Gly Ala Ala Ser
1               5                   10                  15

Arg Pro Ala Ile Leu Tyr Ala Leu Leu Ser Ser Ser Leu Lys Ala Val
            20                  25                  30

Pro Arg Pro Arg Ser Arg Cys Leu Cys Arg Gln His Arg Pro Val Gln
        35                  40                  45

Leu Cys Ala Pro His Arg Thr Cys Arg Glu Ala Leu Asp Val Leu Ala
    50                  55                  60

Lys Thr Val Ala Phe Leu Arg Asn Leu Pro Ser Phe Trp Gln Leu Pro
65                  70                  75                  80

Pro Gln Asp Gln Arg Arg Leu Leu Gln Gly Cys Trp Gly Pro Leu Phe
                85                  90                  95

Leu Leu Gly Leu Ala Gln Asp Ala Val Thr Phe Glu Val Ala Glu Ala
            100                 105                 110

Pro Val Pro Ser Ile Leu Lys Lys Ile Leu Leu Glu Glu Pro Ser Ser
        115                 120                 125
```

Ser Gly Gly Ser Gly Gln Leu Pro Asp Arg Pro Gln Pro Ser Leu Ala
    130                 135                 140

Ala Val Gln Trp Leu Gln Cys Cys Leu Glu Ser Phe Trp Ser Leu Glu
145                 150                 155                 160

Leu Ser Pro Lys Glu Tyr Ala Cys Leu Lys Gly Thr Ile Leu Phe Asn
                165                 170                 175

Pro Asp Val Pro Gly Leu Gln Ala Ala Ser His Ile Gly His Leu Gln
            180                 185                 190

Gln Glu Ala His Trp Val Leu Cys Glu Val Leu Glu Pro Trp Cys Pro
        195                 200                 205

Ala Ala Gln Gly Arg Leu Thr Arg Val Leu Leu Thr Ala Ser Thr Leu
    210                 215                 220

Lys Ser Ile Pro Thr Ser Leu Leu Gly Asp Leu Phe Phe Arg Pro Ile
225                 230                 235                 240

Ile Gly Asp Val Asp Ile Ala Gly Leu Leu Gly Asp Met Leu Leu Leu
                245                 250                 255

Arg

<210> SEQ ID NO 68
<211> LENGTH: 595
<212> TYPE: PRT
<213> ORGANISM: Homo sapiens

<400> SEQUENCE: 68

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

-continued

```
Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595
```

<210> SEQ ID NO 69
<211> LENGTH: 530
<212> TYPE: PRT
<213> ORGANISM: Homo sapiens

<400> SEQUENCE: 69

```
Met Asp Ile Lys Asn Ser Pro Ser Ser Leu Asn Ser Pro Ser Ser Tyr
1               5                   10                  15
```

-continued

```
Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285

Phe Thr Glu Ala Ser Met Met Met Ser Leu Thr Lys Leu Ala Asp Lys
    290                 295                 300

Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430
```

Val Thr Asp Ala Leu Val Trp Val Ile Ala Lys Ser Gly Ile Ser Ser
435 440 445

Gln Gln Gln Ser Met Arg Leu Ala Asn Leu Leu Met Leu Leu Ser His
450 455 460

Val Arg His Ala Ser Asn Lys Gly Met Glu His Leu Leu Asn Met Lys
465 470 475 480

Cys Lys Asn Val Val Pro Val Tyr Asp Leu Leu Leu Glu Met Leu Asn
485 490 495

Ala His Val Leu Arg Gly Cys Lys Ser Ser Ile Thr Gly Ser Glu Cys
500 505 510

Ser Pro Ala Glu Asp Ser Lys Ser Lys Glu Gly Ser Gln Asn Pro Gln
515 520 525

Ser Gln
530

<210> SEQ ID NO 70
<211> LENGTH: 920
<212> TYPE: PRT
<213> ORGANISM: Homo sapiens

<400> SEQUENCE: 70

Met Glu Val Gln Leu Gly Leu Gly Arg Val Tyr Pro Arg Pro Pro Ser
1 5 10 15

Lys Thr Tyr Arg Gly Ala Phe Gln Asn Leu Phe Gln Ser Val Arg Glu
20 25 30

Val Ile Gln Asn Pro Gly Pro Arg His Pro Glu Ala Ala Ser Ala Ala
35 40 45

Pro Pro Gly Ala Ser Leu Leu Leu Leu Gln Gln Gln Gln Gln Gln Gln
50 55 60

Gln Gln Gln Gln Gln Gln Gln Gln Gln Gln Gln Gln Gln Gln Gln Gln
65 70 75 80

Glu Thr Ser Pro Arg Gln Gln Gln Gln Gln Gln Gly Glu Asp Gly Ser
85 90 95

Pro Gln Ala His Arg Arg Gly Pro Thr Gly Tyr Leu Val Leu Asp Glu
100 105 110

Glu Gln Gln Pro Ser Gln Pro Gln Ser Ala Leu Glu Cys His Pro Glu
115 120 125

Arg Gly Cys Val Pro Glu Pro Gly Ala Ala Val Ala Ala Ser Lys Gly
130 135 140

Leu Pro Gln Gln Leu Pro Ala Pro Pro Asp Glu Asp Asp Ser Ala Ala
145 150 155 160

Pro Ser Thr Leu Ser Leu Leu Gly Pro Thr Phe Pro Gly Leu Ser Ser
165 170 175

Cys Ser Ala Asp Leu Lys Asp Ile Leu Ser Glu Ala Ser Thr Met Gln
180 185 190

Leu Leu Gln Gln Gln Gln Gln Glu Ala Val Ser Glu Gly Ser Ser Ser
195 200 205

Gly Arg Ala Arg Glu Ala Ser Gly Ala Pro Thr Ser Ser Lys Asp Asn
210 215 220

Tyr Leu Gly Gly Thr Ser Thr Ile Ser Asp Asn Ala Lys Glu Leu Cys
225 230 235 240

Lys Ala Val Ser Val Ser Met Gly Leu Gly Val Glu Ala Leu Glu His
245 250 255

Leu Ser Pro Gly Glu Gln Leu Arg Gly Asp Cys Met Tyr Ala Pro Leu
260 265 270

-continued

```
Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly Gly Gly
    450                 455                 460

Gly Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685
```

```
Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920


<210> SEQ ID NO 71
<211> LENGTH: 777
<212> TYPE: PRT
<213> ORGANISM: Homo sapiens

<400> SEQUENCE: 71

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140
```

```
Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560
```

```
Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775
```

<210> SEQ ID NO 72
<211> LENGTH: 984
<212> TYPE: PRT
<213> ORGANISM: Homo sapiens

<400> SEQUENCE: 72

```
Met Glu Thr Lys Gly Tyr His Ser Leu Pro Glu Gly Leu Asp Met Glu
1               5                   10                  15

Arg Arg Trp Gly Gln Val Ser Gln Ala Val Glu Arg Ser Ser Leu Gly
            20                  25                  30

Pro Thr Glu Arg Thr Asp Glu Asn Asn Tyr Met Glu Ile Val Asn Val
        35                  40                  45

Ser Cys Val Ser Gly Ala Ile Pro Asn Asn Ser Thr Gln Gly Ser Ser
    50                  55                  60

Lys Glu Lys Gln Glu Leu Leu Pro Cys Leu Gln Gln Asp Asn Asn Arg
65                  70                  75                  80

Pro Gly Ile Leu Thr Ser Asp Ile Lys Thr Glu Leu Glu Ser Lys Glu
                85                  90                  95

Leu Ser Ala Thr Val Ala Glu Ser Met Gly Leu Tyr Met Asp Ser Val
            100                 105                 110

Arg Asp Ala Asp Tyr Ser Tyr Glu Gln Gln Asn Gln Gln Gly Ser Met
        115                 120                 125

Ser Pro Ala Lys Ile Tyr Gln Asn Val Glu Gln Leu Val Lys Phe Tyr
    130                 135                 140

Lys Gly Asn Gly His Arg Pro Ser Thr Leu Ser Cys Val Asn Thr Pro
145                 150                 155                 160
```

-continued

```
Leu Arg Ser Phe Met Ser Asp Ser Gly Ser Ser Val Asn Gly Gly Val
                165                 170                 175

Met Arg Ala Ile Val Lys Ser Pro Ile Met Cys His Glu Lys Ser Pro
            180                 185                 190

Ser Val Cys Ser Pro Leu Asn Met Thr Ser Ser Val Cys Ser Pro Ala
        195                 200                 205

Gly Ile Asn Ser Val Ser Ser Thr Thr Ala Ser Phe Gly Ser Phe Pro
    210                 215                 220

Val His Ser Pro Ile Thr Gln Gly Thr Pro Leu Thr Cys Ser Pro Asn
225                 230                 235                 240

Ala Glu Asn Arg Gly Ser Arg Ser His Ser Pro Ala His Ala Ser Asn
                245                 250                 255

Val Gly Ser Pro Leu Ser Ser Pro Leu Ser Ser Met Lys Ser Ser Ile
            260                 265                 270

Ser Ser Pro Pro Ser His Cys Ser Val Lys Ser Pro Val Ser Ser Pro
        275                 280                 285

Asn Asn Val Thr Leu Arg Ser Ser Val Ser Ser Pro Ala Asn Ile Asn
    290                 295                 300

Asn Ser Arg Cys Ser Val Ser Ser Pro Ser Asn Thr Asn Asn Arg Ser
305                 310                 315                 320

Thr Leu Ser Ser Pro Ala Ala Ser Thr Val Gly Ser Ile Cys Ser Pro
                325                 330                 335

Val Asn Asn Ala Phe Ser Tyr Thr Ala Ser Gly Thr Ser Ala Gly Ser
            340                 345                 350

Ser Thr Leu Arg Asp Val Val Pro Ser Pro Asp Thr Gln Glu Lys Gly
        355                 360                 365

Ala Gln Glu Val Pro Phe Pro Lys Thr Glu Glu Val Glu Ser Ala Ile
    370                 375                 380

Ser Asn Gly Val Thr Gly Gln Leu Asn Ile Val Gln Tyr Ile Lys Pro
385                 390                 395                 400

Glu Pro Asp Gly Ala Phe Ser Ser Ser Cys Leu Gly Gly Asn Ser Lys
                405                 410                 415

Ile Asn Ser Asp Ser Ser Phe Ser Val Pro Ile Lys Gln Glu Ser Thr
            420                 425                 430

Lys His Ser Cys Ser Gly Thr Ser Phe Lys Gly Asn Pro Thr Val Asn
        435                 440                 445

Pro Phe Pro Phe Met Asp Gly Ser Tyr Phe Ser Phe Met Asp Asp Lys
    450                 455                 460

Asp Tyr Tyr Ser Leu Ser Gly Ile Leu Gly Pro Pro Val Pro Gly Phe
465                 470                 475                 480

Asp Gly Asn Cys Glu Gly Ser Gly Phe Pro Val Gly Ile Lys Gln Glu
                485                 490                 495

Pro Asp Asp Gly Ser Tyr Tyr Pro Glu Ala Ser Ile Pro Ser Ser Ala
            500                 505                 510

Ile Val Gly Val Asn Ser Gly Gly Gln Ser Phe His Tyr Arg Ile Gly
        515                 520                 525

Ala Gln Gly Thr Ile Ser Leu Ser Arg Ser Ala Arg Asp Gln Ser Phe
    530                 535                 540

Gln His Leu Ser Ser Phe Pro Pro Val Asn Thr Leu Val Glu Ser Trp
545                 550                 555                 560

Lys Ser His Gly Asp Leu Ser Ser Arg Arg Ser Asp Gly Tyr Pro Val
                565                 570                 575
```

-continued

```
Leu Glu Tyr Ile Pro Glu Asn Val Ser Ser Ser Thr Leu Arg Ser Val
            580                 585                 590

Ser Thr Gly Ser Ser Arg Pro Ser Lys Ile Cys Leu Val Cys Gly Asp
        595                 600                 605

Glu Ala Ser Gly Cys His Tyr Gly Val Val Thr Cys Gly Ser Cys Lys
    610                 615                 620

Val Phe Phe Lys Arg Ala Val Glu Gly Gln His Asn Tyr Leu Cys Ala
625                 630                 635                 640

Gly Arg Asn Asp Cys Ile Ile Asp Lys Ile Arg Arg Lys Asn Cys Pro
                645                 650                 655

Ala Cys Arg Leu Gln Lys Cys Leu Gln Ala Gly Met Asn Leu Gly Ala
            660                 665                 670

Arg Lys Ser Lys Lys Leu Gly Lys Leu Lys Gly Ile His Glu Glu Gln
        675                 680                 685

Pro Gln Gln Gln Gln Pro Pro Pro Pro Pro Pro Pro Pro Gln Ser Pro
    690                 695                 700

Glu Glu Gly Thr Thr Tyr Ile Ala Pro Ala Lys Glu Pro Ser Val Asn
705                 710                 715                 720

Thr Ala Leu Val Pro Gln Leu Ser Thr Ile Ser Arg Ala Leu Thr Pro
                725                 730                 735

Ser Pro Val Met Val Leu Glu Asn Ile Glu Pro Glu Ile Val Tyr Ala
            740                 745                 750

Gly Tyr Asp Ser Ser Lys Pro Asp Thr Ala Glu Asn Leu Leu Ser Thr
        755                 760                 765

Leu Asn Arg Leu Ala Gly Lys Gln Met Ile Gln Val Val Lys Trp Ala
    770                 775                 780

Lys Val Leu Pro Gly Phe Lys Asn Leu Pro Leu Glu Asp Gln Ile Thr
785                 790                 795                 800

Leu Ile Gln Tyr Ser Trp Met Cys Leu Ser Ser Phe Ala Leu Ser Trp
                805                 810                 815

Arg Ser Tyr Lys His Thr Asn Ser Gln Phe Leu Tyr Phe Ala Pro Asp
            820                 825                 830

Leu Val Phe Asn Glu Glu Lys Met His Gln Ser Ala Met Tyr Glu Leu
        835                 840                 845

Cys Gln Gly Met His Gln Ile Ser Leu Gln Phe Val Arg Leu Gln Leu
    850                 855                 860

Thr Phe Glu Glu Tyr Thr Ile Met Lys Val Leu Leu Leu Leu Ser Thr
865                 870                 875                 880

Ile Pro Lys Asp Gly Leu Lys Ser Gln Ala Ala Phe Glu Glu Met Arg
                885                 890                 895

Thr Asn Tyr Ile Lys Glu Leu Arg Lys Met Val Thr Lys Cys Pro Asn
            900                 905                 910

Asn Ser Gly Gln Ser Trp Gln Arg Phe Tyr Gln Leu Thr Lys Leu Leu
        915                 920                 925

Asp Ser Met His Asp Leu Val Ser Asp Leu Leu Glu Phe Cys Phe Tyr
    930                 935                 940

Thr Phe Arg Glu Ser His Ala Leu Lys Val Glu Phe Pro Ala Met Leu
945                 950                 955                 960

Val Glu Ile Ile Ser Asp Gln Leu Pro Lys Val Glu Ser Gly Asn Ala
                965                 970                 975

Lys Pro Leu Tyr Phe His Arg Lys
            980
```

<210> SEQ ID NO 73
<211> LENGTH: 933
<212> TYPE: PRT
<213> ORGANISM: Homo sapiens

<400> SEQUENCE: 73

```
Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Gly Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Val
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380
```

-continued

```
Leu Lys Ile Lys Glu Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
        435                 440                 445

Ser Ser Ala Ser Ser Ser Gly Ser Thr Leu Glu Cys Ile Leu Tyr Lys
    450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
        515                 520                 525

Val Leu Lys Glu Gly Leu Pro Gln Val Tyr Pro Pro Tyr Leu Asn Tyr
    530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
        595                 600                 605

Cys Ile Val Asp Lys Ile Arg Arg Lys Asn Cys Pro Ala Cys Arg Leu
    610                 615                 620

Arg Lys Cys Cys Gln Ala Gly Met Val Leu Gly Gly Arg Lys Phe Lys
625                 630                 635                 640

Lys Phe Asn Lys Val Arg Val Val Arg Ala Leu Asp Ala Val Ala Leu
                645                 650                 655

Pro Gln Pro Val Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
        675                 680                 685

Asn Leu Leu Met Ser Ile Glu Pro Asp Val Ile Tyr Ala Gly His Asp
    690                 695                 700

Asn Thr Lys Pro Asp Thr Ser Ser Ser Leu Leu Thr Ser Leu Asn Gln
705                 710                 715                 720

Leu Gly Glu Arg Gln Leu Leu Ser Val Val Lys Trp Ser Lys Ser Leu
                725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
        755                 760                 765

Lys His Val Ser Gly Gln Met Leu Tyr Phe Ala Pro Asp Leu Ile Leu
    770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
```

```
                805                 810                 815

Glu Phe Leu Cys Met Lys Val Leu Leu Leu Leu Asn Thr Ile Pro Leu
            820                 825                 830

Glu Gly Leu Arg Ser Gln Thr Gln Phe Glu Glu Met Arg Ser Ser Tyr
        835                 840                 845

Ile Arg Glu Leu Ile Lys Ala Ile Gly Leu Arg Gln Lys Gly Val Val
    850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
    930


<210> SEQ ID NO 74
<211> LENGTH: 599
<212> TYPE: PRT
<213> ORGANISM: Mus musculus

<400> SEQUENCE: 74

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Ala Phe Ser Ala Asn
                85                  90                  95

Ser Leu Gly Ala Phe Pro Gln Leu Asn Ser Val Ser Pro Ser Pro Leu
            100                 105                 110

Met Leu Leu His Pro Pro Pro Gln Leu Ser Pro Phe Leu His Pro His
        115                 120                 125

Gly Gln Gln Val Pro Tyr Tyr Leu Glu Asn Glu Pro Ser Ala Tyr Ala
    130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Ser Asn Glu Lys Gly
                165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
        195                 200                 205

Cys Lys Ala Phe Phe Lys Arg Ser Ile Gln Gly His Asn Asp Tyr Met
    210                 215                 220

Cys Pro Ala Thr Asn Gln Cys Thr Ile Asp Lys Asn Arg Arg Lys Ser
225                 230                 235                 240
```

```
Cys Gln Ala Cys Arg Leu Arg Lys Cys Tyr Glu Val Gly Met Met Lys
                245                 250                 255

Gly Gly Ile Arg Lys Asp Arg Arg Gly Gly Arg Met Leu Lys His Lys
            260                 265                 270

Arg Gln Arg Asp Asp Leu Glu Gly Arg Asn Glu Met Gly Ala Ser Gly
        275                 280                 285

Asp Met Arg Ala Ala Asn Leu Trp Pro Ser Pro Leu Val Ile Lys His
    290                 295                 300

Thr Lys Lys Asn Ser Pro Ala Leu Ser Leu Thr Ala Asp Gln Met Val
305                 310                 315                 320

Ser Ala Leu Leu Asp Ala Glu Pro Pro Met Ile Tyr Ser Glu Tyr Asp
                325                 330                 335

Pro Ser Arg Pro Phe Ser Glu Ala Ser Met Met Gly Leu Leu Thr Asn
            340                 345                 350

Leu Ala Asp Arg Glu Leu Val His Met Ile Asn Trp Ala Lys Arg Val
        355                 360                 365

Pro Gly Phe Gly Asp Leu Asn Leu His Asp Gln Val His Leu Leu Glu
    370                 375                 380

Cys Ala Trp Leu Glu Ile Leu Met Ile Gly Leu Val Trp Arg Ser Met
385                 390                 395                 400

Glu His Pro Gly Lys Leu Leu Phe Ala Pro Asn Leu Leu Leu Asp Arg
                405                 410                 415

Asn Gln Gly Lys Cys Val Glu Gly Met Val Glu Ile Phe Asp Met Leu
            420                 425                 430

Leu Ala Thr Ser Ser Arg Phe Arg Met Met Asn Leu Gln Gly Glu Glu
        435                 440                 445

Phe Val Cys Leu Lys Ser Ile Ile Leu Leu Asn Ser Gly Val Tyr Thr
    450                 455                 460

Phe Leu Ser Ser Thr Leu Lys Ser Leu Glu Glu Lys Asp His Ile His
465                 470                 475                 480

Arg Val Leu Asp Lys Ile Thr Asp Thr Leu Ile His Leu Met Ala Lys
                485                 490                 495

Ala Gly Leu Thr Leu Gln Gln Gln His Arg Arg Leu Ala Gln Leu Leu
            500                 505                 510

Leu Ile Leu Ser His Ile Arg His Met Ser Asn Lys Gly Met Glu His
        515                 520                 525

Leu Tyr Asn Met Lys Cys Lys Asn Val Val Pro Leu Tyr Asp Leu Leu
    530                 535                 540

Leu Glu Met Leu Asp Ala His Arg Leu His Ala Pro Ala Ser Arg Met
545                 550                 555                 560

Gly Val Pro Pro Glu Glu Pro Ser Gln Thr Gln Leu Ala Thr Thr Ser
                565                 570                 575

Ser Thr Ser Ala His Ser Leu Gln Thr Tyr Tyr Ile Pro Pro Glu Ala
            580                 585                 590

Glu Gly Phe Pro Asn Thr Ile
        595


<210> SEQ ID NO 75
<211> LENGTH: 530
<212> TYPE: PRT
<213> ORGANISM: Mus musculus

<400> SEQUENCE: 75

Met Glu Ile Lys Asn Ser Pro Ser Ser Leu Thr Ser Pro Ala Ser Tyr
1               5                   10                  15
```

```
Asn Cys Ser Gln Ser Ile Leu Pro Leu Glu His Gly Pro Ile Tyr Ile
            20                  25                  30

Pro Ser Ser Tyr Val Glu Ser Arg His Glu Tyr Ser Ala Met Thr Phe
        35                  40                  45

Tyr Ser Pro Ala Val Met Asn Tyr Ser Val Pro Ser Ser Thr Gly Asn
    50                  55                  60

Leu Glu Gly Gly Pro Val Arg Gln Thr Ala Ser Pro Asn Val Leu Trp
65                  70                  75                  80

Pro Thr Ser Gly His Leu Ser Pro Leu Ala Thr His Cys Gln Ser Ser
                85                  90                  95

Leu Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Leu
        115                 120                 125

Gly Gly Ser Gly Cys Ala Ser Pro Val Thr Ser Pro Ser Ala Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Ile Val Arg Arg Gln Arg Ser Ala Ser Glu Gln Val His
225                 230                 235                 240

Cys Leu Asn Lys Ala Lys Arg Thr Ser Gly His Thr Pro Arg Val Lys
                245                 250                 255

Glu Leu Leu Leu Asn Ser Leu Ser Pro Glu Gln Leu Val Leu Thr Leu
            260                 265                 270

Leu Glu Ala Glu Pro Pro Asn Val Leu Val Ser Arg Pro Ser Met Pro
        275                 280                 285

Phe Thr Glu Ala Ser Met Met Met Ser Leu Thr Lys Leu Ala Asp Lys
    290                 295                 300

Glu Leu Val His Met Ile Gly Trp Ala Lys Lys Ile Pro Gly Phe Val
305                 310                 315                 320

Glu Leu Ser Leu Leu Asp Gln Val Arg Leu Leu Glu Ser Cys Trp Met
                325                 330                 335

Glu Val Leu Met Val Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ala Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Ala Thr Ala
                405                 410                 415

Ser Gln Glu Ala Glu Ser Ser Arg Lys Leu Thr His Leu Leu Asn Ala
            420                 425                 430
```

```
Val Thr Asp Ala Leu Val Trp Val Ile Ser Lys Ser Gly Ile Ser Ser
        435                 440                 445

Gln Gln Gln Ser Val Arg Leu Ala Asn Leu Leu Met Leu Leu Ser His
    450                 455                 460

Val Arg His Ile Ser Asn Lys Gly Met Glu His Leu Leu Ser Met Lys
465                 470                 475                 480

Cys Lys Asn Val Val Pro Val Tyr Asp Leu Leu Leu Glu Met Leu Asn
                485                 490                 495

Ala His Thr Leu Arg Gly Tyr Lys Ser Ser Ile Ser Gly Ser Glu Cys
            500                 505                 510

Cys Ser Thr Glu Asp Ser Lys Ser Lys Glu Gly Ser Gln Asn Leu Gln
        515                 520                 525

Ser Gln
    530


<210> SEQ ID NO 76
<211> LENGTH: 923
<212> TYPE: PRT
<213> ORGANISM: Mus musculus

<400> SEQUENCE: 76

Met Thr Glu Leu Gln Ala Lys Asp Pro Gln Val Leu His Thr Ser Gly
1               5                   10                  15

Ala Ser Pro Ser Pro Pro His Ile Gly Ser Pro Leu Leu Ala Arg Leu
            20                  25                  30

Asp Ser Gly Pro Phe Gln Gly Ser Gln His Ser Asp Val Ser Ser Val
        35                  40                  45

Val Ser Pro Ile Pro Ile Ser Leu Asp Gly Leu Leu Phe Pro Arg Ser
    50                  55                  60

Cys Arg Gly Pro Glu Leu Pro Asp Gly Lys Thr Gly Asp Gln Gln Ser
65                  70                  75                  80

Leu Ser Asp Val Glu Gly Ala Phe Ser Gly Val Glu Ala Thr His Arg
                85                  90                  95

Glu Gly Gly Arg Asn Ser Arg Pro Pro Glu Lys Asp Ser Arg Leu Leu
            100                 105                 110

Asp Ser Val Leu Asp Ser Leu Leu Thr Pro Ser Gly Pro Glu Gln Ser
        115                 120                 125

His Ala Ser Pro Pro Ala Cys Glu Ala Ile Thr Ser Trp Cys Leu Phe
    130                 135                 140

Gly Pro Glu Leu Pro Glu Asp Pro Arg Ser Val Pro Ala Thr Lys Gly
145                 150                 155                 160

Leu Leu Ser Pro Leu Met Ser Arg Pro Glu Ile Lys Val Gly Asp Gln
                165                 170                 175

Ser Gly Thr Gly Arg Gly Gln Lys Val Leu Pro Lys Gly Leu Ser Pro
            180                 185                 190

Pro Arg Gln Leu Leu Leu Pro Thr Ser Gly Ser Ala His Trp Pro Gly
        195                 200                 205

Ala Gly Val Lys Pro Ser Pro Gln Pro Ala Ala Gly Glu Val Glu Glu
    210                 215                 220

Asp Ser Gly Leu Glu Thr Glu Gly Ser Ala Ser Pro Leu Leu Lys Ser
225                 230                 235                 240

Lys Pro Arg Ala Leu Glu Gly Thr Gly Gln Gly Gly Gly Val Ala Ala
                245                 250                 255

Asn Ala Pro Ser Ala Ala Pro Gly Gly Val Thr Leu Val Pro Lys Glu
            260                 265                 270
```

-continued

```
Asp Ser Arg Phe Ser Ala Pro Arg Val Ser Leu Glu Gln Asp Ser Pro
        275                 280                 285

Ile Ala Pro Gly Arg Ser Pro Leu Ala Thr Thr Val Val Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Gly Glu Ser Tyr Asp Gly Gly Ala Thr Ala Gly
                325                 330                 335

Pro Phe Cys Pro Pro Arg Ser Pro Ser Ala Pro Ser Thr Pro Val Pro
            340                 345                 350

Arg Gly Asp Phe Pro Asp Cys Thr Tyr Pro Leu Glu Gly Asp Pro Lys
        355                 360                 365

Glu Asp Val Phe Pro Leu Tyr Gly Asp Phe Gln Thr Pro Gly Leu Lys
    370                 375                 380

Ile Lys Glu Glu Glu Glu Gly Ala Asp Ala Ala Val Arg Ser Pro Arg
385                 390                 395                 400

Pro Tyr Leu Ser Ala Gly Ala Ser Ser Ser Thr Phe Pro Asp Phe Pro
                405                 410                 415

Leu Ala Pro Ala Pro Gln Ala Ala Pro Ser Ser Arg Pro Gly Glu Ala
            420                 425                 430

Ala Val Ala Gly Gly Pro Ser Ser Ala Ala Val Ser Pro Ala Ser Ser
        435                 440                 445

Ser Gly Ser Ala Leu Glu Cys Ile Leu Tyr Lys Ala Glu Ala Pro Pro
    450                 455                 460

Thr Gln Gly Ser Phe Ala Pro Leu Pro Cys Lys Pro Pro Ala Ala Ala
465                 470                 475                 480

Ser Cys Leu Leu Pro Arg Asp Ser Leu Pro Ala Ala Pro Gly Thr Ala
                485                 490                 495

Ala Ala Pro Ala Ile Tyr Gln Pro Leu Gly Leu Asn Gly Leu Pro Gln
            500                 505                 510

Leu Gly Tyr Gln Ala Ala Val Leu Lys Asp Ser Leu Pro Gln Val Tyr
        515                 520                 525

Pro Pro Tyr Leu Asn Tyr Leu Arg Pro Asp Ser Glu Ala Ser Gln Ser
    530                 535                 540

Pro Gln Tyr Gly Phe Asp Ser Leu Pro Gln Lys Ile Cys Leu Ile Cys
545                 550                 555                 560

Gly Asp Glu Ala Ser Gly Cys His Tyr Gly Val Leu Thr Cys Gly Ser
                565                 570                 575

Cys Lys Val Phe Phe Lys Arg Ala Met Glu Gly Gln His Asn Tyr Leu
            580                 585                 590

Cys Ala Gly Arg Asn Asp Cys Ile Val Asp Lys Ile Arg Arg Lys Asn
        595                 600                 605

Cys Pro Ala Cys Arg Leu Arg Lys Cys Cys Gln Ala Gly Met Val Leu
    610                 615                 620

Gly Gly Arg Lys Phe Lys Lys Phe Asn Lys Val Arg Val Met Arg Thr
625                 630                 635                 640

Leu Asp Gly Val Ala Leu Pro Gln Ser Val Gly Leu Pro Asn Glu Ser
                645                 650                 655

Gln Ala Leu Ser Gln Arg Ile Thr Phe Ser Pro Asn Gln Glu Ile Gln
            660                 665                 670

Leu Val Pro Pro Leu Ile Asn Leu Leu Met Ser Ile Glu Pro Asp Val
        675                 680                 685
```

-continued

```
Ile Tyr Ala Gly His Asp Asn Thr Lys Pro Asp Thr Ser Ser Ser Leu
    690                 695                 700

Leu Thr Ser Leu Asn Gln Leu Gly Glu Arg Gln Leu Leu Ser Val Val
705                 710                 715                 720

Lys Trp Ser Lys Ser Leu Pro Gly Phe Arg Asn Leu His Ile Asp Asp
                725                 730                 735

Gln Ile Thr Leu Ile Gln Tyr Ser Trp Met Ser Leu Met Val Phe Gly
            740                 745                 750

Leu Gly Trp Arg Ser Tyr Lys His Val Ser Gly Gln Met Leu Tyr Phe
        755                 760                 765

Ala Pro Asp Leu Ile Leu Asn Glu Gln Arg Met Lys Glu Leu Ser Phe
    770                 775                 780

Tyr Ser Leu Cys Leu Thr Met Trp Gln Ile Pro Gln Glu Phe Val Lys
785                 790                 795                 800

Leu Gln Val Thr His Glu Glu Phe Leu Cys Met Lys Val Leu Leu Leu
                805                 810                 815

Leu Asn Thr Ile Pro Leu Glu Gly Leu Arg Ser Gln Ser Gln Phe Glu
            820                 825                 830

Glu Met Arg Ser Ser Tyr Ile Arg Glu Leu Ile Lys Ala Ile Gly Leu
        835                 840                 845

Arg Gln Lys Gly Val Val Pro Thr Ser Gln Arg Phe Tyr Gln Leu Thr
    850                 855                 860

Lys Leu Leu Asp Ser Leu His Asp Leu Val Lys Gln Leu His Leu Tyr
865                 870                 875                 880

Cys Leu Asn Thr Phe Ile Gln Ser Arg Thr Leu Ala Val Glu Phe Pro
                885                 890                 895

Glu Met Met Ser Glu Val Ile Ala Ala Gln Leu Pro Lys Ile Leu Ala
            900                 905                 910

Gly Met Val Lys Pro Leu Leu Phe His Lys Lys
        915                 920


<210> SEQ ID NO 77
<211> LENGTH: 783
<212> TYPE: PRT
<213> ORGANISM: Mus musculus

<400> SEQUENCE: 77

Met Asp Ser Lys Glu Ser Leu Ala Pro Pro Gly Arg Asp Glu Val Pro
1               5                   10                  15

Ser Ser Leu Leu Gly Arg Gly Arg Gly Ser Val Met Asp Leu Tyr Lys
            20                  25                  30

Thr Leu Arg Gly Gly Ala Thr Val Lys Val Ser Ala Ser Ser Pro Ser
        35                  40                  45

Val Ala Ala Ala Ser Gln Ala Asp Ser Lys Gln Gln Arg Ile Leu Leu
    50                  55                  60

Asp Phe Ser Lys Gly Ser Ala Ser Asn Ala Gln Gln Gln Gln Gln Gln
65                  70                  75                  80

Gln Gln Pro Gln Pro Asp Leu Ser Lys Ala Val Ser Leu Ser Met Gly
                85                  90                  95

Leu Tyr Met Gly Glu Thr Glu Thr Lys Val Met Gly Asn Asp Leu Gly
            100                 105                 110

Tyr Pro Gln Gln Gly Gln Leu Gly Leu Ser Ser Gly Glu Thr Asp Phe
        115                 120                 125

Arg Leu Leu Glu Glu Ser Ile Ala Asn Leu Asn Arg Ser Thr Ser Arg
    130                 135                 140
```

```
Pro Glu Asn Pro Lys Ser Ser Thr Pro Ala Ala Gly Cys Ala Thr Pro
145                 150                 155                 160

Thr Glu Lys Glu Phe Pro Gln Thr His Ser Asp Pro Ser Ser Glu Gln
                165                 170                 175

Gln Asn Arg Lys Ser Gln Pro Gly Thr Asn Gly Gly Ser Val Lys Leu
            180                 185                 190

Tyr Thr Thr Asp Gln Ser Thr Phe Asp Ile Leu Gln Asp Leu Glu Phe
        195                 200                 205

Ser Ala Gly Ser Pro Gly Lys Glu Thr Asn Glu Ser Pro Trp Arg Ser
    210                 215                 220

Asp Leu Leu Ile Asp Glu Asn Leu Leu Ser Pro Leu Ala Gly Glu Asp
225                 230                 235                 240

Asp Pro Phe Leu Leu Glu Gly Asp Val Asn Glu Asp Cys Lys Pro Leu
                245                 250                 255

Ile Leu Pro Asp Thr Lys Pro Lys Ile Gln Asp Thr Gly Asp Thr Ile
            260                 265                 270

Leu Ser Ser Pro Ser Ser Val Ala Leu Pro Gln Val Lys Thr Glu Lys
        275                 280                 285

Asp Asp Phe Ile Glu Leu Cys Thr Pro Gly Val Ile Lys Gln Glu Lys
    290                 295                 300

Leu Gly Pro Val Tyr Cys Gln Ala Ser Phe Ser Gly Thr Asn Ile Ile
305                 310                 315                 320

Gly Asn Lys Met Ser Ala Ile Ser Val His Gly Val Ser Thr Ser Gly
                325                 330                 335

Gly Gln Met Tyr His Tyr Asp Met Asn Thr Ala Ser Leu Ser Gln Gln
            340                 345                 350

Gln Asp Gln Lys Pro Val Phe Asn Val Ile Pro Pro Ile Pro Val Gly
        355                 360                 365

Ser Glu Asn Trp Asn Arg Cys Gln Gly Ser Gly Glu Asp Asn Leu Thr
    370                 375                 380

Ser Leu Gly Ala Met Asn Phe Ala Gly Arg Ser Val Phe Ser Asn Gly
385                 390                 395                 400

Tyr Ser Ser Pro Gly Met Arg Pro Asp Val Ser Ser Pro Pro Ser Ser
                405                 410                 415

Ser Ser Thr Ala Thr Gly Pro Pro Pro Lys Leu Cys Leu Val Cys Ser
            420                 425                 430

Asp Glu Ala Ser Val Cys His Tyr Gly Val Leu Thr Cys Gly Ser Cys
        435                 440                 445

Lys Val Phe Phe Lys Arg Ala Val Glu Gly Gln His Asn Tyr Leu Cys
    450                 455                 460

Ala Gly Arg Asn Asp Cys Ile Ile Asp Lys Ile Arg Arg Lys Asn Cys
465                 470                 475                 480

Pro Ala Cys Arg Tyr Arg Lys Cys Leu Gln Ala Gly Met Asn Leu Glu
                485                 490                 495

Ala Arg Lys Thr Lys Lys Lys Ile Lys Gly Ile Gln Gln Ala Thr Ala
            500                 505                 510

Gly Val Ser Gln Asp Thr Ser Glu Asn Ala Asn Lys Thr Ile Val Pro
        515                 520                 525

Ala Ala Leu Pro Gln Leu Thr Pro Thr Leu Val Ser Leu Leu Glu Val
    530                 535                 540

Ile Glu Pro Glu Val Leu Tyr Ala Gly Tyr Asp Ser Ser Val Pro Asp
545                 550                 555                 560
```

-continued

```
Ser Ala Trp Arg Ile Met Thr Thr Leu Asn Met Leu Gly Gly Arg Gln
            565                 570                 575

Val Ile Ala Ala Val Lys Trp Ala Lys Ala Ile Pro Gly Phe Arg Asn
            580                 585                 590

Leu His Leu Asp Asp Gln Met Thr Leu Leu Gln Tyr Ser Trp Met Phe
        595                 600                 605

Leu Met Ala Phe Ala Leu Gly Trp Arg Ser Tyr Arg Gln Ala Ser Gly
    610                 615                 620

Asn Leu Leu Cys Phe Ala Pro Asp Leu Ile Ile Asn Glu Gln Arg Met
625                 630                 635                 640

Thr Leu Pro Cys Met Tyr Asp Gln Cys Lys His Met Leu Phe Ile Ser
            645                 650                 655

Thr Glu Leu Gln Arg Leu Gln Val Ser Tyr Glu Glu Tyr Leu Cys Met
            660                 665                 670

Lys Thr Leu Leu Leu Leu Ser Ser Val Pro Lys Glu Gly Leu Lys Ser
        675                 680                 685

Gln Glu Leu Phe Asp Glu Ile Arg Met Thr Tyr Ile Lys Glu Leu Gly
    690                 695                 700

Lys Ala Ile Val Lys Arg Glu Gly Asn Ser Ser Gln Asn Trp Gln Arg
705                 710                 715                 720

Phe Tyr Gln Leu Thr Lys Leu Leu Asp Ser Met His Asp Val Val Glu
            725                 730                 735

Asn Leu Leu Ser Tyr Cys Phe Gln Thr Phe Leu Asp Lys Ser Met Ser
            740                 745                 750

Ile Glu Phe Pro Glu Met Leu Ala Glu Ile Ile Thr Asn Gln Ile Pro
        755                 760                 765

Lys Tyr Ser Asn Gly Asn Ile Lys Lys Leu Leu Phe His Gln Lys
    770                 775                 780


<210> SEQ ID NO 78
<211> LENGTH: 899
<212> TYPE: PRT
<213> ORGANISM: Mus musculus

<400> SEQUENCE: 78

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65                  70                  75                  80

Arg Gly Pro Thr Gly Tyr Leu Ala Leu Glu Glu Glu Gln Gln Pro Ser
            85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160
```

Lys Asp Ile Leu Asn Glu Ala Gly Thr Met Gln Leu Leu Gln Gln Gln
165 170 175

Gln Gln Gln Gln Gln His Gln Gln Gln His Gln Gln His Gln Gln Gln
180 185 190

Gln Glu Val Ile Ser Glu Gly Ser Ser Ala Arg Ala Arg Glu Ala Thr
195 200 205

Gly Ala Pro Ser Ser Ser Lys Asp Ser Tyr Leu Gly Gly Asn Ser Thr
210 215 220

Ile Ser Asp Ser Ala Lys Glu Leu Cys Lys Ala Val Ser Val Ser Met
225 230 235 240

Gly Leu Gly Val Glu Ala Leu Glu His Leu Ser Pro Gly Glu Gln Leu
245 250 255

Arg Gly Asp Cys Met Tyr Ala Ser Leu Leu Gly Gly Pro Pro Ala Val
260 265 270

Arg Pro Thr Pro Cys Ala Pro Leu Pro Glu Cys Lys Gly Leu Pro Leu
275 280 285

Asp Glu Gly Pro Gly Lys Ser Thr Glu Glu Thr Ala Glu Tyr Ser Ser
290 295 300

Phe Lys Gly Gly Tyr Ala Lys Gly Leu Glu Gly Glu Ser Leu Gly Cys
305 310 315 320

Ser Gly Ser Ser Glu Ala Gly Ser Ser Gly Thr Leu Glu Ile Pro Ser
325 330 335

Ser Leu Ser Leu Tyr Lys Ser Gly Ala Leu Asp Glu Ala Ala Ala Tyr
340 345 350

Gln Asn Arg Asp Tyr Tyr Asn Phe Pro Leu Ala Leu Ser Gly Pro Pro
355 360 365

His Pro Pro Pro Pro Thr His Pro His Ala Arg Ile Lys Leu Glu Asn
370 375 380

Pro Leu Asp Tyr Gly Ser Ala Trp Ala Ala Ala Ala Ala Gln Cys Arg
385 390 395 400

Tyr Gly Asp Leu Gly Ser Leu His Gly Gly Ser Val Ala Gly Pro Ser
405 410 415

Thr Gly Ser Pro Pro Ala Thr Thr Ser Ser Ser Trp His Thr Leu Phe
420 425 430

Thr Ala Glu Glu Gly Gln Leu Tyr Gly Pro Gly Gly Gly Gly Gly Ser
435 440 445

Ser Ser Pro Ser Asp Ala Gly Pro Val Ala Pro Tyr Gly Tyr Thr Arg
450 455 460

Pro Pro Gln Gly Leu Thr Ser Gln Glu Ser Asp Tyr Ser Ala Ser Glu
465 470 475 480

Val Trp Tyr Pro Gly Gly Val Val Asn Arg Val Pro Tyr Pro Ser Pro
485 490 495

Asn Cys Val Lys Ser Glu Met Gly Pro Trp Met Glu Asn Tyr Ser Gly
500 505 510

Pro Tyr Gly Asp Met Arg Leu Asp Ser Thr Arg Asp His Val Leu Pro
515 520 525

Ile Asp Tyr Tyr Phe Pro Pro Gln Lys Thr Cys Leu Ile Cys Gly Asp
530 535 540

Glu Ala Ser Gly Cys His Tyr Gly Ala Leu Thr Cys Gly Ser Cys Lys
545 550 555 560

Val Phe Phe Lys Arg Ala Ala Glu Gly Lys Gln Lys Tyr Leu Cys Ala
565 570 575

-continued

```
Ser Arg Asn Asp Cys Thr Ile Asp Lys Phe Arg Arg Lys Asn Cys Pro
            580                 585                 590

Ser Cys Arg Leu Arg Lys Cys Tyr Glu Ala Gly Met Thr Leu Gly Ala
        595                 600                 605

Arg Lys Leu Lys Lys Leu Gly Asn Leu Lys Leu Gln Glu Glu Gly Glu
    610                 615                 620

Asn Ser Asn Ala Gly Ser Pro Thr Glu Asp Pro Ser Gln Lys Met Thr
625                 630                 635                 640

Val Ser His Ile Glu Gly Tyr Glu Cys Gln Pro Ile Phe Leu Asn Val
                645                 650                 655

Leu Glu Ala Ile Glu Pro Gly Val Val Cys Ala Gly His Asp Asn Asn
            660                 665                 670

Gln Pro Asp Ser Phe Ala Ala Leu Leu Ser Ser Leu Asn Glu Leu Gly
        675                 680                 685

Glu Arg Gln Leu Val His Val Val Lys Trp Ala Lys Ala Leu Pro Gly
    690                 695                 700

Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
                725                 730                 735

Val Asn Ser Arg Met Leu Tyr Phe Ala Pro Asp Leu Val Phe Asn Glu
            740                 745                 750

Tyr Arg Met His Lys Ser Arg Met Tyr Ser Gln Cys Val Arg Met Arg
        755                 760                 765

His Leu Ser Gln Glu Phe Gly Trp Leu Gln Ile Thr Pro Gln Glu Phe
    770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
                805                 810                 815

Glu Leu Asp Arg Ile Ile Ala Cys Lys Arg Lys Asn Pro Thr Ser Cys
            820                 825                 830

Ser Arg Arg Phe Tyr Gln Leu Thr Lys Leu Leu Asp Ser Val Gln Pro
        835                 840                 845

Ile Ala Arg Glu Leu His Gln Phe Thr Phe Asp Leu Leu Ile Lys Ser
    850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
                885                 890                 895

His Thr Gln


<210> SEQ ID NO 79
<211> LENGTH: 933
<212> TYPE: PRT
<213> ORGANISM: Homo sapiens

<400> SEQUENCE: 79

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45
```

```
Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Ser Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Cys
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380

Leu Lys Ile Lys Glu Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
        435                 440                 445

Ser Ser Ala Ser Ser Ser Gly Ser Thr Leu Glu Cys Ile Leu Tyr Lys
    450                 455                 460

Ala Glu Gly Ala Pro Pro Gln Gln Gly Pro Phe Ala Pro Pro Pro Cys
```

-continued 465 470 475 480

Lys Ala Pro Gly Ala Ser Gly Cys Leu Leu Pro Arg Asp Gly Leu Pro
485 490 495

Ser Thr Ser Ala Ser Ala Ala Ala Ala Gly Ala Ala Pro Ala Leu Tyr
500 505 510

Pro Ala Leu Gly Leu Asn Gly Leu Pro Gln Leu Gly Tyr Gln Ala Ala
515 520 525

Val Leu Lys Glu Gly Leu Pro Gln Val Tyr Pro Pro Tyr Leu Asn Tyr
530 535 540

Leu Arg Pro Asp Ser Glu Ala Ser Gln Ser Pro Gln Tyr Ser Phe Glu
545 550 555 560

Ser Leu Pro Gln Lys Ile Cys Leu Ile Cys Gly Asp Glu Ala Ser Gly
565 570 575

Cys His Tyr Gly Val Leu Thr Cys Gly Ser Cys Lys Val Phe Phe Lys
580 585 590

Arg Ala Met Glu Gly Gln His Asn Tyr Leu Cys Ala Gly Arg Asn Asp
595 600 605

Cys Ile Val Asp Lys Ile Arg Arg Lys Asn Cys Pro Ala Cys Arg Leu
610 615 620

Arg Lys Cys Cys Gln Ala Gly Met Val Leu Gly Gly Arg Lys Phe Lys
625 630 635 640

Lys Phe Asn Lys Val Arg Val Val Arg Ala Leu Asp Ala Val Ala Leu
645 650 655

Pro Gln Pro Leu Gly Val Pro Asn Glu Ser Gln Ala Leu Ser Gln Arg
660 665 670

Phe Thr Phe Ser Pro Gly Gln Asp Ile Gln Leu Ile Pro Pro Leu Ile
675 680 685

Asn Leu Leu Met Ser Ile Glu Pro Asp Val Ile Tyr Ala Gly His Asp
690 695 700

Asn Thr Lys Pro Asp Thr Ser Ser Ser Leu Leu Thr Ser Leu Asn Gln
705 710 715 720

Leu Gly Glu Arg Gln Leu Leu Ser Val Val Lys Trp Ser Lys Ser Leu
725 730 735

Pro Gly Phe Arg Asn Leu His Ile Asp Asp Gln Ile Thr Leu Ile Gln
740 745 750

Tyr Ser Trp Met Ser Leu Met Val Phe Gly Leu Gly Trp Arg Ser Tyr
755 760 765

Lys His Val Ser Gly Gln Met Leu Tyr Phe Ala Pro Asp Leu Ile Leu
770 775 780

Asn Glu Gln Arg Met Lys Glu Ser Ser Phe Tyr Ser Leu Cys Leu Thr
785 790 795 800

Met Trp Gln Ile Pro Gln Glu Phe Val Lys Leu Gln Val Ser Gln Glu
805 810 815

Glu Phe Leu Cys Met Lys Val Leu Leu Leu Leu Asn Thr Ile Pro Leu
820 825 830

Glu Gly Leu Arg Ser Gln Thr Gln Phe Glu Glu Met Arg Ser Ser Tyr
835 840 845

Ile Arg Glu Leu Ile Lys Ala Ile Gly Leu Arg Gln Lys Gly Val Val
850 855 860

Ser Ser Ser Gln Arg Phe Tyr Gln Leu Thr Lys Leu Leu Asp Asn Leu
865 870 875 880

His Asp Leu Val Lys Gln Leu His Leu Tyr Cys Leu Asn Thr Phe Ile
885 890 895

-continued

Gln Ser Arg Ala Leu Ser Val Glu Phe Pro Glu Met Met Ser Glu Val
900 905 910

Ile Ala Ala Gln Leu Pro Lys Ile Leu Ala Gly Met Val Lys Pro Leu
915 920 925

Leu Phe His Lys Lys
930

<210> SEQ ID NO 80
<211> LENGTH: 742
<212> TYPE: PRT
<213> ORGANISM: Homo sapiens

<400> SEQUENCE: 80

Met Asp Ser Lys Glu Ser Leu Thr Pro Gly Arg Glu Glu Asn Pro Ser
1 5 10 15

Ser Val Leu Ala Gln Glu Arg Gly Asp Val Met Asp Phe Tyr Lys Thr
20 25 30

Leu Arg Gly Gly Ala Thr Val Lys Val Ser Ala Ser Ser Pro Ser Leu
35 40 45

Ala Val Ala Ser Gln Ser Asp Ser Lys Gln Arg Arg Leu Leu Val Asp
50 55 60

Phe Pro Lys Gly Ser Val Ser Asn Ala Gln Gln Pro Asp Leu Ser Lys
65 70 75 80

Ala Val Ser Leu Ser Met Gly Leu Tyr Met Gly Glu Thr Glu Thr Lys
85 90 95

Val Met Gly Asn Asp Leu Gly Phe Pro Gln Gln Gly Gln Ile Ser Leu
100 105 110

Ser Ser Gly Glu Thr Asp Leu Lys Leu Leu Glu Glu Ser Ile Ala Asn
115 120 125

Leu Asn Arg Ser Thr Ser Val Pro Glu Asn Pro Lys Ser Ser Ala Ser
130 135 140

Thr Ala Val Ser Ala Ala Pro Thr Glu Lys Glu Phe Pro Lys Thr His
145 150 155 160

Ser Asp Val Ser Ser Glu Gln Gln His Leu Lys Gly Gln Thr Gly Thr
165 170 175

Asn Gly Gly Asn Val Lys Leu Tyr Thr Thr Asp Gln Ser Thr Phe Asp
180 185 190

Ile Leu Gln Asp Leu Glu Phe Ser Ser Gly Ser Pro Gly Lys Glu Thr
195 200 205

Asn Glu Ser Pro Trp Arg Ser Asp Leu Leu Ile Asp Glu Asn Cys Leu
210 215 220

Leu Ser Pro Leu Ala Gly Glu Asp Asp Ser Phe Leu Leu Glu Gly Asn
225 230 235 240

Ser Asn Glu Asp Cys Lys Pro Leu Ile Leu Pro Asp Thr Lys Pro Lys
245 250 255

Ile Lys Asp Asn Gly Asp Leu Val Leu Ser Ser Pro Ser Asn Val Thr
260 265 270

Leu Pro Gln Val Lys Thr Glu Lys Glu Asp Phe Ile Glu Leu Cys Thr
275 280 285

Pro Gly Val Ile Lys Gln Glu Lys Leu Gly Thr Val Tyr Cys Gln Ala
290 295 300

Ser Phe Pro Gly Ala Asn Ile Ile Gly Asn Lys Met Ser Ala Ile Ser
305 310 315 320

Val His Gly Val Ser Thr Ser Gly Gly Gln Met Tyr His Tyr Asp Met

```
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Asn Val Met Trp Leu Lys Pro Glu Ser
                725                 730                 735

Thr Ser His Thr Leu Ile
            740
```

<210> SEQ ID NO 81
<211> LENGTH: 919
<212> TYPE: PRT
<213> ORGANISM: Homo sapiens

<400> SEQUENCE: 81

Met Glu Val Gln Leu Gly Leu Gly Arg Val Tyr Pro Arg Pro Pro Ser
1 5 10 15

Lys Thr Tyr Arg Gly Ala Phe Gln Asn Leu Phe Gln Ser Val Arg Glu
20 25 30

Val Ile Gln Asn Pro Gly Pro Arg His Pro Glu Ala Ala Ser Ala Ala
35 40 45

Pro Pro Gly Ala Ser Leu Leu Leu Leu Gln Gln Gln Gln Gln Gln Gln
50 55 60

Gln Gln Gln Gln Gln Gln Gln Gln Gln Gln Gln Gln Gln Gln Glu Thr
65 70 75 80

Ser Pro Arg Gln Gln Gln Gln Gln Gln Gly Glu Asp Gly Ser Pro Gln
85 90 95

Ala His Arg Arg Gly Pro Thr Gly Tyr Leu Val Leu Asp Glu Glu Gln
100 105 110

Gln Pro Ser Gln Pro Gln Ser Ala Leu Glu Cys His Pro Glu Arg Gly
115 120 125

Cys Val Pro Glu Pro Gly Ala Ala Val Ala Ala Ser Lys Gly Leu Pro
130 135 140

Gln Gln Leu Pro Ala Pro Pro Asp Glu Asp Asp Ser Ala Ala Pro Ser
145 150 155 160

Thr Leu Ser Leu Leu Gly Pro Thr Phe Pro Gly Leu Ser Ser Cys Ser
165 170 175

Ala Asp Leu Lys Asp Ile Leu Ser Glu Ala Ser Thr Met Gln Leu Leu
180 185 190

Gln Gln Gln Gln Gln Glu Ala Val Ser Glu Gly Ser Ser Ser Gly Arg
195 200 205

Ala Arg Glu Ala Ser Gly Ala Pro Thr Ser Ser Lys Asp Asn Tyr Leu
210 215 220

Gly Gly Thr Ser Thr Ile Ser Asp Asn Ala Lys Glu Leu Cys Lys Ala
225 230 235 240

Val Ser Val Ser Met Gly Leu Gly Val Glu Ala Leu Glu His Leu Ser
245 250 255

Pro Gly Glu Gln Leu Arg Gly Asp Cys Met Tyr Ala Pro Leu Leu Gly
260 265 270

Val Pro Pro Ala Val Arg Pro Thr Pro Cys Ala Pro Leu Ala Glu Cys
275 280 285

Lys Gly Ser Leu Leu Asp Asp Ser Ala Gly Lys Ser Thr Glu Asp Thr
290 295 300

Ala Glu Tyr Ser Pro Phe Lys Gly Gly Tyr Thr Lys Gly Leu Glu Gly
305 310 315 320

Glu Ser Leu Gly Cys Ser Gly Ser Ala Ala Ala Gly Ser Ser Gly Thr
325 330 335

Leu Glu Leu Pro Ser Thr Leu Ser Leu Tyr Lys Ser Gly Ala Leu Asp
340 345 350

Glu Ala Ala Ala Tyr Gln Ser Arg Asp Tyr Tyr Asn Phe Pro Leu Ala
355 360 365

Leu Ala Gly Pro Pro Pro Pro Pro Pro Pro Pro His Pro His Ala Arg

```
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
                405                 410                 415

Ala Ala Gly Pro Gly Ser Gly Ser Pro Ser Ala Ala Ala Ser Ser Ser
            420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
    530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
    770                 775                 780

Val Arg Met Arg His Leu Ser Gln Glu Phe Gly Trp Leu Gln Ile Thr
785                 790                 795                 800
```

Pro Gln Glu Phe Leu Cys Met Lys Ala Leu Leu Leu Phe Ser Ile Ile
805 810 815

Pro Val Asp Gly Leu Lys Asn Gln Lys Phe Phe Asp Glu Leu Arg Met
820 825 830

Asn Tyr Ile Lys Glu Leu Asp Arg Ile Ile Ala Cys Lys Arg Lys Asn
835 840 845

Pro Thr Ser Cys Ser Arg Arg Phe Tyr Gln Leu Thr Lys Leu Leu Asp
850 855 860

Ser Val Gln Pro Ile Ala Arg Glu Leu His Gln Phe Thr Phe Asp Leu
865 870 875 880

Leu Ile Lys Ser His Met Val Ser Val Asp Phe Pro Glu Met Met Ala
885 890 895

Glu Ile Ile Ser Val Gln Val Pro Lys Ile Leu Ser Gly Lys Val Lys
900 905 910

Pro Ile Tyr Phe His Thr Gln
915

<210> SEQ ID NO 82
<211> LENGTH: 314
<212> TYPE: PRT
<213> ORGANISM: Artificial Sequence
<220> FEATURE:
<223> OTHER INFORMATION: LBD of estrogen receptor mutant ER(T2)

<400> SEQUENCE: 82

Ser Ala Gly Asp Met Arg Ala Ala Asn Leu Trp Pro Ser Pro Leu Met
1 5 10 15

Ile Lys Arg Ser Lys Lys Asn Ser Leu Ala Leu Ser Leu Thr Ala Asp
20 25 30

Gln Met Val Ser Ala Leu Leu Asp Ala Glu Pro Pro Ile Leu Tyr Ser
35 40 45

Glu Tyr Asp Pro Thr Arg Pro Phe Ser Glu Ala Ser Met Met Gly Leu
50 55 60

Leu Thr Asn Leu Ala Asp Arg Glu Leu Val His Met Ile Asn Trp Ala
65 70 75 80

Lys Arg Val Pro Gly Phe Val Asp Leu Thr Leu His Asp Gln Val His
85 90 95

Leu Leu Glu Cys Ala Trp Leu Glu Ile Leu Met Ile Gly Leu Val Trp
100 105 110

Arg Ser Met Glu His Pro Val Lys Leu Leu Phe Ala Pro Asn Leu Leu
115 120 125

Leu Asp Arg Asn Gln Gly Lys Cys Val Glu Gly Met Val Glu Ile Phe
130 135 140

Asp Met Leu Leu Ala Thr Ser Ser Arg Phe Arg Met Met Asn Leu Gln
145 150 155 160

Gly Glu Glu Phe Val Cys Leu Lys Ser Ile Ile Leu Leu Asn Ser Gly
165 170 175

Val Tyr Thr Phe Leu Ser Ser Thr Leu Lys Ser Leu Glu Glu Lys Asp
180 185 190

His Ile His Arg Val Leu Asp Lys Ile Thr Asp Thr Leu Ile His Leu
195 200 205

Met Ala Lys Ala Gly Leu Thr Leu Gln Gln Gln His Gln Arg Leu Ala
210 215 220

Gln Leu Leu Leu Ile Leu Ser His Ile Arg His Met Ser Asn Lys Gly
225 230 235 240

-continued

```
Met Glu His Leu Tyr Ser Met Lys Cys Lys Asn Val Val Pro Leu Tyr
                245                 250                 255

Asp Leu Leu Leu Glu Ala Ala Asp Ala His Arg Leu His Ala Pro Thr
            260                 265                 270

Ser Arg Gly Gly Ala Ser Val Glu Glu Thr Asp Gln Ser His Leu Ala
        275                 280                 285

Thr Ala Gly Ser Thr Ser Ser His Ser Leu Gln Lys Tyr Tyr Ile Thr
    290                 295                 300

Gly Glu Ala Glu Gly Phe Pro Ala Thr Ala
305                 310


<210> SEQ ID NO 83
<211> LENGTH: 756
<212> TYPE: DNA
<213> ORGANISM: Homo sapiens

<400> SEQUENCE: 83

aagaagaaca gcctggcctt gtccctgacg gccgaccaga tggtcagtgc cttgttggat     60

gctgagcccc ccatactcta ttccgagtat gatcctacca gacccttcag tgaagcttcg    120

atgatgggct tactgaccaa cctggcagac agggagctgg ttcacatgat caactgggcg    180

aagagggtgc caggctttgt ggatttgacc ctccatgatc aggtccacct tctagaatgt    240

gcctggctag agatcctgat gattggactc gtctggcgct ccatggagca cccagggaag    300

ctactgtttg ctcctaactt gctcttggac aggaaccagg gaaaatgtgt agagggcatg    360

gtggagatct tcgacatgct gctggctaca tcatctcggt tccgcatgat gaatctgcag    420

ggagaggagt ttgtgtgcct caaatctatt attttgctta attctggagt gtacacattt    480

ctgtccagca ccctgaagtc tctggaagag aaggaccata tccaccgagt cctggacaag    540

atcacagaca ctttgatcca cctgatggcc aaggcaggcc tgaccctgca gcagcagcac    600

cagcggctgg cccagctcct cctcatcctc tcccacatca ggcacatgag taacaaaggc    660

atggagcatc tgtacagcat gaagtgcaag aacgtggtgc ccctctatga cctgctgctg    720

gagatgctgg acgcccaccg cctacatgcg cccacc                              756


<210> SEQ ID NO 84
<211> LENGTH: 960
<212> TYPE: DNA
<213> ORGANISM: Artificial Sequence
<220> FEATURE:
<223> OTHER INFORMATION: encodes tBID fusion protein C3445 (ESR1-D)

<400> SEQUENCE: 84

atgaagaaga acagcctggc cttgtccctg acggccgacc agatggtcag tgccttgttg     60

gatgctgagc cccccatact ctattccgag tatgatccta ccagaccctt cagtgaagct    120

tcgatgatgg gcttactgac caacctggca gacagggagc tggttcacat gatcaactgg    180

gcgaagaggg tgccaggctt tgtggatttg accctccatg atcaggtcca ccttctagaa    240

tgtgcctggc tagagatcct gatgattgga ctcgtctggc gctccatgga gcacccaggg    300

aagctactgt ttgctcctaa cttgctcttg gacaggaacc agggaaaatg tgtagagggc    360

atggtggaga tcttcgacat gctgctggct acatcatctc ggttccgcat gatgaatctg    420

cagggagagg agtttgtgtg cctcaaatct attattttgc ttaattctgg agtgtacaca    480

tttctgtcca gcaccctgaa gtctctggaa gagaaggacc atatccaccg agtcctggac    540

aagatcacag acactttgat ccacctgatg gccaaggcag gcctgaccct gcagcagcag    600
```

caccagcggc tggcccagct cctcctcatc ctctcccaca tcaggcacat gagtaacaaa 660
ggcatggagc atctgtacag catgaagtgc aagaacgtgg tgcccctcta tgacctgctg 720
ctggagatgc tggacgccca ccgcctacat gcgcccaccg gcagcagtca agaagacatc 780
atccggaata ttgccaggca cctcgcccag gtcggggaca gcatggaccg tagcatccct 840
ccgggcgaga agaccatgct ggtgctggcc ctgctgctgg ccaagaaggt ggccagtcac 900
acgccgtcct tgctccgtga tgtctttcac acaacagtga attttattaa ccagaaccta 960

<210> SEQ ID NO 85
<211> LENGTH: 957
<212> TYPE: DNA
<213> ORGANISM: Artificial Sequence
<220> FEATURE:
<223> OTHER INFORMATION: encodes tBID fusion protein C3454 (D-ESR1)

<400> SEQUENCE: 85
agtcaagaag acatcatccg gaatattgcc aggcacctcg cccaggtcgg ggacagcatg 60
gaccgtagca tccctccggg cgagaagacc atgctggtgc tggccctgct gctggccaag 120
aaggtggcca gtcacacgcc gtccttgctc cgtgatgtct ttcacacaac agtgaatttt 180
attaaccaga acctaggaag caagaagaac agcctggcct tgtccctgac ggccgaccag 240
atggtcagtg ccttgttgga tgctgagccc cccatactct attccgagta tgatcctacc 300
agacccttca gtgaagcttc gatgatgggc ttactgacca acctggcaga cagggagctg 360
gttcacatga tcaactgggc gaagagggtg ccaggctttg tggatttgac cctccatgat 420
caggtccacc ttctagaatg tgcctggcta gagatcctga tgattggact cgtctggcgc 480
tccatggagc acccagggaa gctactgttt gctcctaact tgctcttgga caggaaccag 540
ggaaaatgtg tagagggcat ggtggagatc ttcgacatgc tgctggctac atcatctcgg 600
ttccgcatga tgaatctgca gggagaggag tttgtgtgcc tcaaatctat tattttgctt 660
aattctggag tgtacacatt tctgtccagc accctgaagt ctctggaaga gaaggaccat 720
atccaccgag tcctggacaa gatcacagac actttgatcc acctgatggc caaggcaggc 780
ctgaccctgc agcagcagca ccagcggctg gcccagctcc tcctcatcct ctcccacatc 840
aggcacatga gtaacaaagg catggagcat ctgtacagca tgaagtgcaa gaacgtggtg 900
cccctctatg acctgctgct ggagatgctg gacgcccacc gcctacatgc gcccacc 957

<210> SEQ ID NO 86
<211> LENGTH: 1026
<212> TYPE: DNA
<213> ORGANISM: Artificial Sequence
<220> FEATURE:
<223> OTHER INFORMATION: encodes tBID fusion protein C3443 (ESR1-C)

<400> SEQUENCE: 86
atgaagaaga acagcctggc cttgtccctg acggccgacc agatggtcag tgccttgttg 60
gatgctgagc cccccatact ctattccgag tatgatccta ccagaccctt cagtgaagct 120
tcgatgatgg gcttactgac caacctggca gacagggagc tggttcacat gatcaactgg 180
gcgaagaggg tgccaggctt tgtggatttg accctccatg atcaggtcca ccttctagaa 240
tgtgcctggc tagagatcct gatgattgga ctcgtctggc gctccatgga gcacccaggg 300
aagctactgt ttgctcctaa cttgctcttg gacaggaacc agggaaaatg tgtagagggc 360
atggtggaga tcttcgacat gctgctggct acatcatctc ggttccgcat gatgaatctg 420

```
cagggagagg agtttgtgtg cctcaaatct attattttgc ttaattctgg agtgtacaca    480

tttctgtcca gcaccctgaa gtctctggaa gagaaggacc atatccaccg agtcctggac    540

aagatcacag acactttgat ccacctgatg gccaaggcag gcctgaccct gcagcagcag    600

caccagcggc tggcccagct cctcctcatc ctctcccaca tcaggcacat gagtaacaaa    660

ggcatggagc atctgtacag catgaagtgc aagaacgtgg tgcccctcta tgacctgctg    720

ctggagatgc tggacgccca ccgcctacat gcgcccaccg gcagcagtca agaagacatc    780

atccggaata ttgccaggca cctcgcccag gtcggggaca gcatggaccg tagcatccct    840

ccgggcctgg tgaacggcct ggccctgcag ctcaggaaca ccagccggtc ggaggaggac    900

cggaacaggg acctggccac tgccctggag cagctgctgc aggcctaccc tagagacatg    960

gagaaggaga agaccatgct ggtgctggcc ctgctgctgg ccaagaaggt ggccagtcac   1020

acgccg                                                              1026
```

<210> SEQ ID NO 87
<211> LENGTH: 1026
<212> TYPE: DNA
<213> ORGANISM: Artificial Sequence
<220> FEATURE:
<223> OTHER INFORMATION: encodes tBID fusion protein C3452 (C-ESR1)

<400> SEQUENCE: 87

```
atgagtcaag aagacatcat ccggaatatt gccaggcacc tcgcccaggt cggggacagc     60

atggaccgta gcatccctcc gggcctggtg aacggcctgg ccctgcagct caggaacacc    120

agccggtcgg aggaggaccg gaacagggac ctggccactg ccctggagca gctgctgcag    180

gcctacccta gagacatgga gaaggagaag accatgctgg tgctggccct gctgctggcc    240

aagaaggtgg ccagtcacac gccgggaagc aagaagaaca gcctggcctt gtccctgacg    300

gccgaccaga tggtcagtgc cttgttggat gctgagcccc ccatactcta ttccgagtat    360

gatcctacca gacccttcag tgaagcttcg atgatgggct tactgaccaa cctggcagac    420

agggagctgg ttcacatgat caactgggcg aagagggtgc caggctttgt ggatttgacc    480

ctccatgatc aggtccacct tctagaatgt gcctggctag agatcctgat gattggactc    540

gtctggcgct ccatggagca cccagggaag ctactgtttg ctcctaactt gctcttggac    600

aggaaccagg gaaaatgtgt agagggcatg gtggagatct tcgacatgct gctggctaca    660

tcatctcggt tccgcatgat gaatctgcag ggagaggagt ttgtgtgcct caaatctatt    720

attttgctta attctggagt gtacacattt ctgtccagca ccctgaagtc tctggaagag    780

aaggaccata tccaccgagt cctggacaag atcacagaca ctttgatcca cctgatggcc    840

aaggcaggcc tgaccctgca gcagcagcac cagcggctgg cccagctcct cctcatcctc    900

tcccacatca ggcacatgag taacaaaggc atggagcatc tgtacagcat gaagtgcaag    960

aacgtggtgc ccctctatga cctgctgctg gagatgctgg acgcccaccg cctacatgcg   1020

cccacc                                                              1026
```

<210> SEQ ID NO 88
<211> LENGTH: 18
<212> TYPE: PRT
<213> ORGANISM: Unknown
<220> FEATURE:
<223> OTHER INFORMATION: T2A peptide

<400> SEQUENCE: 88

Glu Gly Arg Gly Ser Leu Leu Thr Cys Gly Asp Val Glu Glu Asn Pro 1 5 10 15

Gly Pro

<210> SEQ ID NO 89
<211> LENGTH: 54
<212> TYPE: DNA
<213> ORGANISM: Unknown
<220> FEATURE:
<223> OTHER INFORMATION: encodes T2A peptide

<400> SEQUENCE: 89
gagggcagag gcagcctgct gacatgtggc gacgtggaag agaaccctgg cccc 54

<210> SEQ ID NO 90
<211> LENGTH: 19
<212> TYPE: PRT
<213> ORGANISM: Unknown
<220> FEATURE:
<223> OTHER INFORMATION: P2A peptide

<400> SEQUENCE: 90

Ala Thr Asn Phe Ser Leu Leu Lys Gln Ala Gly Asp Val Glu Glu Asn
1 5 10 15

Pro Gly Pro

<210> SEQ ID NO 91
<211> LENGTH: 20
<212> TYPE: PRT
<213> ORGANISM: Unknown
<220> FEATURE:
<223> OTHER INFORMATION: E2A peptide

<400> SEQUENCE: 91

Gln Cys Thr Asn Tyr Ala Leu Leu Lys Leu Ala Gly Asp Val Glu Ser
1 5 10 15

Asn Pro Gly Pro
20

<210> SEQ ID NO 92
<211> LENGTH: 22
<212> TYPE: PRT
<213> ORGANISM: Unknown
<220> FEATURE:
<223> OTHER INFORMATION: F2A peptide

<400> SEQUENCE: 92

Val Lys Gln Thr Leu Asn Phe Asp Leu Leu Lys Leu Ala Gly Asp Val
1 5 10 15

Glu Ser Asn Pro Gly Pro
20

<210> SEQ ID NO 93
<211> LENGTH: 78
<212> TYPE: PRT
<213> ORGANISM: Artificial Sequence
<220> FEATURE:
<223> OTHER INFORMATION: tBID polypeptide

<400> SEQUENCE: 93

Ser Gln Glu Asp Ile Ile Arg Asn Ile Ala Arg His Leu Ala Gln Val
1 5 10 15

Gly Asp Ser Met Asp Arg Ser Ile Pro Pro Gly Glu Lys Thr Met Leu
20 25 30

```
Val Leu Ala Leu Leu Leu Ala Lys Lys Val Ala Ser His Thr Pro Ser
        35                  40                  45

Leu Leu Arg Asp Val Phe His Thr Thr Val Asn Phe Ile Asn Gln Asn
    50                  55                  60

Leu Arg Thr Tyr Val Arg Ser Leu Ala Arg Asn Gly Met Asp
65                  70                  75


<210> SEQ ID NO 94
<211> LENGTH: 234
<212> TYPE: DNA
<213> ORGANISM: Artificial Sequence
<220> FEATURE:
<223> OTHER INFORMATION: encodes tBID polypeptide

<400> SEQUENCE: 94

agtcaagaag acatcatccg gaatattgcc aggcacctcg cccaggtcgg ggacagcatg     60

gaccgtagca tccctccggg cgagaagacc atgctggtgc tggccctgct gctggccaag    120

aaggtggcca gtcacacgcc gtccttgctc cgtgatgtct ttcacacaac agtgaatttt    180

attaaccaga acctacgcac ctacgtgagg agcttagcca gaaatgggat ggac          234


<210> SEQ ID NO 95
<211> LENGTH: 74
<212> TYPE: PRT
<213> ORGANISM: Artificial Sequence
<220> FEATURE:
<223> OTHER INFORMATION: tBID polypeptide

<400> SEQUENCE: 95

Met Ser Gln Glu Asp Ile Ile Arg Asn Ile Ala Arg His Leu Ala Gln
1               5                   10                  15

Val Gly Asp Ser Met Asp Arg Ser Ile Pro Pro Gly Ser Glu Glu Asp
            20                  25                  30

Arg Asn Arg Asp Leu Ala Thr Ala Leu Glu Gln Leu Leu Gln Ala Tyr
        35                  40                  45

Pro Arg Asp Met Glu Lys Glu Lys Thr Met Leu Val Leu Ala Leu Leu
    50                  55                  60

Leu Ala Lys Lys Val Ala Ser His Thr Pro
65                  70


<210> SEQ ID NO 96
<211> LENGTH: 219
<212> TYPE: DNA
<213> ORGANISM: Artificial Sequence
<220> FEATURE:
<223> OTHER INFORMATION: encodes tBID polypeptide

<400> SEQUENCE: 96

agtcaagaag acatcatccg gaatattgcc aggcacctcg cccaggtcgg ggacagcatg     60

gaccgtagca tccctccggg ctcggaggag gaccggaaca gggacctggc cactgccctg    120

gagcagctgc tgcaggccta ccctagagac atggagaagg agaagaccat gctggtgctg    180

gccctgctgc tggccaagaa ggtggccagt cacacgccg                           219


<210> SEQ ID NO 97
<211> LENGTH: 328
<212> TYPE: PRT
<213> ORGANISM: Artificial Sequence
<220> FEATURE:
<223> OTHER INFORMATION: tBID fusion protein C3687 (H-ESR1)

<400> SEQUENCE: 97
```

```
Met Ser Gln Glu Asp Ile Ile Arg Asn Ile Ala Arg His Leu Ala Gln
1               5                   10                  15

Val Gly Asp Ser Met Asp Arg Ser Ile Pro Pro Gly Ser Glu Glu Asp
            20                  25                  30

Arg Asn Arg Asp Leu Ala Thr Ala Leu Glu Gln Leu Leu Gln Ala Tyr
        35                  40                  45

Pro Arg Asp Met Glu Lys Glu Lys Thr Met Leu Val Leu Ala Leu Leu
    50                  55                  60

Leu Ala Lys Lys Val Ala Ser His Thr Pro Gly Ser Lys Lys Asn Ser
65                  70                  75                  80

Leu Ala Leu Ser Leu Thr Ala Asp Gln Met Val Ser Ala Leu Leu Asp
                85                  90                  95

Ala Glu Pro Pro Ile Leu Tyr Ser Glu Tyr Asp Pro Thr Arg Pro Phe
            100                 105                 110

Ser Glu Ala Ser Met Met Gly Leu Leu Thr Asn Leu Ala Asp Arg Glu
        115                 120                 125

Leu Val His Met Ile Asn Trp Ala Lys Arg Val Pro Gly Phe Val Asp
    130                 135                 140

Leu Thr Leu His Asp Gln Val His Leu Leu Glu Cys Ala Trp Leu Glu
145                 150                 155                 160

Ile Leu Met Ile Gly Leu Val Trp Arg Ser Met Glu His Pro Gly Lys
                165                 170                 175

Leu Leu Phe Ala Pro Asn Leu Leu Leu Asp Arg Asn Gln Gly Lys Cys
            180                 185                 190

Val Glu Gly Met Val Glu Ile Phe Asp Met Leu Leu Ala Thr Ser Ser
        195                 200                 205

Arg Phe Arg Met Met Asn Leu Gln Gly Glu Glu Phe Val Cys Leu Lys
    210                 215                 220

Ser Ile Ile Leu Leu Asn Ser Gly Val Tyr Thr Phe Leu Ser Ser Thr
225                 230                 235                 240

Leu Lys Ser Leu Glu Glu Lys Asp His Ile His Arg Val Leu Asp Lys
                245                 250                 255

Ile Thr Asp Thr Leu Ile His Leu Met Ala Lys Ala Gly Leu Thr Leu
            260                 265                 270

Gln Gln Gln His Gln Arg Leu Ala Gln Leu Leu Leu Ile Leu Ser His
        275                 280                 285

Ile Arg His Met Ser Asn Lys Gly Met Glu His Leu Tyr Ser Met Lys
    290                 295                 300

Cys Lys Asn Val Val Pro Leu Tyr Asp Leu Leu Leu Glu Met Leu Asp
305                 310                 315                 320

Ala His Arg Leu His Ala Pro Thr
                325
```

<210> SEQ ID NO 98
<211> LENGTH: 984
<212> TYPE: DNA
<213> ORGANISM: Artificial Sequence
<220> FEATURE:
<223> OTHER INFORMATION: encodes tBID fusion protein C3687 (H-ESR1)

<400> SEQUENCE: 98

```
atgagtcaag aagacatcat ccggaatatt gccaggcacc tcgcccaggt cggggacagc      60

atggaccgta gcatccctcc gggctcggag gaggaccgga acagggacct ggccactgcc     120

ctggagcagc tgctgcaggc ctaccctaga gacatggaga aggagaagac catgctggtg     180
```

```
ctggccctgc tgctggccaa gaaggtggcc agtcacacgc cgggaagcaa gaagaacagc    240

ctggccttgt ccctgacggc cgaccagatg gtcagtgcct tgttggatgc tgagcccccc    300

atactctatt ccgagtatga tcctaccaga cccttcagtg aagcttcgat gatgggctta    360

ctgaccaacc tggcagacag ggagctggtt cacatgatca actgggcgaa gagggtgcca    420

ggctttgtgg atttgaccct ccatgatcag gtccaccttc tagaatgtgc ctggctagag    480

atcctgatga ttggactcgt ctggcgctcc atggagcacc cagggaagct actgtttgct    540

cctaacttgc tcttggacag gaaccaggga aaatgtgtag agggcatggt ggagatcttc    600

gacatgctgc tggctacatc atctcggttc cgcatgatga atctgcaggg agaggagttt    660

gtgtgcctca aatctattat tttgcttaat tctggagtgt acacatttct gtccagcacc    720

ctgaagtctc tggaagagaa ggaccatatc caccgagtcc tggacaagat cacagacact    780

ttgatccacc tgatggccaa ggcaggcctg accctgcagc agcagcacca gcggctggcc    840

cagctcctcc tcatcctctc ccacatcagg cacatgagta acaaaggcat ggagcatctg    900

tacagcatga agtgcaagaa cgtggtgccc ctctatgacc tgctgctgga gatgctggac    960

gcccaccgcc tacatgcgcc cacc                                           984
```

<210> SEQ ID NO 99
<211> LENGTH: 30
<212> TYPE: PRT
<213> ORGANISM: Artificial Sequence
<220> FEATURE:
<223> OTHER INFORMATION: polypeptide linker
<220> FEATURE:
<221> NAME/KEY: SITE
<222> LOCATION: (4)..(6)
<223> OTHER INFORMATION: residues, as a group, may be present or absent
<220> FEATURE:
<221> NAME/KEY: SITE
<222> LOCATION: (7)..(9)
<223> OTHER INFORMATION: residues, as a group, may be present or absent
<220> FEATURE:
<221> NAME/KEY: SITE
<222> LOCATION: (10)..(12)
<223> OTHER INFORMATION: residues, as a group, may be present or absent
<220> FEATURE:
<221> NAME/KEY: SITE
<222> LOCATION: (13)..(15)
<223> OTHER INFORMATION: residues, as a group, may be present or absent
<220> FEATURE:
<221> NAME/KEY: SITE
<222> LOCATION: (16)..(18)
<223> OTHER INFORMATION: residues, as a group, may be present or absent
<220> FEATURE:
<221> NAME/KEY: SITE
<222> LOCATION: (19)..(21)
<223> OTHER INFORMATION: residues, as a group, may be present or absentt
<220> FEATURE:
<221> NAME/KEY: SITE
<222> LOCATION: (22)..(24)
<223> OTHER INFORMATION: residues, as a group, may be present or absent
<220> FEATURE:
<221> NAME/KEY: SITE
<222> LOCATION: (25)..(27)
<223> OTHER INFORMATION: residues, as a group, may be present or absent
<220> FEATURE:
<221> NAME/KEY: SITE
<222> LOCATION: (28)..(30)
<223> OTHER INFORMATION: residues, as a group, may be present or absent

<400> SEQUENCE: 99

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
```

20 25 30

<210> SEQ ID NO 100
<211> LENGTH: 40
<212> TYPE: PRT
<213> ORGANISM: Artificial Sequence
<220> FEATURE:
<223> OTHER INFORMATION: polypeptide linker
<220> FEATURE:
<221> NAME/KEY: SITE
<222> LOCATION: (5)..(8)
<223> OTHER INFORMATION: residues, as a group, may be present or absent
<220> FEATURE:
<221> NAME/KEY: SITE
<222> LOCATION: (9)..(12)
<223> OTHER INFORMATION: residues, as a group, may be present or absent
<220> FEATURE:
<221> NAME/KEY: SITE
<222> LOCATION: (13)..(16)
<223> OTHER INFORMATION: residues, as a group, may be present or absent
<220> FEATURE:
<221> NAME/KEY: SITE
<222> LOCATION: (17)..(20)
<223> OTHER INFORMATION: residues, as a group, may be present or absent
<220> FEATURE:
<221> NAME/KEY: SITE
<222> LOCATION: (21)..(24)
<223> OTHER INFORMATION: residues, as a group, may be present or absent
<220> FEATURE:
<221> NAME/KEY: SITE
<222> LOCATION: (25)..(28)
<223> OTHER INFORMATION: residues, as a group, may be present or absent
<220> FEATURE:
<221> NAME/KEY: SITE
<222> LOCATION: (29)..(32)
<223> OTHER INFORMATION: residues, as a group, may be present or absent
<220> FEATURE:
<221> NAME/KEY: SITE
<222> LOCATION: (33)..(36)
<223> OTHER INFORMATION: residues, as a group, may be present or absent
<220> FEATURE:
<221> NAME/KEY: SITE
<222> LOCATION: (37)..(40)
<223> OTHER INFORMATION: residues, as a group, may be present or absent

<400> SEQUENCE: 100

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 101
<211> LENGTH: 50
<212> TYPE: PRT
<213> ORGANISM: Artificial Sequence
<220> FEATURE:
<223> OTHER INFORMATION: polypeptide linker
<220> FEATURE:
<221> NAME/KEY: SITE
<222> LOCATION: (6)..(10)
<223> OTHER INFORMATION: residues, as a group, may be present or absent
<220> FEATURE:
<221> NAME/KEY: SITE
<222> LOCATION: (11)..(15)
<223> OTHER INFORMATION: residues, as a group, may be present or absent
<220> FEATURE:
<221> NAME/KEY: SITE
<222> LOCATION: (16)..(20)
<223> OTHER INFORMATION: residues, as a group, may be present or absent
<220> FEATURE:
<221> NAME/KEY: SITE
<222> LOCATION: (21)..(25)

<223> OTHER INFORMATION: residues, as a group, may be present or absent
<220> FEATURE:
<221> NAME/KEY: SITE
<222> LOCATION: (26)..(30)
<223> OTHER INFORMATION: residues, as a group, may be present or absent
<220> FEATURE:
<221> NAME/KEY: SITE
<222> LOCATION: (31)..(35)
<223> OTHER INFORMATION: residues, as a group, may be present or absent
<220> FEATURE:
<221> NAME/KEY: SITE
<222> LOCATION: (36)..(40)
<223> OTHER INFORMATION: residues, as a group, may be present or absent
<220> FEATURE:
<221> NAME/KEY: SITE
<222> LOCATION: (41)..(45)
<223> OTHER INFORMATION: residues, as a group, may be present or absent
<220> FEATURE:
<221> NAME/KEY: SITE
<222> LOCATION: (46)..(50)
<223> OTHER INFORMATION: residues, as a group, may be present or absent

<400> SEQUENCE: 101

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 102
<211> LENGTH: 5
<212> TYPE: PRT
<213> ORGANISM: Artificial Sequence
<220> FEATURE:
<223> OTHER INFORMATION: polypeptide linker

<400> SEQUENCE: 102

```
Gly Gly Gly Gly Ser
1               5
```

<210> SEQ ID NO 103
<211> LENGTH: 10
<212> TYPE: PRT
<213> ORGANISM: Artificial Sequence
<220> FEATURE:
<223> OTHER INFORMATION: polypeptide linker

<400> SEQUENCE: 103

```
Gly Gly Gly Gly Ser Gly Gly Gly Gly Ser
1               5                   10
```

<210> SEQ ID NO 104
<211> LENGTH: 15
<212> TYPE: PRT
<213> ORGANISM: Artificial Sequence
<220> FEATURE:
<223> OTHER INFORMATION: polypeptide linker

<400> SEQUENCE: 104

```
Gly Gly Gly Gly Ser Gly Gly Gly Gly Ser Gly Gly Gly Gly Ser
1               5                   10                  15
```

<210> SEQ ID NO 105
<211> LENGTH: 20
<212> TYPE: PRT

-continued

```
<213> ORGANISM: Artificial Sequence
<220> FEATURE:
<223> OTHER INFORMATION: polypeptide linker

<400> SEQUENCE: 105

Gly Gly Gly Gly Ser Gly Gly Gly Gly Ser Gly Gly Gly Gly Ser Gly
1               5                   10                  15

Gly Gly Gly Ser
            20


<210> SEQ ID NO 106
<211> LENGTH: 13
<212> TYPE: PRT
<213> ORGANISM: Unknown
<220> FEATURE:
<223> OTHER INFORMATION: myristoylation signal sequence

<400> SEQUENCE: 106

Gly Ser Ser Lys Ser Lys Pro Lys Asp Pro Ser Gln Arg
1               5                   10
```

GENE FUSIONS FOR CONTROL OF GENETICALLY MODIFIED CELLS

CROSS-REFERENCE TO RELATED APPLICATIONS

This application is a National Stage Application filed under 35 U.S.C. § 371 of PCT International Patent Application No. PCT/US21/45704, filed Aug. 12, 2021, which claims the benefit of and priority to U.S. Provisional Patent Application No. 63,065,321 filed Aug. 13, 2020, the contents of which are hereby incorporated by reference in their entireties herein.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: A2BI_001_01WO_SeqList_ST25.txt, date recorded: Aug. 4, 2021, file size ~315 kilobytes).

FIELD OF THE INVENTION

The invention relates generally to cellular and gene therapy for genetic disorders and other disease conditions. In particular, the invention relates to compositions and methods for the control of cell proliferation in the context of cell or gene therapy.

BACKGROUND

Gene and cell therapies confront the risk that cells engineered to provide a specific therapeutic benefit may behave in problematic or unexpected ways after transfer into the body. For example, cells used in an adoptive cell therapy, such as a T cell therapy developed for cancer treatment, may attack normal tissues as well as cancer cells. In the worst-case scenario, this problematic behavior of transplanted cells may cause a patient's death. Therefore, there exists a need for mechanisms that can control or eliminate transplanted, engineered cells within the body.

SUMMARY

The disclosure provides a novel safety mechanism for eliminating genetically engineered cells comprising the fusion of a powerful truncated form of the pro-apoptotic polypeptide, truncated BH3-interacting domain death agonist (tBID), to a steroid hormone receptor domain, such as the estrogen receptor ligand binding domain. This fusion protein, when activated by its cognate ligand, can causes rapid cell death of engineered cells in vitro and in vivo, increasing the safety of adoptive cell therapies.

The disclosure provides fusion proteins comprising a truncated BH3-interacting domain death agonist (tBID) polypeptide and a steroid hormone receptor (SHR) domain that can control proliferation of cells expressing the fusion proteins. Administration of the corresponding steroid hormone activates tBID, which induces apoptosis of the cells.

The disclosure provides polynucleotides comprising a sequence encoding a fusion protein, the fusion protein comprising a truncated BH3-interacting domain death agonist (tBID) polypeptide and a steroid hormone receptor (SHR) domain polypeptide, wherein the tBID polypeptide comprises a deletion of BID helix 1 and BID helix 2.

The disclosure provides vectors comprising the polynucleotides described herein, such as lentiviral vectors, and immune cells comprising same.

The disclosure provides methods of treating a disease or disorder in a subject in need thereof, comprising administering immune cells comprising the fusion proteins of the disclosure to the subject, and later administering a hormone that specifically binds the SHR domain, wherein the hormone causes activation of the fusion protein resulting in apoptosis of the immune cells. In some embodiments, the immune cells are T cells. In some embodiments, the immune cells further comprise a chimeric antigen receptor or T cell receptor.

The disclosure provides methods of controlling proliferation of transplanted immune cells in a subject previously transplanted with the immune cells comprising the fusion proteins of the disclosure, the methods comprising administering a hormone that specifically binds the SHR domain of the fusion protein.

The disclosure provides methods of making the immune cells comprising the polynucleotides, vectors and polypeptides described herein.

DETAILED DESCRIPTION

Figure 1:
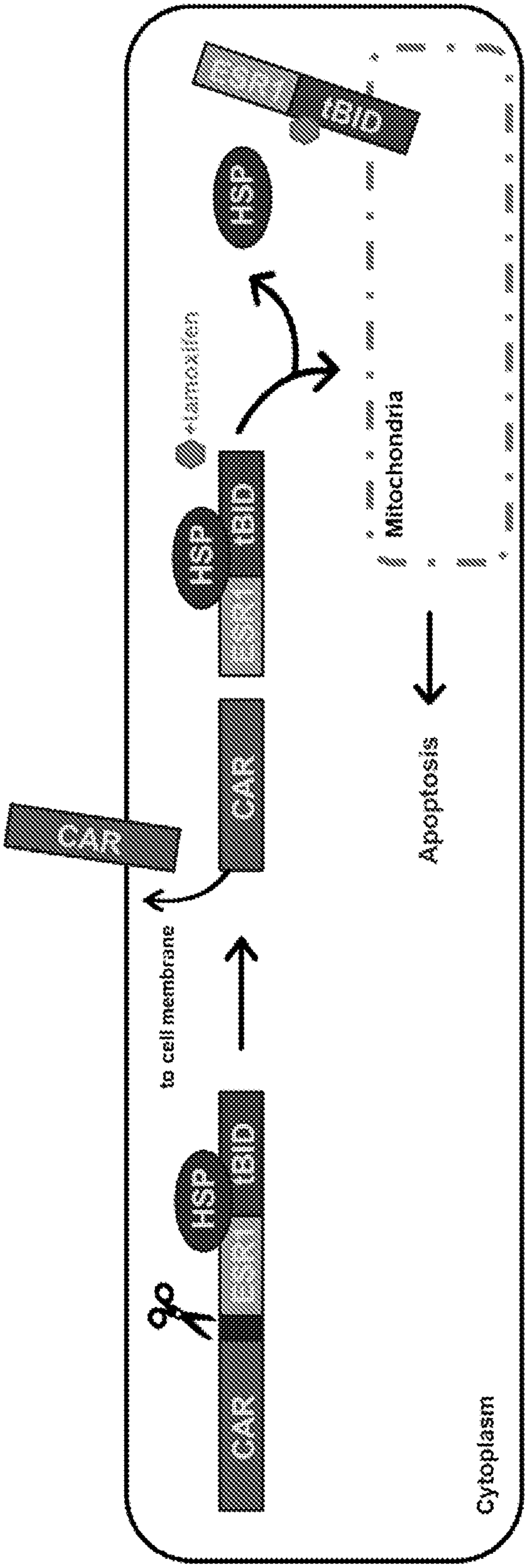
FIG. 1 shows that a safety switch can improve the safety of CAR-T/TCR-T cell therapies. Features of the safety switch shown in FIG. 1 include small construct size, the rapid induction of cell death, and that the switch can be induced by a well-biodistributed, widely used and well-tolerated small molecule (tamoxifen).

Gene and cell therapies have potential on-target and off-target risks. On-target toxicities result from excessive and harmful modulation of host physiology that overlaps with the intended therapeutic mechanism. An example of this problem involves the expression of cancer targets by normal tissues. Off-target toxicities may be caused by cross-reaction with molecules structurally related to the target, and can be physiologically similar to the therapeutic mechanism employed, or completely unrelated to the therapeutic mechanism. Because of the risks associated with exposing humans to new therapies that involve genetic modification of cells, either in vivo or ex vivo, it is desirable to regulate such modified cells.

Disclosed herein are fusion proteins for use as a molecular safety switch. The disclosed fusion proteins comprise a ligand binding domain of a steroid hormone receptor (SHR) and the cytolytic protein and potent death agonist, truncated BH3 interacting domain death agonist (tBID), or a functional fragment or variant thereof.

Currently, there are several types of synthetic regulatory circuits under investigation for tuning viability of genetically engineered cells, as well as other control systems designed to modulate the level of recombinant protein expressed by the modified cell, for example the so-called rheostats. Viability tuners fall into three main categories: (i) monoclonal antibodies (mAbs) that mediate complement-dependent cytotoxicity (CDC) or antibody-dependent cell-mediated cytotoxicity (ADCC) when bound to a surface epitope expressed uniquely on the genetically engineered cell; (ii) small-molecule substrates that are converted into metabolic poisons by exogenous enzymes; and, (iii) small-molecule inducers of apoptosis, similar to the kill switch described here (see Tey 2014, Clin Transl Immunology 3(6): e17; Bonifant et al. 2016, Mol Ther Oncolytics 3: 16011; and Zhou and Brenner 2016 Exp Hematol 44(11): 1013-1019). mAbs are by far the simplest means by which engineered cells can be targeted. The antigen/mAb pairs range from large surface proteins (e.g., CD19/rituximab) to small epitopes added to cargo genes (e.g., RQR8/rituximab). Metabolic suicide substrates used in kill switches originated with ganciclovir, a selective substrate for herpes simplex virus thymidylate kinase (HSV tk), which can be engineered into cells. Ganciclovir is harmless to normal cells, but is phosphorylated by HSV tk to create a toxic nucleoside metabolite that kills dividing cells engineered with the gene. The approach of commandeering the apoptotic machinery with a small molecule inducer was pioneered by M. Brenner and colleagues, based on work by Wandless and coworkers, using the combination of a split caspase9 engineered into cells and a rapalog to induce dimerization via FKBP (see Spencer et al. 1993 Science 262(5136): 1019-1024; Clackson et al. 1998 Proc Natl Acad Sci USA 95(18): 10437-10442; Straathof et al. 2005 Blood 105(11): 4247-4254; Tey et al. 2007 Biol Blood Marrow Transplant 13(8): 913-924; Di Stasi et al. 2011, N Engl J Med 365(18): 1673-1683).

The fusion proteins of the disclosure may have several advantages over such methods of controlling genetically-engineered cells in vivo. Though mAb-mediated cytotoxicity has technical feasibility, its utility is seriously compromised by reliance on a large molecule effector that is poorly biodistributed, as well as cellular effectors (NK cells, macrophages, and the like) that may not be homogeneously distributed in the body. Suicide metabolites generally require cell division, constraining their kinetics and breadth of activity. Finally, the rapalogs of the rapalog-inducible caspase9 system do not permeate the brain effectively, removing this important organ from their regulatory reach.

Accordingly, the disclosure provides a safety switch comprising a ligand binding domain of a steroid hormone receptor (SHR), and a truncated BH3 interacting domain death agonist (tBID). The disclosure provides polypeptides comprising a tBID polypeptide sequence and a steroid hormone receptor (SHR) domain polypeptide sequence, wherein the tBID polypeptide comprises a deletion of BID helix 1 and BID helix 2. The disclosure provides polynucleotides encoding these fusion proteins. The disclosure further provides cells, for example T cells, comprising the polynucleotides and polypeptides described herein, for example for use in adoptive cell therapies.

Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

The terms "subject," "patient" and "individual" are used interchangeably herein to refer to a vertebrate, preferably a mammal, more preferably a human. Tissues, cells, and their progeny of a biological entity obtained in vivo or cultured in vitro are also encompassed. A "subject," "patient" or "individual" as used herein, includes any animal that exhibits pain that can be treated with the vectors, compositions, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included.

"Ligand-receptor binding," "ligand binding," and "binding" are used interchangeably herein to mean physical interaction between a ligand binding domain and a ligand or a synthetic ligand. Ligand binding can be measured by a variety of methods known in the art (e.g., detection of association with a radioactively labeled ligand, or surface plasmon resonance).

As used herein, the terms "specific binding affinity" or "specifically binds" or "specifically bound" or "specific binding" are used interchangeably throughout the specification and claims and refer to that binding which occurs between a paired species of molecules, e.g., ligand-binding domain and ligand. When the interaction of the two species produces a non-covalently bound complex, the binding which occurs is typically electrostatic, hydrogen-bonding, or the result of lipophilic interactions. In various embodiments, the specific binding between one or more species is direct. In one embodiment, the affinity of specific binding is about 2 times greater than background binding (non-specific binding), about 5 times greater than background binding, about 10 times greater than background binding, about 20 times greater than background binding, about 50 times greater than background binding, about 100 times greater than background binding, or about 1000 times greater than background binding or more.

In general, "sequence identity" or "sequence homology" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993).

The term "exogenous" is used herein to refer to any molecule, including nucleic acids, protein or peptides, small molecular compounds, and the like that originate from outside the organism. In contrast, the term "endogenous" refers to any molecule that originates from inside the organism (i.e., naturally produced by the organism).

The term "MOI" is used herein to refer to multiplicity of infection, which is the ratio of agents (e.g. viral particles) to infection targets (e.g. cells).

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

The terms "functionally active variant" or "functional variant" refer to proteins or nucleic acids comprising sequence changes with respect to a reference sequence yet retaining the functional attributes of the reference sequence. In the case of a ligand-binding domain (LBD), a functional variant retains both ligand binding activity and any activity responsible for regulation of activity of a gene fusion partner—that is in embodiments of the present invention, an effector protein. For example, a LBD that represses the activity of a gene fusion partner in the absence of ligand and de-represses that activity in the presence of ligand would be a functional variant if it retains both the ligand binding and repression/de-repression activities of the reference sequence. As a further example, a function variant or functionally active variant of tBID retains the apoptotic function of tBID.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

BH3 Interacting Domain Death Agonist (BID)

The disclosure provides fusion proteins (polypeptides) comprising a truncated BH3 interacting domain death agonist (tBID) polypeptide (See Li et al. 1998 Cell 94(4): 491-501; Luo et al. 1998 Cell 94(4): 481-490; Gross et al. 1999 J Biol Chem 274(2): 1156-1163) and a steroid hormone receptor (SHR) domain polypeptide. In some embodiments, the SHR domain is a ligand binding domain of a nuclear hormone receptor, and the tBID polypeptide comprises a deletion of BID alpha helices 1 and 2.

BH3 interacting domain death agonist (BID) is a pro-apoptotic member of the Bcl-2 family. Bcl-2 family members act as anti- or pro-apoptotic regulators involved in a variety of cellular functions. BID cleavage is required for BID-mediated initiation of the mitochondrial apoptosis. Pro-apoptotic signaling leads to Caspase-8 cleavage of inactive, full length, cytosolic BID (p22 BID) to produce a 15 kilodalton BID fragment (p15 truncated BID, or tBID) encompassing amino acids 62-195 of SEQ ID NO: 9. This fragment induces mitochondrial outer membrane permeabilization. p15 tBID works with another Bcl-2 family member, BCL2 associated X, apoptosis regulator (Bax), leading to insertion of Bax into organelle membranes, including the outer mitochondrial membrane. Insertion of Bax in the outer mitochondrial membrane induces mitochondrial voltage-dependent anion channels (VDAC) to open, releasing cytochrome c and other pro-apoptotic factors from the mitochondria. These factors activate caspases, leading to apoptosis. Caspase cleavage of p22 BID also results in two minor fragments, p13 and p11, spanning amino acids 77-195 and 100-195 of SEQ ID NO: 9, respectively.

An exemplary human BH3 interacting domain death agonist (BID) polypeptide is described at NCBI accession number NM 197966.2 (isoform 1), and comprises a sequence of:

(SEQ ID NO: 8)
1 MCSGAGVMMA RWAARGRAGW RSTVRILSPL
GHCEPGVSRS CRAAQAMDCE VNNGSSLRDE
61 CITNLLVFGF LQSCSDNSFR RELDALGHEL
PVLAPQWEGY DELQTDGNRS SHSRLGRIEA
121 DSESQEDIIR NIARHLAQVG DSMDRSIPPG
LVNGLALQLR NTSRSEEDRN RDLATALEQL
181 LQAYPRDMEK EKTMLVLALL LAKKVASHTP
SLLRDVFHTT VNFINQNLRT YVRSLARNGM
241 D.

The BID polypeptide of SEQ ID NO: 8 includes, inter alia, 8 alpha helices which are underlined in SEQ ID NO: 8. In some embodiments, a tBID polypeptide comprises a polypeptide sequence having at least 80%, at least 90%, at least 95%, at least 96%, at least 97%, at least 98%, at least 99% identity or that is identical to a subsequence of SEQ ID NO: 8. In some embodiments, a tBID polypeptide consists essentially of a polypeptide sequence having at least 80%, at least 90%, at least 95%, at least 96%, at least 97%, at least 98%, at least 99% identity or that is identical to a subsequence of SEQ ID NO: 8.

A further exemplary human BID polypeptide is described at NCBI accession number NP 001187.1 (isoform 2), and comprises a sequence of:

(SEQ ID NO: 9)
1 MDCEVNNGSS LRDECITNLL VFGFLQSCSD
NSFRRELDAL GHELPVLAPQ WEGYDELQTD
61 GNRSSHSRLG RIEADSESQE DIIRNIARHL
AQVGDSMDRS IPPGLVNGLA LQLRNTSRSE
121 EDRNRDLATA LEQLLQAYPR DMEKEKTMLV
LALLLAKKVA SHTPSLLRDV FHTTVNFINQ
181 NLRTYVRSLA RNGMD.

In some embodiments, a tBID polypeptide comprises a polypeptide sequence having at least 80%, at least 90%, at least 95%, at least 96%, at least 97%, at least 98%, at least 99% identity or that is identical to a subsequence of SEQ ID NO: 9. In some embodiments, a tBID polypeptide consists essentially of a polypeptide sequence having at least 80%, at least 90%, at least 95%, at least 96%, at least 97%, at least 98%, at least 99% identity, or that is identical to a subsequence of SEQ ID NO: 9.

The BID polypeptide of SEQ ID NO: 9 includes, inter alia, 8 alpha helices, which are underlined in SEQ ID NO: 9. Sequences and positions of the BID alpha helixes of the relative to the BID polypeptide of SEQ ID NO: 9 are shown in Table 1 below:

TABLE 1

BID isoform 2 alpha helices

| Alpha Helix | Position (relative to SEQ ID NO: 9) | Sequence |
|---|---|---|
| 1 | 15-27 | CITNLLVFGFLQS (SEQ ID NO: 11) |
| 2 | 34-43 | RRELDALGHE (SEQ ID NO: 12) |
| 3 | 79-101 | QEDIIRNIARHLAQVGDSMDRSI (SEQ ID NO: 13) |
| 4 | 105-114 | LVNGLALQLR (SEQ ID NO: 14) |
| 5 | 119-136 | SEEDRNRDLATALEQLLQ (SEQ ID NO: 15) |
| 6 | 145-162 | EKTMLVLALLLAKKVASH (SEQ ID NO: 16) |
| 7 | 167-180 | LRDVFHTTVNFINQ (SEQ ID NO: 17) |
| 8 | 183-192 | RTYVRSLARN (SEQ ID NO: 18) |

A further exemplary human BID polypeptide is described at NCBI accession number NP 932071.1 (isoform 3), and comprises a sequence of:

(SEQ ID NO: 10)
1 MDRSIPPGLV NGLALQLRNT SRSEEDRNRD LATALEQLLQ
AYPRDMEKEK TMLVLALLLA
61 KKVASHTPSL LRDVFHTTVN FINQNLRTYV RSLARNGMD.

Alpha helices in SEQ ID NO: 10 are underlined. In some embodiments, a tBID polypeptide comprises a polypeptide sequence having at least 80%, at least 90%, at least 95%, at least 96%, at least 97%, at least 98%, at least 99% identity, or that is identical to a subsequence of SEQ ID NO: 10. In some embodiments, a tBID polypeptide consists essentially of a polypeptide sequence having at least 80%, at least 90%, at least 95%, at least 96%, at least 97%, at least 98%, at least 99% identity, or that is identical to a subsequence of SEQ ID NO: 10.

In some embodiments of the fusion proteins provided herein, the fusion protein comprises a truncated BID (tBID) polypeptide. In some embodiments, the tBID polypeptide comprises a polypeptide having at least 80%, at least 90%, at least 95%, at least 96%, at least 97%, at least 98%, at least 99% identity or that is identical to amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9. In some embodiments, the tBID polypeptide comprises amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9. In some embodiments, the tBID polypeptide consists essentially of a polypeptide sequence having at least 80%, at least 90%, at least 95%, at least 96%, at least 97%, at least 98%, at least 99% identity, or that is identical to amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9. In some embodiments, the tBID polypeptide consists essentially of amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9.

In some embodiments, the tBID polypeptides of the disclosure comprise a one or more deletions encompassing of any one of BID alpha helices 1, 2, 4, 5, 7, 8 or any combination thereof. Without wishing to be bound by theory, it is thought that –α-helix 3 and 6 are required for tBID to cause apoptosis.

In some embodiments, the tBID polypeptides of the disclosure comprise a deletion of BID alpha helices 1 and 2, i.e. the tBID polypeptide does not comprise sequences of SEQ ID NO: 11 and SEQ ID NO: 12.

In some embodiments, the tBID polypeptides of the disclosure comprise a deletion of BID alpha helix 8, i.e. the tBID polypeptides do not comprise a sequence of SEQ ID NO: 18. In some embodiments, the tBID polypeptides do not comprise the sequences of SEQ ID NO: 11, SEQ ID NO: 12 and SEQ ID NO: 18.

In some embodiments, the tBID polypeptides of the disclosure comprise a deletion of BID alpha helix 4 and/or BID helix 5. For example, a tBID polypeptide does not comprise the sequences of SEQ ID NO: 14, SEQ ID NO: 15, or both SEQ ID NO: 14 and SEQ ID NO: 15. In some embodiments, the tBID polypeptides do not comprise the sequences of SEQ ID NO: 11, SEQ ID NO: 12, and SEQ ID NO: 14. In some embodiments, the tBID polypeptides do not comprise the sequences of SEQ ID NO: 11, SEQ ID NO: 12, and SEQ ID NO: 15. In some embodiments, the tBID polypeptides do not comprise the sequences of SEQ ID NO: 11, SEQ ID NO: 12, SEQ ID NO: 14 and SEQ ID NO: 15. In some embodiments, the tBID polypeptides do not comprise the sequences of SEQ ID NO: 11, SEQ ID NO: 12, SEQ ID NO: 14, SEQ ID NO: 15 and SEQ ID NO: 18. For example, a tBID polypeptide comprising only alpha helices 3, 6, 7 and 8 (SEQ ID NO: 13, SEQ ID NO: 16, SEQ ID NO: 17 and SEQ ID NO: 18), a tBID polypeptide comprising only alpha helices 3, 6 and 7 (SEQ ID NO: 13, SEQ ID NO: 16, and SEQ ID NO: 17), a tBID polypeptide comprising only alpha helices 3 and 6 (SEQ ID NO: 13 and SEQ ID NO: 16), only alpha helix 3 (SEQ ID NO: 13), or only alpha helix 6 (SEQ ID NO: 16) do not comprise BID helices 4 and/or 5.

In some embodiments, the tBID polypeptides of the disclosure comprise a deletion of BID helix 7, i.e. the tBID polypeptide does not comprise a sequence of SEQ ID NO: 17. In some embodiments, a tBID polypeptide does not comprise alpha helices 1, 2, and 7, i.e. a tBID polypeptide does not comprise the sequences of SEQ ID NO: 11, SEQ ID NO: 12 and SEQ ID NO: 17. In some embodiments, a tBID polypeptide does not comprise alpha helices 1, 2, 7, and 8, i.e. the tBID polypeptide does not comprise the sequences of SEQ ID NO: 11, SEQ ID NO: 12, SEQ ID NO: 17 and SEQ ID NO: 18. For example, a tBID polypeptide comprising only alpha helices 3, 4, 5, and 6 (SEQ ID NO: 13, SEQ ID NO: 14, SEQ ID NO: 15 and SEQ ID NO: 16), a tBID polypeptide comprising only alpha helices 3 and 6 (SEQ ID NO: 13 and SEQ ID NO: 16), a tBID polypeptide comprising only alpha helix 3 (SEQ ID NO: 13), or a tBID polypeptide comprising only alpha helix 6 (SEQ ID NO: 16) does not comprise BID helix 7.

In some embodiments, the tBID polypeptides comprise sequences of BID alpha helices 3, 4, 5, 6, 7 and 8, or sequences having at least 80% identity, at least 90% identity, at least 95% identity or at least 99% identity thereto. In some embodiments, the tBID polypeptide comprises sequences of BID alpha helices 3, 4, 5, 6, 7 and 8. In some embodiments, the tBID polypeptides comprise sequences of SEQ ID NO: 13, SEQ ID NO: 14, SEQ ID NO: 15, SEQ ID NO: 16, SEQ ID NO: 17 and SEQ ID NO: 18, or sequences having at least 80% identity, at least 90% identity, at least 95% identity or at least 99% identity thereto. In some embodiments, the tBID polypeptides comprise sequences identical to SEQ ID NO: 13, SEQ ID NO: 14, SEQ ID NO: 15, SEQ ID NO: 16, SEQ ID NO: 17 and SEQ ID NO: 18. In some embodiments, the tBID polypeptides comprise a deletion of BID helices 1 and 2, i.e. the tBID polypeptides do not comprise sequences of SEQ ID NO: 11 and SEQ ID NO: 12. In some embodiments, the tBID polypeptides comprise, or consist essentially of, a sequence of 1 QEDIIRNIAR HLAQVGDSMD RSIPPGLVNG LALQLRNTSR SEEDRNRDLA TALEQLLQAY 61 PRDMEKEKTM LVLALLLAKK VASHTPSLLR DVFHTTVNFI NQNLRTYVRS LARN (SEQ ID NO: 19), or a sequence having at least 80% identity, at least 90% identity, at least 95% identity or at least 99% identity thereto. In some embodiments, the tBID polypeptides comprise, or consist essentially of, SEQ ID NO: 19. In some embodiments, the tBID polypeptides comprise, or consist essentially of, a sequence of 1 NRSSHSRLGR IEADSESQED IIRNIARHLA QVGDSMDRSI PPGLVNGLAL QLRNTSRSEE 61 DRNRDLATAL EQLLQAYPRD MEKEKTMLVL ALLLAKKVAS HTPSLLRDVF HTTVNFINQN 121 LRTYVRSLAR NGMD (SEQ ID NO: 20), or a sequence having at least 80% identity, at least 90% identity, at least 95% identity or at least 99% identity thereto. In some embodiments, the tBID polypeptides comprise, or consist essentially of, SEQ ID NO: 20. In some embodiments, the tBID polypeptides comprise, or consist essentially of, a sequence of 1 DGNRSSHSRL GRIEADSESQ EDIIRNIARH LAQVGDSMDR SIPPGLVNGL ALQLRNTSRS 61 EEDRNRDLAT ALEQLLQAYP RDMEKEKTML VLALLLAKKV ASHTPSLLRD VFHTTVNFIN 121 QNLRTYVRSL ARNGMD (SEQ ID NO: 21), or a sequence having at least 80% identity, at least 90% identity, at least 95% identity or at least 99% identity thereto. In some embodiments, the tBID polypeptides comprise, or consist essentially of, SEQ ID NO: 21.

In some embodiments, the tBID polypeptide comprises sequences of BID alpha helices 3, 6, 7 and 8, or sequences having at least 80% identity, at least 90% identity, at least 95% identity or at least 99% identity thereto. In some embodiments, the tBID polypeptide comprises sequences of BID alpha helices 3, 6, 7 and 8. In some embodiments, the tBID polypeptide comprises sequences of SEQ ID NO: 13, SEQ ID NO: 16, SEQ ID NO: 17 and SEQ ID NO: 18, or sequences having at least 80% identity, at least 90% identity, at least 95% identity or at least 99% identity thereto. In some embodiments, the tBID polypeptide comprises sequences identical to SEQ ID NO: 13, SEQ ID NO: 16, SEQ ID NO: 17 and SEQ ID NO: 18. In some embodiments, the tBID polypeptides do not comprise sequences of BID helices 1 and 2, i.e. the tBID polypeptides do not comprise sequences of SEQ ID NO: 11 and SEQ ID NO: 12. In some embodiments, the tBID polypeptides do not comprise sequences of BID helices 1, 2, 4 and 5, i.e. the tBID polypeptides do not comprise sequences of SEQ ID NO: 11, SEQ ID NO: 12, SEQ ID NO: 14, and SEQ ID NO: 15. In some embodiments, the tBID polypeptides comprise, or consist essentially of, a sequence of (SEQ ID NO: 93, alpha helices are underlined)
SQEDIIRNIARHLAQVGDSMDRSIPPGEKTMLVLALLLAK

KVASHTPSLLRDVFHTTVNFINQNLRTYVRSLARNGMD, or a sequence having at least 80% identity, at least 90% identity, at least 95% identity or at least 99% identity thereto. In some embodiments, the tBID polypeptides comprise a sequence identical to SEQ ID NO: 93. In some embodiments, the tBID polypeptides consist essentially of a sequence identical to SEQ ID NO: 93. In some embodiments, the tBID polypeptide is at least 85% identical, at least 90% identical, at least 95% identical, at least 96% identical, at least 97% identical, at least 98% identical, at least 99% identical or identical to SEQ ID NO: 93. In some embodiments, the tBID polypeptide is at least 95% identical to SEQ ID NO: 93. In some embodiments, a tBID polypeptide is encoded by a polynucleotide having a sequence of (SEQ ID NO: 94, sequences encoding alpha helices are underlined)
AGTCAAGAAGACATCATCCGGAATATTGCCAGGCACCTC

GCCCAGGTCGGGGACAGCATGGACCGTAGCATCCCTCCG

GGCGAGAAGACCATGCTGGTGCTGGCCCTGCTGCTGGCC

AAGAAGGTGGCCAGTCACACGCCGTCCTTGCTCCGTGAT

GTCTTTCACACAACAGTGAATTTTATTAACCAGAACCTA

CGCACCTACGTGAGGAGCTTAGCCAGAAATGGGATGGAC, or a sequence having at least 70% identity, at least 80% identity, at least 90% identity, at least 95% identity or at least 99% identity thereto. In some embodiments, a tBID polypeptide is encoded by a polynucleotide having a sequence of SEQ ID NO: 94.

In some embodiments, the tBID polypeptide comprises sequences of BID alpha helices 3, 5 and 6, or sequences having at least 80% identity, at least 90% identity, at least 95% identity or at least 99% identity thereto. In some embodiments, the tBID polypeptide comprises sequences of BID alpha helices 3, 5 and 6. In some embodiments, the tBID polypeptide comprises sequences of SEQ ID NO: 13, SEQ ID NO: 15 and SEQ ID NO: 16, or sequences having at least 80% identity, at least 90% identity, at least 95% identity or at least 99% identity thereto. In some embodiments, the tBID polypeptide comprises sequences identical to SEQ ID NO: 13, SEQ ID NO: 15 and SEQ ID NO: 16. In some embodiments, the tBID polypeptides do not comprise sequences of BID helices 1-2, 4 and 7-8, i.e. the tBID polypeptides do not comprise sequences of SEQ ID NOs: 11, 12, 14 and 17-18. In some embodiments, the tBID polypeptides comprise, or consist essentially of, a sequence of (SEQ ID NO: 95, alpha helices are underlined)
MSQEDIIRNIARHLAQVGDSMDRSIPPGSEEDRNRDLATALEQ

LLQAYPRDMEKEKTMLVLALLLAKKVASHTP, or a sequence having at least 80% identity, at least 90% identity, at least 95% identity or at least 99% identity thereto. In some embodiments, the tBID polypeptides comprise a sequence identical to SEQ ID NO: 95. In some embodiments, the tBID polypeptides consist essentially of a sequence identical to SEQ ID NO: 95. In some embodiments, the tBID polypeptide is at least 85% identical, at least 90% identical, at least 95% identical, at least 96% identical, at least 97% identical, at least 98% identical, at least 99% identical or identical to SEQ ID NO: 95. In some embodiments, the tBID polypeptide is at least 95% identical to SEQ ID NO: 95. In some embodiments, a tBID polypeptide is encoded by a polynucleotide having a sequence of (SEQ ID NO: 96, sequences encoding alpha helices are underlined)
AGTCAAGAAGACATCATCCGGAATATTGCCAGGCACCTCGCCC

AGGTCGGGGACAGCATGGACCGTAGCATCCCTCCGGGCTCGGA

GGAGGACCGGAACAGGGACCTGGCCACTGCCCTGGAGCAGCTG

CTGCAGGCCTACCCTAGAGACATGGAGAAGGAGAAGACCATGC

TGGTGCTGGCCCTGCTGCTGGCCAAGAAGGTGGCCAGTCACAC

GCCG, or a sequence having at least 70% identity, at least 80% identity, at least 90% identity, at least 95% identity or at least 99% identity thereto. In some embodiments, a tBID polypeptide is encoded by a polynucleotide having a sequence of SEQ ID NO: 96.

In some embodiments, the tBID polypeptides comprise sequences of BID alpha helices 3, 4, 5, and 6, or sequences having at least 80% identity, at least 90% identity, at least 95% identity or at least 99% identity thereto. In some embodiments, the tBID polypeptides comprise sequences of BID alpha helices 3, 4, 5 and 6. In some embodiments, the tBID polypeptides comprise sequences of SEQ ID NO: 13, SEQ ID NO: 14, SEQ ID NO: 15 and SEQ ID NO: 16, or sequences having at least 80% identity, at least 90% identity, at least 95% identity or at least 99% identity thereto. In some embodiments, the tBID polypeptides comprise sequences identical to SEQ ID NO: 13, SEQ ID NO: 14, SEQ ID NO: 15 and SEQ ID NO: 16. In some embodiments, the tBID polypeptides do not comprise sequences of BID helices 1 and 2, i.e. the tBID polypeptides do not comprise sequences of SEQ ID NO: 11 and SEQ ID NO: 12. In some embodiments, the tBID polypeptides do not comprise sequences of BID helices 1, 2, 7 and 8, i.e. the tBID polypeptides do not comprise sequences of SEQ ID NO: 11, SEQ ID NO: 12, SEQ ID NO: 17 and SEQ ID NO: 18. In some embodiments, the tBID polypeptides comprise, or consist essentially of, a sequence of 1 QEDIIRNIAR HLAQVGDSMD RSIPPGLVNG LALQLRNTSR SEEDRNRDLA TALEQLLQAY 61 PRDMEKEKTM LVLALLLAKK VASHTP (SEQ ID NO: 22), or a sequence having at least 80% identity, at least 90% identity, at least 95% identity or at least 99% identity thereto. In some embodiments, the tBID polypeptides comprise, or consist essentially of, SEQ ID NO: 22.

In some embodiments, the tBID polypeptides comprise, or consist essentially of, a sequence of

```
(SEQ ID NO: 2, alpha helices are underlined)
SQEDIIRNIARHLAQVGDSMDRSIPPGLVNGLALQLRNTSRSEEDRNRDL

ATALEQLLQAYPRDMEKEKTMLVLALLLAKKVASHTP,
```

or a sequence having at least 80% identity, at least 90% identity, at least 95% identity or at least 99% identity thereto. In some embodiments, the tBID polypeptides comprise a sequence identical to SEQ ID NO: 2. In some embodiments, the tBID polypeptides consist essentially of a sequence identical to SEQ ID NO: 2. In some embodiments, the tBID polypeptide is at least 85% identical, at least 90% identical, at least 95% identical, at least 96% identical, at least 97% identical, at least 98% identical, at least 99% identical or identical to SEQ ID NO: 2. In some embodiments, the tBID polypeptide is at least 95% identical to SEQ ID NO: 2. In some embodiments, a tBID polypeptide is encoded by a polynucleotide having a sequence of

```
(SEQ ID NO: 23, sequences encoding alpha helices
are underlined)
AGTCAAGAAGACATCATCCGGAATATTGCCAGGCACCTCGCCCAGGTCGG

GGACAGCATGGACCGTAGCATCCCTCCGGGCCTGGTGAACGGCCTGGCCC

TGCAGCTCAGGAACACCAGCCGGTCGGAGGAGGACCGGAACAGGGACCTG

GCCACTGCCCTGGAGCAGCTGCTGCAGGCCTACCCTAGAGACATGGAGAA

GGAGAAGACCATGCTGGTGCTGGCCCTGCTGCTGGCCAAGAAGGTGGCCA

GTCACACGCCG,
```

or a sequence having at least 70% identity, at least 80% identity, at least 90% identity, at least 95% identity or at least 99% identity thereto. In some embodiments, a tBID polypeptide is encoded by a polynucleotide having a sequence of SEQ ID NO: 23.

In some embodiments, the tBID polypeptides comprise sequences of BID alpha helices 3, 6 and 7, or sequences having at least 80% identity, at least 90% identity, at least 95% identity or at least 99% identity thereto. In some embodiments, the tBID polypeptides comprise sequences of BID alpha helices 3, 6 and 7. In some embodiments, the tBID polypeptides comprises sequences of SEQ ID NO: 13, SEQ ID NO: 16 and SEQ ID NO: 17, or sequences having at least 80% identity, at least 90% identity, at least 95% identity or at least 99% identity thereto. In some embodiments, the tBID polypeptides comprise sequences identical SEQ ID NO: 13, SEQ ID NO: 16 and SEQ ID NO: 17. In some embodiments, the tBID polypeptides do not comprise sequences of BID helices 1 and 2, i.e. the tBID polypeptides do not comprise sequences of SEQ ID NO: 11 and SEQ ID NO: 12. In some embodiments, the tBID polypeptides do not comprise sequences of BID helices 1, 2, 5, 6 and 8, i.e. the tBID polypeptides do not comprise sequences of SEQ ID NO: 11, SEQ ID NO: 12, SEQ ID NO: 15, SEQ ID NO: 16 and SEQ ID NO: 18. In some embodiments, the tBID polypeptides comprise, or consist essentially of, a sequence of

```
(SEQ ID NO: 1, alpha helices are underlined)
SQEDIIRNIARHLAQVGDSMDRSIPPGEKTMLVLALLLAKKVASHTPSLL

RDVFHTTVNFINQNL,
```

or a sequence having at least 80% identity, at least 90% identity, at least 95% identity or at least 99% identity thereto. In some embodiments, the tBID polypeptides comprise a sequence identical to SEQ ID NO: 1. In some embodiments, the tBID polypeptides consist essentially of a sequence identical to SEQ ID NO: 1. In some embodiments, the tBID polypeptide is at least 85% identical, at least 90% identical, at least 95% identical, at least 96% identical, at least 97% identical, at least 98% identical, at least 99% identical or identical to SEQ ID NO: 1. In some embodiments, the tBID polypeptide is at least 95% identical to SEQ ID NO: 1. In some embodiments, a tBID polypeptide is encoded by a polynucleotide having a sequence of

```
(SEQ ID NO: 24, sequences encoding alpha helices
are underlined)
AGTCAAGAAGACATCATCCGGAATATTGCCAGGCACCTCGCCCAGGTCGG

GGACAGCATGGACCGTAGCATCCCTCCGGGCGAGAAGACCATGCTGGTGC

TGGCCCTGCTGCTGGCCAAGAAGGTGGCCAGTCACACGCCGTCCTTGCTC

CGTGATGTCTTTCACACAACAGTGAATTTTATTAACCAGAACCTA
```

or a sequence having at least 70% identity, at least 80% identity, at least 90% identity, at least 95% identity or at least 99% identity thereto. In some embodiments, a tBID polypeptide is encoded by a polynucleotide having a sequence of SEQ ID NO: 24.

In some embodiments, the tBID polypeptide comprises sequences of BID alpha helices 3, and 6, or sequences having at least 80% identity, at least 90% identity, at least 95% identity or at least 99% identity thereto. In some embodiments, the tBID polypeptide comprises sequences of BID alpha helices 3 and 6. In some embodiments, the tBID polypeptide comprises sequences of SEQ ID NO: 13 and SEQ ID NO: 16, or sequences having at least 80% identity, at least 90% identity, at least 95% identity or at least 99% identity thereto. In some embodiments, the tBID polypeptide comprises sequences of SEQ ID NO: 13 and SEQ ID NO: 16. In some embodiments, the tBID polypeptide does not comprise sequences of BID helices 1 and 2. In some embodiments, the tBID polypeptide does not comprise sequences of SEQ ID NO: 11 and SEQ ID NO: 12. In some embodiments, the tBID polypeptide does not comprise sequences of SEQ ID NO: 11, SEQ ID NO: 12, SEQ ID NO: 14, SEQ ID NO: 15, SEQ ID NO: 17 and SEQ ID NO: 18.

In some embodiments, the tBID polypeptide comprises a sequence of BID alpha helix 3, or sequences having at least 80% identity, at least 90% identity, at least 95% identity or at least 99% identity thereto. In some embodiments, the tBID polypeptide comprises sequences of BID alpha helix 3. In some embodiments, the tBID polypeptide comprises a sequence of SEQ ID NO: 13, or a sequence having at least 80% identity, at least 90% identity, at least 95% identity or at least 99% identity thereto. In some embodiments, the tBID polypeptide comprises a sequence of SEQ ID NO: 13. In some embodiments, the tBID polypeptide does not comprise sequences of SEQ ID NO: 11 and SEQ ID NO: 12. In some embodiments, the tBID polypeptide does not comprise sequences of SEQ ID NO: 11, SEQ ID NO: 12, SEQ ID NO: 14, SEQ ID NO: 15, SEQ ID NO: 16, SEQ ID NO: 17, SEQ ID NO: 18 or any combination thereof.

In some embodiments, the tBID polypeptide comprises a sequence of BID alpha helix 6 of BID, or sequences having at least 80% identity, at least 90% identity, at least 95% identity or at least 99% identity thereto. In some embodiments, the tBID polypeptide comprises a sequence of BID alpha helix 6. In some embodiments, the tBID polypeptide comprises a sequence of SEQ ID NO: 16, or a sequence having at least 80% identity, at least 90% identity, at least 95% identity or at least 99% identity thereto. In some embodiments, the tBID polypeptide comprises sequences of SEQ ID NO: 16. In some embodiments, the tBID polypeptide does not comprise sequences of BID helices 1 and 2. In some embodiments, the tBID polypeptide does not comprise sequences of SEQ ID NO: 11 and SEQ ID NO: 12. In some embodiments, the tBID polypeptide does not comprise sequences of SEQ ID NO: 11, SEQ ID NO: 12, SEQ ID NO: 13, SEQ ID NO: 14, SEQ ID NO: 15, SEQ ID NO: 17, SEQ ID NO: 18 or any combination thereof.

Steroid Hormone Receptors

The disclosure provides fusion proteins comprising a truncated BID polypeptide and a steroid hormone receptor (SHR) domain. In some embodiments, the SHR domain comprises a ligand binding domain (LBD) of the SHR.

Steroid hormone receptors are a type of receptor found in the nucleus, cytosol and plasma membrane of cells. Steroid hormone receptors are generally intracellular, and initiate signal transduction in response to steroid hormones, leading to changes in gene expression in the cell. One type of steroid hormone receptor is the nuclear hormone receptor.

LBDs for use in the tBID fusion proteins of the instant disclosure can be isolated or derived from any suitable steroid hormone receptor. In some embodiments, the steroid hormone receptor is a nuclear hormone receptor. In some embodiments, the steroid hormone receptor is a mammalian nuclear hormone receptor. In some embodiments, the steroid hormone receptor is a human nuclear hormone receptor. In some embodiments, the steroid hormone receptor is a mouse nuclear hormone receptor.

Nuclear hormone receptors are a class of protein that, in their native state, regulate transcription of target genes in response to a variety of ligands. (Alexander et al. The Concise Guide to PHARMACOLOGY 2017/18: Nuclear hormone receptors. *British Journal of Pharmacology* (2017) 174, S208-S224). Table 2 lists nuclear hormone receptors for used in embodiments of the present invention along with information on agonist or antagonists used as ligands in embodiments of the present invention.

TABLE 2

Nuclear Hormone Receptors (ligand binding domains are underlined)

| Name | Agonists | Antagonists | Sequence |
|---|---|---|---|
| Thyroid hormone receptor-α (NR1A1) (LBD at 163-407) | Dextrothyroxine | — | MEQKPSKVECGSDPEENSARSPDGKRKRKNGQCSLKTS<br>MSGYIPSYLDKDEQCVVCGDKATGYHYRCITCEGCKGF<br>FRRTIQKNLHPTYSCKYDSCCVIDKITRNQCQLCRFKK<br>CIAVGMAMDLVLDDSKRVAKRKLIEQNRERRRKEEMIR<br>SLQQRPEPTPEEWDLIHIATEAHRSTNAQGSHWKQRRK<br>FLPDDIGQSPIVSMPDGDKVDLEAFSEFTKIITPAITR<br>VVDFAKKLPMFSELPCEDQIILLKGCCMEIMSLRAAVR<br>YDPESDTLTLSGEMAVKREQLKNGGLGVVSDAIFELGK<br>SLSAFNLDDTEVALLQAVLLMSTDRSGLLCVDKIEKSQ<br>EAYLLAFEHYVNHRKHNIPHFWPKLLMKEREVQSSILY<br>KGAAAEGRPGGSLGVHPEGQQLLGMHVVQGPQVRQLEQ<br>QLGEAGSLQGPVLQHQSPKSPQQRLLELLHRSGILHAR<br>AVCGEDDSSEADSPSSSEEEPEVCEDLAGNAASP<br>(SEQ ID NO: 25) |
| Thyroid hormone receptor-β (NR1A2) (LBD at 217-461) | Dextrothyroxine, sobetirome | — | MTPNSMTENGLTAWDKPKHCPDREHDWKLVGMSEACLH<br>RKSHSERRSTLKNEQSSPHLIQTTWTSSIFHLDHDDVN<br>DQSVSSAQTFQTEEKKCKGYIPSYLDKDELCVVCGDKA<br>TGYHYRCITCEGCKGFFRRTIQKNLHPSYSCKYEGKCV<br>IDKVTRNQCQECRFKKCIYVGMATDLVLDDSKRLAKRK<br>LIEENREKRRREELQKSIGHKPEPTDEEWELIKTVTEA<br>HVATNAQGSHWKQKRKFLPEDIGQAPIVNAPEGGKVDL<br>EAFSHFTKIITPAITRVVDFAKKLPMFCELPCEDQIIL<br>LKGCCMEIMSLRAAVRYDPESETLTLNGEMAVTRGQLK<br>NGGLGVVSDAIFDLGMSLSSFNLDDTEVALLQAVLLMS<br>SDRPGLACVERIEKYQDSFLLAFEHYINYRKHHVTHFW<br>PKLLMKVTDLRMIGACHASRFLHMKVECPTELFPPLFL<br>EVFED (SEQ ID NO: 26) |

TABLE 2-continued

Nuclear Hormone Receptors (ligand binding domains are underlined)

| Name | Agonists | Antagonists | Sequence |
|---|---|---|---|
| Retinoic acid receptor-α (NR1B1) (LBD at 183-417) | tretinoin, tazarotene, BMS753 (CAS 215307-86-1), tamibarotene, Ro 40-6055 (CAS 102121-60-8) | Ro 41-5253 ($pIC_{50}$ 6.3-7.2) (CAS 144092-31-9) | MASNSSSCPTPGGGHLNGYPVPPYAFFFPPMLGGLSPP<br>GALTTLQHQLPVSGYSTPSPATIETQSSSSEEIVPSPP<br>SPPPLPRIYKPCFVCQDKSSGYHYGVSACEGCKGFFRR<br>SIQKNMVYTCHRDKNCIINKVTRNRCQYCRLQKCFEVG<br>MSKESVRNDRNKKKKEVPKPECSESYTLTPEVGELIEK<br>VRKAHQETFPALCQLGKYTTNNSSEQRVSLDIDLWDKF<br>SELSTKCIIKTVEFAKQLPGFTTLTIADQITLLKAACL<br>DILILRICTRYTPEQDTMTFSDGLTLNRTQMHNAGFGP<br>LTDLVFAFANQLLPLEMDDAETGLLSAICLICGDRQDL<br>EQPDRVDMLQEPLLEALKVYVRKRRPSRPHMFPKMLMK<br>ITDLRSISAKGAERVITLKMEIPGSMPPLIQEMLENSE<br>GLDTLSGQPGGGGRDGGGLAPPPGSCSPSLSPSSNRSS<br>PATHSP (SEQ ID NO: 27) |
| Retinoic acid receptor-β (NR1B2) (LBD at 183-417) | tretinoin, tazarotene, adapalene, AC261066 (CAS 870773-76-5), AC55649 (CAS 59662-49-6) | — | MTTSGHACPVPAVNGHMTHYPATPYPLLFPPVIGGLSL<br>PPLHGLHGHPPPSGCSTPSPATIETQSTSSEELVPSPP<br>SPLPPPRVYKPCFVCQDKSSGYHYGVSACEGCKGFFRR<br>SIQKNMIYTCHRDKNCVINKVTRNRCQYCRLQKCFEVG<br>MSKESVRNDRNKKKKETSKQECTESYEMTAELDDLTEK<br>IRKAHQETFPSLCQLGKYTTNSSADHRVRLDLGLWDKF<br>SELATKCIIKIVEFAKRLPGFTGLTIADQITLLKAACL<br>DILILRICTRYTPEQDTMTFSDGLTLNRTQMHNAGFGP<br>LTDLVFTFANQLLPLEMDDTETGLLSAICLICGDRQDL<br>EEPTKVDKLQEPLLEALKIYIRKRRPSKPHMFPKILMK<br>ITDLRSISAKGAERVITLKMEIPGSMPPLIQEMLENSE<br>GHEPLTPSSSGNTAEHSPSISPSSVENSGVSQSPLVQ<br>(SEQ ID NO: 28) |
| Retinoic acid receptor-γ (NR1B3) (LBD at 185-419) | Tretinoin, tazarotene, adapalene, AHPN (CAS 125316-60-1) | MM 11253 (CAS 35952-44-5) | MATNKERLFAAGALGPGSGYPGAGFPFAFPGALRGSPP<br>FEMLSPSFRGLGQPDLPKEMASLSVETQSTSSEEMVPS<br>SPSPPPPPRVYKPCFVCNDKSSGYHYGVSSCEGCKGFF<br>RRSIQKNMVYTCHRDKNCIINKVTRNRCQYCRLQKCFE<br>VGMSKEAVRNDRNKKKKEVKEEGSPDSYELSPQLEELI<br>TKVSKAHQETFPSLCQLGKYTTNSSADHRVQLDLGLWD<br>KFSELATKCIIKIVEFAKRLPGFTGLSIADQITLLKAA<br>CLDILMLRICTRYTPEQDTMTFSDGLTLNRTQMHNAGF<br>GPLTDLVFAFAGQLLPLEMDDTETGLLSAICLICGDRM<br>DLEEPEKVDKLQEPLLEALRLYARRRRPSQPYMFPRML<br>MKITDLRGISTKGAERAITLKMEIPGPMPPLIREMLEN<br>PEMFEDDSSQPGPHPNASSEDEVPGGQGKGGLKSPA<br>(SEQ ID NO: 29) |
| Peroxisome proliferator-activated receptor-α (NR1C1) (LBD at 239-466) | GW7647 (CAS 265129-71-3), CP-775146 (CAS 702680-17-9), pirinixic acid, gemfibrozil | GW6471 ($pIC_{50}$ 6.6) (CAS 880635-03-0) | MVDTESPLCPLSPLEAGDLESPLSEEFLQEMGNIQEIS<br>QSIGEDSSGSFGFTEYQYLGSCPGSDGSVITDTLSPAS<br>SPSSVTYPVVPGSVDESPSGALNIECRICGDKASGYHY<br>GVHACEGCKGFFRRTIRLKLVYDKCDRSCKIQKKNRNK<br>CQYCRFHKCLSVGMSHNAIRFGRMPRSEKAKLKAEILT<br>CEHDIEDSETADLKSLAKRIYEAYLKNFNMNKVKARVI<br>LSGKASNNPPFVIHDMETLCMAEKTLVAKLVANGIQNK<br>EAEVRIFHCCQCTSVETVTELTEFAKAIPGFANLDLND<br>QVTLLKYGVYEAIFAMLSSVMNKDGMLVAYGNGFITRE<br>FLKSLRKPFCDIMEPKFDFAMKFNALELDDSDISLFVA<br>AIICCGDRPGLLNVGHIEKMQEGIVHVLRLHLQSNHPD<br>DIFLFPKLLQKMADLRQLVTEHAQLVQIIKKTESDAAL<br>HPLLQEIYRDMY (SEQ ID NO: 30) |
| Peroxisome proliferator-activated receptor-β/δ (NR1C2) (LBD at 211-439) | GW0742X (CAS 317318-84-6), GW501516 (CAS 317318-70-0) | GSK0660 ($pIC_{50}$ 6.5) (CAS 1014691-61-2) | MEQPQEEAPEVREEEEKEEVAEAEGAPELNGGPQHALP<br>SSSYTDLSRSSSPPSLLDQLQMGCDGASCGSLNMECRV<br>CGDKASGFHYGVHACEGCKGFFRRTIRMKLEYEKCERS<br>CKIQKKNRNKCQYCRFQKCLALGMSHNAIRFGRMPEAE<br>KRKLVAGLTANEGSQYNPQVADLKAFSKHIYNAYLKNF<br>NMTKKKARSILTGKASHTAPFVIHDIETLWQAEKGLVW<br>KQLVNGLPPYKEISVHVFYRCQCTTVETVRELTEFAKS<br>IPSFSSLFLNDQVTLLKYGVHEAIFAMLASIVNKDGLL<br>VANGSGFVTREFLRSLRKPFSDIIEPKFEFAVKFNALE<br>LDDSDLALFIAAIILCGDRPGLMNVPRVEAIQDTILRA<br>LEFHLQANHPDAQYLFPKLLQKMADLRQLVTEHAQMMQ<br>RIKKTETETSLHPLLQEIYKDMY (SEQ ID NO: 31) |
| Peroxisome proliferator-activated receptor-γ | GW1929 (CAS 1217446-21-1), | T0070907 ($pK_i$ 9) (CAS 313516-66-4), GW9662 | MGETLGDSPIDPESDSFTDTLSANISQEMTMVDTEMPF<br>WPTNFGISSVDLSVMEDHSHSFDIKPFTTVDFSSISTP<br>HYEDIPFTRTDPVVADYKYDLKLQEYQSAIKVEPASPP<br>YYSEKTQLYNKPHEEPSNSLMAIECRVCGDKASGFHYG |

TABLE 2-continued

| Nuclear Hormone Receptors (ligand binding domains are underlined) | | | |
|---|---|---|---|
| Name | Agonists | Antagonists | Sequence |
| (NR1C3)<br>(LBD at 238-503) | bardoxolone (Partial agonist), rosiglitazone, troglitazone, pioglitazone, ciglitazone | (Irreversible inhibition) ($pIC_{50}$ 8.1) (CAS 22978-25-2), CDDO-Me (Bardoxolone methyl) ($pK_i$ 6.9) | VHACEGCKGFFRRTIRLKLIYDRCDLNCRIHKKSRNKC<br>QYCRFQKCLAVGMSHNAIRFGRMPQAEKEKLLAEISSD<br>IDQLNPESADLRALAKHLYDSYIKSFPLTKAKARAILT<br>GKTTDKSPFVIYDMNSLMMGEDKIKFKHITPLQEQSKE<br>VAIRIFQGCQFRSVEAVQEITEYAKSIPGFVNLDLNDQ<br>VTLLKYGVHEIIYTMLASLMNKDGVLISEGQGFMTREF<br>LKSLRKPFGDFMEPKFEFAVKFNALELDDSDLAIFIAV<br>IILSGDRPGLLNVKPIEDIQDNLLQALELQLKLNHPES<br>SQLFAKLLQKMTDLRQIVTEHVQLLQVIKKTETDMSLH<br>PLLQEIYKDLY (SEQ ID NO: 32) |
| Rev-Erb-α<br>(NR1D1)<br>(LBD at 284-614) | Heme (endogenous), GSK4112 (CAS 1216744-19-2) | SR8278 ($pIC_{50}$ 6.5) (CAS 1254944-66-5) | MTTLDSNNNTGGVITYIGSSGSSPSRTSPESLYSDNSN<br>GSFQSLTQGCPTYFPPSPTGSLTQDPARSFGSIPPSLS<br>DDGSPSSSSSSSSSSSSFYNGSPPGSLQVAMEDSSRVS<br>PSKSTSNITKLNGMVLLCKVCGDVASGFHYGVHACEGC<br>KGFFRRSIQQNIQYKRCLKNENCSIVRINRNRCQQCRF<br>KKCLSVGMSRDAVRFGRIPKREKQRMLAEMQSAMNLAN<br>NQLSSQCPLETSPTQHPTPGPMGPSPPPAPVPSPLVGF<br>SQFPQQLTPPRSPSPEPTVEDVISQVARAHREIFTYAH<br>DKLGSSPGNFNANHASGSPPATTPHRWENQGCPPAPND<br>NNTLAAQRHNEALNGLRQAPSSYPPTWPPGPAHHSCHQ<br>SNSNGHRLCPTHVYAAPEGKAPANSPRQGNSKNVLLAC<br>PMNMYPHGRSGRTVQEIWEDFSMSFTPAVREVVEFAKH<br>IPGFRDLSQHDQVTLLKAGTFEVLMVRFASLFNVKDQT<br>VMFLSRTTYSLQELGAMGMGDLLSAMFDFSEKLNSLAL<br>TEEELGLFTAVVLVSADRSGMENSASVEQLQETLLRAL<br>RALVLKNRPLETSRFTKLLLKLPDLRTLNNMHSEKLLS<br>FRVDAQ (SEQ ID NO: 33) |
| Rev-Erb-β<br>(NR1D2)<br>(LBD at 369-579) | Heme (endogenous) | — | MEVNAGGVIAYISSSSSASSPASCHSEGSENSFQSSSS<br>SVPSSPNSSNSDTNGNPKNGDLANIEGILKNDRIDCSM<br>KTSKSSAPGMTKSHSGVTKFSGMVLLCKVCGDVASGFH<br>YGVHACEGCKGFFRRSIQQNIQYKKCLKNENCSIMRMN<br>RNRCQQCRFKKCLSVGMSRDAVRFGRIPKREKQRMLIE<br>MQSAMKTMMNSQFSGHLQNDTLVEHHEQTALPAQEQLR<br>PKPQLEQENIKSSSPPSSDFAKEEVIGMVTRAHKDTFM<br>YNQEQQENSAESMQPQRGERIPKNMEQYNLNHDHCGNG<br>LSSHFPCSESQQHLNGQFKGRNIMHYPNGHAICIANGH<br>CMNFSNAYTQRVCDRVPIDGFSQNENKNSYLCNTGGRM<br>HLVCPLSKSPYVDPHKSGHEIWEEFSMSFTPAVKEVVE<br>FAKRIPGFRDLSQHDQVNLLKAGTFEVLMVRFASLFDA<br>KERTVTFLSGKKYSVDDLHSMGAGDLLNSMFEFSEKLN<br>ALQLSDEEMSLFTAVVLVSADRSGIENVNSVEALQETL<br>IRALRTLIMKNHPNEASIFTKLLLKLPDLRSLNNMHSE<br>ELLAFKVHP (SEQ ID NO: 34) |
| RAR-related orphan receptor-α<br>(NR1F1)<br>(LBD at 272-510) | Cholesterol (endogenous), 7-hydroxycholesterol, cholesterol sulphate | — | MESAPAAPDPAASEPGSSGADAAAGSRETPLNQESARK<br>SEPPAPVRRQSYSSTSRGISVTKKTHTSQIEIIPCKIC<br>GDKSSGIHYGVITCEGCKGFFRRSQQSNATYSCPRQKN<br>CLIDRTSRNRCQHCRLQKCLAVGMSRDAVKFGRMSKKQ<br>RDSLYAEVQKHRMQQQQRDHQQQPGEAEPLTPTYNISA<br>NGLTELHDDLSNYIDGHTPEGSKADSAVSSFYLDIQPS<br>PDQSGLDINGIKPEPICDYTPASGFFPYCSFTNGETSP<br>TVSMAELEHLAQNISKSHLETCQYLREELQQITWQTFL<br>QEEIENYQNKQREVMWQLCAIKITEAIQYVVEFAKRID<br>GFMELCQNDQIVLLKAGSLEVVFIRMCRAFDSQNNTVY<br>FDGKYASPDVFKSLGCEDFISFVFEFGKSLCSMHLTED<br>EIALFSAFVLMSADRSWLQEKVKIEKLQQKIQLALQHV<br>LQKNHREDGILTKLICKVSTLRALCGRHTEKLMAFKAI<br>YPDIVRLHFPPLYKELFTSEFEPAMQIDG (SEQ ID NO: 35) |
| RAR-related orphan receptor-β<br>(NR1F2)<br>(LBD at 222-460) | — | — | MCENQLKTKADATAQIEVIPCKICGDKSSGIHYGVITC<br>EGCKGFFRRSQQNNASYSCPRQRNCLIDRTNRNRCQHC<br>RLQKCLALGMSRDAVKFGRMSKKQRDSLYAEVQKHQQR<br>LQEQRQQQSGEAEALARVYSSSISNGLSNLNNETSGTY<br>ANGHVIDLPKSEGYYNVDSGQPSPDQSGLDMTGIKQIK<br>QEPIYDLTSVPNLFTYSSFNNGQLAPGITMTEIDRIAQ<br>NIIKSHLETCQYTMEELHQLAWQTHTYEEIKAYQSKSR<br>EALWQQCAIQITHAIQYVVEFAKRITGFMELCQNDQIL<br>LLKSGCLEVVLVRMCRAFNPLNNTVLFEGKYGGMQMFK<br>ALGSDDLVNEAFDFAKNLCSLQLTEEEIALFSSAVLIS<br>PDRAWLIEPRKVQKLQEKIYFALQHVIQKNHLDDETLA<br>KLIAKIPTITAVCNLHGEKLQVFKQSHPEIVNTLFPPL<br>YKELFNPDCATGCK (SEQ ID NO: 36) |

TABLE 2-continued

Nuclear Hormone Receptors (ligand binding domains are underlined)

| Name | Agonists | Antagonists | Sequence |
|---|---|---|---|
| RAR-related<br>orphan<br>receptor-γ<br>(NR1F3)<br>(LBD at 269-<br>508) | — | — | MDRAPQRQHRASRELLAAKKTHTSQIEVIPCKICGDKS<br>SGIHYGVITCEGCKGFFRRSQRCNAAYSCTRQQNCPID<br>RTSRNRCQHCRLQKCLALGMSRDAVKFGRMSKKQRDSL<br>HAEVQKQLQQRQQQQQEPVVKTPPAGAQGADTLTYTLG<br>LPDGQLPLGSSPDLPEASACPPGLLKASGSGPSYSNNL<br>AKAGLNGASCHLEYSPERGKAEGRESFYSTGSQLTPDR<br>CGLRFEEHRHPGLGELGQGPDSYGSPSFRSTPEAPYAS<br>LTEIEHLVQSVCKSYRETCQLRLEDLLRQRSNIFSREE<br>VTGYQRKSMWEMWERCAHHLTEAIQYVVEFAKRLSGFM<br>ELCQNDQIVLLKAGAMEVVLVRMCRAYNADNRTVFFEG<br>KYGGMELFRALGCSELISSIFDFSHSLSALHFSEDEIA<br>LYTALVLINAHRPGLQEKRKVEQLQYNLELAFHHHLCK<br>THRQSILAKLPPKGKLRSLCSQHVERLQIFQHLHPIVV<br>QAAFPPLYKELFSTETESPVGLSK (SEQ ID NO:<br>37) |
| Farnesoid X<br>receptor<br>(NR1H4)<br>(LBD at 262-<br>486) | chenodeoxyc<br>holic acid,<br>lithocholic<br>acid,<br>deoxycholic<br>acid,<br>GW4064<br>(CAS 278779-<br>30-9),<br>obeticholic<br>acid,<br>fexaramine | guggulsterone<br>($pIC_{50}$ 5.7-<br>6) | MVMQFQGLENPIQISPHCSCTPSGFFMEMMSMKPAKGV<br>LTEQVAGPLGQNLEVEPYSQYSNVQFPQVQPQISSSSY<br>YSNLGFYPQQPEEWYSPGIYELRRMPAETLYQGETEVA<br>EMPVTKKPRMGASAGRIKGDELCVVCGDRASGYHYNAL<br>TCEGCKGFFRRSITKNAVYKCKNGGNCVMDMYMRRKCQ<br>ECRLRKCKEMGMLAECMYTGLLTEIQCKSKRLRKNVKQ<br>HADQTVNEDSEGRDLRQVTSTTKSCREKTELTPDQQTL<br>LHFIMDSYNKQRMPQEITNKILKEEFSAEENFLILTEM<br>ATNHVQVLVEFTKKLPGFQTLDHEDQIALLKGSAVEAM<br>FLRSAEIFNKKLPSGHSDLLEERIRNSGISDEYITPMF<br>SFYKSIGELKMTQEEYALLTAIVILSPDRQYIKDREAV<br>EKLQEPLLDVLQKLCKIHQPENPQHFACLLGRLTELRT<br>FNHHHAEMLMSWRVNDHKFTPLLCEIWDVQ (SEQ ID<br>NO: 38) |
| Farnesoid X<br>receptor-β<br>(NR1H5)<br>(Mouse)<br>(LBD at 248-<br>503) | Lanosterol<br>(endogenous,<br>mouse) | — | MANTYVATSDGYYLAEPTQYYDILPEQFHYQLCDTDFQ<br>EPPYCQYSTAQFPPALQSPSLQSHFNTHGLDPQYSGGS<br>WCGLDARESGQSTYVVVHDDEDEFPGAQRCRATCSLRW<br>KGQDDMLCMVCGDKASGYHYNALTCEGCKGFFRRSITK<br>NAVYSCKNGGHCEMDMYMRRKCQECRLKKCKAVGMLAE<br>CLLTEIQCKSKRLRKNFKHGPALYPAIQVEDEGADTKH<br>VSSSTRSGKGVQDNMTLTQEEHRLLNTIVTVHQKSMIP<br>LGETSKLLQEGSNPELSFLRLSEVSVLHIQGLMKFTKG<br>LPGFENLTTEDQAALQKASKTEVMFLHVAQLYGGKDST<br>SGSTMRPAKPSAGTLEVHNPSADESVHSPENFLKEGYP<br>SAPLTDITKEFIASLSYFYRRMSELHVSDTEYALLTAT<br>TVLFSDRPCLKNKQHIENLQEPVLQLLFKFSKMYHPED<br>PQHFAHLIGRLTELRTLSHSHSEILRMWKTKDPRLVML<br>FSEKWDLHSFS (SEQ ID NO: 39) |
| Liver X<br>receptor-α<br>(NR1H3)<br>(LBD at 209-<br>447) | 20S-<br>hydroxychole<br>sterol,<br>22R-<br>hydroxychole<br>sterol,<br>24(S)-<br>hydroxychole<br>sterol,<br>25-<br>hydroxychole<br>sterol,<br>27-<br>hydroxychole<br>sterol | — | MSLWLGAPVPDIPPDSAVELWKPGAQDASSQAQGGSSC<br>ILREEARMPHSAGGTAGVGLEAAEPTALLTRAEPPSEP<br>TEIRPQKRKKGPAPKMLGNELCSVCGDKASGFHYNVLS<br>CEGCKGFFRRSVIKGAHYICHSGGHCPMDTYMRRKCQE<br>CRLRKCRQAGMREECVLSEEQIRLKKLKRQEEEQAHAT<br>SLPPRASSPPQILPQLSPEQLGMIEKLVAAQQQCNRRS<br>FSDRLRVTPWPMAPDPHSREARQQRFAHFTELAIVSVQ<br>EIVDFAKQLPGFLQLSREDQIALLKTSAIEVMLLETSR<br>RYNPGSESITFLKDFSYNREDFAKAGLQVEFINPIFEF<br>SRAMNELQLNDAEFALLIAISIFSADRPNVQDQLQVER<br>LQHTYVEALHAYVSIHHPHDRLMFPRMLMKLVSLRTLS<br>SVHSEQVFALRLQDKKLPPLLSEIWDVHE (SEQ ID<br>NO: 40) |
| Liver X<br>receptor-β<br>(NR1H2)<br>(LBD at 222-<br>460) | 20S-<br>hydroxychole<br>sterol,<br>22R-<br>hydroxychole<br>sterol,<br>24(S)-<br>hydroxychole<br>sterol,<br>25- | — | MSSPTTSSLDTPLPGNGPPQPGAPSSSPTVKEEGPEPW<br>PGGPDPDVPGTDEASSACSTDWVIPDPEEEPERKRKKG<br>PAPKMLGHELCRVCGDKASGFHYNVLSCEGCKGFFRRS<br>VVRGGARRYACRGGGTCQMDAFMRRKCQQCRLRKCKEA<br>GMREQCVLSEEQIRKKKIRKQQQESQSQSQSPVGPQGS<br>SSSASGPGASPGGSEAGSQGSGEGEGVQLTAAQELMIQ<br>QLVAAQLQCNKRSFSDQPKVTPWPLGADPQSRDARQQR<br>FAHFTELAIISVQEIVDFAKQVPGFLQLGREDQIALLK<br>ASTIEIMLLETARRYNHETECITFLKDFTYSKDDFHRA<br>GLQVEFINPIFEFSRAMRRLGLDDAEYALLIAINIFSA |

TABLE 2-continued

| Name | Agonists | Antagonists | Sequence |
| --- | --- | --- | --- |
| Nuclear Hormone Receptors (ligand binding domains are underlined) | | | |
| | hydroxycholesterol, 27-hydroxycholesterol | | DRPNVQEPGRVEALQQPYVEALLSYTRIKRPQDQLRFPRMLMKLVSLRTLSSVHSEQVFALRLQDKKLPPLLSEIWDVHE (SEQ ID NO: 41) |
| Vitamin D receptor (NR1\|1) (LBD at 127-423) | 1,25-dihydroxyvitamin D3 (endogenous), seocalcitol, doxercalciferol | TEI-9647 ($pIC_{50}$ 8.2) (Chicken) (CAS 173388-20-0), ZK159222 ($pIC_{50}$ 7.5) | MEAMAASTSLPDPGDFDRNVPRICGVCGDRATGFHFNAMTCEGCKGFFRRSMKRKALFTCPFNGDCRITKDNRRHCQACRLKRCVDIGMMKEFILTDEEVQRKREMILKRKEEEALKDSLRPKLSEEQQRIIAILLDAHHKTYDPTYSDFCQFRPPVRVNDGGGSHPSRPNSRHTPSFSGDSSSSCSDHCITSSDMMDSSSFSNLDLSEEDSDDPSVTLELSQLSMLPHLADLVSYSIQKVIGFAKMIPGFRDLTSEDQIVLLKSSAIEVIMLRSNESFTMDDMSWTCGNQDYKYRVSDVTKAGHSLELIEPLIKFQVGLKKLNLHEEEHVLLMAICIVSPDRPGVQDAALIEAIQDRLSNTLQTYIRCRHPPPGSHLLYAKMIQKLADLRSLNEEHSKQYRCLSFQPECSMKLTPLVLEVFGNEIS (SEQ ID NO: 42) |
| Pregnane X receptor (NR1\|2) (LBD at 146-433) | 17β-estradiol (endogenous), hyperforin, 5β-pregnane-3,20-dione, lovastatin, rifampicin | — | MEVRPKESWNHADFVHCEDTESVPGKPSVNADEEVGGPQICRVCGDKATGYHFNVMTCEGCKGFFRRAMKRNARLRCPFRKGACEITRKTRRQCQACRLRKCLESGMKKEMIMSDEAVEERRALIKRKKSERTGTQPLGVQGLTEEQRMMIRELMDAQMKTFDTTFSHFKNFRLPGVLSSGCELPESLQAPSREEAAKWSQVRKDLCSLKVSLQLRGEDGSVWNYKPPADSGGKEIFSLLPHMADMSTYMFKGIISFAKVISYFRDLPIEDQISLLKGAAFELCQLRFNTVFNAETGTWECGRLSYCLEDTAGGFQQLLLEPMLKFHYMLKKLQLHEEEYVLMQAISLFSPDRPGVLQHRVVDQLQEQFAITLKSYIECNRPQPAHRFLFLKIMAMLTELRSINAQHTQRLLRIQDIHPFATPLMQELFGITGS (SEQ ID NO: 43) |
| Constitutive androstane receptor (NR1\|3) (LBD at 109-352) | TCPOBOP (Mouse) (CAS 76150-91-9), CITCO (CAS 338408-52-7) | Lotrimazole, T0901317 (CAS 293754-55-9) | MASREDELRNCVVCGDQATGYHFNALTCEGCKGFFRRTVSKSIGPTCPFAGSCEVSKTQRRHCPACRLQKCLDAGMRKDMILSAEALALRRAKQAQRRAQQTPVQLSKEQEELIRTLLGAHTRHMGTMFEQFVQFRPPAHLFIHHQPLPTLAPVLPLVTHFADINTFMVLQVIKFTKDLPVFRSLPIEDQISLLKGAAVEICHIVLNTTFCLQTQNFLCGPLRYTIEDGARVSPTVGFQVEFLELLFHFHGTLRKLQLQEPEYVLLAAMALFSPDRPGVTQRDEIDQLQEEMALTLQSYIKGQQRRPRDRFLYAKLLGLLAELRSINEAYGYQIQHIQGLSAMMPLLQEICS (SEQ ID NO: 44) |
| Hepatocyte nuclear factor-4-α (NR2A1) (LBD at 147-377) | linoleic acid | BI6015 (CAS 93987-29-2) | MRLSKTLVDMDMADYSAALDPAYTTLEFENVQVLTMGNDTSPSEGTNLNAPNSLGVSALCAICGDRATGKHYGASSCDGCKGFFRRSVRKNHMYSCRFSRQCVVDKDKRNQCRYCRLKKCFRAGMKKEAVQNERDRISTRRSSYEDSSLPSINALLQAEVLSRQITSPVSGINGDIRAKKIASIADVCESMKEQLLVLVEWAKYIPAFCELPLDDQVALLRAHAGEHLLLGATKRSMVFKDVLLLGNDYIVPRHCPELAEMSRVSIRILDELVLPFQELQIDDNEYAYLKAIIFFDPDAKGLSDPGKIKRLRSQVQVSLEDYINDRQYDSRGRFGELLLLLPTLQSITWQMIEQIQFIKLFGMAKIDNLLQEMLLGGSPSDAPHAHHPLHPHLMQEHMGTNVIVANTMPTHLSNGQMCEWPRPRGQAATPETPQPSPPGGSGSEPYKLLPGAVATIVKPLSAIPQPTITKQEVI (SEQ ID NO: 45) |
| Hepatocyte nuclear factor-4-γ (NR2A2) (LBD at 99-328) | — | — | MNTTDNGVNCLCAICGDRATGKHYGASSCDGCKGFFRRSIRKSHVYSCRFSRQCVVDKDKRNQCRYCRLRKCFRAGMKKEAVQNERDRISTRRSTFDGSNIPSINTLAQAEVRSRQISVSSPGSSTDINVKKIASIGDVCESMKQQLLVLVEWAKYIPAFCELPLDDQVALLRAHAGEHLLLGATKRSMMYKDILLLGNNYVIHRNSCEVEISRVANRVLDELVRPFQEIQIDDNEYACLKAIVFFDPDAKGLSDPVKIKNMRFQVQIGLEDYINDRQYDSRGRFGELLLLLPTLQSITWQMIEQIQFVKLFGMVKIDNLLQEMLLGGASNDGSHLHHPMHPHLSQDPLTGQTILLGPMSTLVHADQISTPETPLPSPPQGSGQEQYKIAANQASVISHQHLSKQKQL (SEQ ID NO: 46) |
| Retinoid X receptor-α (NR2B1) (LBD at 227-458) | Bexarotene, CD3254 (CAS 196961-43-0) | — | MDTKHFLPLDFSTQVNSSLTSPTGRGSMAAPSLHPSLGPGIGSPGQLHSPISTLSSPINGMGPPFSVISSPMGPHSMSVPTTPTLGFSTGSPQLSSPMNPVSSSEDIKPPLGLNGVLKVPAHPSGNMASFTKHICAICGDRSSGKHYGVYSCEGCKGFFKRTVRKDLTYTCRDNKDCLIDKRQRNRCQYCRYQKCLAMGMKREAVQEERQRGKDRNENEVESTSSANE |

TABLE 2-continued

| Nuclear Hormone Receptors (ligand binding domains are underlined) | | | |
|---|---|---|---|
| Name | Agonists | Antagonists | Sequence |
| | | | DMPVERILEAELAVEPKTETYVEANMGLNPSSPNDPVT<br>NICQAADKQLFTLVEWAKRIPHFSELPLDDQVILLRAG<br>WNELLIASFSHRSIAVKDGILLATGLHVHRNSAHSAGV<br>GAIFDRVLTELVSKMRDMQMDKTELGCLRAIVLFNPDS<br>KGLSNPAEVEALREKVYASLEAYCKHKYPEQPGRFAKL<br>LLRLPALRSIGLKCLEHLFFFKLIGDTPIDTFLMEMLE<br>APHQMT (SEQ ID NO: 47) |
| Retinoid X receptor-β (NR2B2) (LBD at 296-529) | Bexarotene | — | MSWAARPPFLPQRHAAGQCGPVGVRKEMHCGVASRWRR<br>RRPWLDPAAAAAAAVAGGEQQTPEPEPGEAGRDGMGDS<br>GRDSRSPDSSSPNPLPQGVPPPSPPGPPLPPSTAPSLG<br>GSGAPPPPPMPPPPLGSPFPVISSSMGSPGLPPPAPPG<br>FSGPVSSPQINSTVSLPGGGSGPPEDVKPPVLGVRGLH<br>CPPPPGGPGAGKRLCAICGDRSSGKHYGVYSCEGCKGF<br>FKRTIRKDLTYSCRDNKDCTVDKRQRNRCQYCRYQKCL<br>ATGMKREAVQEERQRGKDKDGDGEGAGGAPEEMPVDRI<br>LEAELAVEQKSDQGVEGPGGTGGSGSSPNDPVTNICQA<br>ADKQLFTLVEWAKRIPHFSSLPLDDQVILLRAGWNELL<br>IASFSHRSIDVRDGILLATGLHVHRNSAHSAGVGAIFD<br>RVLTELVSKMRDMRMDKTELGCLRAIILFNPDAKGLSN<br>PSEVEVLREKVYASLETYCKQKYPEQQGRFAKLLLRLP<br>ALRSIGLKCLEHLFFFKLIGDTPIDTFLMEMLEAPHQL<br>A (SEQ ID NO: 48) |
| Retinoid X receptor-γ (NR2B3) (LBD at 231-459) | Bexarotene | — | MYGNYSHFMKFPAGYGGSPGHTGSTSMSPSAALSTGKP<br>MDSHPSYTDTPVSAPRTLSAVGTPLNALGSPYRVITSA<br>MGPPSGALAAPPGINLVAPPSSQLNVVNSVSSSEDIKP<br>LPGLPGIGNMNYPSTSPGSLVKHICAICGDRSSGKHYG<br>VYSCEGCKGFFKRTIRKDLIYTCRDNKDCLIDKRQRNR<br>CQYCRYQKCLVMGMKREAVQEERQRSRERAESEAECAT<br>SGHEDMPVERILEAELAVEPKTESYGDMNMENSTNDPV<br>TNICHAADKQLFTLVEWAKRIPHFSDLTLEDQVILLRA<br>GWNELLIASFSHRSVSVQDGILLATGLHVHRSSAHSAG<br>VGSIFDRVLTELVSKMKDMQMDKSELGCLRAIVLFNPD<br>AKGLSNPSEVETLREKVYATLEAYTKQKYPEQPGRFAK<br>LLLRLPALRSIGLKCLEHLFFFKLIGDTPIDTFLMEML<br>ETPLQIT (SEQ ID NO: 49) |
| Testicular receptor 2 (NR2C1) (LBD at 348-590) | — | — | MATIEEIAHQIIEQQMGEIVTEQQTGQKIQIVTALDHN<br>TQGKQFILTNHDGSTPSKVILARQDSTPGKVFLTTPDA<br>AGVNQLFFTTPDLSAQHLQLLTDNSPDQGPNKVFDLCV<br>VCGDKASGRHYGAVTCEGCKGFFKRSIRKNLVYSCRGS<br>KDCIINKHHRNRCQYCRLQRCIAFGMKQDSVQCERKPI<br>EVSREKSSNCAASTEKIYIRKDLRSPLTATPTFVTDSE<br>STRSTGLLDSGMFMNIHPSGVKTESAVLMTSDKAESCQ<br>GDLSTLANVVTSLANLGKTKDLSQNSNEMSMIESLSND<br>DTSLCEFQEMQTNGDVSRAFDTLAKALNPGESTACQSS<br>VAGMEGSVHLITGDSSINYTEKEGPLLSDSHVAFRLTM<br>PSPMPEYLNVHYIGESASRLLFLSMHWALSIPSFQALG<br>QENSISLVKAYWNELFTLGLAQCWQVMNVATILATFVN<br>CLHNSLQQDKMSTERRKLLMEHIFKLQEFCNSMVKLCI<br>DGYEYAYLKAIVLFSPDHPSLENMEQIEKFQEKAYVEF<br>QDYITKTYPDDTYRLSRLLLRLPALRLMNATITEELFF<br>KGLIGNIRIDSVIPHILKMEPADYNSQIIGHSI (SEQ<br>ID NO: 50) |
| Testicular receptor 4 (NR2C2) (LBD at 341-583) | retinol (endogenous), tretinoin (endogenous) | | MTSPSPRIQIISTDSAVASPQRIQIVTDQQTGQKIQIV<br>TAVDASGSPKQQFILTSPDGAGTGKVILASPETSSAKQ<br>LIFTTSDNLVPGRIQIVTDSASVERLLGKTDVQRPQVV<br>EYCVVCGDKASGRHYGAVSCEGCKGFFKRSVRKNLTYS<br>CRSNQDCIINKHHRNRCQFCRLKKCLEMGMKMESVQSE<br>RKPFDVQREKPSNCAASTEKIYIRKDLRSPLIATPTFV<br>ADKDGARQTGLLDPGMLVNIQQPLIREDGTVLLATDSK<br>AETSQGALGTLANVVTSLANLSESLNNGDTSEIQPEDQ<br>SASEITRAFDTLAKALNTTDSSSSPSLADGIDTSGGGS<br>IHVISRDQSTPIIEVEGPLLSDTHVTFKLTMPSPMPEY<br>LNVHYICESASRLLFLSMHWARSIPAFQALGQDCNTSL<br>VRACWNELFTLGLAQCAQVMSLSTILAAIVNHLQNSIQ<br>EDKLSGDRIKQVMEHIWKLQEFCNSMAKLDIDGYEYAY<br>LKAIVLFSPDHPGLTSTSQIEKFQEKAQMELQDYVQKT<br>YSEDTYRLARILVRLPALRLMSSNITEELFFTGLIGNV<br>SIDSIIPYILKMETAEYNGQITGASL (SEQ ID NO:<br>51) |

TABLE 2-continued

| Nuclear Hormone Receptors (ligand binding domains are underlined) | | | |
|---|---|---|---|
| Name | Agonists | Antagonists | Sequence |
| TLX (NR2E1) (LBD at 155-383) | — | — | MSKPAGSTSRILDIPCKVCGDRSSGKHYGVYACDGCSG<br>FFKRSIRRNRTYVCKSGNQGGCPVDKTHRNQCRACRLK<br>KCLEVNMNKDAVQHERGPRTSTIRKQVALYFRGHKEEN<br>GAAAHFPSAALPAPAFFTAVTQLEPHGLELAAVSTTPE<br>RQTLVSLAQPTPKYPHEVNGTPMYLYEVATESVCESAA<br>RLLFMSIKWAKSVPAFSTLSLQDQLMLLEDAWRELFVL<br>GIAQWAIPVDANTLLAVSGMNGDNTDSQKLNKIISEIQ<br>ALQEVVARFRQLRLDATEFACLKCIVTFKAVPTHSGSE<br>LRSFRNAAAIAALQDEAQLTLNSYTHTRYPTQPCRFGK<br>LLLLLPALRSISPSTIEEVFFKKTIGNVPITRLLSDMY<br>KSSDI (SEQ ID NO: 52) |
| PNR (NR2E3) (LBD at 169-410) | — | — | METRPTALMSSTVAAAAPAAGAASRKESPGRWGLGEDP<br>TGVSPSLQCRVCGDSSSGKHYGIYACNGCSGFFKRSVR<br>RRLIYRCQVGAGMCPVDKAHRNQCQACRLKKCLQAGMN<br>QDAVQNERQPRSTAQVHLDSMESNTESRPESLVAPPAP<br>AGRSPRGPTPMSAARALGHHFMASLITAETCAKLEPED<br>ADENIDVTSNDPEFPSSPYSSSSPCGLDSTHETSARLL<br>FMAVKWAKNLPVFSSLPFRDQVILLEEAWSELFLLGAI<br>QWSLPLDSCPLLAPPEASAAGGAQGRLTLASMETRVLQ<br>ETISRFRALAVDPTEFACMKALVLFKPETRGLKDPEHV<br>EALQDQSQVMLSQHSKAHHPSQPVRFGKLLLLLPSLRF<br>ITAERIELLFFRKTIGNTPMEKLLCDMFKN (SEQ ID<br>NO: 53) |
| COUP transcription factor 1 (NR2F1) (LBD at 184-410) | — | — | MAMVVSSWRDPQDDVAGGNPGGPNPAAQAARGGGGGAG<br>EQQQQAGSGAPHTPQTPGQPGAPATPGTAGDKGQGPPG<br>SGQSQQHIECVVCGDKSSGKHYGQFTCEGCKSFFKRSV<br>RRNLTYTCRANRNCPIDQHHRNQCQYCRLKKCLKVGMR<br>REAVQRGRMPPTQPNPGQYALTNGDPLNGHCYLSGYIS<br>LLLRAEPYPTSRYGSQCMQPNNIMGIENICELAARLLF<br>SAVEWARNIPFFPDLQITDQVSLLRLTWSELFVLNAAQ<br>CSMPLHVAPLLAAAGLHASPMSADRVVAFMDHIRIFQE<br>QVEKLKALHVDSAEYSCLKAIVLFTSDACGLSDAAHIE<br>SLQEKSQCALEEYVRSQYPNQPSRFGKLLLRLPSLRTV<br>SSSVIEQLFFVRLVGKTPIETLIRDMLLSGSSFNWPYM<br>SIQCS (SEQ ID NO: 54) |
| COUP transcription factor 2 (NR2F2) (LBD at 177-403) | — | — | MAMVVSTWRDPQDEVPGSQGSQASQAPPVPGPPPGAPH<br>TPQTPGQGGPASTPAQTAAGGQGGPGGPGSDKQQQQQH<br>IECVVCGDKSSGKHYGQFTCEGCKSFFKRSVRRNLSYT<br>CRANRNCPIDQHHRNQCQYCRLKKCLKVGMRREAVQRG<br>RMPPTQPTHGQFALTNGDPLNCHSYLSGYISLLLRAEP<br>YPTSRFGSQCMQPNNIMGIENICELAARMLFSAVEWAR<br>NIPFFPDLQITDQVALLRLTWSELFVLNAAQCSMPLHV<br>APLLAAAGLHASPMSADRVVAFMDHIRIFQEQVEKLKA<br>LHVDSAEYSCLKAIVLFTSDACGLSDVAHVESLQEKSQ<br>CALEEYVRSQYPNQPTRFGKLLLRLPSLRTVSSSVIEQ<br>LFFVRLVGKTPIETLIRDMLLSGSSFNWPYMAIQ<br>(SEQ ID NO: 55) |
| V-erbA-related gene (NR2F6) (LBD at 165-393) | — | — | MAMVTGGWGGPGGDTNGVDKAGGYPRAAEDDSASPPGA<br>ASDAEPGDEERPGLQVDCVVCGDKSSGKHYGVFTCEGC<br>KSFFKRSIRRNLSYTCRSNRDCQIDQHHRNQCQYCRLK<br>KCFRVGMRKEAVQRGRIPHSLPGAVAASSGSPPGSALA<br>AVASGGDLFPGQPVSELIAQLLRAEPYPAAAGRFGAGG<br>GAAGAVLGIDNVCELAARLLFSTVEWARHAPFFPELPV<br>ADQVALLRLSWSELFVLNAAQAALPLHTAPLLAAAGLH<br>AAPMAAERAVAFMDQVRAFQEQVDKLGRLQVDSAEYGC<br>LKAIALFTPDACGLSDPAHVESLQEKAQVALTEYVRAQ<br>YPSQPQRFGRLLLRLPALRAVPASLISQLFFMRLVGKT<br>PIETLIRDMLLSGSTFNWPYGSGQ (SEQ ID NO:<br>56) |
| Estrogen-related receptor-α (NR3B1) (LBD at 193-421) | GSK4716 (CAS 101574-65-6) | XCT790 (CAS 725247-18-7) | MSSQVVGIEPLYIKAEPASPDSPKGSSETETEPPVALA<br>PGPAPTRCLPGHKEEEDGEGAGPGEQGGGKLVLSSLPK<br>RLCLVCGDVASGYHYGVASCEACKAFFKRTIQGSIEYS<br>CPASNECEITKRRRKACQACRFTKCLRVGMLKEGVRLD<br>RVRGGRQKYKRRPEVDPLPFPGPFPAGPLAVAGGPRKT<br>AAPVNALVSHLLVVEPEKLYAMPDPAGPDGHLPAVATL<br>CDLFDREIVVTISWAKSIPGFSSLSLSDQMSVLQSVWM<br>EVLVLGVAQRSLPLQDELAFAEDLVLDEEGARAAGLGE |

TABLE 2-continued

Nuclear Hormone Receptors (ligand binding domains are underlined)

| Name | Agonists | Antagonists | Sequence |
| --- | --- | --- | --- |
| | | | LGAALLQLVRRLQALRLEREEYVLLKALALANSDSVHIEDAEAVEQLREALHEALLEYEAGRAGPGGGAERRRAGRLLLTLPLLRQTAGKVLAHFYGVKLEGKVPMHKLFLEMLEAMMD (SEQ ID NO: 57) |
| Estrogen-related receptor-β (NR3B2) (LBD at 208-432) | DY131 (CAS 95167-41-2) | — | MSSDDRHLGSSCGSFIKTEPSSPSSGIDALSHHSPSGSSDASGGFGLALGTHANGLDSPPMFAGAGLGGTPCRKSYEDCASGIMEDSAIKCEYMLNAIPKRLCLVCGDIASGYHYGVASCEACKAFFKRTIQGNIEYSCPATNECEITKRRRKSCQACRFMKCLKVGMLKEGVRLDRVRGGRQKYKRRLDSESSPYLSLQISPPAKKPLTKIVSYLLVAEPDKLYAMPPPGMPEGDIKALTTLCDLADRELVVIIGWAKHIPGFSSLSLGDQMSLLQSAWMEILILGIVYRSLPYDDKLVYAEDYIMDEEHSRLAGLLELYRAILQLVRRYKKLKVEKEEFVTLKALALANSDSMYIEDLEAVQKLQDLLHEALQDYELSQRHEEPWRTGKLLLTLPLLRQTAAKAVQHFYSVKLQGKVPMHKLFLEMLEAKV (SEQ ID NO: 58) |
| Estrogen-related receptor-γ (NR3B3) (LBD at 233-457) | DY131 (CAS 95167-41-2) | — | MDSVELCLPESFSLHYEEELLCRMSNKDRHIDSSCSSFIKTEPSSPASLTDSVNHHSPGGSSDASGSYSSTMNGHQNGLDSPPLYPSAPILGGSGPVRKLYDDCSSTIVEDPQTKCEYMLNSMPKRLCLVCGDIASGYHYGVASCEACKAFFKRTIQGNIEYSCPATNECEITKRRRKSCQACRFMKCLKVGMLKEGVRLDRVRGGRQKYKRRIDAENSPYLNPQLVQPAKKPYNKIVSHLLVAEPEKIYAMPDPTVPDSDIKALTTLCDLADRELVVIIGWAKHIPGFSTLSLADQMSLLQSAWMEILILGVVYRSLSFEDELVYADDYIMDEDQSKLAGLLDLNNAILQLVKKYKSMKLEKEEFVTLKAIALANSDSMHIEDVEAVQKLQDVLHEALQDYEAGQHMEDPRRAGKMLMTLPLLRQTSTKAVQHFYNIKLEGKVPMHKLFLEMLEAKV (SEQ ID NO: 59) |
| Nerve Growth factor IB (NR4A1) (LBD at 360-595) | cytosporone B (endogenous) | — | MPCIQAQYGTPAPSPGPRDHLASDPLTPEFIKPTMDLASPEAAPAAPTALPSFSTFMDGYTGEFDTFLYQLPGTVQPCSSASSSASSTSSSSATSPASASFKFEDFQVYGCYPGPLSGPVDEALSSSGSDYYGSPCSAPSPSTPSFQPPQLSPWDGSFGHFSPSQTYEGLRAWTEQLPKASGPPQPPAFFSFSPPTGPSPSLAQSPLKLFPSQATHQLGEGESYSMPTAFPGLAPTSPHLEGSGILDTPVTSTKARSGAPGGSEGRCAVCGDNASCQHYGVRTCEGCKGFFKRTVQKNAKYICLANKDCPVDKRRRNRCQFCRFQKCLAVGMVKEVVRTDSLKGRRGRLPSKPKQPPDASPANLLTSLVRAHLDSGPSTAKLDYSKFQELVLPHFGKEDAGDVQQFYDLLSGSLEVIRKWAEKIPGFAELSPADQDLLLESAFLELFILRLAYRSKPGEGKLIFCSGLVLHRLQCARGFGDWIDSILAFSRSLHSLLVDVPAFACLSALVLITDRHGLQEPRRVEELQNRIASCLKEHVAAVAGEPQPASCLSRLLGKLPELRTLCTQGLQRIFYLKLEDLVPPPPIIDKIFMDTLPF (SEQ ID NO: 60) |
| Nuclear receptor related 1 (NR4A2) (LBD at 360-595) | — | — | MPCVQAQYGSSPQGASPASQSYSYHSSGEYSSDFLTPEFVKFSMDLTNTEITATTSLPSFSTFMDNYSTGYDVKPPCLYQMPLSGQQSSIKVEDIQMHNYQQHSHLPPQSEEMMPHSGSVYYKPSSPPTPTTPGFQVQHSPMWDDPGSLHNFHQNYVATTHMIEQRKTPVSRLSLFSFKQSPPGTPVSSCQMRFDGPLHVPMNPEPAGSHHVVDGQTFAVPNPIRKPASMGFPGLQIGHASQLLDTQVPSPPSRGSPSNEGLCAVCGDNAACQHYGVRTCEGCKGFFKRTVQKNAKYVCLANKNCPVDKRRRNRCQYCRFQKCLAVGMVKEVVRTDSLKGRRGRLPSKPKSPQEPSPPSPPVSLISALVRAHVDSNPAMTSLDYSRFQANPDYQMSGDDTQHIQQFYDLLTGSMEIIRGWAEKIPGFADLPKADQDLLFESAFLELFVLRLAYRSNPVEGKLIFCNGVVLHRLQCVRGFGEWIDSIVEFSSNLQNMNIDISAFSCIAALAMVTERHGLKEPKRVEELQNKIVNCLKDHVTFNNGGLNRPNYLSKLLGKLPELRTLCTQGLQRIFYLKLEDLVPPPAIIDKLFLDTLPF (SEQ ID NO: 61) |
| Neuron-derived orphan receptor 1 (NR4A3) (LBD at 394-623) | — | — | MPCVQAQYSPSPPGSSYAAQTYSSEYTTEIMNPDYTKLTMDLGSTEITATATTSLPSISTFVEGYSSNYELKPSCVYQMQRPLIKVEEGRAPSYHHHHHHHHHHHHHHQQQHQQPSIPPASSPEDEVLPSTSMYFKQSPPSTPTTPAFPPQAGALWDEALPSAPGCIAPGPLLDPPMKAVPTVAGARFPLFHFKPSPPHPPAPSPAGGHHLGYDPTAAAALSLPLGAAAAAGSQAAALESHPYGLPLAKRAAPLAFPPLGLTPSPTASSLLGESPSLPSPPSRSSSSGEGTCAVCGDNAACQHY |

TABLE 2-continued

| Nuclear Hormone Receptors (ligand binding domains are underlined) | | | |
|---|---|---|---|
| Name | Agonists | Antagonists | Sequence |
| | | | GVRTCEGCKGFFKRTVQKNAKYVCLANKNCPVDKRRRN<br>RCQYCRFQKCLSVGMVKEVVRTDSLKGRRGRLPSKPKS<br>PLQQEPSQPSPPSPPICMMNALVRALTDSTPRDLDYSR<br>YCPTDQAAAGTDAEHVQQFYNLLTASIDVSRSWAEKIP<br>GFTDLPKEDQTLLIESAFLELFVLRLSIRSNTAEDKFV<br>FCNGLVLHRLQCLRGFGEWLDSIKDFSLNLQSLNLDIQ<br>ALACLSALSMITERHGLKEPKRVEELCNKITSSLKDHQ<br>SKGQALEPTESKVLGALVELRKICTLGLQRIFYLKLED<br>LVSPPSIIDKLFLDTLPF (SEQ ID NO: 62) |
| Steroidogenic<br>factor 1<br>(NR5A1)<br>(LBD at 22-<br>459) | — | AC45594<br>(CAS 13037-<br>86-0),<br>SID7969543<br>(CAS 868224-<br>64-0) | MDYSYDEDLDELCPVCGDKVSGYHYGLLTCESCKGFFK<br>RTVQNNKHYTCTESQSCKIDKTQRKRCPFCRFQKCLTV<br>GMRLEAVRADRMRGGRNKFGPMYKRDRALKQQKKAQIR<br>ANGFKLETGPPMGVPPPPPPAPDYVLPPSLHGPEPKGL<br>AAGPPAGPLGDFGAPALPMAVPGAHGPLAGYLYPAFPG<br>RAIKSEYPEPYASPPQPGLPYGYPEPFSGGPNVPELIL<br>QLLQLEPDEDQVRARILGCLQEPTKSRPDQPAAFGLLC<br>RMADQTFISIVDWARRCMVFKELEVADQMTLLQNCWSE<br>LLVFDHIYRQVQHGKEGSILLVTGQEVELTTVATQAGS<br>LLHSLVLRAQELVLQLLALQLDRQEFVCLKFIILFSLD<br>LKFLNNHILVKDAQEKANAALLDYTLCHYPHCGDKFQQ<br>LLLCLVEVRALSMQAKEYLYHKHLGNEMPRNNLLIEML<br>QAKQT (SEQ ID NO: 63) |
| Liver<br>receptor<br>homolog-1<br>(NR5A2)<br>(LBD at 300-<br>539) | — | — | MSSNSDTGDLQESLKHGLTPIGAGLPDRHGSPIPARGR<br>LVMLPKVETEALGLARSHGEQGQMPENMQVSQFKMVNY<br>SYDEDLEELCPVCGDKVSGYHYGLLTCESCKGFFKRTV<br>QNNKRYTCIENQNCQIDKTQRKRCPYCRFQKCLSVGMK<br>LEAVRADRMRGGRNKFGPMYKRDRALKQQKKALIRANG<br>LKLEAMSQVIQAMPSDLTISSAIQNIHSASKGLPLNHA<br>ALPPTDYDRSPFVTSPISMTMPPHGSLQGYQTYGHFPS<br>RAIKSEYPDPYTSSPESIMGYSYMDSYQTSSPASIPHL<br>ILELLKCEPDEPQVQAKIMAYLQQEQANRSKHEKLSTF<br>GLMCKMADQTLFSIVEWARSSIFFRELKVDDQMKLLQN<br>CWSELLILDHIYRQVVHGKEGSIFLVTGQQVDYSIIAS<br>QAGATLNNLMSHAQELVAKLRSLQFDQREFVCLKFLVL<br>FSLDVKNLENFQLVEGVQEQVNAALLDYTMCNYPQQTE<br>KFGQLLLRLPEIRAISMQAEEYLYYKHLNGDVPYNNLL<br>IEMLHAKRA (SEQ ID NO: 64) |
| Germ cell<br>nuclear<br>factor<br>(NR6A1)<br>(LBD at 249-<br>480) | — | — | MERDEPPPSGGGGGGGSAGFLEPPAALPPPPRNGFCQD<br>ELAELDPGTISVSDDRAEQRTCLICGDRATGLHYGIIS<br>CEGCKGFFKRSICNKRVYRCSRDKNCVMSRKQRNRCQY<br>CRLLKCLQMGMNRKAIREDGMPGGRNKSIGPVQISEEE<br>IERIMSGQEFEEEANHWSNHGDSDHSSPGNRASESNQP<br>SPGSTLSSSRSVELNGFMAFREQYMGMSVPPHYQYIPH<br>LFSYSGHSPLLPQQARSLDPQSYSLIHQLLSAEDLEPL<br>GTPMLIEDGYAVTQAELFALLCRLADELLFRQIAWIKK<br>LPFFCELSIKDYTCLLSSTWQELILLSSLTVYSKQIFG<br>ELADVTAKYSPSDEELHRFSDEGMEVIERLIYLYHKFH<br>QLKVSNEEYACMKAINFLNQDIRGLTSASQLEQLNKRY<br>WYICQDFTEYKYTHQPNRFPDLMMCLPEIRYIAGKMVN<br>VPLEQLPLLFKVVLHSCKTSVGKE (SEQ ID NO:<br>65) |
| DAX1<br>(NR0B1)<br>(LBD at 205-<br>469) | — | — | MAGENHQWQGSILYNMLMSAKQTRAAPEAPETRLVDQC<br>WGCSCGDEPGVGREGLLGGRNVALLYRCCFCGKDHPRQ<br>GSILYSMLTSAKQTYAAPKAPEATLGPCWGCSCGSDPG<br>VGRAGLPGGRPVALLYRCCFCGEDHPRQGSILYSLLTS<br>SKQTHVAPAAPEARPGGAWWDRSYFAQRPGGKEALPGG<br>RATALLYRCCFCGEDHPQQGSTLYCVPTSTNQAQAAPE<br>ERPRAPWWDTSSGALRPVALKSPQVVCEAASAGLLKTL<br>RFVKYLPCFQVLPLDQQLVLVRNCWASLLMLELAQDRL<br>QFETVEVSEPSMLQKILTTRRRETGGNEPLPVPTLQHH<br>LAPPAEARKVPSASQVQAIKCFLSKCWSLNISTKEYAY<br>LKGTVLFNPDVPGLQCVKYIQGLQWGTQQILSEHTRMT<br>HQGPHDRFIELNSTLFLLRFINANVIAELFFRPIIGTV<br>SMDDMMLEMLCTKI (SEQ ID NO: 66) |

TABLE 2-continued

| Nuclear Hormone Receptors (ligand binding domains are underlined) | | | |
|---|---|---|---|
| Name | Agonists | Antagonists | Sequence |
| SHP (NR0B2) (LBD at 16-257) | — | — | MSTSQPGACPCQGAASRPAILYALLSSSLKAVPRPRSR<br>CLCRQHRPVQLCAPHRTCREALDVLAKTVAFLRNLPSF<br>WQLPPQDQRRLLQGCWGPLFLLGLAQDAVTFEVAEAPV<br>PSILKKILLEEPSSSGGSGQLPDRPQPSLAAVQWLQCC<br>LESFWSLELSPKEYACLKGTILFNPDVPGLQAASHIGH<br>LQQEAHWVLCEVLEPWCPAAQGRLTRVLLTASTLKSIP<br>TSLLGDLFFRPIIGDVDIAGLLGDMLLLR (SEQ ID NO: 67) |
| Estrogen receptor-α (NR3A1) (LBD at 302-553) | estriol (endogenous), estrone (endogenous), propylpyrazo-letriol, ethinylestradiol | Bazedoxifene ($pIC_{50}$ 7.6), clomiphene ($pK_i$ 8.9), methyl-piperidino-pyrazole ($pK_i$ 8.6) | MTMTLHTKASGMALLHQIQGNELEPLNRPQLKIPLERP<br>LGEVYLDSSKPAVYNYPEGAAYEFNAAAAANAQVYGQT<br>GLPYGPGSEAAAFGSNGLGGFPPLNSVSPSPLMLLHPP<br>PQLSPFLQPHGQQVPYYLENEPSGYTVREAGPPAFYRP<br>NSDNRRQGGRERLASTNDKGSMAMESAKETRYCAVCND<br>YASGYHYGVWSCEGCKAFFKRSIQGHNDYMCPATNQCT<br>IDKNRRKSCQACRLRKCYEVGMMKGGIRKDRRGGRMLK<br>HKRQRDDGEGRGEVGSAGDMRAANLWPSPLMIKRSKKN<br>SLALSLTADQMVSALLDAEPPILYSEYDPTRPFSEASM<br>MGLLTNLADRELVHMINWAKRVPGFVDLTLHDQVHLLE<br>CAWLEILMIGLVWRSMEHPGKLLFAPNLLLDRNQGKCV<br>EGMVEIFDMLLATSSRFRMMNLQGEEFVCLKSIILLNS<br>GVYTFLSSTLKSLEEKDHIHRVLDKITDTLIHLMAKAG<br>LTLQQQHQRLAQLLLILSHIRHMSNKGMEHLYSMKCKN<br>VVPLYDLLLEMLDAHRLHAPTSRGGASVEETDQSHLAT<br>AGSTSSHSLQKYYITGEAEGFPATV (SEQ ID NO: 68) |
| Estrogen receptor-β (NR3A2) (LBD at 264-498) | WAY200070 (CAS 440122-66-7), diarylpropionitrile, prinaberel | bazedoxifene ($pIC_{50}$ 7.1), R,R-THC ($pK_i$ 8.4) (CAS 138090-06-9), PHTPP ($pK_i$ 6.9) (CAS 805239-56-9) | MDIKNSPSSLNSPSSYNCSQSILPLEHGSIYIPSSYVD<br>SHHEYPAMTFYSPAVMNYSIPSNVTNLEGGPGRQTTSP<br>NVLWPTPGHLSPLVVHRQLSHLYAEPQKSPWCEARSLE<br>HTLPVNRETLKRKVSGNRCASPVTGPGSKRDAHFCAVC<br>SDYASGYHYGVWSCEGCKAFFKRSIQGHNDYICPATNQ<br>CTIDKNRRKSCQACRLRKCYEVGMVKCGSRRERCGYRL<br>VRRQRSADEQLHCAGKAKRSGGHAPRVRELLLDALSPE<br>QLVLTLLEAEPPHVLISRPSAPFTEASMMMSLTKLADK<br>ELVHMISWAKKIPGFVELSLFDQVRLLESCWMEVLMMG<br>LMWRSIDHPGKLIFAPDLVLDRDEGKCVEGILEIFDML<br>LATTSRFRELKLQHKEYLCVKAMILLNSSMYPLVTATQ<br>DADSSRKLAHLLNAVTDALVWVIAKSGISSQQQSMRLA<br>NLLMLLSHVRHASNKGMEHLLNMKCKNVVPVYDLLLEM<br>LNAHVLRGCKSSITGSECSPAEDSKSKEGSQNPQSQ<br>(SEQ ID NO: 69) |
| Androgen receptor (NR3C4) (LBD at 669-900) | Dihydrotesto sterone, testosterone, testosterone propionate, mibolerone, fluoxymesterone, methyltrienolone, dromostanolone propionate, | bicalutamide ($pK_i$ 7.7), PF0998425 ($pIC_{50}$ 7.1-7.5) (CAS 845861-39-4), enzalutamide ($pIC_{50}$ 7.4), nilutamide (pIC50 7.1-7.1), hydroxyflutamide (pEC506.6), galeterone ($pIC_{50}$ 6.4), flutamide ($pK_i$ 5.4) | MEVQLGLGRVYPRPPSKTYRGAFQNLFQSVREVIQNPG<br>PRHPEAASAAPPGASLLLLQQQQQQQQQQQQQQQQQQQ<br>QQQQETSPRQQQQQQGEDGSPQAHRRGPTGYLVLDEEQ<br>QPSQPQSALECHPERGCVPEPGAAVAASKGLPQQLPAP<br>PDEDDSAAPSTLSLLGPTFPGLSSCSADLKDILSEAST<br>MQLLQQQQQEAVSEGSSSGRAREASGAPTSSKDNYLGG<br>TSTISDNAKELCKAVSVSMGLGVEALEHLSPGEQLRGD<br>CMYAPLLGVPPAVRPTPCAPLAECKGSLLDDSAGKSTE<br>DTAEYSPFKGGYTKGLEGESLGCSGSAAAGSSGTLELP<br>STLSLYKSGALDEAAAYQSRDYYNFPLALAGPPPPPPP<br>PHPHARIKLENPLDYGSAWAAAAAQCRYGDLASLHGAG<br>AAGPGSGSPSAAASSSWHTLFTAEEGQLYGPCGGGGGG<br>GGGGGGGGGGGGGGGGGEAGAVAPYGYTRPPQGLAGQE<br>SDFTAPDVWYPGGMVSRVPYPSPTCVKSEMGPWMDSYS<br>GPYGDMRLETARDHVLPIDYYFPPQKTCLICGDEASGC<br>HYGALTCGSCKVFFKRAAEGKQKYLCASRNDCTIDKFR<br>RKNCPSCRLRKCYEAGMTLGARKLKKLGNLKLQEEGEA<br>SSTTSPTEETTQKLTVSHIEGYECQPIFLNVLEAIEPG<br>VVCAGHDNNQPDSFAALLSSLNELGERQLVHVVKWAKA<br>LPGFRNLHVDDQMAVIQYSWMGLMVFAMGWRSFTNVNS<br>RMLYFAPDLVFNEYRMHKSRMYSQCVRMRHLSQEFGWL<br>QITPQEFLCMKALLLFSIIPVDGLKNQKFFDELRMNYI<br>KELDRIIACKRKNPTSCSRRFYQLTKLLDSVQPIAREL<br>HQFTFDLLIKSHMVSVDFPEMMAEIISVQVPKILSGKV<br>KPIYFHTQ (SEQ ID NO: 70) |

TABLE 2-continued

Nuclear Hormone Receptors (ligand binding domains are underlined)

| Name | Agonists | Antagonists | Sequence |
| --- | --- | --- | --- |
| Glucocorticoid receptor (NR3C1) (LBD at 524-758) | cortisol, corticosterone, aldosterone, deoxycortisone, fluticasone propionate, beclometasone, methylprednisolone, fluocinonide, betamethasone, budesonide | onapristone ($pIC_{50}$ 7.6), ZK112993 (CAS 105114-63-4) | MDSKESLTPGREENPSSVLAQERGDVMDFYKTLRGGATVKVSASSPSLAVASQSDSKQRRLLVDFPKGSVSNAQQPDLSKAVSLSMGLYMGETETKVMGNDLGFPQQGQISLSSGETDLKLLEESIANLNRSTSVPENPKSSASTAVSAAPTEKEFPKTHSDVSSEQQHLKGQTGTNGGNVKLYTTDQSTFDILQDLEFSSGSPGKETNESPWRSDLLIDENCLLSPLAGEDDSFLLEGNSNEDCKPLILPDTKPKIKDNGDLVLSSPSNVTLPQVKTEKEDFIELCTPGVIKQEKLGTVYCQASFPGANIIGNKMSAISVHGVSTSGGQMYHYDMNTASLSQQQDQKPIFNVIPPIPVGSENWNRCQGSGDDNLTSLGTLNFPGRTVFSNGYSSPSMRPDVSSPPSSSSTATTGPPPKLCLVCSDEASGCHYGVLTCGSCKVFFKRAVEGQHNYLCAGRNDCIIDKIRRKNCPACRYRKCLQAGMNLEARKTKKKIKGIQQATTGVSQETSENPGNKTIVPATLPQLTPTLVSLLEVIEPEVLYAGYDSSVPDSTWRIMTTLNMLGGRQVIAAVKWAKAIPGFRNLHLDDQMTLLQYSWMFLMAFALGWRSYRQSSANLLCFAPDLIINEQRMTLPCMYDQCKHMLYVSSELHRLQVSYEEYLCMKTLLLLSSVPKDGLKSQELFDEIRMTYIKELGKAIVKREGNSSQNWQRFYQLTKLLDSMHEVVENLLNYCFQTFLDKTMSIEFPEMLAEIITNQIPKYSNGNIKKLLFHQK (SEQ ID NO: 71) |
| Mineralocorticoid receptor (NR3C2) (LBD at 726-964) | corticosterone, cortisol, aldosterone, progesterone | finerenone ($pIC_{50}$ 7.7), eplerenone ($pK_i$ 6.9), onapristone ($pIC_{50}$ 6.3), RU28318 (CAS 76676-34-1), ZK112993 (CAS 105114-63-4) | METKGYHSLPEGLDMERRWGQVSQAVERSSLGPTERTDENNYMEIVNVSCVSGAIPNNSTQGSSKEKQELLPCLQQDNNRPGILTSDIKTELESKELSATVAESMGLYMDSVRDADYSYEQQNQQGSMSPAKIYQNVEQLVKFYKGNGHRPSTLSCVNTPLRSFMSDSGSSVNGGVMRAIVKSPIMCHEKSPSVCSPLNMTSSVCSPAGINSVSSTTASFGSFPVHSPITQGTPLTCSPNAENRGSRSHSPAHASNVGSPLSSPLSSMKSSISSPPSHCSVKSPVSSPNNVTLRSSVSSPANINNSRCSVSSPSNTNNRSTLSSPAASTVGSICSPVNNAFSYTASGTSAGSSTLRDVVPSPDTQEKGAQEVPFPKTEEVESAISNGVTGQLNIVQYIKPEPDGAFSSSCLGGNSKINSDSSFSVPIKQESTKHSCSGTSFKGNPTVNPFPFMDGSYFSFMDDKDYYSLSGILGPPVPGFDGNCEGSGFPVGIKQEPDDGSYYPEASIPSSAIVGVNSGGQSFHYRIGAQGTISLSRSARDQSFQHLSSFPPVNTLVESWKSHGDLSSRRSDGYPVLEYIPENVSSSTLRSVSTGSSRPSKICLVCGDEASGCHYGVVTCGSCKVFFKRAVEGQHNYLCAGRNDCIIDKIRRKNCPACRLQKCLQAGMNLGARKSKKLGKLKGIHEEQPQQQQPPPPPPPPQSPEEGTTYIAPAKEPSVNTALVPQLSTISRALTPSPVMVLENIEPEIVYAGYDSSKPDTAENLLSTLNRLAGKQMIQVVKWAKVLPGFKNLPLEDQITLIQYSWMCLSSFALSWRSYKHTNSQFLYFAPDLVFNEEKMHQSAMYELCQGMHQISLQFVRLQLTFEEYTIMKVLLLLSTIPKDGLKSQAAFEEMRTNYIKELRKMVTKCPNNSGQSWQRFYQLTKLLDSMHDLVSDLLEFCFYTFRESHALKVEFPAMLVEIISDQLPKVESGNAKPLYFHRK (SEQ ID NO: 72) |
| Progesterone receptor (NR3C3) (LBD at 679-913) | Progesterone, medroxyprogesterone (Affinity at human PR-A), ORG2058 (CAS 24320-06-7), levonorgestrel | ulipristal acetate ($pIC_{50}$ 9.7), mifepristone (Mixed) ($pK_i$ 9), onapristone ($pK_i$ 7.7), ZK112993 (CAS 105114-63-4) | MTELKAKGPRAPHVAGGPPSPEVGSPLLCRPAAGPFPGSQTSDTLPEVSAIPISLDGLLFPRPCQGQDPSDEKTQDQQSLSDVEGAYSRAEATRGAGGSSSSPPEKDSGLLDSVLDTLLAPSGPGQSQPSPPACEVTSSWCLFGPELPEDPPAAPATQRVLSPLMSRSGCKVGDSSGTAAAHKVLPRGLSPARQLLLPASESPHWSGAPVKPSPQAAAVEVEEEDGSESEESAGPLLKGKPRALGGAAAGGGAAAVPPGAAAGGVALVPKEDSRFSAPRVALVEQDAPMAPGRSPLATTVMDFIHVPILPLNHALLAARTRQLLEDESYDGGAGAASAFAPPRSSPCASSTPVAVGDFPDCAYPPDAEPKDDAYPLYSDFQPPALKIKEEEEGAEASARSPRSYLVAGANPAAFPDFPLGPPPPLPPRATPSRPGEAAVTAAPASASVSSASSSGSTLECILYKAEGAPPQQGPFAPPPCKAPGASGCLLPRDGLPSTSASAAAAGAAPALYPALGLNGLPQLGYQAAVLKEGLPQVYPPYLNYLRPDSEASQSPQYSFESLPQKICLICGDEASGCHYGVLTCGSCKVFFKRAMEGQHNYLCAGRNDCIVDKIRRKNCPACRLRKCCQAGMVLGGRKFKKFNKVRVVRALDAVALPQPVGVPNESQALSQRFTFSPGQDIQLIPPLINLLMSIEPDVIYAGHDNTKPDTSSSLLTSLNQLGERQLLSVVKWSKSLPGFRNLHIDDQITLIQYSWMSLMV |

TABLE 2-continued

| Nuclear Hormone Receptors (ligand binding domains are underlined) | | | |
|---|---|---|---|
| Name | Agonists | Antagonists | Sequence |
| | | | FGLGWRSYKHVSGQMLYFAPDLILNEQRMKESSFYSLCLTMWQIPQEFVKLQVSQEEFLCMKVLLLLNTIPLEGLRSQTQFEEMRSSYIRELIKAIGLRQKGVVSSSQRFYQLTKLLDNLHDLVKQLHLYCLNTFIQSRALSVEFPEMMSEVIAAQLPKILAGMVKPLLFHKK (SEQ ID NO: 73) |

Sequences in Table 2 are human sequences, unless indicated otherwise.

Table 3 lists additional nuclear hormone receptors for used in embodiments of the present invention, along with domain information.

TABLE 3

| Nuclear Hormone Receptors (underlining refers to ligand binding domains) | | |
|---|---|---|
| Name | Sequence | Domains (residue range) |
| Mouse | | |
| mouse estrogen receptor alpha (ESR1, NR3A1) | MTMTLHTKASGMALLHQIQGNELEPLNRPQLKMPMERALGEVYVDNSKPTVFNYPEGAAYEFNAAAAAAAAASAPVYGQSGIAYGPGSEAAAFSANSLGAFPQLNSVSPSPLMLLHPPPQLSPFLHPHGQQVPYYLENEPSAYAVRDTGPPAFYRSNSDNRRQNGRERLSSSNEKGNMIMESAKETRYCAVCNDYASGYHYGVWSCEGCKAFFKRSIQGHNDYMCPATNQCTIDKNRRKSCQACRLRKCYEVGMMKGGIRKDRRGGRMLKHKRQRDDLEGRNEMGASGDMRAANLWPSPLVIKHTKKNSPALSLTADQMVSALLDAEPPMIYSEYDPSRPFSEASMMGLLTNLADRELVHMINWAKRVPGFGDLNLHDQVHLLECAWLEILMIGLVWRSMEHPGKLLFAPNLLLDRNQGKCVEGMVEIFDMLLATSSRFRMMNLQGEEFVCLKSIILLNSGVYTFLSSTLKSLEEKDHIHRVLDKITDTLIHLMAKAGLTLQQQHRRLAQLLLILSHIRHMSNKGMEHLYNMKCKNVVPLYDLLLEMLDAHRLHAPASRMGVPPEEPSQTQLATTSSTSAHSLQTYYIPPEAEGFPNTI (SEQ ID NO: 74) | LBD can contain amino acids 355-547, or larger portions of mouse ESR1 Exemplary mouse ESR1 LBD fragments: amino acids 306-557 (underlined); amino acids 309-553, 355-547 |
| Mouse estrogen receptor beta (ESR2, NR3A2) | MEIKNSPSSLTSPASYNCSQSILPLEHGPIYIPSSYVESRHEYSAMTFYSPAVMNYSVPSSTGNLEGGPVRQTASPNVLWPTSGHLSPLATHCQSSLLYAEPQKSPWCEARSLEHTLPVNRETLKRKLGGSGCASPVTSPSAKRDAHFCAVCSDYASGYHYGVWSCEGCKAFFKRSIQGHNDYICPATNQCTIDKNRRKSCQACRLRKCYEVGMVKCGSRRERCGYRIVRRQRSASEQVHCLNKAKRTSGHTPRVKELLLNSLSPEQLVLTLLEAEPPNVLVSRPSMPFTEASMMMSLTKLADKELVHMIGWAKKIPGFVELSLLDQVRLLESCWMEVLMVGLMWRSIDHPGKLIFAPDLVLDRDEGKCVEGILEIFDMLLATTARFRELKLQHKEYLCVKAMILLNSSMYPLATASQEAESSRKLTHLLNAVTDALVWVISKSGISSQQQSVRLANLLMLLSHVRHISNKGMEHLLSMKCKNVVPVYDLLLEMLNAHTLRGYKSSISGSECCSTEDSKSKEGSQNLQSQ (SEQ ID NO: 75) | Exemplary LBD fragment: 264-498 |
| Mouse progesterone receptor (NR3C3) | MTELQAKDPQVLHTSGASPSPPHIGSPLLARLDSGPFQGSQHSDVSSVVSPIPISLDGLLFPRSCRGPELPDGKTGDQQSLSDVEGAFSGVEATHREGGRNSRPPEKDSRLLDSVLDSLLTPSGPEQSHASPPACEAITSWCLFGPELPEDPRSVPATKGLLSPLMSRPEIKVGDQSGTGRGQKVLPKGLSPPRQLLLPTSGSAHWPGAGVKPSPQPAAGEVEEDSGLETEGSASPLLKSKPRALEGTGQGGGVAANAPSAAPGGVTLVPKEDSRFSAPRVSLEQDSPIAPGRSPLATTVVDFIHVPILPLNHALLAARTRQLLEGESYDGGATAGPFCPPRSPSAPSTPVPRGDFPDCTYPLEGDPKEDVFPLYGDFQTPGLKIKEEEEGADAAVRSPRPYLSAGASSSTFPDFPLAPAPQAAPSSRPGEAAVAGGPSSAAVSPASSSGSALECILYKAEAPPTQGSFAPLPCKPPAAASCLLPRDSLPAAPGTAAAPAIYQPLGLNGLPQLGYQAAVLKDSLPQVYPPYLNYLRPDSEASQSPQYGFDSLPQKICLICGDEASGCHYGVLTCGSCKVFFKRAMEGQHNYLCAGRNDCIVDKIRRKNCPACRLRKCCQAGMVLGGRKFKKFNKVRVMRTLDGVALPQSVGLPNESQALSQRITFSPNQEIQLVPPLINLLMSIEPDVIYAGHDNTKPDTSSSLLTSLNQLGERQLLSVVKWSKSLPGFRNLHIDDQITLIQYSWMSLMVFGLGWRSYKHVSGQMLYFAPDLILNEQRMKELSFYSLCLTMWQIPQEFVKLQVTHEEFLCMKVLLLLNTIPLEGLRSQSQFEEMRSSYIRELIKAIGLRQKGVVPTSQRFYQLTKLLDSLHDLVKQLHLYCLNTFIQSRTLAVEFPEMMSEVIAAQLPKILAGMVKPLLFHKK (SEQ ID NO: 76) | Exemplary LBD fragments: 641-891, 672-906 |

TABLE 3-continued

Nuclear Hormone Receptors (underlining refers to ligand binding domains)

| Name | Sequence | Domains (residue range) |
| --- | --- | --- |
| murine glucocorticoid receptor (NR3C1) | MDSKESLAPPGRDEVPSSLLGRGRGSVMDLYKTLRGGATVKVSA<br>SSPSVAAASQADSKQQRILLDFSKGSASNAQQQQQQQPQPDL<br>SKAVSLSMGLYMGETETKVMGNDLGYPQQGQLGLSSGETDFRL<br>LEESIANLNRSTSRPENPKSSTPAAGCATPTEKEFPQTHSDPSSEQ<br>QNRKSQPGTNGGSVKLYTTDQSTFDILQDLEFSAGSPGKETNESP<br>WRSDLLIDENLLSPLAGEDDPFLLEGDVNEDCKPLILPDTKPKIQD<br>TGDTILSSPSSVALPQVKTEKDDFIELCTPGVIKQEKLGPVYCQASF<br>SGTNIIGNKMSAISVHGVSTSGGQMYHYDMNTASLSQQQDQK<br>PVFNVIPPIPVGSENWNRCQGSGEDNLTSLGAMNFAGRSVFSN<br>GYSSPGMRPDVSSPPSSSSTATGPPPKLCLVCSDEASVCHYGVLT<br>CGSCKVFFKRAVEGQHNYLCAGRNDCIIDKIRRKNCPACRYRKCL<br>QAGMNLEARKTKKKIKGIQQATAGVSQDTSENANKTIVPAALPQ<br>LTPTLVSLLEVIEPEVLYAGYDSSVPDSAWRIMTTLNMLGGRQVI<br>AAVKWAKAIPGFRNLHLDDQMTLLQYSWMFLMAFALGWRSY<br>RQASGNLLCFAPDLIINEQRMTLPCMYDQCKHMLFISTELQRLQ<br>VSYEEYLCMKTLLLLSSVPKEGLKSQELFDEIRMTYIKELGKAIVKR<br>EGNSSQNWQRFYQLTKLLDSMHDVVENLLSYCFQTFLDKSMSIE<br>FPEMLAEIITNQIPKYSNGNIKKLLFHQK (SEQ ID NO: 77) | Exemplary LBD fragments: 530-764, 500-777 |
| murine androgen receptor (NR3C4) | MEVQLGLGRVYPRPPSKTYRGAFQNLFQSVREAIQNPGPRHPEA<br>ANIAPPGACLQQRQETSPRRRRRQQHTEDGSPQAHIRGPTGYL<br>ALEEEQQPSQQQAASEGHPESSCLPEPGAATAPGKGLPQQPPA<br>PPDQDDSAAPSTLSLLGPTFPGLSSCSADIKDILNEAGTMQLLQQ<br>QQQQQQHQQQHQQHQQQQEVISEGSSARAREATGAPSSSKD<br>SYLGGNSTISDSAKELCKAVSVSMGLGVEALEHLSPGEQLRGDC<br>MYASLLGGPPAVRPTPCAPLPECKGLPLDEGPGKSTEETAEYSSF<br>KGGYAKGLEGESLGCSGSSEAGSSGTLEIPSSLSLYKSGALDEAAA<br>YQNRDYYNFPLALSGPPHPPPPTHPHARIKLENPLDYGSAWAAA<br>AAQCRYGDLGSLHGGSVAGPSTGSPPATTSSSWHTLFTAEEGQL<br>YGPGGGGGSSSPSDAGPVAPYGYTRPPQGLTSQESDYSASEVW<br>YPGGVVNRVPYPSPNCVKSEMGPWMENYSGPYGDMRLDSTR<br>DHVLPIDYYFPPQKTCLICGDEASGCHYGALTCGSCKVFFKRAAE<br>GKQKYLCASRNDCTIDKFRRKNCPSCRLRKCYEAGMTLGARKLKK<br>LGNLKLQEEGENSNAGSPTEDPSQKMTVSHIEGYECQPIFLNVLE<br>AIEPGVVCAGHDNNQPDSFAALLSSLNELGERQLVHVVKWAKA<br>LPGFRNLHVDDQMAVIQYSWMGLMVFAMGWRSFTNVNSRM<br>LYFAPDLVFNEYRMHKSRMYSQCVRMRHLSQEFGWLQITPQEF<br>LCMKALLLFSIIPVDGLKNQKFFDELRMNYIKELDRIIACKRKNPTS<br>CSRRFYQLTKLLDSVQPIARELHQFTFDLLIKSHMVSVDFPEMMA<br>EIISVQVPKILSGKVKPIYFHTQ (SEQ ID NO: 78) | Exemplary LBD fragment: 648-879 |
| | Human (variants and mutants) | |
| Humane progesterone receptor | MTELKAKGPRAPHVAGGPPSPEVGSPLLCRPAAGPFPGSQ<br>TSDTLPEVSAIPISLDGLLFPRPCQGQDPSDEKTQDQQSL<br>SDVEGAYSRAEATRGAGGSSSSPPEKDSGLLDSVLDTLLA<br>PSGPGQSQPSPPACEVTSSWCLFGPELPEDPPAAPATQRV<br>LSPLMSRSGCKVGDSSGTAAAHKVLPRGLSPARQLLLPAS<br>ESPHWSGAPVKPSPQAAAVEVEEEDSSESEESAGPLLKGK<br>PRALGGAAAGGGAAACPPGAAAGGVALVPKEDSRFSAPRV<br>ALVEQDAPMAPGRSPLATTVMDFIHVPILPLNHALLAART<br>RQLLEDESYDGGAGAASAFAPPRSSPCASSTPVAVGDFPD<br>CAYPPDAEPKDDAYPLYSDFQPPALKIKEEEEGAEASARS<br>PRSYLVAGANPAAFPDFPLGPPPPLPPRATPSRPGEAAVT<br>AAPASASVSSASSSGSTLECILYKAEGAPPQQGPFAPPPC<br>KAPGASGCLLPRDGLPSTSASAAAAGAAPALYPALGLNGL<br>PQLGYQAAVLKEGLPQVYPPYLNYLRPDSEASQSPQYSFE<br>SLPQKICLICGDEASGCHYGVLTCGSCKVFFKRAMEGQHN<br>YLCAGRNDCIVDKIRRKNCPACRLRKCCQAGMVLGGRKFK<br>KFNKVRVVRALDAVALPQPLGVPNESQALSQRFTFSPGQD<br>IQLIPPLINLLMSIEPDVIYAGHDNTKPDTSSSLLTSLNQ<br>LGERQLLSVVKWSKSLPGFRNLHIDDQITLIQYSWMSLMV<br>FGLGWRSYKHVSGQMLYFAPDLILNEQRMKESSFYSLCLT<br>MWQIPQEFVKLQVSQEEFLCMKVLLLLNTIPLEGLRSQTQ<br>FEEMRSSYIRELIKAIGLRQKGVVSSSQRFYQLTKLLDNL<br>HDLVKQLHLYCLNTFIQSRALSVEFPEMMSEVIAAQLPKI<br>LAGMVKPLLFHKK (SEQ ID NO: 79) | Exemplary LBD fragments: 641-933, 679-913 |
| human glucocorticoid receptor | MDSKESLTPGREENPSSVLAQERGDVMDFYKTLRGGATVK<br>VSASSPSLAVASQSDSKQRRLLVDFPKGSVSNAQQPDLSK<br>AVSLSMGLYMGETETKVMGNDLGFPQQGQISLSSGETDLK<br>LLEESIANLNRSTSVPENPKSSASTAVSAAPTEKEFPKTH<br>SDVSSEQQHLKGQTGTNGGNVKLYTTDQSTFDILQDLEFS | Modulating N-terminal domain (1-420)<br>DNA-binding domain (420-487) |

TABLE 3-continued

Nuclear Hormone Receptors (underlining refers to ligand binding domains)

| Name | Sequence | Domains (residue range) |
|---|---|---|
| | SGSPGKETNESPWRSDLLIDENCLLSPLAGEDDSFLLEGN SNEDCKPLILPDTKPKIKDNGDLVLSSPSNVTLPQVKTEK EDFIELCTPGVIKQEKLGTVYCQASFPGANIIGNKMSAIS VHGVSTSGGQMYHYDMNTASLSQQQDQKPIFNVIPPIPVG SENWNRCQGSGDDNLTSLGTLNFPGRTVFSNGYSSPSMRP DVSSPPSSSSTATTGPPPKLCLVCSDEASGCHYGVLTCGS CKVFFKRAVEGQHNYLCAGRNDCIIDKIRRKNCPACRYRK CLQAGMNLEARKTKKKIKGIQQATTGVSQETSENPGNKTI VPATLPQLTPTLVSLLEVIEPEVLYAGYDSSVPDSTWRIM TTLNMLGGRQVIAAVKWAKAIPGFRNLHLDDQMTLLQYSW MFLMAFALGWRSYRQSSANLLCFAPDLIINEQRMTLPCMY DQCKHMLYVSSELHRLQVSYEEYLCMKTLLLLSSVPKDGL KSQELFDEIRMTYIKELGKAIVKREGNSSQNWQRFYQLTK LLDSMHENVMWLKPESTSHTLI (SEQ ID NO: 80) | Hinge (487-523) Exemplary LBDs: 524-777, 524- 758 (of WT) |
| human androgen receptor | MEVQLGLGRVYPRPPSKTYRGAFQNLFQSVREVIQNPGPR SPRQQQQQQGEDGSPQAHRRGPTGYLVLDEEQQPSQPQSA LECHPERGCVPEPGAAVAASKGLPQQLPAPPDEDDSAAPS TLSLLGPTFPGLSSCSADLKDILSEASTMQLLQQQQQEAV SEGSSSGRAREASGAPTSSKDNYLGGTSTISDNAKELCKA VSVSMGLGVEALEHLSPGEQLRGDCMYAPLLGVPPAVRPT PCAPLAECKGSLLDDSAGKSTEDTAEYSPFKGGYTKGLEG ESLGCSGSAAAGSSGTLELPSTLSLYKSGALDEAAAYQSR DYYNFPLALAGPPPPPPPPHPHARIKLENPLDYGSAWAAA AAQCRYGDLASLHGAGAAGPGSGSPSAAASSSWHTLFTAE EGQLYGPCGGGGGGGGGGGGGGGGGGGGGGGGEAGAVAPY GYTRPPQGLAGQESDFTAPDVWYPGGMVSRVPYPSPTCVK SEMGPWMDSYSGPYGDMRLETARDHVLPIDYYFPPQKTCL ICGDEASGCHYGALTCGSCKVFFKRAAEGKQKYLCASRND CTIDKFRRKNCPSCRLRKCYEAGMTLGARKLKKLGNLKLQ EEGEASSTTSPTEETTQKLTVSHIEGYECQPIFLNVLEAI EPGVVCAGHDNNQPDSFAALLSSLNELGERQLVHVVKWAK ALPGFRNLHVDDQMAVIQYSWMGLMVFAMGWRSFTNVNSR MLYFAPDLVFNEYRMHKSRMYSQCVRMRHLSQEFGWLQIT PQEFLCMKALLLFSIIPVDGLKNQKFFDELRMNYIKELDR I TACKRKNPTSCSRRFYQLTKLLDSVQPIARELHQFTFDL LIKSHMVSVDFPEMMAEIISVQVPKILSGKVKPIYFHTQ (SEQ ID NO: 81) | |
| LBD of estrogen receptor mutant ER(T2) with amino acid exchanges from Glycine to Valine at position 400 (G400V), from Methionine to Alanine at position 543 (M543A), from Leucine to Alanine at position 544 | SAGDMRAANLWPSPLMIKRSKKNSLALSLTADQMVSALLD AEPPILYSEYDPTRPFSEASMMGLLTNLADRELVHMINWA KRVPGFVDLTLHDQVHLLECAWLEILMIGLVWRSMEHPVK LLFAPNLLLDRNQGKCVEGMVEIFDMLLATSSRFRMMNLQ GEEFVCLKSIILLNSGVYTFLSSTLKSLEEKDHIHRVLDK ITDTLIHLMAKAGLTLQQQHQRLAQLLLILSHIRHMSNKG MEHLYSMKCKNVVPLYDLLLEAADAHRLHAPTSRGGASVE ETDQSHLATAGSTSSHSLQKYYITGEAEGFPATA (SEQ ID NO: 82) | |

Illustrative ligand binding domains based on UniProt database annotation of the nuclear hormone receptors described in Table 2 and Table 3 are underlined in the sequences in the tables. The person of ordinary skill in the art will understand that boundaries of exemplary LBDs used in the tBID fusion proteins described herein may vary from those indicated in Table 2 and Table 3, without loss of function of the ligand binding domain. For example, the N and/or C terminal boundaries of the LBDs of the tBID fusion proteins of the disclosure may vary by about 1, 2, 3, 4, 5, 6 7, 8, 9, 10, 11, 12, 13, 14, 15, 16 17, 18, 19, 20, 25, 30, 35, 40, 45 or 50 amino acids from the N and/or C terminal boundaries of the LBDs described in Table 2 and Table 3.

Suitable LBDs can be identified by the person of ordinary skill in the by their structure. The structure of the LBD of nuclear steroid receptors comprises a conserved arrangement of a series of 11-12 alpha-helices closely folded in a similar manner (Kumar and Thompson, Steroids, 64, 310-319 (1999)). Suitable LBDs can also be identified by the person of ordinary skill in the by alignment with known LBDs, for example using algorithms such as the basic local alignment search tool (BLAST).

In various embodiments, the ligand-binding domain (LBD) of the present invention is selected from the LBDs of the members of the nuclear receptor superfamily of proteins (Mangelsdorf, et al., Cell, 83, 835-839 (1995)). In some embodiments, the LBD of the tBID fusion proteins described herein comprises a LBD isolated or derived from a nuclear hormone receptor selected from the group consisting of Thyroid hormone receptor-α (NR1A1), Thyroid hormone receptor-β (NR1A2), Retinoic acid receptor-α (NR1B1), Retinoic acid receptor-β (NR1B2), Retinoic acid receptor-γ (NR1B3), Peroxisome proliferator-activated receptor-α (NR1C1), Peroxisome proliferator-activated receptor-β/δ (NR1C2), Peroxisome proliferator-activated receptor-γ (NR1C3), Rev-Erb-α (NR1D1), Rev-Erb-β (NR1D2), RAR-related orphan receptor-α (NR1F1), RAR-related orphan receptor-β (NR1F2), RAR-related orphan receptor-γ (NR1F3), Farnesoid X receptor (NR1H4), Farnesoid X receptor-β (NR1H5), Liver X receptor-α (NR1H3), Liver X receptor-β (NR1H2), Vitamin D receptor (NR1I1), Pregnane X receptor (NR1I2), Constitutive androstane receptor (NR1I3), Hepatocyte nuclear factor-4-α (NR2A1), Hepatocyte nuclear factor-4-γ (NR2A2), Retinoid X receptor-α (NR2B1), Retinoid X receptor-β (NR2B2), Retinoid X receptor-γ (NR2B3), Testicular receptor 2 (NR2C1), Testicular receptor 4 (NR2C2), TLX (NR2E1), PNR (NR2E3), COUP transcription factor 1 (NR2F1), COUP transcription factor 2 (NR2F2), V-erbA-related gene (NR2F6), Estrogen-related receptor-α (NR3B1), Estrogen-related receptor-β (NR3B2), Estrogen-related receptor-γ (NR3B3), Nerve Growth factor IB (NR4A1), Nuclear receptor related 1 (NR4A2), Neuron-derived orphan receptor 1 (NR4A3), Steroidogenic factor 1 (NR5A1), Liver receptor homolog-1 (NR5A2), Germ cell nuclear factor (NR6A1), DAX1 (NR0B1), SHP (NR0B2), Estrogen receptor-α (NR3A1), Estrogen receptor-β (NR3A2), Androgen receptor (NR3C4), Glucocorticoid receptor (NR3C1), Mineralocorticoid receptor (NR3C2) and Progesterone receptor (NR3C3). In some embodiments, the LBD is an LBD isolated or derived from a nuclear hormone receptor described in Table 2 or Table 3. In some embodiments, the LBD comprises a LBD having at least at least 85% identity, at least 90% identity, at least 95% identity, at least 96% identity, at least 97% identity, at least 98% identity, at least 99% identity or that is identical to the sequence of a LBD isolated or derived from a nuclear hormone receptor selected from the group consisting of NR1A1, NR1A2, NR1B1, NR1B2, NR1B3, NR1C1, NR1C2, NR1C3, NR1D1, NR1D2, NR1F1, NR1F2, NR1F3, NR1H4, NR1H5, NR1H3, NR1H2, NR1I1, NR1I2, NR1I3, NR2A1, NR2A2, NR2B1, NR2B2, NR2B3, NR2C1, NR2C2, NR2E1, NR2E3, NR2F1, NR2F2, NR2F6, NR3B1, NR3B2, NR3B3, NR4A1, NR4A2, NR4A3, NR5A1, NR5A2, NR6A1, NR0B1, NR0B2, NR3A1, NR3A2, NR3C4, GNR3C1, NR3C2 and NR3C3. n some embodiments, the LBD comprises a LBD having at least at least 85% identity, at least 90% identity, at least 95% identity, at least 96% identity, at least 97% identity, at least 98% identity, at least 99% identity or that is identical to the sequence of a LBD isolated or derived from a nuclear hormone receptor described in Table 2 or Table 3.

In some embodiments, LBDs isolated or derived from mutants or variants of steroid hormone receptors can be used in the fusion proteins of the instant disclosure. Suitable steroid hormone receptors include, without limitation, a mutant human progesterone receptor (Wang, et al., Proc Natl Acad Sci USA, 91, 8180-8184 (1994), Kellendonk, et al., Nucleic Acids Res, 24, 1404-1411 (1996), Kellendonk, et al., J Mol Biol, 285, 175-182 (1999)); a mutant glucocorticoid receptor (Brocard, et al., Nucleic Acids Res, 26, 4086-4090 (1998)); and a mutant androgen receptor (Kaczmarczyk and Green, Nucleic Acids Res, 31, e86 (2003)). Various natural and modified receptors are described in U.S. Pat. No. 8,530,168 and U.S. Patent Application Publication No. 2003/109683, which are incorporated by reference. Exemplary, but non-limiting, mutants or variants of steroid hormone receptors that may be used in the tBID fusion proteins of the disclosure are described in Table 3.

In some embodiments, the steroid hormone receptor is selected from the group consisting of an estrogen receptor, a progesterone receptor, a glucocorticoid receptor, an androgen receptor, and a functionally active variant thereof. In some embodiments, the steroid hormone receptor is selected from the group consisting of an estrogen receptor, a progesterone receptor, a glucocorticoid receptor, an androgen receptor, and a functionally active variant thereof.

In some embodiments, the SHR domain of the fusion proteins of the disclosure comprises an SHR domain isolated or derived from an estrogen receptor, for example Estrogen receptor-α (NR3A1, also known as ESR1, ESR, ERA and ESTRR) or Estrogen receptor-β (NR3A2, also known as Erb, ESRB, ODG8, ESTRB, ER-Beta and ESR-Beta).

Using a ligand binding from a nuclear hormone receptor such as ESR1 brings the activity of tBID under control of a ligand such as tamoxifen. This system is based on well-known properties of estrogen-regulated activation. First, estrogen is known to regulate gene expression via its binding to ER, which consists of two structural domains, one that binds the estrogen ligand (~250 amino acids), and the other that binds specific DNA sequences within the genome. In the absence of estrogen, ESR1 binds Hsp90, a large chaperone protein that prevents it from interacting with genomic elements in associated with estrogen-responsive genes (Dalman et al., 1991; Scherrer et al., 1993). However, when ESR1 binds estrogen, it is not able to bind Hsp90, unleashing its DNA-binding properties. This feature of ESR1, the capacity to bind Hsp90 only in the absence of estrogen, creates an estrogen-regulated switching or tuning mechanism. Second, artificial agents including tamoxifen can substitute or even enhance the switching mechanism of ESR1. This creates the opportunity to regulate ESR1 activity with compounds that lack other biological properties of estrogen itself. Third, the switching behavior of ESR1 depends solely on its ligand-binding domain; and furthermore, the ligand-binding domain can be fused artificially to other proteins, potentially conferring on those proteins the capacity to be regulated by tamoxifen; i.e., fusions between the ER ligand-binding domain and a second protein may bind Hsp90 in the absence of tamoxifen, blocking the function of this second protein unless tamoxifen is present. Thus, the fusion protein mimics ESR1 in its sensitivity to tamoxifen, insofar as ligand-binding frees it from Hsp90 and unmasks its activity.

In some embodiments, the SHR domain of the fusion proteins of the disclosure comprises an SHR domain isolated or derived from Estrogen receptor-α (NR3A1). The human estrogen receptor (ES1R, or ER) can be either in its wild type form that responds to the natural ligand estradiol or a receptor mutant that exhibits strongly reduced estradiol binding but can be activated by synthetic ligands like 4-OH-Tamoxifen. The structure of tamoxifen is shown below:

(I)

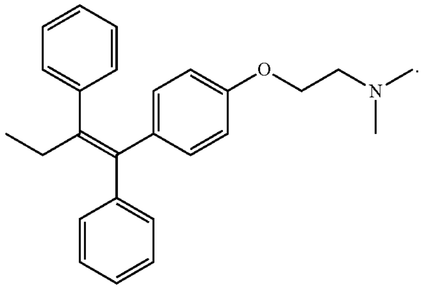

Tamoxifen is metabolized into the more active 4-hydroxytamoxifen (4-OH-TAM or 4OHT) and endoxifen by cytochrome P450 enzymes.

In some embodiments, for example those embodiments where the SHR domain is an ESR1 ligand binding domain or a variant thereof, the fusion proteins are activated by tamoxifen or an analogue or derivative thereof. Suitable tamoxifen analogues and derivatives will be known to persons of ordinary skill in the art, and described, for example, in U.S. Pat. No. 5,192,525, and Farzaneh and Zarghi, Sci. Pharm. (2016) 84(3):409-427, the contents of each of which are incorporated by reference herein. Tamoxifen analogues include, for example, chlorinated derivatives of tamoxifen (e.g. toremifene), phenolic analogues of tamoxifen (e.g. droloxifene), idoxifene, TAT-59 (miproxifene, a phosphorylated derivative of 4-hydroxytamoxifen), and GW5638 (a carboxylic acid derivative of tamoxifen).

Additional ESR1 ligands may be suitable for use in the instant disclosure, and include, for example, steroid ligands (e.g. 11β-ether-17α-ethinyl-3,17ß-estradiol and derivatives), non-steroidal ligands and modulators (e.g. 2,3-diaryl isoquinolinone derivatives, raloxifene and its derivatives LY353381 and LY357489), deoxybenzoin analogues, hydrazide derivatives, 7-hydroxyfluoren-3-one derivatives, and triphenylethylene-coumarin derivatives. Additional ESR1 ligands include prodigiosene and fulvestrant.

In some embodiments, the use of a mutant ER avoids spontaneous activation of a fusion partner by endogenous estrogen.

In some embodiments, the LBD comprises one or more mutations. For example, the LBD may be modified to bind a synthetic ligand rather than only a natural ligand or in preference to a natural ligand. In particular embodiments, a LBD of murine ER comprises a single point mutation replacing a glycine by an arginine residue at position 525 of the mouse or the analogous position 521 of the human estrogen receptor, which is termed ER(T). (Brocard, et al., Proc Natl Acad Sci USA, 94, 14559-14563 (1997)) (Danielian, et al., Mol Endocrinol, 7, 232-240 (1993)). ER(T) dimerizes in response to the ligand 4-OH-Tamoxifen (Danielian, et al., Mol Endocrinol, 7, 232-240 (1993)). In particular embodiments, the recombinant gene comprises a sequence at least partially identical to a human ER LBD and comprising point mutations G400V/M543A/L544A, which is termed ER(T2). (Feil, et al., Biochem Biophys Res Commun, 237, 752-757 (1997).) ER(T2) is roughly 10-fold more sensitive to 4-OH-Tamoxifen than the ER(T) mutant (Indra, et al., Nucleic Acids Res, 27, 4324-4327 (1999)).

Variants of the ESR1 LBD have been identified that modulate its properties. These include substitutions that alter its relative affinity for tamoxifen compared to estrogen, as well as those that destabilize ER in the absence of ligand binding ((Miyazaki et al., 2012, J. Am. Chem. Soc. 134(9): 3942-45). All variants of the ESR1 LBD are contemplated as within the scope of the instant disclosure. An exemplary variant ESR1 LBD is included in Table 3 as SEQ ID NO: 82.

In some embodiments the SHR domain is an ESR1 domain. In some embodiments, the ESR1 domain is an ESR1 ligand binding domain or a functional variant thereof. An exemplary wild type ESR1 human sequence is shown in Table 2 as SEQ ID NO: 68. The full length ESR1 sequence of SEQ ID NO: 68 includes an AF1 transaction domain spanning approximately amino acids 1-180, a DNA binding domain spanning approximately amino acids 180-253, a hinge domain spanning approximately amino acids 263-302, and an AF2 transactivation domain spanning approximately amino acids 302-595 of SEQ ID NO: 68. ESR1 also comprises a C-terminal ligand binding domain, which minimally contains amino acids 311-548 of SEQ ID NO: 68, but can extend up to amino acids 250-595 of SEQ ID NO: 68. In some embodiments, the LBD comprises a sequence having at least 85% identity, at least 90% identity, at least 95% identity, at least 96% identity, at least 97% identity, at least 98% identity, at least 99% identity or that is identical to a subsequence of SEQ ID NO: 68. In some embodiments, the LBD consists essentially a sequence having at least at least 85% identity, at least 90% identity, at least 95% identity, at least 96% identity, at least 97% identity, at least 98% identity, at least 99% identity or that is identical to a subsequence of SEQ ID NO: 68. In some embodiments, the LBD comprises, or consists essentially of, a subsequence of SEQ ID NO: 68. Exemplary fragments of SEQ ID NO: 68 comprising the LBD of ESR1 which can be used in the fusion proteins of the disclosure include amino acids 302-553 of SEQ ID NO: 68, amino acids 305-559 of SEQ ID NO: 68, amino acids 311-547 of SEQ ID NO: 68 or a sequence having a having at least 85% identity, at least 90% identity, at least 95% identity, at least 96% identity, at least 97% identity, at least 98% identity, or at least 99% identity thereto.

In some embodiments, the SHR domain is isolated or derived from ESR1. In some embodiments, the SHR domain comprises a sequence having at least 85% identity, at least 90% identity, at least 95% identity, at least 96% identity, at least 97% identity, at least 98% identity, at least 99% identity or is identical to a sequence of

```
                                                         (SEQ ID NO: 3)
  1 KKNSLALSLT ADQMVSALLD AEPPILYSEY DPTRPFSEAS MMGLLTNLAD RELVHMINWA

 61 KRVPGFVDLT LHDQVHLLEC AWLEILMIGL VWRSMEHPGK LLFAPNLLLD RNQGKCVEGM

121 VEIFDMLLAT SSRFRMMNLQ GEEFVCLKSI ILLNSGVYTF LSSTLKSLEE KDHIHRVLDK

181 ITDTLIHLMA KAGLTLQQQH QRLAQLLLIL SHIRHMSNKG MEHLYSMKCK NVVPLYDLLL

241 EMLDAHRLHA PT.
```

In some embodiments, the SHR domain comprises a sequence having at least 95% identity to SEQ ID NO: 3. In some embodiments, the SHR domain comprises SEQ ID NO: 3. In some embodiments, the SHR domain consists essentially of a sequence having at least 85% identity, at least 90% identity, at least 95% identity, at least 96% identity, at least 97% identity, at least 98% identity, at least 99% identity or that is identical to a sequence of SEQ ID NO: 3. In some embodiments, the SHR domain consists essentially of a sequence having at least 95% identity to SEQ ID NO: 3. In some embodiments, the SHR domain consists essentially of SEQ ID NO: 3. In some embodiments, a SHR domain polypeptide is encoded by a polynucleotide having a sequence of residues in the SHR domain polypeptide or the tBID polypeptide may be reversed when compared to wild type SHR or BID.

In some embodiments, the SHR domain polypeptide is fused to the N-terminus of the tBID polypeptide. In some embodiments, the SHR domain is fused to the C-terminus of the tBID polypeptide.

Optionally, a short oligo- or polypeptide linker, for example, between 2 and 40 amino acids (e.g., 2, 3, 4, 5, 6, 7, 8, 9, or 10 amino acids) in length may form the linkage between the domains.

In some embodiments, the polypeptide linker comprises at most 2, 3, 4, 5, 6, 8, 9, 10, 12, 15, 16, 18 or 20 amino acids. In some embodiments, the polypeptide linker comprises or

```
                                              (SEQ ID NO: 83)
  1 AAGAAGAACA GCCTGGCCTT GTCCCTGACG GCCGACCAGA TGGTCAGTGC CTTGTTGGAT

 61 GCTGAGCCCC CCATACTCTA TTCCGAGTAT GATCCTACCA GACCCTTCAG TGAAGCTTCG

121 ATGATGGGCT TACTGACCAA CCTGGCAGAC AGGGAGCTGG TTCACATGAT CAACTGGGCG

181 AAGAGGGTGC CAGGCTTTGT GGATTTGACC CTCCATGATC AGGTCCACCT TCTAGAATGT

241 GCCTGGCTAG AGATCCTGAT GATTGGACTC GTCTGGCGCT CCATGGAGCA CCCAGGGAAG

301 CTACTGTTTG CTCCTAACTT GCTCTTGGAC AGGAACCAGG GAAAATGTGT AGAGGGCATG

361 GTGGAGATCT TCGACATGCT GCTGGCTACA TCATCTCGGT TCCGCATGAT GAATCTGCAG

421 GGAGAGGAGT TTGTGTGCCT CAAATCTATT ATTTTGCTTA ATTCTGGAGT GTACACATTT

481 CTGTCCAGCA CCCTGAAGTC TCTGGAAGAG AAGGACCATA TCCACCGAGT CCTGGACAAG

541 ATCACAGACA CTTTGATCCA CCTGATGGCC AAGGCAGGCC TGACCCTGCA GCAGCAGCAC

601 CAGCGGCTGG CCCAGCTCCT CCTCATCCTC TCCCACATCA GGCACATGAG TAACAAAGGC

661 ATGGAGCATC TGTACAGCAT GAAGTGCAAG AACGTGGTGC CCCTCTATGA CCTGCTGCTG

721 GAGATGCTGG ACGCCCACCG CCTACATGCG CCCACC
```

or a sequence having at least 70% identity, at least 80% identity, at least 90% identity, at least 95% identity or at least 99% identity thereto. In some embodiments, the SHR domain polypeptide is encoded by a polynucleotide having a sequence of SEQ ID NO: 83.

Linkers

Provided herein are linkers that, in some embodiments, can be used link the domains of the fusion proteins described herein. Linkers can be used to link the SHR domain polypeptides to the tBID polypeptides. Any suitable linker is envisaged within the scope of the instant disclosure. Linkers include, inter alia, peptide linkers.

The terms "linker" as used in the context of linking protein domains refers to a peptide linker that consists of amino acids such as glycine and/or serine residues used alone or in combination, to link two domains together.

The tBID and SHR domains may be linked together in any order. For example, the tBID domain can be located N-terminal of the SHR domain, or vice versa. For example, the C-terminus of the SHR domain polypeptide may be linked to the N-terminus of the tBID domain polypeptide. Alternatively, C-terminus of the tBID domain polypeptide may be linked to the N-terminus of the SHR domain polypeptide.

The tBID and SHR domains may linked together in any orientation with respect to each other, or the endogenous proteins from which they are derived. For example, the SHR domain polypeptide and the tBID polypeptide may be in the original N to C orientation when compared to wild type SHR or BID. Alternatively, the N to C order of the amino acid consists essentially of 2 amino acids. In some embodiments, the polypeptide linker comprises or consists essentially of 3 amino acids. In some embodiments, the amino acids are glycine (Gly) and serine (Ser).

In some embodiments, the linker consists essentially of neutral amino acids. An exemplary linker is composed of the glycine, serine, alanine and/or valine. Other exemplary linkers include the sequences Ala-Asp-Gln, Gly-Ser-Gly, Gly-Gly-Ser, Ser-Gly-Gly. An alternative linker comprises a part of the nuclear hormone receptor D and F domain sequences flanking the ligand binding domain (Metzger, et al., Proc Natl Acad Sci USA, 92, 6991-6995 (1995)).

In some embodiments, the polypeptide linker is a Gly/Ser linker and comprises the amino acid sequence (Gly-Gly-Ser (SEQ ID NO: 99)), (Gly-Gly-Gly-Ser (SEQ ID NO: 100)), or (Gly-Gly-Gly-Gly-Ser (SEQ ID NO: 101)) which can be repeated n times, where n is a positive integer equal to or greater than 1. For example, n=1, n=2, n=3, n=4, n=5, n=6, n=7, n=8, n=9 and n=10. In some embodiments, the flexible polypeptide linkers include, but are not limited to, GS, GGS, GGGGS (SEQ ID NO: 102), GGGGS GGGGS (SEQ ID NO: 103), GGGGSGGGGSGGGGS (SEQ ID NO: 104) or GGGGSGGGGSGGGGSGGGGS (SEQ ID NO: 105).

In some embodiments, the linkers include multiple repeats of (Gly Gly Ser (SEQ ID NO: 99)), (Gly Ser) or (Gly Gly Gly Ser (SEQ ID NO: 100)). Also included within the scope of the invention are linkers described in WO2012/138475 (incorporated herein by reference).

A glycine-serine doublet can be used as a suitable linker. In some embodiments, the linker sequence comprises GS. In some embodiments, the linker sequence consists essential of GS. In some embodiments, the linker sequence comprises SG. In some embodiments, the linker sequence consists essential of SG.

In some embodiments, the tBID and SHR domain polypeptides are fused directly to each other via peptide bonds without use of a linker.

Additional Polypeptide Sequences

In addition to the components listed and specified above, the fusion protein of the disclosure may comprise further components. For example, fusion proteins of the disclosure may comprise a myristoylation signal sequence such as GSSKSKPKDPSQR (SEQ ID NO: 106), a subcellular targeting signal like a nuclear localization sequence or any other suitable sequence, such as a tag, e.g. for purification. Other suitable sequences are known to skilled persons and it is within the knowledge of the skilled person to select and combine further sequences with the components of the fusion protein as defined above.

Myristoylation is an irreversible, post-translational protein modification found in animals, plants, fungi and viruses. In this protein modification a myristoyl group (derived from myristic acid) is covalently attached via an amide bond to the alpha-amino group of an N-terminal glycine residue of a nascent polypeptide. The modification is catalyzed by the enzyme N-myristoyltransferase, and occurs most commonly on glycine residues exposed during co-translational N-terminal methionine removal. Myristoylation plays a vital role in membrane targeting and signal transduction in plant responses to environmental stress. A myristoylation signal sequence may be included in order to increase the local concentration of the fusion protein at membranes which might lead to faster and more efficient induction of apoptosis.

A nuclear localization signal sequence provides for the active transport into the nucleus of eukaryotic cells. Such a signal peptide domain preferably has a length of 5 to 74, preferably 7 to 15 amino acid residues. More preferably, the signal peptide domain comprises a segment of 6 amino acid residues wherein at least 2 amino acid residues, preferably at least 3 amino acid residues are positively charged basic amino acids. Basic amino acids include, but are not limited to, lysine, arginine, and histidine.

Fusion Proteins

The disclosure provides fusion proteins comprising the tBID polypeptides and SHR domain polypeptides described herein. The tBID polypeptide may be fused to the SHR domain polypeptide in any order or orientation, with or without a linker.

Sequences of exemplary, but non limiting, fusion proteins comprising a tBID polypeptide and an ESR1 ligand binding domain are provided in Table 4 below. Nucleotide Sequences encoding these fusion proteins are also provided in Table 4.

TABLE 4

| | tBID Fusion Proteins. | |
|---|---|---|
| Name | Protein Sequence | Nucleotide Sequence |
| C3445 (ESR1-D) | MKKNSLALSLTADQMVS ALLDAEPPILYSEYDPT RPFSEASMMGLLTNLAD RELVHMINWAKRVPGFV DLTLHDQVHLLECAWLE ILMIGLVWRSMEHPGKL LFAPNLLLDRNQGKCVE GMVEIFDMLLATSSRFR MMNLQGEEFVCLKSIIL LNSGVYTFLSSTLKSLE EKDHIHRVLDKITDTLI HLMAKAGLTLQQQHQRL AQLLLILSHIRHMSNKG MEHLYSMKCKNVVPLYD LLLEMLDAHRLHAPTGS SQEDIIRNIARHLAQVG DSMDRSIPPGEKTMLVL ALLLAKKVASHTPSLLR DVFHTTVNFINQNL (SEQ ID NO: 4) | ATGAAGAAGAACAGCCTGGCCTTGTCCCTGACGGCCGACCAGA TGGTCAGTGCCTTGTTGGATGCTGAGCCCCCCATACTCTATTC CGAGTATGATCCTACCAGACCCTTCAGTGAAGCTTCGATGATG GGCTTACTGACCAACCTGGCAGACAGGGAGCTGGTTCACATGA TCAACTGGGCGAAGAGGGTGCCAGGCTTTGTGGATTTGACCCT CCATGATCAGGTCCACCTTCTAGAATGTGCCTGGCTAGAGATC CTGATGATTGGACTCGTCTGGCGCTCCATGGAGCACCCAGGGA AGCTACTGTTTGCTCCTAACTTGCTCTTGGACAGGAACCAGGG AAAATGTGTAGAGGGCATGGTGGAGATCTTCGACATGCTGCTG GCTCACATCATCTCGGTTCCGCATGATGAATCTGCAGGGAGAGG AGTTTGTGTGCCTCAAATCTATTATTTTGCTTAATTCTGGAGT GTACACATTTCTGTCCAGCACCCTGAAGTCTCTGGAAGAGAAG GACCATATCCACCGAGTCCTGGACAAGATCACAGACACTTTGA TCCACCTGATGGCCAAGGCAGGCCTGACCCTGCAGCAGCAGCA CCAGCGGCTGGCCCAGCTCCTCCTCATCCTCTCCCACATCAGG CACATGAGTAACAAAGGCATGGAGCATCTGTACAGCATGAAGT GCAAGAACGTGGTGCCCCTCTATGACCTGCTGCTGGAGATGCT GGACGCCCACCGCCTACATGCGCCCACCGGCAGCAGTCAAGAA GACATCATCCGGAATATTGCCAGGCACCTCGCCCAGGTCGGGG ACAGCATGGACCGTAGCATCCCTCCGGGCGAGAAGACCATGCT GGTGCTGGCCCTGCTGCTGGCCAAGAAGGTGGCCAGTCACACG CCGTCCTTGCTCCGTGATGTCTTTCACACAACAGTGAATTTTA TTAACCAGAACCTA (SEQ ID NO: 84) |
| C3454 (D-ESR1) | SQEDIIRNIARHLAQVG DSMDRSIPPGEKTMLVL ALLLAKKVASHTPSLLR DVFHTTVNFINQNLGSK KNSLALSLTADQMVSAL LDAEPPILYSEYDPTRP FSEASMMGLLTNLADRE LVHMINWAKRVPGFVDL TLHDQVHLLECAWLEIL MIGLVWRSMEHPGKLLF APNLLLDRNQGKCVEGM VEIFDMLLATSSRFRMM NLQGEEFVCLKSIILLN SGVYTFLSSTLKSLEEK DHIHRVLDKITDTLIHL MAKAGLTLQQQHQRLAQ | AGTCAAGAAGACATCATCCGGAATATTGCCAGGCACCTCGCCC AGGTCGGGGACAGCATGGACCGTAGCATCCCTCCGGGCGAGAA GACCATGCTGGTGCTGGCCCTGCTGCTGGCCAAGAAGGTGGCC AGTCACACGCCGTCCTTGCTCCGTGATGTCTTTCACACAACAG TGAATTTTATTAACCAGAACCTAGGAAGCAAGAAGAACAGCCT GGCCTTGTCCCTGACGGCCGACCAGATGGTCAGTGCCTTGTTG GATGCTGAGCCCCCCATACTCTATTCCGAGTATGATCCTACCA GACCCTTCAGTGAAGCTTCGATGATGGGCTTACTGACCAACCT GGCAGACAGGGAGCTGGTTCACATGATCAACTGGGCGAAGAGG GTGCCAGGCTTTGTGGATTTGACCCTCCATGATCAGGTCCACC TTCTAGAATGTGCCTGGCTAGAGATCCTGATGATTGGACTCGT CTGGCGCTCCATGGAGCACCCAGGGAAGCTACTGTTTGCTCCT AACTTGCTCTTGGACAGGAACCAGGGAAAATGTGTAGAGGGCA TGGTGGAGATCTTCGACATGCTGCTGGCTACATCATCTCGGTT CCGCATGATGAATCTGCAGGGAGAGGAGTTTGTGTGCCTCAAA TCTATTATTTTGCTTAATTCTGGAGTGTACACATTTCTGTCCA |

TABLE 4-continued tBID Fusion Proteins.

| Name | Protein Sequence | Nucleotide Sequence |
| --- | --- | --- |
| | LLLILSHIRHMSNKGME<br>HLYSMKCKNVVPLYDLL<br>LEMLDAHRLHAPT<br>(SEQ ID NO: 5) | GCACCCTGAAGTCTCTGGAAGAGAAGGACCATATCCACCGAGT<br>CCTGGACAAGATCACAGACACTTTGATCCACCTGATGGCCAAG<br>GCAGGCCTGACCCTGCAGCAGCAGCACCAGCGGCTGGCCCAGC<br>TCCTCCTCATCCTCTCCCACATCAGGCACATGAGTAACAAAGG<br>CATGGAGCATCTGTACAGCATGAAGTGCAAGAACGTGGTGCCC<br>CTCTATGACCTGCTGCTGGAGATGCTGGACGCCCACCGCCTAC<br>ATGCGCCCACC (SEQ ID NO: 85) |
| C3443<br>(ESR1-C) | MKKNSLALSLTADOMVS<br>ALLDAEPPILYSEYDPT<br>RPFSEASMMGLLTNLAD<br>RELVHMINWAKRVPGFV<br>DLTLHDQVHLLECAWLE<br>ILMIGLVWRSMEHPGKL<br>LFAPNLLLDRNQGKCVE<br>GMVEIFDMLLATSSRFR<br>MMNLQGEEFVCLKSIIL<br>LNSGVYTFLSSTLKSLE<br>EKDHIHRVLDKITDTLI<br>HLMAKAGLTLQQQHQRL<br>AQLLLILSHIRHMSNKG<br>MEHLYSMKCKNVVPLYD<br>LLLEMLDAHRLHAPTGS<br>SQEDIIRNIARHLAQVG<br>DSMDRSIPPGLVNGLAL<br>QLRNTSRSEEDRNRDLA<br>TALEQLLQAYPRDMEKE<br>KTMLVLALLLAKKVASH<br>TP (SEQ ID NO: 6) | ATGAAGAAGAACAGCCTGGCCTTGTCCCTGACGGCCGACCAGA<br>TGGTCAGTGCCTTGTTGGATGCTGAGCCCCCCATACTCTATTC<br>CGAGTATGATCCTACCAGACCCTTCAGTGAAGCTTCGATGATG<br>GGCTTACTGACCAACCTGGCAGACAGGGAGCTGGTTCACATGA<br>TCAACTGGGCGAAGAGGGTGCCAGGCTTTGTGGATTTGACCCT<br>CCATGATCAGGTCCACCTTCTAGAATGTGCCTGGCTAGAGATC<br>CTGATGATTGGACTCGTCTGGCGCTCCATGGAGCACCCAGGGA<br>AGCTACTGTTTGCTCCTAACTTGCTCTTGGACAGGAACCAGGG<br>AAAATGTGTAGAGGGCATGGTGGAGATCTTCGACATGCTGCTG<br>GCTACATCATCTCGGTTCCGCATGATGAATCTGCAGGGAGAGG<br>AGTTTGTGTGCCTCAAATCTATTATTTTGCTTAATTCTGGAGT<br>GTACACATTTCTGTCCAGCACCCTGAAGTCTCTGGAAGAGAAG<br>GACCATATCCACCGAGTCCTGGACAAGATCACAGACACTTTGA<br>TCCACCTGATGGCCAAGGCAGGCCTGACCCTGCAGCAGCAGCA<br>CCAGCGGCTGGCCCAGCTCCTCCTCATCCTCTCCCACATCAGG<br>CACATGAGTAACAAAGGCATGGAGCATCTGTACAGCATGAAGT<br>GCAAGAACGTGGTGCCCCTCTATGACCTGCTGCTGGAGATGCT<br>GGACGCCCACCGCCTACATGCGCCCACCGGCAGCAGTCAAGAA<br>GACATCATCCGGAATATTGCCAGGCACCTCGCCCAGGTCGGGG<br>ACAGCATGGACCGTAGCATCCCTCCGGGCCTGGTGAACGGCCT<br>GGCCCTGCAGCTCAGGAACACCAGCCGGTCGGAGGAGGACCGG<br>AACAGGGACCTGGCCACTGCCCTGGAGCAGCTGCTGCAGGCCT<br>ACCCTAGAGACATGGAGAAGGAGAAGACCATGCTGGTGCTGGC<br>CCTGCTGCTGGCCAAGAAGGTGGCCAGTCACACGCCG (SEQ<br>ID NO: 86) |
| C3452<br>(C-ESR1) | MSQEDIIRNIARHLAQV<br>GDSMDRSIPPGLVNGLA<br>LQLRNTSRSEEDRNRDL<br>ATALEQLLQAYPRDMEK<br>EKTMLVLALLLAKKVAS<br>HTPGSKKNSLALSLTAD<br>QMVSALLDAEPPILYSE<br>YDPTRPFSEASMMGLLT<br>NLADRELVHMINWAKRV<br>PGFVDLTLHDQVHLLEC<br>AWLEILMIGLVWRSMEH<br>PGKLLFAPNLLLDRNQG<br>KCVEGMVEIFDMLLATS<br>SRFRMMNLQGEEFVCLK<br>SIILLNSGVYTFLSSTL<br>KSLEEKDHIHRVLDKIT<br>DTLIHLMAKAGLTLQQQ<br>HQRLAQLLLILSHIRHM<br>SNKGMEHLYSMKCKNVV<br>PLYDLLLEMLDAHRLHA<br>PT (SEQ ID NO: 7) | ATGAGTCAAGAAGACATCATCCGGAATATTGCCAGGCACCTCG<br>CCCAGGTCGGGGACAGCATGGACCGTAGCATCCCTCCGGGCCT<br>GGTGAACGGCCTGGCCCTGCAGCTCAGGAACACCAGCCGGTCG<br>GAGGAGGACCGGAACAGGGACCTGGCCACTGCCCTGGAGCAGC<br>TGCTGCAGGCCTACCCTAGAGACATGGAGAAGGAGAAGACCAT<br>GCTGGTGCTGGCCCTGCTGCTGGCCAAGAAGGTGGCCAGTCAC<br>ACGCCGGGAAGCAAGAAGAACAGCCTGGCCTTGTCCCTGACGG<br>CCGACCAGATGGTCAGTGCCTTGTTGGATGCTGAGCCCCCCAT<br>ACTCTATTCCGAGTATGATCCTACCAGACCCTTCAGTGAAGCT<br>TCGATGATGGGCTTACTGACCAACCTGGCAGACAGGGAGCTGG<br>TTCACATGATCAACTGGGCGAAGAGGGTGCCAGGCTTTGTGGA<br>TTTGACCCTCCATGATCAGGTCCACCTTCTAGAATGTGCCTGG<br>CTAGAGATCCTGATGATTGGACTCGTCTGGCGCTCCATGGAGC<br>ACCCAGGGAAGCTACTGTTTGCTCCTAACTTGCTCTTGGACAG<br>GAACCAGGGAAAATGTGTAGAGGGCATGGTGGAGATCTTCGAC<br>ATGCTGCTGGCTACATCATCTCGGTTCCGCATGATGAATCTGC<br>AGGGAGAGGAGTTTGTGTGCCTCAAATCTATTATTTTGCTTAA<br>TTCTGGAGTGTACACATTTCTGTCCAGCACCCTGAAGTCTCTG<br>GAAGAGAAGGACCATATCCACCGAGTCCTGGACAAGATCACAG<br>ACACTTTGATCCACCTGATGGCCAAGGCAGGCCTGACCCTGCA<br>GCAGCAGCACCAGCGGCTGGCCCAGCTCCTCCTCATCCTCTCC<br>CACATCAGGCACATGAGTAACAAAGGCATGGAGCATCTGTACA<br>GCATGAAGTGCAAGAACGTGGTGCCCCTCTATGACCTGCTGCT<br>GGAGATGCTGGACGCCCACCGCCTACATGCGCCCACC (SEQ<br>ID NO: 87) |
| C3687<br>(H-ESR1) | MSQEDIIRNIARHLAQV<br>GDSMDRSIPPGSEEDRN<br>RDLATALEQLLQAYPRD<br>MEKEKTMLVLALLLAKK<br>VASHTPGSKKNSLALSL<br>TADQMVSALLDAEPPIL<br>YSEYDPTRPFSEASMMG<br>LLTNLADRELVHMINWA<br>KRVPGFVDLTLHDQVHL<br>LECAWLEILMIGLVWRS<br>MEHPGKLLFAPNLLLDR<br>NOGKCVEGMVEIFDMLL<br>ATSSRFRMMNLQGEEFV<br>CLKSIILLNSGVYTFLS<br>STLKSLEEKDHIHRVLD<br>KITDTLIHLMAKAGLTL | ATGAGTCAAGAAGACATCATCCGGAATATTGCCAGGCACCTCG<br>CCCAGGTCGGGGACAGCATGGACCGTAGCATCCCTCCGGGCTC<br>GGAGGAGGACCGGAACAGGGACCTGGCCACTGCCCTGGAGCAG<br>CTGCTGCAGGCCTACCCTAGAGACATGGAGAAGGAGAAGACCA<br>TGCTGGTGCTGGCCCTGCTGCTGGCCAAGAAGGTGGCCAGTCA<br>CACGCCGGGAAGCAAGAAGAACAGCCTGGCCTTGTCCCTGACG<br>GCCGACCAGATGGTCAGTGCCTTGTTGGATGCTGAGCCCCCCA<br>TACTCTATTCCGAGTATGATCCTACCAGACCCTTCAGTGAAGC<br>TTCGATGATGGGCTTACTGACCAACCTGGCAGACAGGGAGCTG<br>GTTCACATGATCAACTGGGCGAAGAGGGTGCCAGGCTTTGTGG<br>ATTTGACCCTCCATGATCAGGTCCACCTTCTAGAATGTGCCTG<br>GCTAGAGATCCTGATGATTGGACTCGTCTGGCGCTCCATGGAG<br>CACCCAGGGAAGCTACTGTTTGCTCCTAACTTGCTCTTGGACA<br>GGAACCAGGGAAAATGTGTAGAGGGCATGGTGGAGATCTTCGA<br>CATGCTGCTGGCTACATCATCTCGGTTCCGCATGATGAATCTG<br>CAGGGAGAGGAGTTTGTGTGCCTCAAATCTATTATTTTGCTTA |

TABLE 4-continued

| tBID Fusion Proteins. | | |
|---|---|---|
| Name | Protein Sequence | Nucleotide Sequence |
| | QQQHQRLAQLLLILSHI RHMSNKGMEHLYSMKCK NVVPLYDLLLEMLDAHR LHAPT (SEQ ID NO: 97) | ATTCTGGAGTGTACACATTTCTGTCCAGCACCCTGAAGTCTCT GGAAGAGAAGGACCATATCCACCGAGTCCTGGACAAGATCACA GACACTTTGATCCACCTGATGGCCAAGGCAGGCCTGACCCTGC AGCAGCAGCACCAGCGGCTGGCCCAGCTCCTCCTCATCCTCTC CCACATCAGGCACATGAGTAACAAAGGCATGGAGCATCTGTAC AGCATGAAGTGCAAGAACGTGGTGCCCCTCTATGACCTGCTGC TGGAGATGCTGGACGCCCACCGCCTACATGCGCCCACC (SEQ ID NO: 98) |

In some embodiments of the fusion proteins of the disclosure, the fusion protein shares at least 85% identity, at least 90% identity, at least 95% identity, at least 96% identity, at least 97% identity, at least 98% identity, at least 99% identity or is identical to ESR1-D (SEQ ID NO: 4). In some embodiments, the fusion protein shares at least 95% identity to ESR1-D (SEQ ID NO: 4). In some embodiments, the fusion protein comprises SEQ ID NO: 4. In some embodiments, the fusion protein consists essentially of SEQ ID NO: 4.

In some embodiments of the fusion proteins of the disclosure, the fusion protein shares at least 85% identity, at least 90% identity, at least 95% identity, at least 96% identity, at least 97% identity, at least 98% identity, at least 99% identity or is identical to D-ESR1 (SEQ ID NO: 5). In some embodiments, the fusion protein shares at least 95% identity to D-ESR1 (SEQ ID NO: 5). In some embodiments, the fusion protein comprises SEQ ID NO: 5. In some embodiments, the fusion protein consists essentially of SEQ ID NO: 5.

In some embodiments of the fusion proteins of the disclosure, the fusion protein shares at least 85% identity, at least 90% identity, at least 95% identity, at least 96% identity, at least 97% identity, at least 98% identity, at least 99% identity or is identical to ESR1-C (SEQ ID NO: 6). In some embodiments, the fusion protein shares at least 95% identity to ESR1-C(SEQ ID NO: 6). In some embodiments, the fusion protein comprises SEQ ID NO: 6. In some embodiments, the fusion protein consists essentially of SEQ ID NO: 6.

In some embodiments of the fusion proteins of the disclosure, the fusion protein shares at least 85% identity, at least 90% identity, at least 95% identity, at least 96% identity, at least 97% identity, at least 98% identity, at least 99% identity or is identical to C-ESR1 (SEQ ID NO: 7). In some embodiments, the fusion protein shares at least 95% identity to C-ESR1 (SEQ ID NO: 7). In some embodiments, the fusion protein comprises SEQ ID NO: 7. In some embodiments, the fusion protein consists essentially of SEQ ID NO: 7.

Polynucleotides and Vectors

In other aspects, the disclosure provides polynucleotides encoding the fusion proteins described herein. In some embodiments, the polynucleotides encode a fusion protein comprising a tBID polypeptide and an SHR polypeptide. In some embodiments, the SHR polypeptide is a ligand binding domain isolated or derived from a steroid hormone receptor such as ESR1. In some embodiments, the polynucleotides encode a fusion protein further comprising a linker between the tBID polypeptide and the SHR polypeptide.

The term nucleic acid, or polynucleotide, includes DNA and RNA such as genomic DNA, cDNA and mRNA, or combinations thereof. The nucleic acid may comprise, in addition to the sequence coding for the fusion proteins of the disclosure, further sequences such as those required for the transcription and/or translation of the nucleic acid coding for the fusion protein. This may include a promoter, enhancer, transcription and/or translation initiation and/or termination sequences, selection markers, sequences protecting or directing the RNA or fusion protein within the cell. The selection and combination of these sequences is within the knowledge of the person skilled in the art and may be selected in accordance with the cell the nucleic acid or fusion protein is intended for.

In some embodiments, the polynucleotides comprise a sequence encoding a tBID domain. In some embodiments, the polynucleotides comprise a sequence encoding a tBID polypeptide that is at least 80%, at least 90%, at least 95%, at least 96%, at least 97%, at least 98%, at least 99% identity or that is identical to a subsequence of SEQ ID NO: 8. In some embodiments, a the polynucleotides comprise a sequence encoding a tBID polypeptide consisting essentially of a polypeptide sequence having at least 80%, at least 90%, at least 95%, at least 96%, at least 97%, at least 98%, at least 99% identity or that is identical to a subsequence of SEQ ID NO: 8.

In some embodiments, the polynucleotides comprise a sequence encoding a tBID domain. In some embodiments, the polynucleotides comprise a sequence encoding a tBID polypeptide that is at least 80%, at least 90%, at least 95%, at least 96%, at least 97%, at least 98%, at least 99% identity or that is identical to a subsequence of SEQ ID NO: 9. In some embodiments, a the polynucleotides comprise a sequence encoding a tBID polypeptide consisting essentially of a polypeptide sequence having at least 80%, at least 90%, at least 95%, at least 96%, at least 97%, at least 98%, at least 99% identity or that is identical to a subsequence of SEQ ID NO: 9.

In some embodiments, the polynucleotides comprise a sequence encoding a tBID domain. In some embodiments, the polynucleotides comprise a sequence encoding a tBID polypeptide that is at least 80%, at least 90%, at least 95%, at least 96%, at least 97%, at least 98%, at least 99% identity or that is identical to a subsequence of SEQ ID NO: 10. In some embodiments, a the polynucleotides comprise a sequence encoding a tBID polypeptide consisting essentially of a polypeptide sequence having at least 80%, at least 90%, at least 95%, at least 96%, at least 97%, at least 98%, at least 99% identity or that is identical to a subsequence of SEQ ID NO: 10.

In some embodiments of the polynucleotides of the disclosure, the polynucleotides comprise a sequence encoding a tBID polypeptide having at least 80%, at least 90%, at least 95%, at least 96%, at least 97%, at least 98%, at least 99% identity or that is identical to amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9. In some embodiments, the polynucleotides comprise a sequence encoding a tBID polypeptide comprising or consisting essentially of amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9. In some embodiments, the polynucleotides comprise a sequence encoding a tBID polypeptide consisting essentially of amino acid residues 60-195 of SEQ ID NO: 9, residues 62-195 of SEQ ID NO: 9, residues 60-195 of SEQ ID NO: 9, residues 79-192 of SEQ ID NO: 9, residues 70-195 of SEQ ID NO: 9, residues 78-195 of SEQ ID NO: 9, or residues 60-142 of SEQ ID NO: 9.

In some embodiments of the polynucleotides of the disclosure, the polynucleotides comprise a sequence encoding a tBID polypeptide comprising one or more deletions encompassing of any one of BID alpha helices 1, 2, 4, 5, 7, 8 or any combination thereof. For example, the polynucleotides may encode a tBID polypeptide comprising a deletion of BID alpha helices 1 and 2, i.e. the tBID polypeptide does not comprise sequences of SEQ ID NO: 11 and SEQ ID NO: 12.

In some embodiments of the polynucleotides of the disclosure, the polynucleotides comprise a sequence encoding a tBID polypeptide comprising a deletion of BID alpha helix 8 (SEQ ID NO: 18). In some embodiments, the polynucleotides comprise a sequence encoding a tBID polypeptide comprising a deletion of BID alpha helix 4 and/or BID helix 5 (SEQ ID NO: 14, SEQ ID NO: 15, or both SEQ ID NO: 14 and SEQ ID NO: 15). In some embodiments, the polynucleotides comprise a sequence encoding a tBID polypeptide comprising a deletion of BID helix 7 (SEQ ID NO: 17).

In some embodiments of the polynucleotides of the disclosure, the polynucleotides comprise a sequence encoding a tBID polypeptide comprising BID alpha helices 3, 4, 5, 6, 7 and 8 (SEQ ID NO: 13, SEQ ID NO: 14, SEQ ID NO: 15, SEQ ID NO: 16, SEQ ID NO: 17 and SEQ ID NO: 18), or sequences having at least 80% identity, at least 90% identity, at least 95% identity or at least 99% identity thereto. In some embodiments, the polynucleotides encode a tBID polypeptide comprising sequences of BID alpha helices 3, 4, 5, 6, 7 and 8 (SEQ ID NO: 13, SEQ ID NO: 14, SEQ ID NO: 15, SEQ ID NO: 16, SEQ ID NO: 17 and SEQ ID NO: 18). In some embodiments, the polynucleotides comprise a sequence encoding a tBID polypeptide comprising or consisting essentially of SEQ ID NO: 19, or a sequence having at least 80% identity, at least 90% identity, at least 95% identity or at least 99% identity thereto. In some embodiments, the polynucleotides comprise a sequence encoding a tBID polypeptide comprising or consisting essentially of, SEQ ID NO: 19. In some embodiments, the polynucleotides comprise a sequence encoding a tBID polypeptide comprising or consisting essentially of SEQ ID NO: 20, or a sequence having at least 80% identity, at least 90% identity, at least 95% identity or at least 99% identity thereto. In some embodiments, the polynucleotides comprise a sequence encoding a tBID polypeptide comprising or consisting essentially of SEQ ID NO: 20. In some embodiments, the polynucleotides comprise a sequence encoding a tBID polypeptide comprising or consisting essentially of SEQ ID NO: 21, or a sequence having at least 80% identity, at least 90% identity, at least 95% identity or at least 99% identity thereto. In some embodiments, the polynucleotides comprise a sequence encoding a tBID polypeptide comprising or consisting essentially of, SEQ ID NO: 21.

In some embodiments of the polynucleotides of the disclosure, the polynucleotides comprise a sequence encoding a tBID polypeptide comprising BID alpha helices 3, 6, 7 and 8 (SEQ ID NO: 13, SEQ ID NO: 16, SEQ ID NO: 17 and SEQ ID NO: 18), or sequences having at least 80% identity, at least 90% identity, at least 95% identity or at least 99% identity thereto. In some embodiments, the polynucleotides comprise a sequence encoding a tBID polypeptide comprising sequences identical to SEQ ID NO: 13, SEQ ID NO: 16, SEQ ID NO: 17 and SEQ ID NO: 18. In some embodiments, the tBID polypeptides do not comprise sequences of BID helices 1 and 2, i.e. the tBID polypeptides do not comprise sequences of SEQ ID NO: 11 and SEQ ID NO: 12.

In some embodiments of the polynucleotides of the disclosure, the polynucleotides comprise a sequence encoding a tBID polypeptide comprising sequences of BID alpha helices 3, 4, 5, and 6 (SEQ ID NO: 13, SEQ ID NO: 14, SEQ ID NO: 15 and SEQ ID NO: 16), or sequences having at least 80% identity, at least 90% identity, at least 95% identity or at least 99% identity thereto. In some embodiments, the polynucleotides comprise a sequence encoding a tBID polypeptide comprising sequences of BID alpha helices 3, 4, 5 and 6 (SEQ ID NO: 13, SEQ ID NO: 14, SEQ ID NO: 15 and SEQ ID NO: 16). In some embodiments, the tBID polypeptides do not comprise sequences of BID helices 1 and 2, i.e. the tBID polypeptides do not comprise sequences of SEQ ID NO: 11 and SEQ ID NO: 12. In some embodiments, the polynucleotides comprise a sequence encoding a tBID polypeptide comprising or consisting essentially of SEQ ID NO: 22, or a sequence having at least 80% identity, at least 90% identity, at least 95% identity or at least 99% identity thereto. In some embodiments, the polynucleotides comprise a sequence encoding a tBID polypeptide comprising or consisting essentially of SEQ ID NO: 22. In some embodiments, the polynucleotides comprise a sequence encoding a tBID polypeptide comprising or consisting essentially of SEQ ID NO: 22, or a sequence having at least 80% identity, at least 90% identity, at least 95% identity or at least 99% identity thereto. In some embodiments, the polynucleotides comprise a sequence encoding a tBID polypeptide comprising or consisting essentially of SEQ ID NO: 2. In some embodiments, the polynucleotides comprise a sequence encoding a tBID polypeptide comprising or consisting essentially of a sequence at least 95% identical to SEQ ID NO: 2. In some embodiments, the polynucleotides comprise a polynucleotide sequence of SEQ ID NO: 23, or a sequence having at least 70% identity, at least 80% identity, at least 90% identity, at least 95% identity or at least 99% identity thereto. In some embodiments, a he polynucleotides comprise a polynucleotide sequence SEQ ID NO: 23.

In some embodiments of the polynucleotides of the disclosure, the polynucleotides comprise a sequence encoding a tBID polypeptide comprising sequences of BID alpha helices 3, 6 and 7 (SEQ ID NO: 13, SEQ ID NO: 16 and SEQ ID NO: 17), or sequences having at least 80% identity, at least 90% identity, at least 95% identity or at least 99% identity thereto. In some embodiments, the polynucleotides comprise a sequence encoding a tBID polypeptide comprising sequences identical SEQ ID NO: 13, SEQ ID NO: 16 and SEQ ID NO: 17. In some embodiments, the tBID polypeptides do not comprise sequences of BID helices 1 and 2, i.e. the tBID polypeptides do not comprise sequences of SEQ ID NO: 11 and SEQ ID NO: 12. In some embodiments, the polynucleotides comprise a sequence encoding a tBID polypeptide comprising or consisting essentially of a sequence of SEQ ID NO: 1, or a sequence having at least 80% identity, at least 90% identity, at least 95% identity or at least 99% identity thereto. In some embodiments, the tBID polypeptides comprise a sequence identical to SEQ ID NO: 1. In some embodiments, the polynucleotides comprise a sequence encoding a tBID polypeptide comprising or consisting essentially of a sequence identical to SEQ ID NO: 1. In some embodiments, the polynucleotides comprise a tBID polynucleotide sequence of SEQ ID NO: 24, or a sequence having at least 70% identity, at least 80% identity, at least 90% identity, at least 95% identity or at least 99% identity thereto. In some embodiments, the polynucleotides comprise a tBID polynucleotide sequence of SEQ ID NO: 24.

In some embodiments of the polynucleotides of the disclosure, the polynucleotides comprise a sequence encoding a tBID polypeptide comprising sequences of BID alpha helices 3, and 6 (SEQ ID NO: 13 and SEQ ID NO: 16), or sequences having at least 80% identity, at least 90% identity, at least 95% identity or at least 99% identity thereto. In some embodiments, the polynucleotides comprise a sequence encoding a tBID polypeptide comprising sequences of EQ ID NO: 13 and SEQ ID NO: 16. In some embodiments, the tBID polypeptide does not comprise sequences of SEQ ID NO: 11 and SEQ ID NO: 12.

In some embodiments of the polynucleotides of the disclosure, the polynucleotides comprise a sequence encoding a tBID polypeptide comprising a sequence of BID alpha helix 3 (SEQ ID NO: 13), or a sequence having at least 80% identity, at least 90% identity, at least 95% identity or at least 99% identity thereto. In some embodiments, the polynucleotides comprise a sequence encoding a tBID polypeptide comprising a sequence of BID alpha helix 3 (SEQ ID NO: 13). In some embodiments, the tBID polypeptide does not comprise sequences of SEQ ID NO: 11 and SEQ ID NO: 12.

In some embodiments of the polynucleotides of the disclosure, the polynucleotides comprise a sequence encoding a tBID polypeptide comprising a sequence of BID alpha helix 6 of BID (SEQ ID NO: 16), or a sequence having at least 80% identity, at least 90% identity, at least 95% identity or at least 99% identity thereto. In some embodiments, the polynucleotides comprise a sequence encoding a tBID polypeptide comprising a sequence of BID alpha helix 6 (SEQ ID NO: 16). In some embodiments, the tBID polypeptide does not comprise sequences of SEQ ID NO: 11 and SEQ ID NO: 12.

In some embodiments of the polynucleotides of the disclosure, the polynucleotides comprise a sequence encoding a SHR domain. In some embodiments, the polynucleotides comprise a sequence encoding a ligand binding domain of a steroid hormone receptor. In some embodiments, the polynucleotides comprise a sequence encoding a LBD isolated or derived from NR1A1, NR1A2, NR1B1, NR1B2, NR1B3, NR1C1, NR1C2, NR1C3, NR1D1, NR1D2, NR1F1, NR1F2, NR1F3, NR1H4, NR1H5, NR1H3, NR1H2, NR1I1, NR1I2, NR1I3, NR2A1, NR2A2, NR2B1, NR2B2, NR2B3, NR2C1, NR2C2, NR2E1, NR2E3, NR2F1, NR2F2, NR2F6, NR3B1, NR3B2, NR3B3, NR4A1, NR4A2, NR4A3, NR5A1, NR5A2, NR6A1, NR0B1, NR0B2, NR3A1, NR3A2, NR3C4, GNR3C1, NR3C2 or NR3C3. In some embodiments, the polynucleotides comprise a sequence encoding a LBD having at least at least 85% identity, at least 90% identity, at least 95% identity, at least 96% identity, at least 97% identity, at least 98% identity, at least 99% identity or that is identical to the sequence of a LBD isolated or derived from a nuclear hormone receptor selected from the group consisting of NR1A1, NR1A2, NR1B1, NR1B2, NR1B3, NR1C1, NR1C2, NR1C3, NR1D1, NR1D2, NR1F1, NR1F2, NR1F3, NR1H4, NR1H5, NR1H3, NR1H2, NR1I1, NR1I2, NR1I3, NR2A1, NR2A2, NR2B1, NR2B2, NR2B3, NR2C1, NR2C2, NR2E1, NR2E3, NR2F1, NR2F2, NR2F6, NR3B1, NR3B2, NR3B3, NR4A1, NR4A2, NR4A3, NR5A1, NR5A2, NR6A1, NR0B1, NR0B2, NR3A1, NR3A2, NR3C4, GNR3C1, NR3C2 and NR3C3. In some embodiments, the polynucleotides comprise a sequence encoding a LBD having at least at least 85% identity, at least 90% identity, at least 95% identity, at least 96% identity, at least 97% identity, at least 98% identity, at least 99% identity or is identical to the sequence of a LBD isolated or derived from a nuclear hormone receptor described in Table 2 or Table 3.

In some embodiments of the polynucleotides of the disclosure, the polynucleotides comprise a sequence encoding an SHR domain isolated or derived from an estrogen receptor, for example ESR1.

In some embodiments of the polynucleotides of the disclosure, the polynucleotides comprise a sequence encoding an ESR1 domain. In some embodiments, the polynucleotides comprise a sequence encoding a subsequence of SEQ ID NO: 68, or a sequence having at least 85% identity, at least 90% identity, at least 95% identity, at least 96% identity, at least 97% identity, at least 98% identity, at least 99% identity or is identical thereto. In some embodiments, the polynucleotides comprise a sequence encoding amino acids 302-553 of SEQ ID NO: 68, amino acids 305-559 of SEQ ID NO: 68, amino acids 311-547 of SEQ ID NO: 68 or a sequence having a having at least 85% identity, at least 90% identity, at least 95% identity, at least 96% identity, at least 97% identity, at least 98% identity, or at least 99% identity thereto.

In some embodiments of the polynucleotides of the disclosure, the polynucleotides comprise a sequence encoding a polypeptide having at least 85% identity, at least 90% identity, at least 95% identity, at least 96% identity, at least 97% identity, at least 98% identity, at least 99% identity or that is identical to SEQ ID NO: 3. In some embodiments, the polynucleotides comprise a sequence encoding a polypeptide having at least 95% identity to SEQ ID NO: 3. In some embodiments, the polynucleotides comprise a sequence encoding a polypeptide of SEQ ID NO: 3. In some embodiments, the polynucleotides comprise a sequence encoding an ESR1 LBD that consists essentially of SEQ ID NO: 3. In some embodiments, the polynucleotides comprise SEQ ID NO: 83 or a sequence having at least 70% identity, at least 80% identity, at least 90% identity, at least 95% identity or at least 99% identity thereto. In some embodiments, the polynucleotides comprise SEQ ID NO: 83. In some embodiments, the polynucleotides comprise an ESR1 polynucleotide sequence consisting essentially of SEQ ID NO: 83.

Receptors

The disclosure provides polynucleotides comprising a sequence encoding a chimeric antigen receptor (CAR). The disclosure provides polynucleotides comprising a sequence encoding an T cell receptor (TCR). Any suitable CAR or TCR is envisaged as within the scope of the instant disclosure.

The term "chimeric antigen receptors (CARs)," as used herein, may refer to artificial receptors derived from T cell receptors, and encompasses engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising an antigen binding region. In particular aspects, CARs comprise fusions of single-chain variable fragments (scFv) derived from monoclonal antibodies, fused to CD3 a transmembrane domain and endodomain. The specificity of other CAR designs may be derived from ligands of receptors (e.g., peptides and their cognate antigen binding domains). In certain cases, CARs comprise domains for additional co-stimulatory signaling, such as CD3, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, cytokines, and cytokine receptors.

The term "T cell receptor" as used herein refers to a T cell receptor, optionally one that has been modified to recognize a particular antigen.

As used herein, the term "antigen" is a molecule capable of being bound by an antibody or T-cell receptor. An antigen is additionally capable of inducing a humoral immune response and/or cellular immune response leading to the production of B and/or T lymphocytes.

Any suitable antigen binding domain may be used with the CARs and TCRs of the disclosure. For example, the antigen binding domain many be an scFv, an sdAb, a Vβ-only domain or an antibody fragment.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')2, and Fv fragments, single-chain (sc)Fv ("scFv") antibody fragments, linear antibodies, single domain antibodies (abbreviated "sdAb") (either VL or VH), camelid VHH domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "VH" (or, in the case of single domain antibodies, e.g., nanobodies, "VHH") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

The term "antibody light chain," refers to the smaller of the two types of polypeptide chains present in antibody molecules in their naturally occurring conformations. Kappa ("K") and lambda ("k") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "VP domain", "VP-only domain", "β chain variable domain" or "single variable domain TCR (svd-TCR)" refers to an antigen binding domain that consists essentially of a single T Cell Receptor (TCR) beta variable domain that specifically binds to an antigen in the absence of a second TCR variable domain. In some embodiments, the first, activator LBD comprises or consists essentially of a Vβ-only domain. In some embodiments, the second, inhibitor LBD comprises or consists essentially of a Vβ-only domain.

In some embodiments, the CAR or TCR is used to treat a proliferative disorder such as cancer, and the CAR or TCR recognizes a cancer antigen. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

In some embodiments, the polynucleotides comprise a sequence encoding a self-cleaving peptide. For example, when the polynucleotides encode a tBID fusion protein and a CAR or TCR, the polynucleotide may further comprise a sequence encoding a self-cleaving between the CAR or TCR and the tBID fusion protein.

Exemplary self-cleaving polypeptides include the 2A peptides, which include T2A, E2A, F2A and P2A. In some embodiments, the cleavage site comprises a T2A peptide. In some embodiments, the T2A peptide comprises an amino acid sequence having at least 80% identity, at least 90% identity, at least 95% identity, at least 99% identity or is identical to a sequence of EGRGSLLTCGDVEENPGP (SEQ ID NO: 88). In some embodiments, the T2A peptide comprises or consists essentially of SEQ ID NO: 88. In some embodiments, the T2A peptide is encoded by a nucleotide sequence having at least 80% identity, at least 90% identity, at least 95% identity, at least 99% identity or is identical to a sequence of GAGGGCAGAGGCAGCCTGCTGACATGTGGCGACGTGGAAGAGAACCCTGGCCCC (SEQ ID NO: 89). In some embodiments, the T2A peptide is encoded by SEQ ID NO: 89.

In some embodiments, the cleavage site comprises P2A polypeptide. In some embodiments, the P2A peptide comprises an amino acid sequence of ATNFSLLKQAGDVEENPGP (SEQ ID NO: 90). In some embodiments, the P2A peptide comprises or consists essentially of SEQ ID NO: 90. In some embodiments, the cleavage site comprises E2A peptide. In some embodiments, the E2A peptide comprises an amino acid sequence of QCTNYALLKLAGDVESNPGP (SEQ ID NO: 91). In some embodiments, the E2A peptide comprises or consists essentially of SEQ ID NO: 91. In some embodiments, the cleavage site comprises F2A peptide. In some embodiments, the F2A peptide comprises an amino acid sequence of VKQTLNFDLLKLAGDVESNPGP (SEQ ID NO: 92). In some embodiments, the F2A peptide comprises or consists essentially of SEQ ID NO: 92. An exemplary 2A peptide and related vectors are described in WO2017040815A1, which is incorporated herein by reference in its entirety.

Vectors

Polynucleotides of the disclosure may be delivered to cells as an isolated nucleic acid or in a vector. The isolated nucleic acid or the vector may be delivered in lipid- or lipid-based delivery system, such as a liposome. Alternatively, the vector may comprise viral proteins, such as when the vector is a viral vector. The term "vector" as used herein refers to a construction comprised of genetic material designed to direct transformation or transductions of a targeted cell. A vector contains multiple genetic elements positionally and sequentially oriented with other necessary elements such that the nucleic acid in a nucleic acid cassette can be transcribed and when necessary translated in the transfected cells. The term vector as used herein can refer to nucleic acid, e.g., DNA derived from a plasmid, cosmid, phagemid, bacteriophage, virus, retrovirus, adenovirus, adeno-associated virus, lentivirus, or other type of virus into which one or more fragments of nucleic acid may be inserted or cloned which encode for particular proteins. The term "plasmid" as used herein refers to a construction comprised of extrachromosomal genetic material, usually of a circular duplex of DNA which can replicate independently of chromosomal DNA. The plasmid does not necessarily replicate.

The disclosure provides vectors comprising the polynucleotides encoding the fusion proteins of the disclosure. Any suitable vectors are envisaged as within the scope of the instant disclosure. The polynucleotides encoding the fusion proteins can be cloned into a number of types of vectors. For example, the polynucleotides can be cloned into a vector including, but not limited to a plasmid, a phagemid, a phage derivative, an animal virus, and a cosmid. Vectors of particular interest include expression vectors, replication vectors, probe generation vectors, and sequencing vectors. Expression vectors may be provided to cells, such as immune cells, in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

The vector can contain one or more unique restriction sites, and may be capable of autonomous replication in a defined host or organism such that the cloned sequence is reproduced. The vector molecule can confer some well-defined phenotype on the host organism which is either selectable or readily detected. The vector may have a linear or circular configuration. The components of a vector can contain but is not limited to a DNA molecule incorporating: (1) DNA; (2) a sequence encoding the fusion protein of the invention; and (3) regulatory elements for transcription, translation, RNA processing, RNA stability, and replication.

The purpose of the vector is to provide expression of a nucleic acid sequence in cells or tissue. Expression includes the efficient transcription of an inserted gene or nucleic acid sequence. Expression products may be proteins, polypeptides, or RNA. The nucleic acid sequence can be contained in a nucleic acid cassette. Expression of the nucleic acid can be continuous, constitutive, or regulated. The vector can also be used as a prokaryotic element for replication of plasmid in bacteria and selection for maintenance of plasmid in bacteria.

In one embodiment, the vector comprises the following elements linked sequentially at an appropriate distance to allow functional expression: a promoter, a 5' mRNA leader sequence, a translation initiation site, a nucleic acid cassette containing the sequence of the fusion protein to be expressed, a 3' mRNA untranslated region, and a polyadenylation signal sequence. As used herein the term "expression vector" refers to a DNA vector that contains all of the information necessary to produce a recombinant protein in a heterologous cell.

In addition, the term "vector" as used herein can also include viral vectors. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a vector of the present invention, that portion does not cause incorporation of the vector into a viral particle and thus is unable to produce an infective viral particle. A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentiviral vectors are used.

A vector as used herein can also include DNA sequence elements which enable extra-chromosomal (episomal) replication of the DNA. Vectors capable of episomal replication are maintained as extra-chromosomal molecules and can replicate. These vectors are not eliminated by simple degradation but continue to be copied. These elements may be derived from a viral or mammalian genome. These provide prolonged or "persistent" expression.

In some embodiments, the vector is a "lentiviral" vector or "lentivirus," the terms being used interchangeably. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. Further, they do not transfer viral genes, therefore avoiding the problem of generating transduced cells that can be destroyed by cytotoxic T-cells. Furthermore, they have a relatively large cloning capacity, sufficient for most envisioned clinical applications. In addition, lentiviruses, in contrast to other retroviruses, are capable of transducing non-dividing cells. This is very important in the context of gene-therapy for tissues such as the hematopoietic system, the brain, liver, lungs and muscle. For example, vectors derived from HIV-1 allow efficient in vivo and ex vivo delivery, integration and stable expression of transgenes into cells such a neurons, hepatocytes, and myocytes.

Lentiviral vectors are known in the art, see U.S. Pat. Nos. 6,013,516; and 5,994,136, which are incorporated herein by reference. In general, these vectors are plasmid-based or virus-based, and are configured to carry the essential sequences for incorporating foreign nucleic acid, for selection and for transfer of the nucleic acid into a host cell.

In some cases, a lentiviral vector is introduced into a cell concurrently with one or more lentiviral packaging plasmids, which may include, without limitation, pMD2.G, pRSV-rev, pMDLG-pRRE, and pRRL-GOI. Introduction of a lentiviral vector alone or in combination with lentiviral packaging plasmids into a cell may cause the lentiviral vector to be packaged into a lentiviral particle.

As used herein, the term "lentiviral vector" is intended to mean a nucleic acid that encodes a lentiviral cis nucleic acid sequence required for genome packaging. A lentiviral vector also can encode other cis nucleic acid sequences beneficial for gene delivery, including for example, cis sequences required for reverse transcription, proviral integration or genome transcription. A lentiviral vector performs transduction functions of a lentiviral vector. As such, the exact makeup of a vector genome will depend on the genetic material desired to be introduced into a target cell. Therefore, a vector genome can encode, for example, additional polypeptides or functions other than that required for packaging, reverse transcription, integration, or transcription. Such functions generally include coding for cis elements required for expression of a nucleic acid of interest. The lentiviral cis sequences or elements can be derived from a lentivirus genome or other virus or vector genome so long as the lentiviral vector genome can be packaged by a packaging cell line into a lentiviral particle and introduced into a target cell.

In some embodiments, the vector is a recombinant adeno-associated virus (AAV). The AAV can be any serotype, for example AAV1, AAV2, AAV3, AAV4, AAV5, AAV6, AAV7, AAV8, AAV9, AAV-10, AAV-11, AAV-12, AAV-13 or AAV rh74. In some embodiments, the vector comprises a self-complementary AAV. In some embodiments, the vector comprises a single-stranded AAV. In some embodiments, the AAV is a wild-type AAV or a modified AAV. In some embodiments, the AAV comprises a capsid protein having at least 95% identity to wild-type VP1, VP2, or VP3 capsid protein. In some embodiments, an AAV vector comprises the inverted terminal repeat (ITR) sequences of AAV2. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

In some embodiments, the vector is a recombinant adenovirus. Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation. In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Improved methods for culturing 293 cells and propagating adenovirus are known in the art. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

The adenoviruses of the disclosure are replication defective, or at least conditionally replication defective. The adenovirus may be of any of the 42 different known serotypes or subgroups A-F. Adenovirus type 5 of subgroup C is the preferred starting material in order to obtain the conditional replication-defective adenovirus vector for use in the present disclosure.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of the deleted E3 region in E3 replacement vectors, or in the E4 region where a helper cell line or helper virus complements the E4 defect.

Adenovirus is easy to grow and manipulate and exhibits broad host range in vitro and in vivo. This group of viruses can be obtained in high titers, e.g., 109-1012 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

Adenovirus vectors have been used in eukaryotic gene expression and vaccine development. Animal studies suggested that recombinant adenovirus could be used for gene therapy. Studies in administering recombinant adenovirus to different tissues include trachea instillation, muscle injection, peripheral intravenous injections and stereotactic inoculation into the brain.

The expression of polynucleotides encoding the fusion proteins described herein can be achieved by operably linking a nucleic acid encoding a fusion protein to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters are also contemplated. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of fusion proteins, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). One method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the fusion protein, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or other assays.

Immune Cells

Provided herein are isolated immune cells comprising the polynucleotides, vectors and fusion proteins described herein. In some embodiments, the immune cells comprise a CAR or TCR as described herein. The immune cells of the disclosure can be used in adoptive cell therapy.

In some embodiments, the immune cells comprise a first activator receptor, such as a CAR or TCR, and a second inhibitory receptor, a dual receptor system. In some embodiments, the first activator is specific to a ligand expressed by cancer cells in a subject, such as a cancer antigen, and the second inhibitory receptor is specific to ligand expressed by wild type cells of the subject but not by cancer cells, for example a ligand lost on the cancer cells through loss of heterozygosity. Differential expression of ligands for the first and second receptors, for example through loss of heterozygosity of the locus encoding the inhibitory ligand, mediates activation of immune cells by target cells that express the first activator ligand but not the second inhibitory ligand. Thus, in this two receptor system, the first receptor acts to activate, or promote activation of the immune cells in the presence of the cancer cells, while the second receptor acts to inhibit activation by the first receptor in the presence of wild type cells. Exemplary ligands lost in cancer cells through loss of heterozygosity include HLA class I alleles and minor histocompatibility antigens (MiHA). Targeting cancer cells using a two receptor system is described in WO2021030149, filed on Aug. 6, 2020, and PCT/US2021/036627, filed on Jun. 9, 2021, the contents each of which are incorporated by reference herein in their entireties. LIR1 based inhibitory receptors for use in the dual receptor system are described in WO2021119489, filed on Dec. 11, 2020, and PAG1 based inhibitory receptors for use in the dual receptor system are described in PCT/US2021/029907, filed on Apr. 29, 2021, the contents of each of which are incorporated by reference herein in their entireties. TCRs for use in the dual receptor system are described in WO2021030153, filed on Aug. 6, 2021, and WO2021096868, filed on Nov. 20, 2020, the contents of each of which are incorporated by reference herein in their entireties.

As used herein, the term "immune cell" refers to a cell involved in the innate or adaptive (acquired) immune systems. Exemplary innate immune cells include phagocytic cells such as neutrophils, monocytes and macrophages, Natural Killer (NK) cells, polymophonuclear leukocytes such as neutrophils eosinophils and basophils and mononuclear cells such as monocytes, macrophages and mast cells. Immune cells with roles in acquired immunity include lymphocytes such as T-cells and B-cells.

As used herein, a "T-cell" refers to a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T-cells can be distinguished by the ordinarily skilled artisan based on their expression of markers. Methods of distinguishing between T-cell types will be readily apparent to the ordinarily skilled artisan.

In some embodiments, the engineered immune cell comprising the fusion protein, and optionally CAR or TCR of the disclosure, is a T cell. In some embodiments, the T cell is an effector T cell or a regulatory T cell.

Methods transforming populations of immune cells, such as T cells, with the vectors of the instant disclosure will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of 1×10^6 cells/mL in X-Vivo 15 media supplemented with 5% human A/B serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment. Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example excellent viral transduction of peripheral blood mononuclear cells can be achieved after 5 days of growth to generate a >99% CD3+ highly transduced cell population.

Methods of activating and culturing populations of T cells comprising the TCRs, CARs, fusion proteins or vectors encoding same, will be readily apparent to the person of ordinary skill in the art.

Whether prior to or after genetic modification of T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10040846; and U.S. Pat. Appl. Pub. No. 2006/0121005.

In some embodiments, T cells of the instant disclosure are expanded and activated in vitro. Generally, the T cells of the instant disclosure are expanded in vitro by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. In some embodiments, a ratio of 1:1 cells to beads is used. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the T cells. In one embodiment the cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. In some embodiments, cells that are cultured at a density of $1\times10^6$ cells/mL are used.

In some embodiments, the mixture may be cultured for several hours (about 3 hours) to about 14 days or any hourly integer value in between. In another embodiment, the beads and T cells are cultured together for 2-3 days. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some embodiments, the media comprises X-VIVO-15 media supplemented with 5% human A/B serum, 1% penicillin/streptomycin (pen/strep) and 300 Units/ml of IL-2 (Miltenyi).

The T cells are maintained under conditions necessary to support growth, for example, an appropriate temperature (e.g., 37° C.) and atmosphere (e.g., air plus 5% CO2).

In some embodiments, the T cells comprising CARs, TCRs and fusion proteins are autologous. In some embodiments, the T cells comprising CARs, TCRs and fusion proteins are allogeneic. Prior to expansion and genetic modification, a source of T cells is obtained from a subject. Immune cells such as T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation.

In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In alternative embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In some embodiments, immune cells such as T cells are isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, in one embodiment, T cells are isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immuneadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD 11b, CD 16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

In some embodiments, the cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Pharmaceutical Compositions

The disclosure provides pharmaceutical compositions comprising immune cells comprising the fusion proteins of the disclosure and a pharmaceutically acceptable diluent, carrier or excipient. In some embodiments, the immune cells further comprise a CAR or TCR.

Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; and preservatives.

Methods of Treating Disease

Provided herein are methods of treating a disease or disorder in a subject in need thereof, comprising administering to an immune cell of the disclosure, and later administering a hormone that specifically binds the SHR domain, wherein the hormone causes activation of the fusion protein resulting in apoptosis of the immune cell. In some embodiments, the immune cell further comprises a CAR or TCR. For example, the immune cell is an immune cell that has been genetically modified to express a CAR or TCR that targets the immune cell to a particular cell or tissue type in the subject to treat the disease or disorder.

In some embodiments of the methods of the disclosure, the immune cell is a T cell. In some embodiments, the T cell is a regulatory T cell (Treg). Tregs are a subpopulation of T cells that modulate the immune system, maintain tolerance to self-antigens, and prevent autoimmune disease. Populations of Tregs can enriched through use of appropriate surface makers, for example CD4+ and CD25+.

In some embodiments, the disease or disorder is a proliferative disease or disorder, such as cancer. Cancer is a disease in which abnormal cells divide without control and spread to nearby tissue. In some embodiments, the cancer comprises a liquid tumor or a solid tumor. Exemplary liquid tumors include leukemias and lymphomas. Further cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CIVIL), and hairy cell leukemia. Exemplary solid tumors include sarcomas and carcinomas. Cancers can arise in virtually an organ in the body, including blood, bone marrow, lung, breast, colon, bone, central nervous system, pancreas, prostate and ovary. Further cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

In some embodiments of the methods of the disclosure, the disease or disorder is an autoimmune disease or disorder. Exemplary autoimmune diseases include, but are not limited to, systemic lupus erythematous, type-1 diabetes mellitus, multiple sclerosis, rheumatoid arthritis, psoriasis, chronic inflammatory demylelinating polyneuropathy and vasculitis.

As used herein "treatment" or "treating," includes any beneficial or desirable effect, and may include even minimal improvement in symptoms. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of a symptom of disease. It also refers to delaying the onset or recurrence of a disease or condition or delaying the occurrence or recurrence of the symptoms of a disease. As used herein, "prevention" and similar words also includes reducing the intensity, effect, symptoms and/or burden of disease prior to onset or recurrence.

As used herein, the term "amount" refers to "an amount effective" or "an effective amount" of a polynucleotide or cell to achieve a beneficial or desired prophylactic or therapeutic result, including clinical results.

A "prophylactically effective amount" refers to an amount of a polynucleotide or cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a polynucleotide or cell may vary according to factors such as the disease state, age, sex, and weight of the individual, and the ability of the virus or cell to elicit a desired response in the individual. A therapeutically effective amount is also one in which any toxic or detrimental effects of the polynucleotide or cell are outweighed by the therapeutically beneficial effects. The term "therapeutically effective amount" includes an amount that is effective to "treat" a subject (e.g., a patient).

An "increased" or "enhanced" amount of a physiological response, e.g., electrophysiological activity or cellular activity, is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated cell.

A "decrease" or "reduced" amount of a physiological response, e.g., electrophysiological activity or cellular activity, is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated cell.

By "maintain," or "preserve," or "maintenance," or "no change," or "no substantial change," or "no substantial decrease" refers generally to a physiological response that is comparable to a response caused by either vehicle, or a control molecule/composition. A comparable response is one that is not significantly different or measurable different from the reference response.

The disclosure provides methods of controlling proliferation of transplanted immune cells in a subject previously transplanted with the immune cells of the disclosure, comprising administering a hormone that specifically binds the SHR domain of the fusion protein. For example, if a subject develops graft versus host disease following immune cell transplant, or develops off target effects or other potentially lethal side effects of immune therapy, the tBID fusion proteins described herein provide a way to control the proliferation of the transplanted immune cells in the subject through tBID induced apoptosis under the control of a steroid hormone.

Kits and Articles of Manufacture

The disclosure provides kits and articles of manufacture comprising the polynucleotides and vectors encoding the fusion proteins described herein, and immune cells comprising the fusion proteins described herein. In some embodiments, the immune cells further comprise a CAR or TCR, or a polynucleotide or vector encoding same. In some embodiments, the kit comprises articles such as vials, syringes and instructions for use. The instructions for use may be instructions for use in treating a disease or disorder. In some embodiments, the kit comprises a hormone that specifically binds the SHR of the fusion protein.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

EXAMPLES

Example 1: ESR1 LBD Fused to Truncated tBID Induced Apoptosis in HEK293T Cells Human Embryonic Kidney (HEK) 293T cells were transfected with 1 ug per 1E6 cells using Lipofectamine 3000 and incubated in DMEM+10% FBS+1% Pen/Strep media for 4 hours before adding 1 uM 4-hydroxytamoxifen (+4OHT) or solvent control (No 4OHT). The cells were incubated with 4OHT for 18-24 hours. The cells were then stained with Annexin V to detect apoptotic cells, as well as DAPI to detect dead cells.

Figure 2:
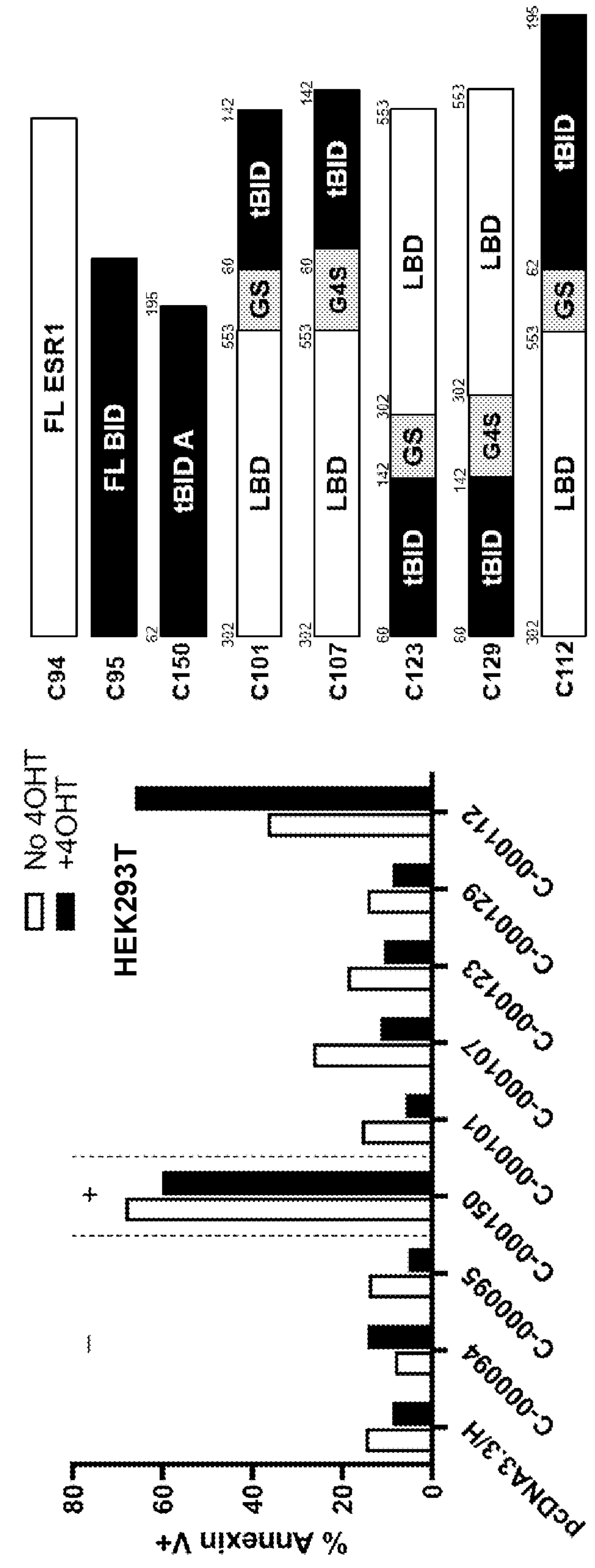
FIG. 2 shows that in HEK293T, full length tBID fused to the C-terminus of the estrogen receptor 1 (ESR1) ligand binding domain (LBD) showed high background and inducible killing. Cells were treated with 1 uM 4-hydroxytamoxifen (+4OHT) or solvent control (No 4OHT).

In cells expressing full length ESR1 or full length Bid alone, negligible death was observed (FIG. 2). In cells expressing the truncated BID (tBID), a potent apoptosis inducer, significant death was observed regardless of the presence of tamoxifen (C150; 60-70% Annexin V+) (FIGS. 2 and 3). Fusing tBID to the C-terminus of the ligand binding domain (LBD) of ESR1 resulted in inducible cell death (C112, FIG. 2). This construct showed ~1.5× inducible apoptosis in the presence of 4OHT as opposed to the solvent control. Truncating the C-terminal region of tBID (amino acids 60-142, constructs C123 and C129) resulted in lack of death (FIG. 2).

Example 2: The ESR1 LBD Fused to Truncated tBID in Jurkat Cells

Jurkat immortalized T lymphocytes were transfected with 1 ug per 1E6 cells using Neon electroporation and incubated in RPMI+20% FBS+0.1% Pen/Strep media for 4 hours before adding 1 uM 4-hydroxytamoxifen (+4OHT) or solvent control (No 4OHT). The cells were incubated with 4OHT for 18-24 hours. The cells were then stained with Annexin V to detect apoptotic cells, as well as propidium iodide (PI) to detect dead cells.

Figure 3A:
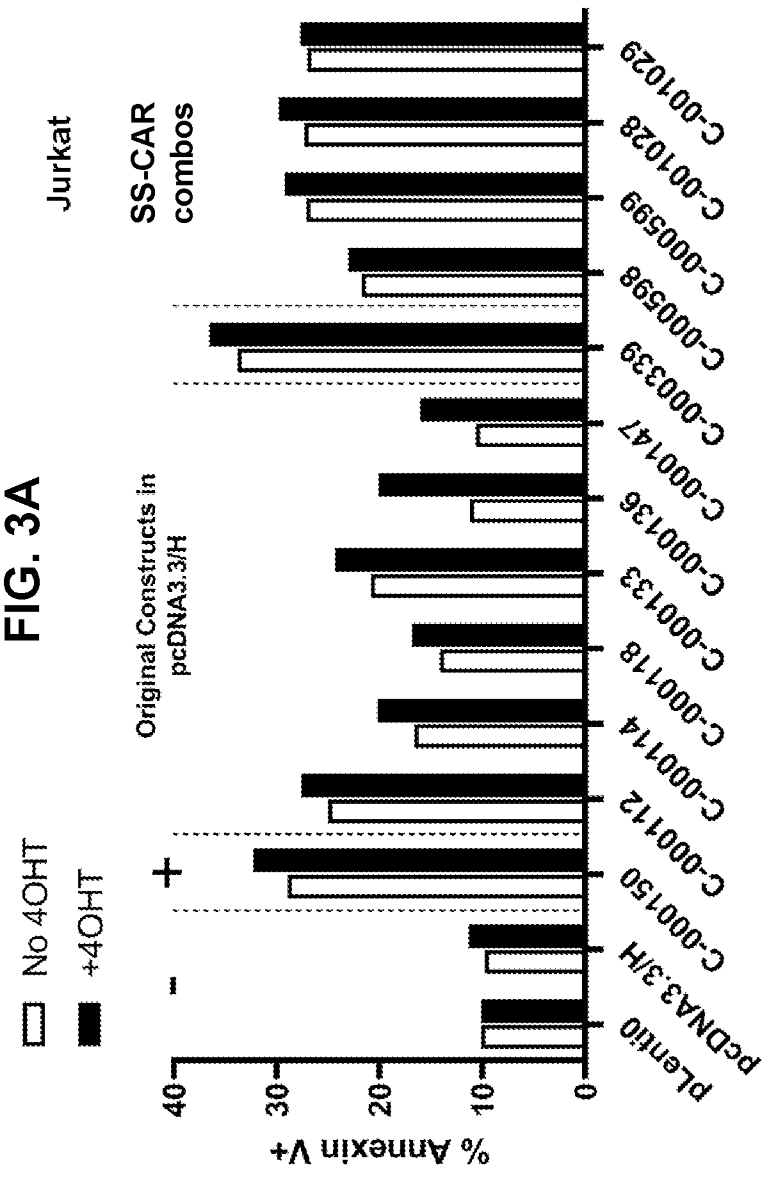
FIG. 3A is a plot showing that, in Jurkat cells, full length tBID fused to the C-terminus of the ESR LBD did not show inducible killing.
Figure 3B:
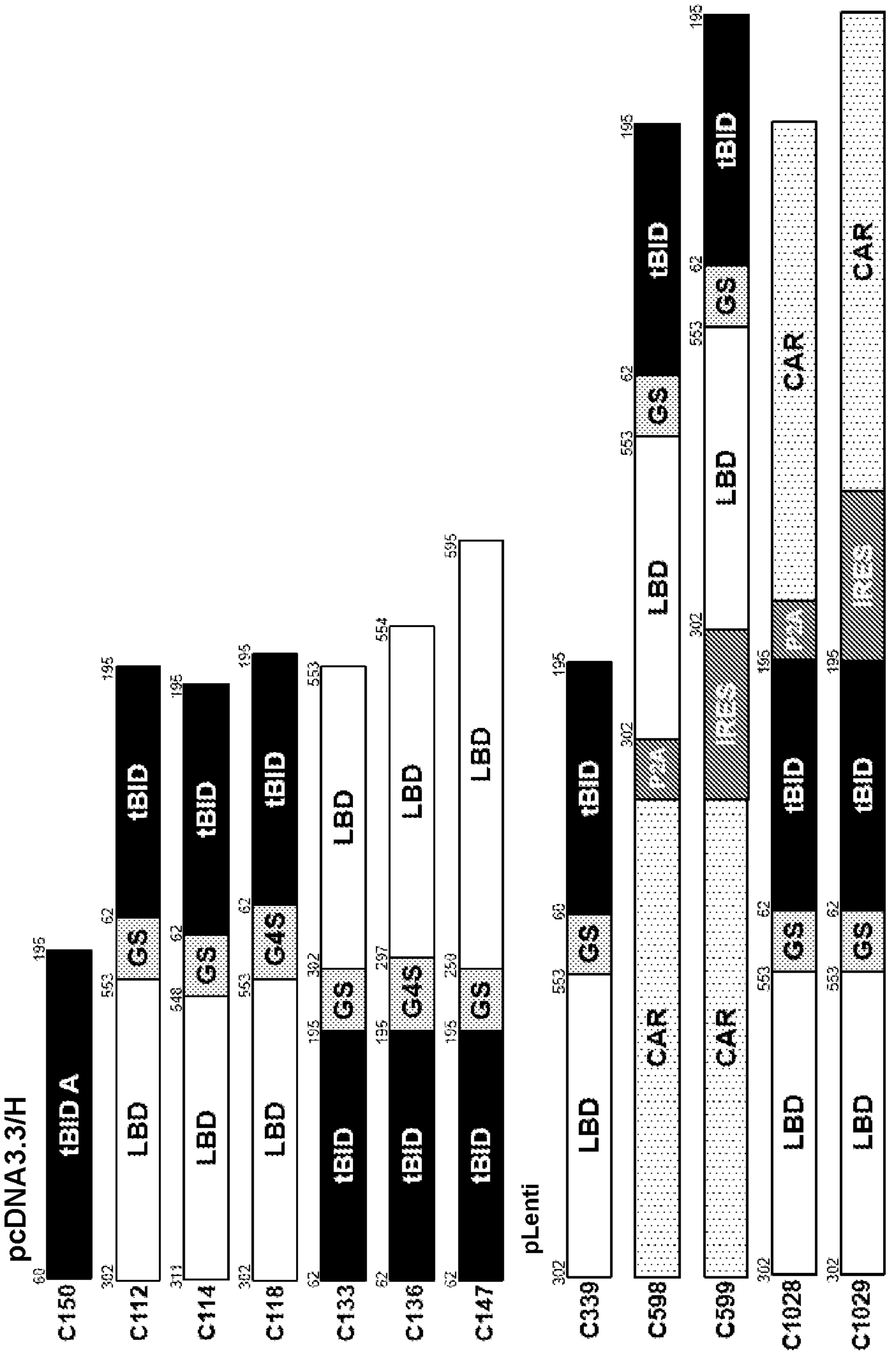
FIG. 3B is a diagram showing the constructs corresponding to FIG. 3A.

Unlike in HEK293T cells, the C112 did not show inducible apoptosis in Jurkat cells (FIG. 3A). In order to test these constructions in primary T cells, ESR1-tBid fusion constructs were cloned into a vector containing anti-NY-ESO-1 chimeric antigen receptor (CAR). Transfection of all of the tBID Safety Switch (SS)-CAR combination constructs shown in FIG. 3B resulted in high background killing and lack of inducible apoptosis (FIG. 3A).

Example 3: Mutations in the ESR1 LBD that Change ESR1 Affinity for Estrogen, 4OHT or Hsp90

Figure 4:
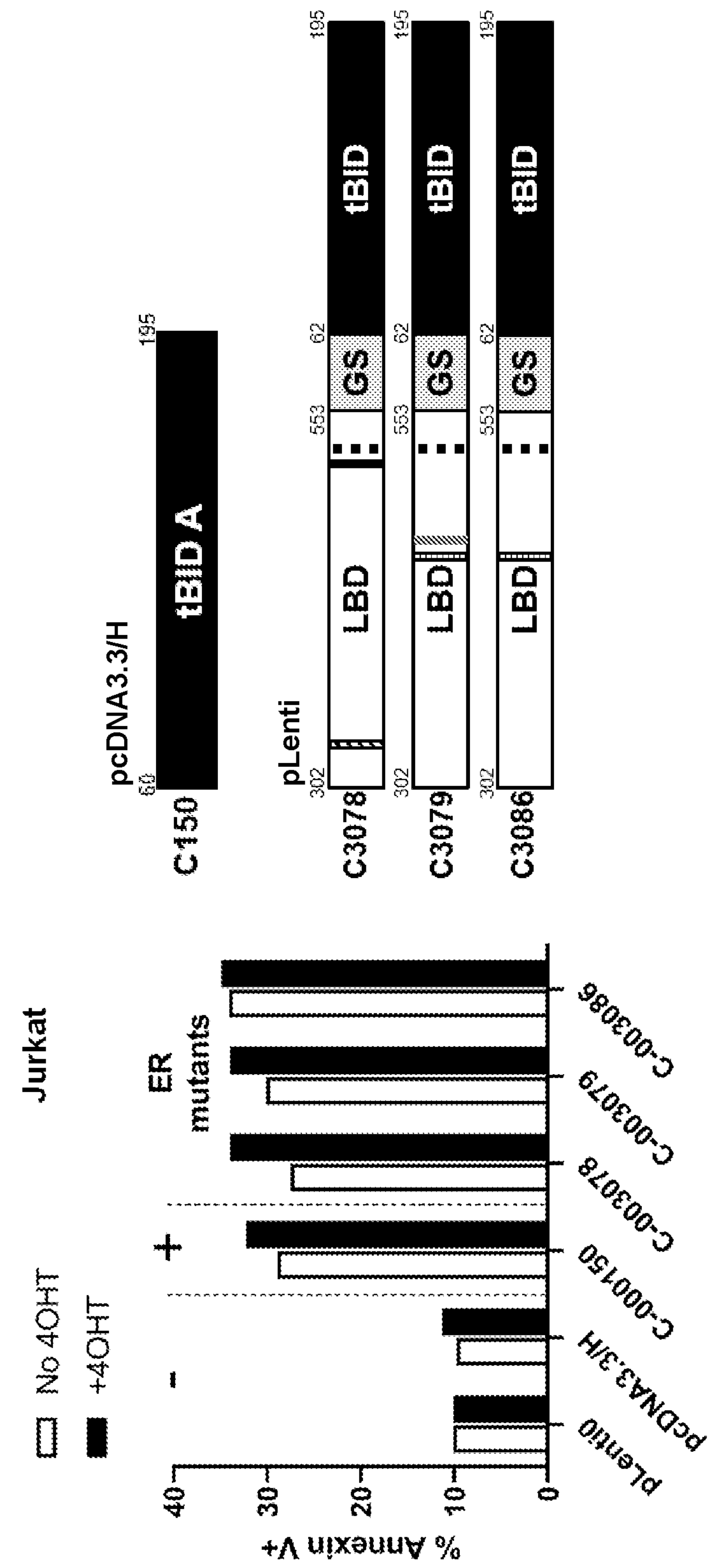
FIG. 4 shows that in Jurkat cells, mutant ESR1 constructs that were assayed for an increase in ESR1 LBD affinity for either active 4-hydroxytamoxifen (4OHT) or Hsp90 did not reduce background killing.

One possibility is that the affinity of the ESR1 LBD for estrogen may be causing the high background level of apoptosis in these constructs. Therefore, we generated mutants in the ESR1 LBD that either increase ESR1 LBD affinity for 4OHT vs. estrogen (mutations E352A, shown in FIG. 4 as a line with thick diagonal stripes; G521T, shown in FIG. 4 as a solid black line; and H524A, shown in FIG. 4 as a dotted line), or increase ESR1 LBD affinity for Hsp90 (G400V, shown in FIG. 4 as a line with thin, horizontal stripes). A C447A mutation was included to remove a potential palmitoylation site, which, when palmitoylated, is thought to recruit ESR1 to the plasma membrane (shown in FIG. 4 as a gray line). However, as can be seen from FIG. 4 these mutations did not reduce background apoptosis or improve inducibility of apoptosis.

Example 4: Assaying N-Terminal Truncations of BID

The NMR structure of tBID suggested that the full length tBID is extended, with its two functional domains, the BH3 domain and the membrane tethering domain, being far apart. Without wishing to be bound by theory, this extended structure of tBID may have reduced its dependence on the ESR1 LBD to induce apoptosis.

The N-terminal region of tBID, which is flexible and likely unnecessary for its apoptotic function. Therefore we sequentially truncated this region (producing truncations starting at amino acids 62, 70, 78, see FIG. 5B) and tested the effect on apoptosis when fused to the ESR1 LBD in either the N or C terminal orientation.

Figure 5A:
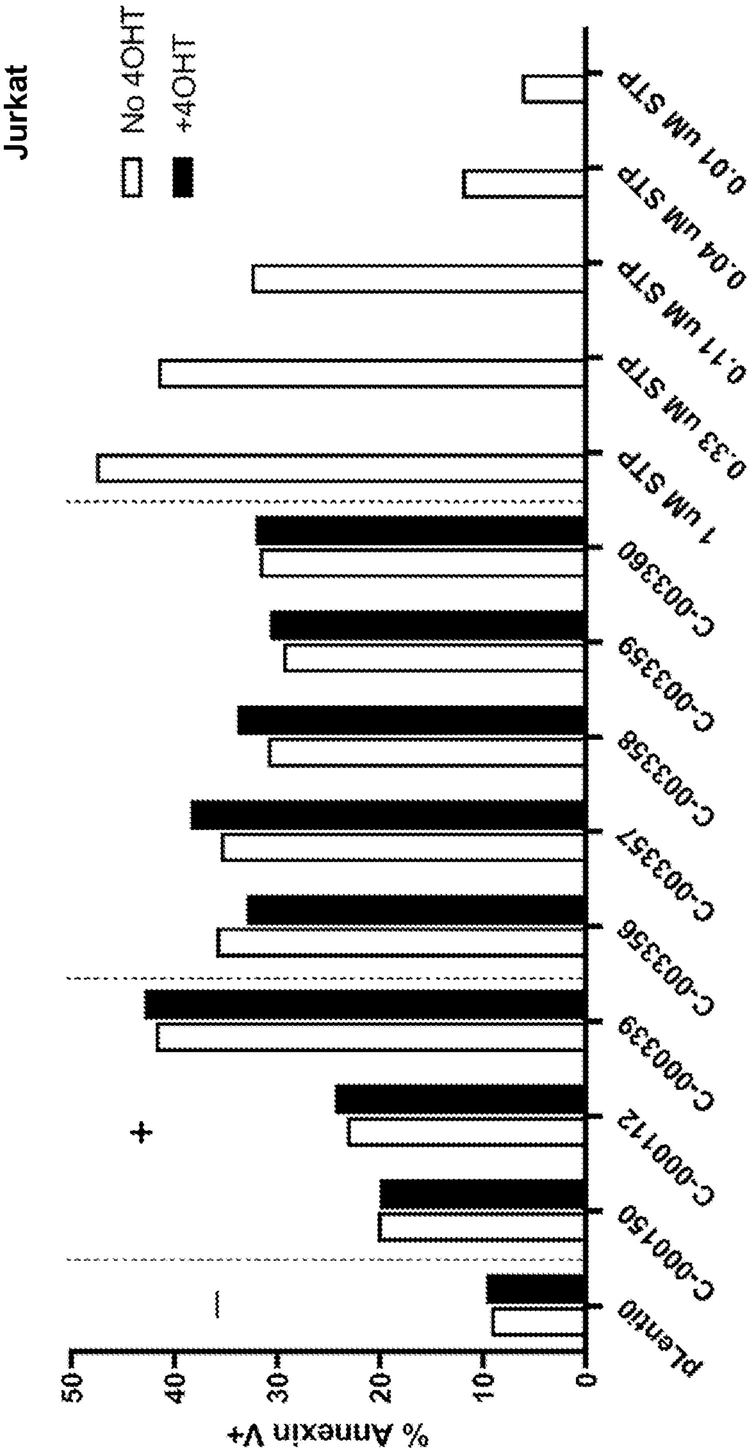
FIG. 5A is a plot showing that the N-terminal loop of tBID is dispensable for tBID killing function.
Figure 5B:
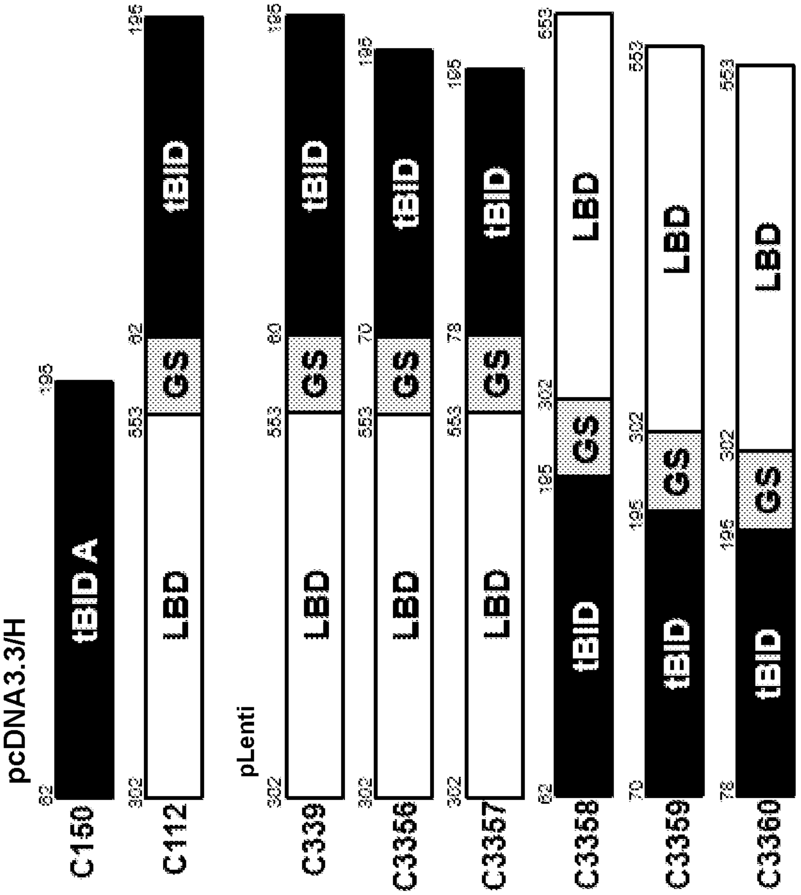
FIG. 5B is a diagram showing the constructs corresponding to FIG. 5A.

Jurkat cells were transfected with 1 ug of DNA per 1E6 cells using Neon electroporation, treated +/−4OHT for 18-24 hrs, and stained with Annexin V to detect apoptotic cells, as well as PI to detect dead cells (FIG. 5A). These tBID N-terminal truncation constructs did not result in significant reduction of background apoptosis or improvement in inducibility.

Example 5: Identification of the Minimal tBID Necessary for Apoptosis

Figure 6:
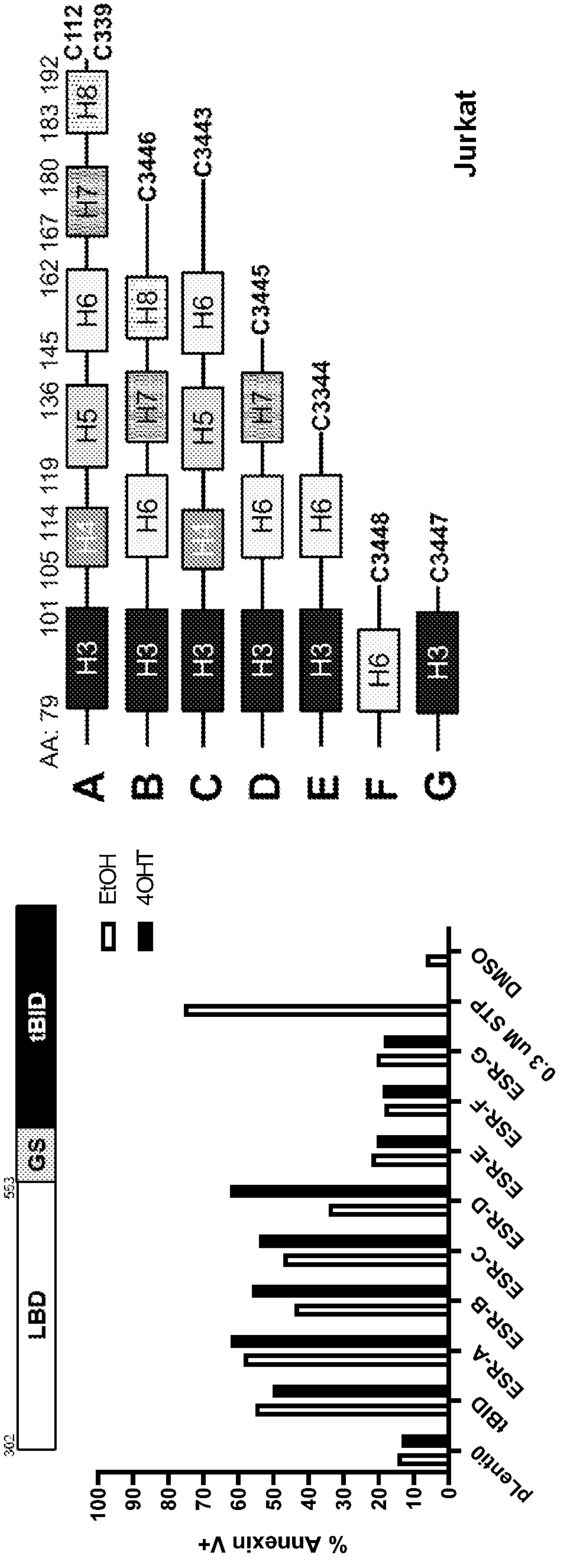
FIG. 6 shows that ESR1-tBID safety switch construct H3, 6-7 (truncation D) has low background killing and high inducibility in Jurkat cells.

One possibility is that the BID α3 and α6 helices are necessary and sufficient for tBID function. Therefore, we made various truncations that included α3 and α6, as well as various other helices. Jurkat cells were transfected with 1 ug DNA per 1E6 cells, treated with 4OHT or solvent control, then stained as in Example 4. When these various tBID truncations were fused to the C-terminus of ESR1, (ESR1-tBid orientation, i.e. the ESR1 LBD is fused to the N-terminus of the tBID domain via a Gly-Ser linker), all constructs displayed similar levels of background apoptosis and negligible inducible apoptosis (FIG. 6). One exception was the ESR-D tBID fusion construct, which has the Bid α3, α6 and α7 helices (FIG. 6). 0.3 uM staurosporine (STP) and DMSO solvent control were included as controls.

Example 6: Effect of Orientation on Inducible and Background Apoptosis

Figure 7:
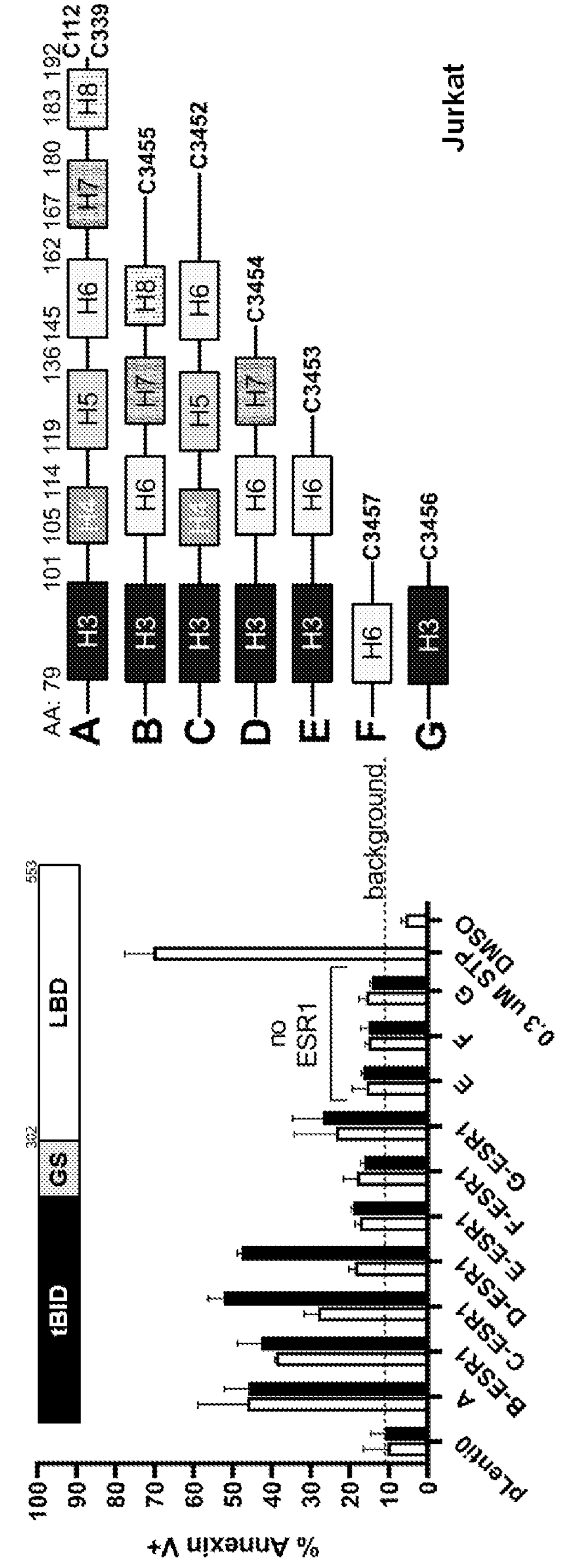
FIG. 7 shows that decreasing tBID domain length to minimal tBID (mintBID) improves inducibility in Jurkat cells when tBID is fused to the N-terminus of ESR1.
Figure 11A:
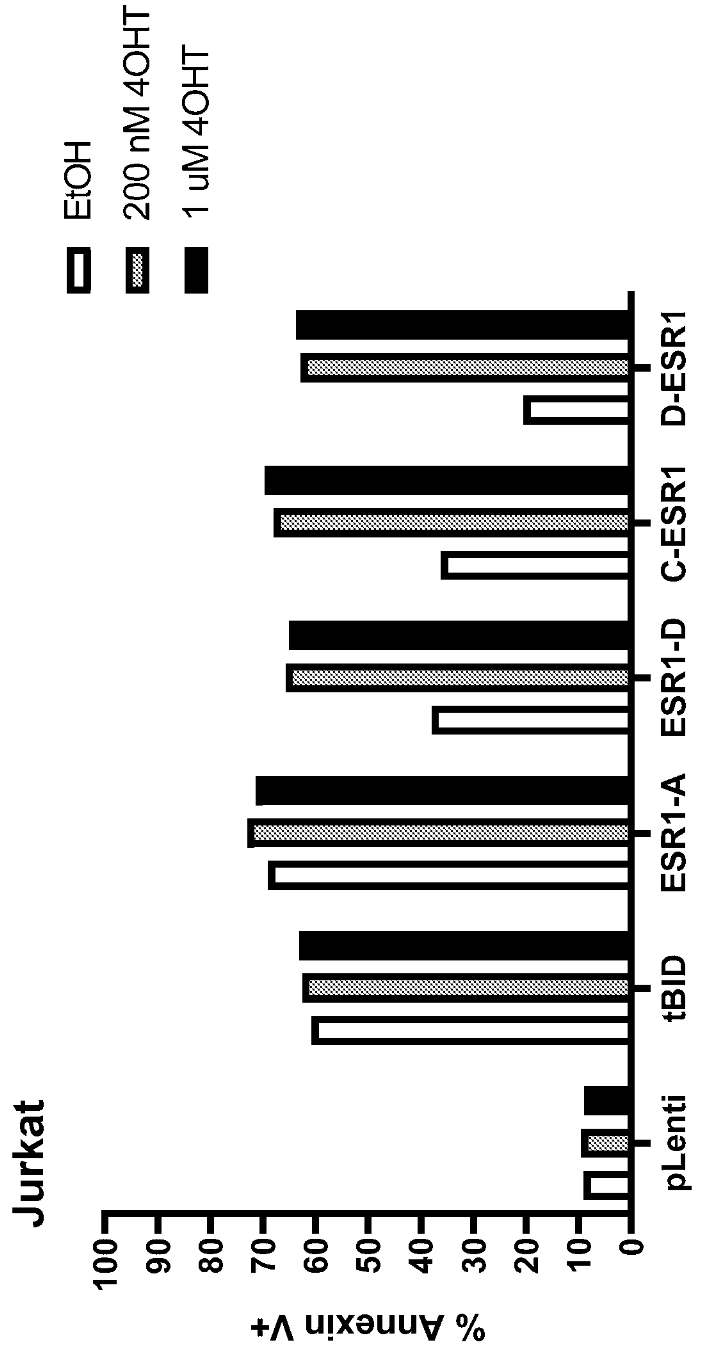
FIG. 11A is a plot showing that apoptosis is induced at intermediate doses of tamoxifen in Jurkat cells.

The tBID truncations from Example 5 were fused to the N-terminus of ESR1 (tBid-ESR1 orientation). In this orientation, two constructs showed inducible apoptosis: C and D (FIG. 7). Construct C-ESR1 contains tBID helices α3, α4, α5 and α6, while construct D-ESR1 contains tBID helices α3, α6 and α7 (see FIG. 7). These results indicate that α3 and 6 are required for apoptosis in transfected Jurkat cells treated with 4OHT. However, surprisingly, the tBID α3 and a 6-only construct (E-ESR1) did not have significant levels of background or induced apoptosis (FIG. 7). In contrast, D-ESR1 (C3454) reproducibly showed low background apoptosis in solvent control-treated Jurkat cells, while inducing apoptosis in 4OHT-treated Jurkat cells (FIGS. 7 and 11A).

Example 7: Determining Fold Change in Apoptosis Upon 4OHT Addition

Figure 8:
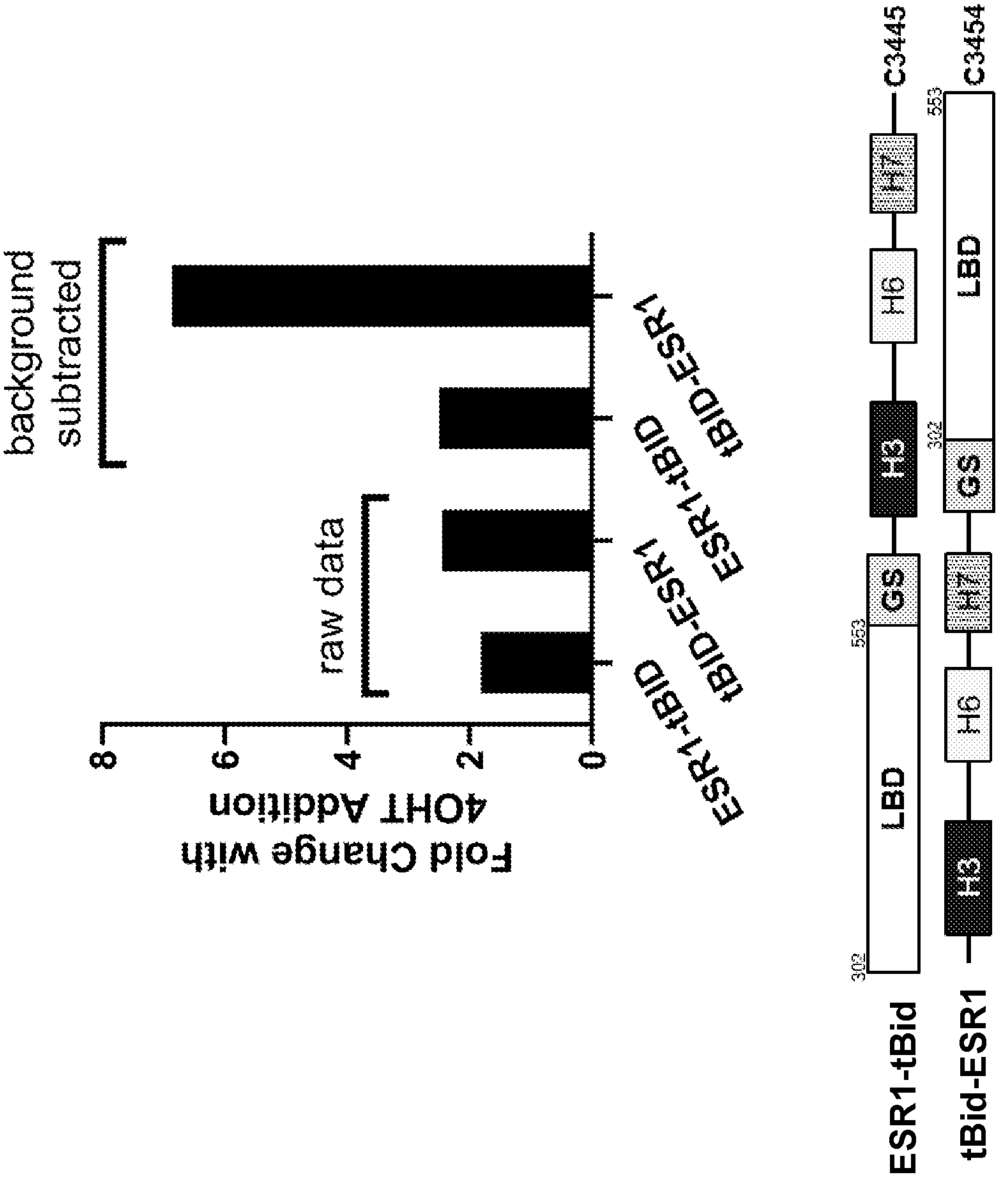
FIG. 8 shows that a construct with a tBID-ESR1 orientation shows greater inducibility than a construct with an ESR1-tBID orientation in Jurkat cells.

Jurkat cells were transfected with 1 ug DNA per 1E6 cells, treated with 4OHT or solvent control, then stained as in Example 4. The fold change in in apoptosis upon 4OHT addition was determined by dividing the percent Annexin V positive cells treated with 4OHT by the percent Annexin V positive cells treated with a solvent control (FIG. 8). The fold change was calculated from one experiment. As electroporation of empty vector always results in some background death of cells, percent Annexin V positive cells of pLenti was used as the background and subtracted from total percentage to obtain “background subtracted” fold change values. As seen clearly in the bar graph representation in FIG. 8, tBID-ESR1 orientation produces a greater fold change in apoptosis upon 4OHT induction than the ESR1-tBID orientation.

Figure 9:
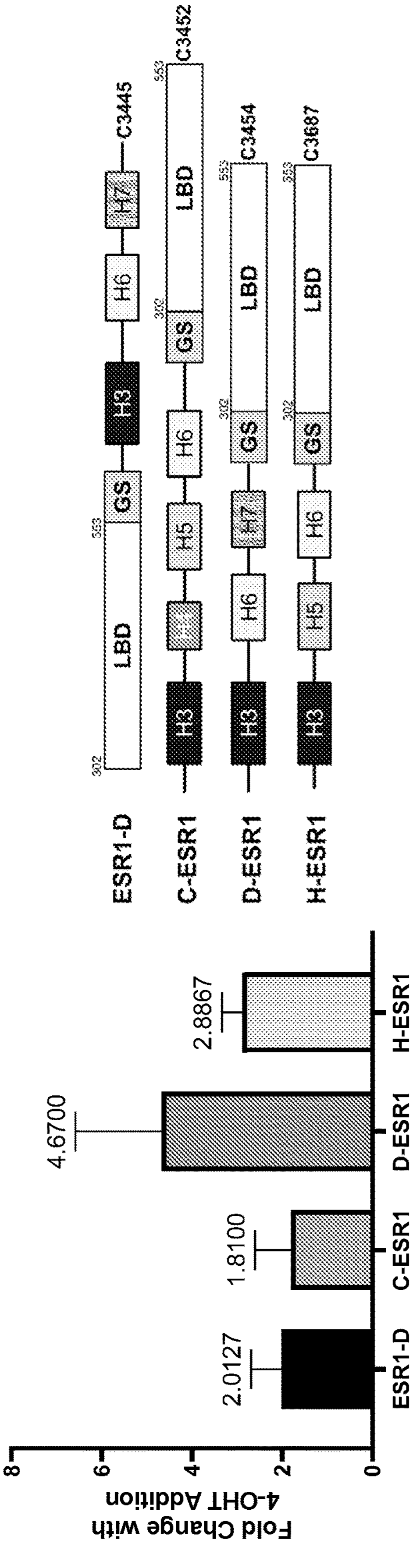
FIG. 9 is a plot and a diagram of constructs showing that additional tBID truncations are inducible using 4OHT.

Based on previous results showing the necessity of helices H3 and H6 for inducible killing activity additional tBID constructs that contained H3 and H6 helices were generated, and assayed for fold change in apoptosis with 4OHT addition (FIG. 9). In FIGS. 8-9, fold change was determined with background subtraction.

Example 8: Effect of Tamoxifen Dose and DNA Amount on Inducibility

The amount of Tamoxifen, and the amount of tBID construct DNA used during transfection, were assayed for their effects on apoptosis in HEK293T cells.

HEK293T cells were transfected with varying amounts of DNA of a vector control (pLenti), with construct A tBID (lacking a LBD, C150, see FIG. 5B), or with C-ESR1 or D-ESR1 (FIG. 10, bottom), and assayed for apoptosis using either 200 nM OHT or 1 μM 4OHT.

Figure 10:
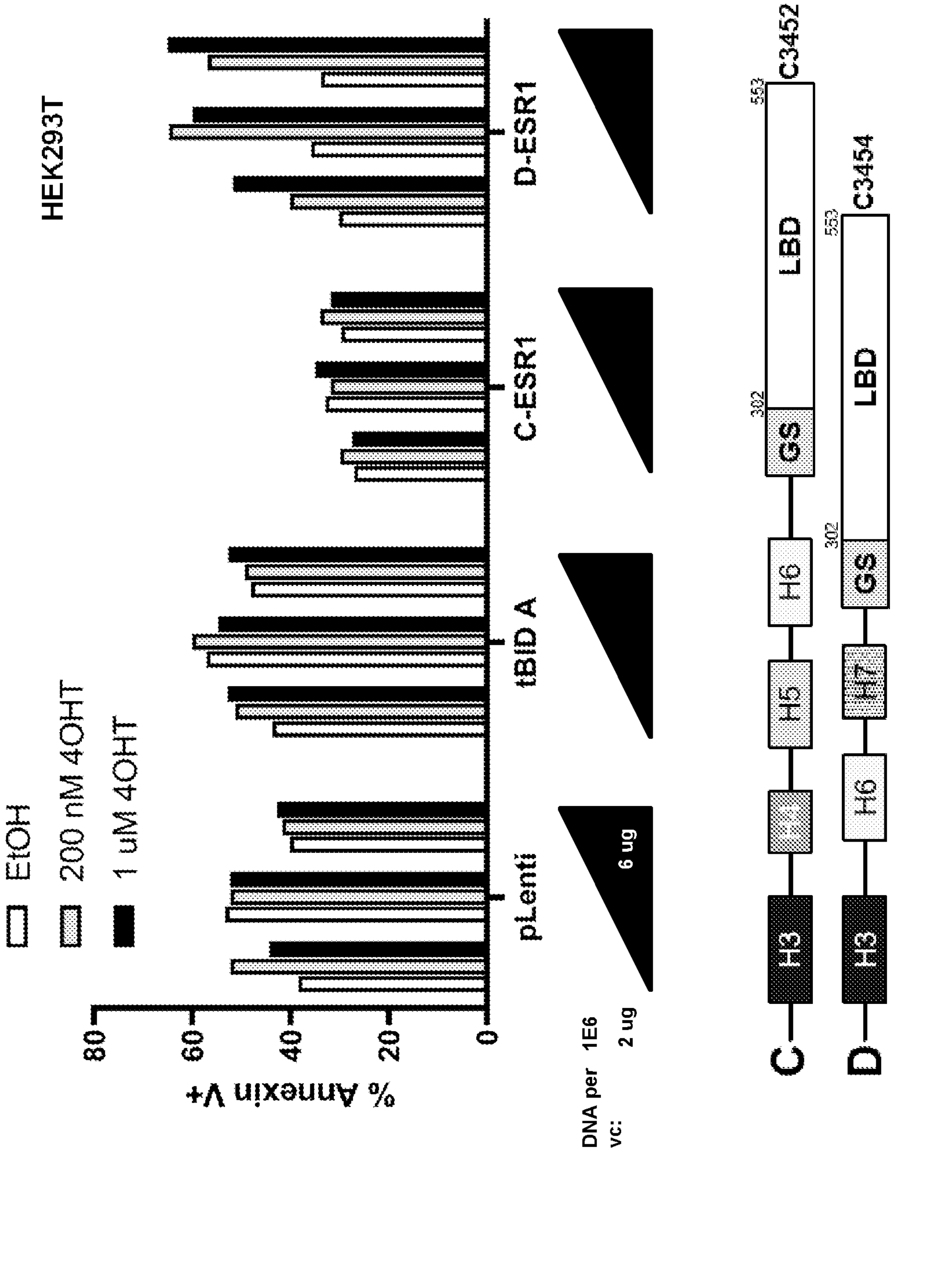
FIG. 10 shows the effect of tamoxifen dose and amount of DNA used during transfection on inducibility in HEK293T cells.
Figure 11B:
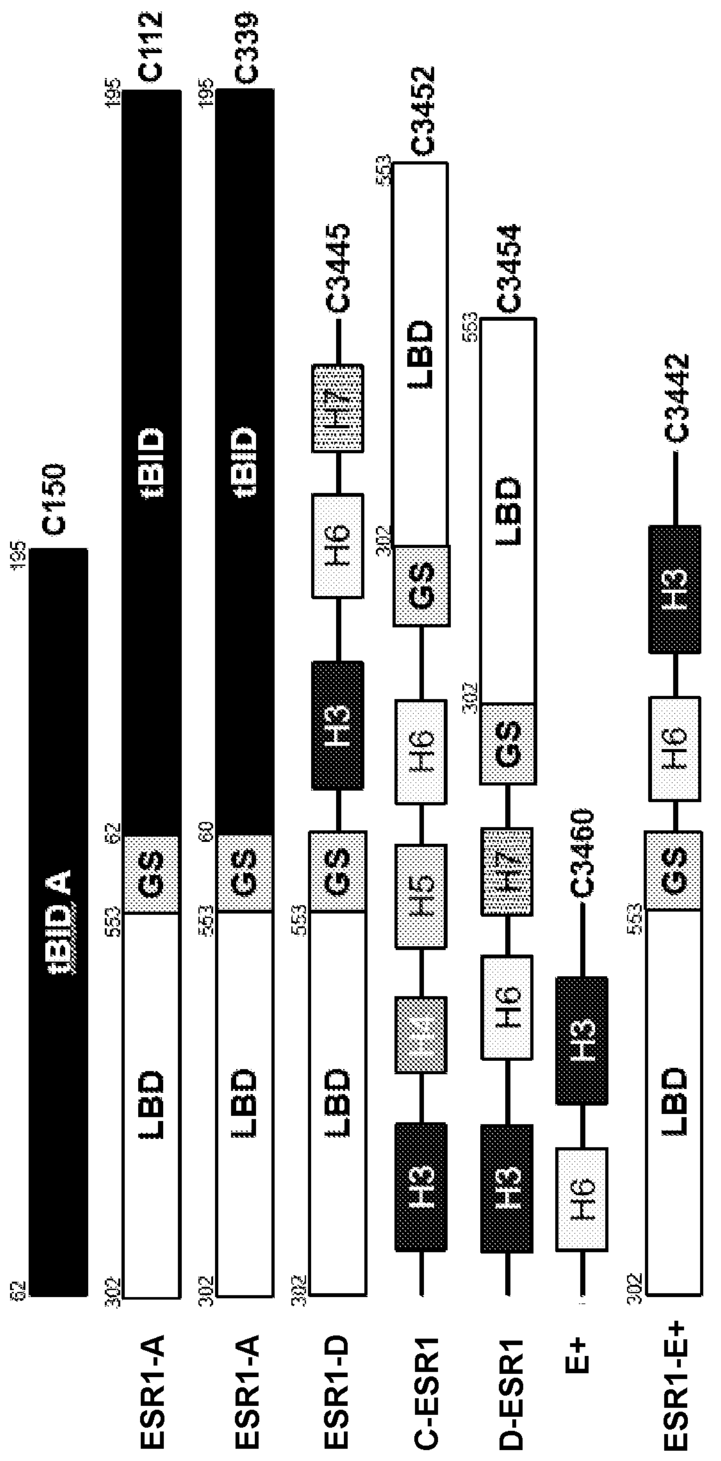
FIG. 11B is a diagram showing the constructs corresponding to FIG. 11A.

Induction of apoptosis was achieved at intermediate doses of tamoxifen, and the amount of DNA used during transfection had negligible effect on inducibility. To determine the effect of amount of DNA as well as 4OHT concentration on apoptosis induction, we titrated both the amount of DNA (2, 3, or 6 ug DNA per 1E6 cells) and the concentration of 4OHT. 500,000 cells HEK293T cells were plated in a 24-well plate. ~2 hours after plating, appropriate amounts of DNA were transfected using Lipofectamine 3000 and incubated for 4 hours. Either ethanol solvent control, 200 nM 4OHT, or 1 uM 4OHT was added to the transfected cells then incubated for ~18-24 hours. The cells were then stained as in Example 4. Intriguingly, C-ESR1 was not inducible in HEK293 Ts, unlike in Jurkat cells (Example 6, FIGS. 7 and 11A-B). This cell type specific effect was also observed in the case of ESR1-A, which was effective in HEK293T but not in Jurkat cells (FIGS. 2 and 3, C112). However, construct C3454 (D-ESR1, FIG. 10 bottom) retained activity across cell types. Increasing the absolute amount of DNA does not increase background in HEK29 Ts but increases the window of induction (FIG. 10, D-ESR1, from left to right).

To determine the effect of 4OHT concentration on apoptosis induction in Jurkat cells, Jurkat cells were transfected with 2 ug DNA per 1E6 cells. 4 hours post-transfection, either ethanol solvent control, 200 nM 4OHT, or 1 uM 4OHT was added to the transfected cells then incubated for 20 hours. The cells were then stained with Annexin V and PI to measure cell death. As shown in FIG. 11A, D-ESR1 consistently induced apoptosis, while the ESR1-C and ESR1-D constructs resulted in relatively high background levels of cell death. Apoptosis was robustly induced at either 200 nM or 1 uM 4OHT using ESR1-D, suggesting that even at 200 nM 4 OHT, the system was saturated, and potentially lower doses of 4OHT can be used to induce apoptosis.

Figure 12:
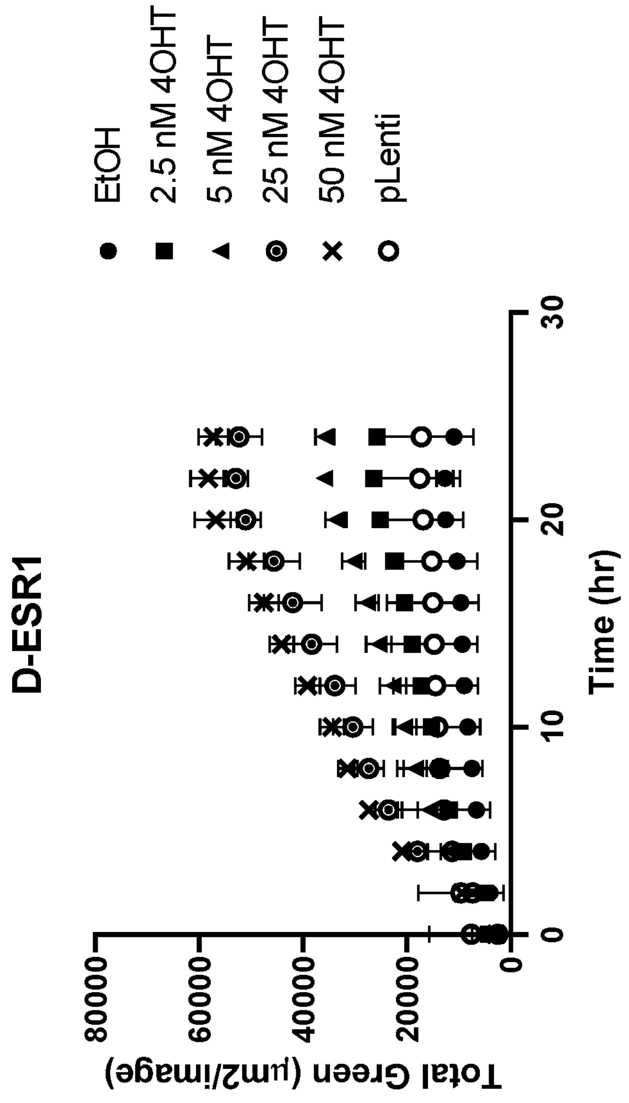
FIG. 12 is a plot showing a time-course of tamoxifen-mediated killing of Jurkat cells transfected with D-ESR1. Total Green (in $\mu m^2$/image) is used as an indicator of apoptosis, as cells turn green in this assay when caspase-3/7-mediated apoptosis occurs.

Example 9: Time Course of Tamoxifen-Mediated Killing of D-ESR1 Containing Jurkat Cells To characterize tamoxifen-induced killing activity in transfected Jurkat cells over time, Jurkat cells were transfected with 1 ug DNA per 1 E6 cells as described previously above. 24 hours post-transfection, Jurkat cells were harvested and resuspended in complete RPMI media containing 10% FBS, 1% Pen/Strep, and 5 uM Caspase-3/7 Green Reagent (Essen Bioscience 4440). The resuspended cells were plated onto poly-L-ornithine treated 384-well plates and left at room temperature for 30 minutes. Then, RPMI+10% FBS+1% Pen/Strep+5 uM Caspase-3/7 Green Reagent containing appropriate 2×4OHT or EtOH was added to the cells. Induction of apoptosis was measured using the Caspase-3/7 dye, which couples caspase-3/7 recognition motif with a DNA intercalating dye. Cells turn green if and only if caspase-3/7-mediated apoptosis occurs. The cells were imaged using the IncuCyte S3 Live-Cell Analysis System. The results are shown in FIG. 12.

Example 10: Background and Induced Apoptosis in Primary T Cells Transduced with D-ESR1

Figure 13B:
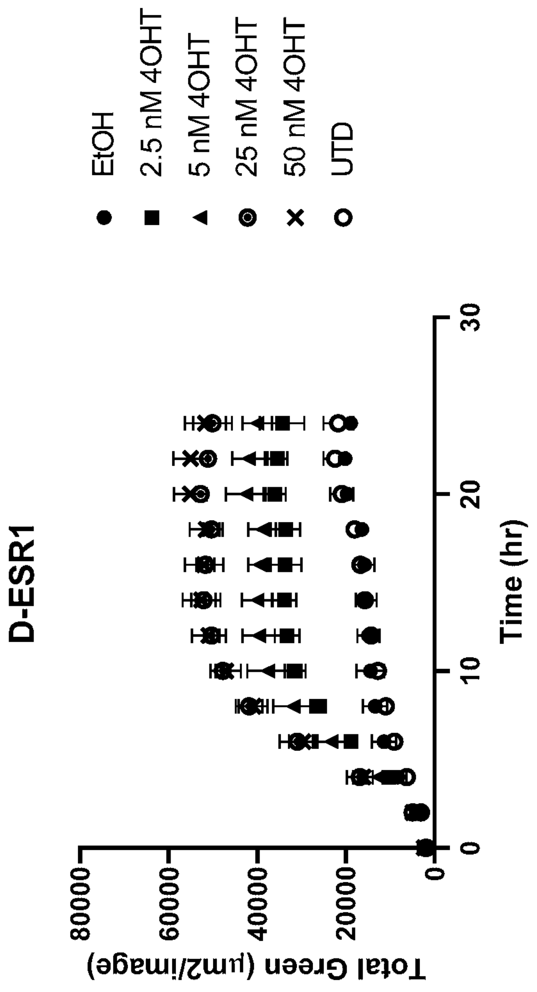
FIG. 13B is a plot showing a time-course of tamoxifen-mediated killing of primary T cells transduced with D-ESR1. UTD: untransduced.
Figure 13A:
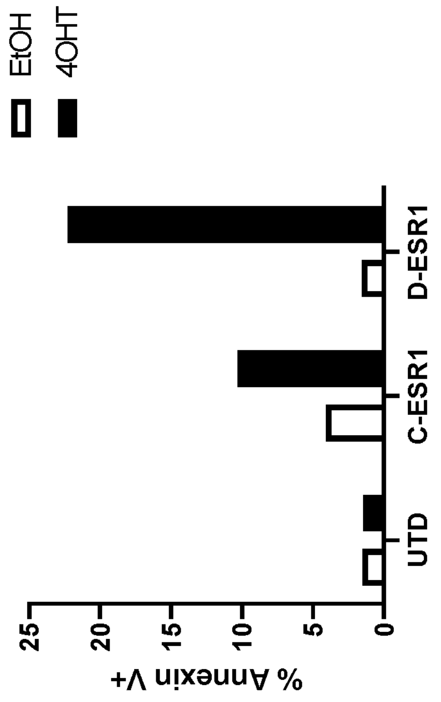
FIG. 13A is a plot showing percent Annexin V positive primary T cells following induction of apoptosis using 4OHT. Primary T cells were transduced with D-ESR1 or C-ESR1. UTD: untransduced.

To characterize tBID-ESR1 safety switch function in primary T cells, D504C cells were transduced with lentiviral constructs containing either C-ESR1 or D-ESR1. The cells were maintained and expanded in media containing 300 IU/mL IL-2. To induce apoptosis, 1E6 cells were resuspended in 1 mL of LymphoONE media containing 1% human serum and 1 uM 4OHT. As a solvent control, same volume of ethanol was added to the cells. 20 hours after 4OHT addition, cells were stained with Annexin V and PI to measure cell death as described in Example 9. The results are shown in FIG. 13A. The results mirror what was seen in transiently-transfected Jurkat cells, with D-ESR1 showing greatest inducible killing as well as low background.

Primary T cells transduced with D-ESR1 were prepared similarly to Jurkat cells in Example 9 and 4OHT-mediated death was measured using the Caspase-3/7 Green Reagent as described in Example 9. Results are shown in FIG. 13B. In transduced primary T cells, there is low background and inducible apoptosis is seen for D-ESR1, similar to Jurkat cells.

The invention claimed is:

1. A polynucleotide comprising a polynucleotide sequence encoding a fusion protein, the fusion protein comprising a truncated BH3-interacting domain death agonist (tBID) polypeptide and a steroid hormone receptor (SHR) domain polypeptide, wherein the tBID polypeptide comprises a deletion of BID helix 1 and BID helix 2, and wherein any of A-D is true:

a) wherein the tBID polypeptide shares at least 95% identity to SEQ ID NO: 1;

b) wherein the tBID polypeptide shares at least 95% identity to SEQ ID NO: 93;

c) wherein the fusion protein shares at least 95% identity to ESR1-D (SEQ ID NO: 4);

d) wherein the fusion protein shares at least 95% identity to D-ESR1 (SEQ ID NO: 5);

e) wherein the fusion protein shares at least 95% identity to ESR1-C(SEQ ID NO: 6);

f) wherein the fusion protein shares at least 95% identity to C-ESR1 (SEQ ID NO: 7); or g) wherein the fusion protein shares at least 95% identity to H-ESR1 (SEQ ID NO: 97).

2. A vector comprising the polynucleotide of claim 1.

3. The vector of claim 2, wherein the vector is a lentiviral vector.

4. An isolated immune cell comprising the polynucleotide of claim 1.

5. A method of controlling proliferation of transplanted immune cells in a subject previously transplanted with the immune cell of claim 4, comprising administering a hormone that specifically binds the SHR domain polypeptide of the fusion protein.

6. A method of making an immune cell, comprising introducing the polynucleotide of claim 1 into an immune cell.

* * * * *